US009273055B2

(12) United States Patent
Gregor

(10) Patent No.: US 9,273,055 B2
(45) Date of Patent: Mar. 1, 2016

(54) TYROSINE KINASE INHIBITORS

(71) Applicant: Chembridge Corporation, San Diego, CA (US)

(72) Inventor: Vlad Edward Gregor, Del Mar, CA (US)

(73) Assignee: CHEMBRIDGE CORPORATION, San Diego, CA (US)

(*) Notice: Subject to any disclaimer, the term of this patent is extended or adjusted under 35 U.S.C. 154(b) by 0 days.

(21) Appl. No.: 14/308,088

(22) Filed: Jun. 18, 2014

(65) Prior Publication Data

US 2015/0038536 A1 Feb. 5, 2015

Related U.S. Application Data

(60) Division of application No. 13/231,797, filed on Sep. 13, 2011, now Pat. No. 8,822,500, which is a continuation-in-part of application No. 12/922,891, filed as application No. PCT/US2009/001691 on Mar. 18, 2009, now Pat. No. 8,815,906.

(60) Provisional application No. 61/038,032, filed on Mar. 19, 2008, provisional application No. 61/382,485, filed on Sep. 13, 2010.

(51) Int. Cl.
*A61K 31/4439* (2006.01)
*C07D 487/04* (2006.01)

(52) U.S. Cl.
CPC .................................... *C07D 487/04* (2013.01)

(58) Field of Classification Search
CPC .................................................. A61K 31/4439
USPC .......................................................... 514/338
See application file for complete search history.

(56) References Cited

U.S. PATENT DOCUMENTS

| | | | |
|---|---|---|---|
| 3,536,809 | A | 10/1970 | Applezineig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie et al. |
| 5,073,543 | A | 12/1991 | Marshall et al. |
| 5,120,548 | A | 6/1992 | McClelland et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis et al. |
| 8,063,225 | B2 | 11/2011 | Gregor et al. |
| 8,815,906 | B2 | 8/2014 | Gregor et al. |
| 8,822,500 | B2 | 9/2014 | Gregor |
| 2012/0065233 | A1 | 3/2012 | Gregor |
| 2015/0011539 | A1 | 1/2015 | Gregor |
| 2015/0038536 | A1 | 2/2015 | Gregor |

FOREIGN PATENT DOCUMENTS

| | | |
|---|---|---|
| AU | 2009226153 B2 | 9/2009 |
| CA | 2109993 | 5/1994 |
| EP | 2262807 A1 | 12/2010 |
| WO | WO 2004/063151 | 7/2004 |
| WO | WO 2004/096807 | 11/2004 |
| WO | WO 2005/009389 | 2/2005 |
| WO | WO 2006/115452 | 2/2006 |
| WO | WO 2006/108488 | 10/2006 |
| WO | WO 2008/021369 | 2/2008 |
| WO | WO 2008/022747 | 2/2008 |

OTHER PUBLICATIONS

LeRoith et al., The insulin-like growth factor system and cancer, Cancer Letters, 195, pp. 127-137 (2003).*
Simone, Oncology:Introduction, Cecil Textbook of Medicine, ed Bennett et al. W.B.Saunders CO. 20th ed, vol. 1, 1996, pp. 1004-1010.*
Robinson, Medical Therapy of Inflammatory Bowel Disease for the 21st century, Eur. J. Surg. 164, Suppl. 582, pp. 90-98, (1998).*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Lodish et al., "Endocrine side, etc.," Endocrine-Related Cancer (2010) 17, R233-R244.*
Dietz et al., "HDAC inhibitors, etc.," Pharmacological Research 62 (2010) 11-17.*
Ouaissi et al., "Rationale for Possible, etc.," Journal of Biomedicine and Biotechnology, 2011, Article: ID 315939, 1-8.*
Golub et al, Science, vol. 286, Oct. 15, 1999, pp. 531-537.*
Carstensen, Drug Stability: Principles & Practice, 2d. Ed., Marcel Dekker, NY, NY, 1995, pp. 379-380.
Gunby et al., "An enzyme-linked immunosorbent assay to screen for inhibitors of the oncogenic anaplastic lymphoma kinase," Haematologica, 2005, 90, 988-990.
Bonvini et al., "Nucleophosmin-Anaplastic Lymphoma Kinase (NPM-ALK), a Novel Hsp90-Client Tyrosine Kinase: Down-Regulation of NPM-ALK Expression and Tyrosine Phosphorylation in ALK+ CD30+ Lymphoma Cells by the Hsp90 Antagonist 17-Allylamino,17-demethoxygeldanamycin ," Cancer. Res. 2002, 62, 1559-1566.
Turturro et al., "Model of Inhibition of the NPM-ALK Kinase Activity by Herbimycin A," Clin. Cancer Res. 2002, 8, 240-245.
Morris et al., "ALK, the chromosome 2 gene locus altered by the t(2;5) in non-Hodgkin's lymphoma, encodes a novel neural receptor tyrosine kinase that is highly related to leukocyte tyrosine kinase (LTK)," Oncogene, 1997, 14:2175-2188.
Iwahara et al., "Molecular characterization of ALK, a receptor tyrosine kinase expressed specifically in the nervous system," Oncogene, 1997, 14:439-449.
Stoica et al., "Identification of anaplastic lymphoma kinase as a receptor for the growth factor pleiotrophin," J Biol Chem, 2001 , 276(20): 16772-16779.
Stoica et al., "Pleiotrophin Signaling through Anaplastic Lymphoma Kinase Is Rate-limiting for Glioblastoma Growth," J Biol Chem, 2002, 277(16):14153-14158.

(Continued)

*Primary Examiner* — Patricia L Morris
(74) *Attorney, Agent, or Firm* — Mark S. Cohen; Pearl Cohen; Zedek Latzer Baratz LLP

(57) ABSTRACT

The present disclosure relates to the field of tyrosine kinase enzyme inhibition, in particular anaplastic lymphoma kinase (ALK) inhibition using novel small molecules. Provided are compounds capable to modulate ALK activity, compositions that comprise the compounds, and methods of using the compounds for the treatment or prevention of diseases or conditions that are characterized by ALK activity or expression.

3 Claims, 9 Drawing Sheets

(56) References Cited

OTHER PUBLICATIONS

Morris et al., "Fusion of a kinase gene, ALK, to a nucleolar protein gene, NPM, in non-Hodgkin's lymphoma," Science, 1994, 263: 1281-1284.
Pulford et al, "Anaplastic lymphoma kinase proteins in growth control and cancer," J Cell Physiol, 2004, 199:330-358.
Sauville et al, J. CHn. Oncol, 2001, 19, 2319-2333.
International Search Report of corresponding PCT Application No. PCT/US09/01691 dated Sep. 24, 2009.
Cahn et al., "Specification of Molecular Chirality" 1966, Angew. Chem. 78: 413-447, Angew Chem. Int. Ed. Engl. 5: 385-414.
Prelog et al., "Basic principles of the CIP-system and proposals for a revision" 1982, Angew. Chem. 94:614-631, Angew. Chem. Int. Ed. Engl. 21:567-583.
Mata et al., "The CIP sequence rules: analysis and proposal for a revision",1993, Tetrahedron: Asymmetry 4:657-668.
Wagner, "Stereospecific synthesis of amphetamines", 2003, Tetrahedron: Asymmetry 14(15), 2119-2125.
Goodman, "Synthesis and evaluation of radioiodinated 2-(2(RS)-aminopropyl)-5-iodothiophenes as brain imaging agents" J. Med. Chem. Jan. 24, 1992;35(2):280-5.
Yu et al., "Physical characterization of, etc.," PSTT, vl. 1(3), 118-127 (1998).
Kirk-Othmer Encyclopedia of Chemical Technology, 8, pp. 95-147 (2002).
Vippagunta et al., "Crystalline Solids", Advanced Drug Delivery Reviews 48 (2001) 3-26.
Guillory (in Brittain ed.), "Polymorphism in Pharmaceutical Solids.," NY: Marcel Dekker, Inc., 1999, 1-2, 125-181, 183-226.
Jain et al., "Polymorphism in Pharmacy", Indian Drugs, 1986, 23(6) 315-329.
West "Solid State Chemistry and its Applications", Wiley, NY 1988, pp. 358 & 365.
Wu et al. "Regulatory perspectives of Type II prodrug development and time-dependent toxicity management: Nonclinical Pharm/Tox analysis and the role of comparative toxicology", Toxicology 236 (2007, pp. 1-6.
European Search Report for European Application No. 15177176.3 dated Dec. 3, 2015.

* cited by examiner

TYROSINE KINASE INHIBITORS

CROSS-REFERENCE TO RELATED APPLICATIONS

This Application is a divisional application of application Ser. No. 13/231,797, filed Sep. 13, 2011, which is a Continuation-In-Part of application Ser. No. 12/922,891, filed Sep. 16, 2010, which is a National Stage of International Application No. PCT/US09/01691, filed Mar. 18, 2009, which claims the benefit of U.S. Provisional Application Ser. No. 61/038,032, filed Mar. 19, 2008, and application Ser. No. 13/231,797, filed Sep. 13, 2011 claims the benefit of U.S. Provisional Application Ser. No. 61/382,485, filed Sep. 13, 2010, all of which are incorporated herein by reference in their entirety.

FIELD OF THE INVENTION

The present disclosure relates to the field of tyrosine kinase enzyme inhibition, in particular anaplastic lymphoma kinase (ALK) inhibition using novel small molecules. Provided are compounds capable to modulate ALK activity, compositions that comprise the compounds, and methods of using the compounds for the treatment or prevention of diseases or conditions that are characterized by ALK activity or expression.

BACKGROUND OF THE INVENTION

The anaplastic lymphoma kinase (ALK) is a receptor tyrosine kinase that belongs to the insulin receptor superfamily and is normally expressed in neural tissues during embryogenesis (Morris et al., *Oncogene,* 1997, 14:2175-2188; Iwahara et al., *Oncogene,* 1997, 14:439-449). In particular, transcripts of ALK gene are highly expressed in specific regions of the central nervous system, including the diencephalon, midbrain, and the ventral half of the spinal cord. In the peripheral nervous system, ALK expression has been detected in the trigeminal, sympathetic, and enteric ganglia. After birth, expression diminishes, but still persists in certain areas such as the olfactory bulb and thalamus. Despite the apparent function of ALK in the development of the nervous system, the physiologic role of ALK is still largely unclear. While the recent studies are proposing that pleiotrophin (PTN) and midkine (MK) are cognate ligands for ALK (Stoica et al., *J Biol Chem,* 2001, 276(20):16772-16779; Stoica et al., *J Biol Chem,* 2002, 277(16):14153-14158), exact mechanisms and biological consequences of ligand-dependent ALK activation are not fully understood at this time.

ALK was initially identified because of its involvement in the human non-Hodgkin lymphoma subtype known as anaplastic large cell lymphoma (ALCL). Many cases of ALCL are associated with a reciprocal translocation, t(2;5)(p23;q35), which juxtaposes the gene at 5q35 encoding nucleophosmin (NPM), a nucleolar-associated phosphoprotein, with the gene for a receptor tyrosine kinase, the anaplastic lymphoma kinase (ALK), at 2p23. The resulting fusion gene encodes a chimeric 80-kD protein in which 40% of the N-terminal portion of NPM is fused to the complete intracytoplasmic portion of ALK containing the functional tyrosine kinase domain (Morris et al., *Science,* 1994, 263:1281-1284). Constitutive activation of the NPM-ALK kinase domain stimulates anti-apoptotic and mitogenic signaling pathways such as PI3K-AKT, JAK-STAT, and PLCγ, resulting in cellular transformation (Bai, 1998; Slupianek, 2001; Zamo 2002). The transforming activity of NPM/ALK is dependent on its kinase activity (Bischof 1997). While the most frequently occurring oncogenic ALK fusion in ALK-positive ALCL cases ("ALKomas") is the NPM-ALK (~80% of ALK-positive ALCL cases), other ALK gene fusions have been consequently identified in human hematological and solid cancers. These include TPM3-ALK (fusion of non-muscle tropomyosin 3 with ALK), TPM4-ALK, ATIC-ALK, CLTC-ALK, RanBP2-ALK, TFGL/S-ALK, CARS-ALK, MSN-ALK and others.

All known ALK fusion proteins (These include ALK-positive ALCL, NPM-ALK, TPM3-ALK (fusion of non-muscle tropomyosin 3 with ALK), TPM4-ALK, ATIC-ALK, CLTC-ALK, RanBP2-ALK, TFGL/S-ALK, CARS-ALK, MSN-ALK and others) share the essential feature of having some type of the oligomerization domain in the sequence of the ALK fusion partner which mediates constitutive self-association of the ALK fusion that causes constant, ligand-independent ALK kinase domain activation. Similarly to NPM-ALK, the related ALK fusion proteins have been shown to possess transforming and oncogenic potential, apparently mediated by their constitutive kinase activity. Although ALK-positive lymphomas have a relatively benign prognosis, about 40% of patients do not respond or relapse after the standard therapy (CHOP). CHOP (cyclophosphamide, hydroxydoxorubicin, oncovin, prednisone) and CHOP-like multi-agent combination chemotherapy regimens that are used for conventional treatment of non-Hodgkin lymphomas including ALCL are associated with considerable acute and chronic toxicities, a problem specifically bothersome in pediatric patients. Therefore, a highly effective and targeted therapy would be beneficial and highly warranted not only for relapsed patients but also as first-line therapy if well tolerated and efficacious.

In addition to ALKomas, several research groups have also described the presence of the NPM-ALK and the related fusion proteins like CLTC-ALK in a rare form of B-cell non-Hodgkin lymphoma. Rearrangements of ALK gene have been also identified in the inflammatory fibroblastic tumors (IMT). These rare spindle cell proliferations involve malignant myofibroblasts and infiltrating non-malignant inflammatory cells in a collagenous matrix and occur primarily in the soft tissue of children and young adults.

More recently, a novel oncogenic ALK fusion, EML4-ALK, comprising portions of the echinoderm microtubule-associated protein-like 4 (EML4) gene and the anaplastic lymphoma kinase (ALK) gene, has been implicated in a subset of non-small cell lung cancer (NSCLC) (Soda, 2007). Mouse 3T3 fibroblast cells forced to express this fusion tyrosine kinase generated transformed foci in culture and subcutaneous tumors in nude mice. The EML4-ALK fusion transcript was detected in 6.7% of the 75 NSCLC patients examined; these individuals were distinct from those harboring mutations in the epidermal growth factor receptor gene. Presence of the oncogenic TPM4-ALK fusion was also detected by proteomics methods in esophageal cancer samples from patients in Iran (Jazii, 2006) and China (Du, 2007). These findings strongly suggest that EML4-ALK and TPM4-ALK fusions are promising candidates for a therapeutic target in a sizable subset of NSCLC and possibly in some esophageal carcinomas.

Certain additional facts concerning the possible relevance of deregulated full-length ALK signaling in some types of cancer and utility of the non-rearranged, full-length ALK as a therapeutic target are noteworthy. The small secreted growth factors pleiotrophin (PTN) and midkine (MK) have been shown to activate signaling of the normal, full-length ALK receptor protein (Stoica et al., 2001, supra; Stoica et al., 2002, supra). While the exact mechanism and biological significance of ALK stimulation by the different molecular forms of these ligands are not completely understood at this time (Lu, 2005; Perez-Pinera, 2007), a functional connection between PTN and/or midkine and ALK is well established. A large number of studies provide evidence that PTN and MK contribute to tumor growth, abnormal tumor-associated angiogenesis and metastasis (Kadamatsu, 2004; Bernard-Pierrot 2002). For example, both PTN and ALK have been found to be overexpressed in human glioblastomas, and downregulation of ALK expression by ribozymes was shown to suppress human glioblastoma xenograft growth in mice and to prolong the survival of the tumor-bearing animals (Powers 2002; Grzhelinsky 2005). Expression or overexpression of the full-length ALK receptor in certain neuroblastomas, diffuse large B-cell non-Hodgkin lymphomas, leiomyosarcomas, and malignant peripheral nerve sheath sarcomas have been reported (Pullford et al., *J Cell Physiol*, 2004, 199:330-358). Similarly, it has been reported that cell lines established from common solid tumors of ectodermal origin, such as melanoma and breast cancer, exhibit ALK receptor mRNA expression (Pulford, 2004, supra). Additional analyses should elucidate the role of ALK signaling in the genesis and progression of these various cancers over the next few years.

Studies in which the mouse Alk gene was knocked-out demonstrate that ALK-negative mice show no evident gross anatomical, histological or functional abnormalities and have a normal lifespan (Pulford, 2004, supra). Therefore, the physiological functions of Alk, which is normally expressed primarily in neural tissues, appear to be largely redundant. These observations suggest that therapeutic approaches targeting the aberrant oncogenic functions of ALK are not likely to be associated with limiting toxicities due to concomitant inhibition of normal ALK functions.

Therefore, both the various cytoplasmic ALK fusion proteins and the full-length ALK in its transmembrane receptor form are valid molecular targets for anticancer drugs. Consequently, small-molecule inhibitors of ALK kinase are likely to be a drug for suppressing of tumor growth and angiogenesis.

Recently reported preclinical studies have provided compelling proof of principle for the efficacy of the inhibition of NPM-ALK in ALK-positive ALCL, with marked anti-tumor activity observed experimentally. For instance, studies performed by Novartis demonstrated regression of established lymphoma tumors formed by subcutaneous injection of the human NPM-ALK-positive ALCL cell line Karpas-299 in mice when the animals were treated with the small molecule ALK kinase inhibitor NVP-TAE684 (Galkin, 2007).

Other experimental approaches for the inhibition of oncogenic ALK signaling have also indicated that the agents blocking this signaling are likely to possess very potent anticancer capabilities. Piva and colleagues recently showed that siRNA (small inhibitory ribonucleic acid)-mediated inhibition of NPM-ALK signaling markedly diminished the development of ALCL xenografts in mice (Piva, 2006). Collectively, these data indicate that the inhibition of the aberrant, cancer-causing activity of ALK fusion proteins in ALCL, as well as other ALK-driven malignancies, using small molecule inhibitors is very likely to produce marked anti-tumor responses.

WO 2004/063151 reported a tyrosine kinase inhibitory activity of pyridones. Pyrroloquinixalinediones and their derivatives were shown to exhibit HIV integrase inhibitory activity (WO2004/096807).

Only a few inhibitors with activity against ALK have been reported. Sauville (Sauville et al, *J. Clin. Oncol.*, 2001, 19, 2319-2333) disclosed a derivative of the natural product staurosporine having an anti-tumor activity in a patient with an ALK-positive anaplastic large cell lymphoma that was refractory to conventional chemo- and radio-therapy. It is important to note that the compound's ability to inhibit ALK was not tested in this study, thus, it has not been formally proven that it is an ALK inhibitor. Indeed, a recent report suggests that staurosporine possesses minimal ability to directly inhibit ALK (Gunby et al., *Haematologica*, 2005, 90, 988-990). The naturally occurring, structurally related benzoquinone analogues, geldanamycin and 17-allylamino-17-demethoxygeldanamycin (Bonvini et al., *Cancer. Res.* 2002, 62, 1559-1566) and herbimycin A (Turturro et al., *Clin. Cancer Res.* 2002, 8, 240-245) have been reported to exert ALK inhibition via heat shock protein pathways, enhancing the proteasome-mediated degradation of the ALK protein. Most recently, a series of pyrazolo[3,4-c]isoquinoline derivatives with ALK-inhibitory activity was published in WO 2005009389.

One of the challenges of developing an ATP-competitive small-molecule ALK inhibitor is to provide sufficient selectivity of the compound for ALK versus inhibition of other structurally related protein kinases. Due to the existence of about 520 evolutionary related protein kinases in the human genome, this could be a demanding task. In particular, inhibition of the insulin receptor kinase which is closely structurally related to ALK is highly undesirable due to the risk of blocking insulin action and the resultant hyperglycemia.

Another highly related RTK is Insulin-Like Growth Factor Receptor I (IGF1R). In the recent years, IGF1R emerged as an attractive oncology target in a broad variety of malignancies (Riedman and Macaulay, 2006; Tao et al. 2007). However, suppression of IGF1R signaling may potentially have undesirable side-effects in a clinical context where normal cell/tissue proliferation and development are essential, such as treating pediatric patients (ALCL). Therefore, a sufficiently high selectivity of ALK inhibition versus inhibition of such related RTKs as Insulin Receptor and IGF1R is likely to be a desirable trait in a clinical ALK inhibitor. Conversely, inhibition of a small subset of therapeutically relevant PTKs (multitargeting), in addition to ALK, can improve the efficacy of an oncology drug, especially for solid tumors which are often heterogeneous and have complicated tumor biology.

Another group of tyrosine kinases evolutionary and structurally related to ALK is, Ret, Ros, Axl, and kinases that are members of Trk family (Trk A, B and C).

RET is a receptor tyrosine kinase that has a role in transducing growth and differentiation signals in tissues derived from the neural crest and is required for normal development of the sympathetic, parasympathetic and enteric nervous systems and the kidney. Gain of function mutations of Ret are associated with the development of several types of human cancers, including medullar thyroid carcinoma and multiple endocrine neoplasias type II and III (or MEN2A and MEN2B). RET mutations have been also identified in a small percentage of pheochromocytomas. Chromosomal rearrangements involving the RET gene are one of the most common causes of a sporadic form of thyroid cancer called papillary thyroid carcinoma (also known as RET/PTC). There is a compelling experimental evidence that thyroid cell transformation to PTC is driven by hyperactivated Ret (Santoro, 2004]. Kinase inhibitors with activity against RET are currently in preclinical or clinical development for these types of cancers.

ROS or ROS1 is a receptor tyrosine kinase that has been found to be constitutively activated in a subset of glioblastomas as a result of genomic translocations (Charest, 2003; Charest, 2006) and may represent an emerging therapeutic target in this highly malignant and deadly brain tumor.

AXL is a unique tyrosine kinase receptor, implicated in the inhibition of apoptosis as well as promoting neovascularization, and it is emerging as a viable therapeutic target in a number of malignancies, both solid and hematologic (Holland, 2005). In particular, it is a chronic myelogenous leukemia-associated oncogene (O'Bryan, 1991; Jannsen, 1991) and is also associated with colon, prostate cancer and melanoma (Van Ginkel, 2004; Sainaghi, 2005). Overexpression of Axl in myeloid cells has been shown to be involved in Type II diabetes (Augustine, 1999). Modulation of Axl activity by small-molecule kinase inhibitors may have utility in therapy of the disease states mentioned above.

TrkA is a receptor tyrosine kinase that belongs to a subfamily of tyrosine kinases that also includes TrkB, and TrkC. TrkB and TrkC are structurally closely related to TrkA, but respond to different ligands in the neurotrophin (NT) family. Nerve growth factor (NGF) signaling through TrkA has been well characterized and is similar to signal transduction mechanisms of other tyrosine kinase receptors. As outlined in more detail below, TrkA is a well validated or a potential drug target in a variety of malignancies as well as in neuropathic pain and certain inflammatory diseases. The roles of the two other members of the neurothropin receptor TK family, TrkB and TrkC, in disease states has received less attention, however the emerging evidence implicates both of them in several types of neoplasias.

TrkA gene was originally described as a chimeric oncogene in colon cancer (Martin-Zanca, 1986] and its activating genomic translocations are common in papillary thyroid carcinomas (Bongarzone, 1989; Pierotti, 2006) and occur in breast cancer as well (Brzezianska, 2007). Hyperactivating deletion or fusion mutations of TrkA and TrkC were also identified in some acute myeloid leukemias as well as solid tumors (Reuther, 2000; Eguchi, 2005).

Overexpression of TrkA in malignant versus normal tissues and association with poor prognosis was shown in prostate, pancreatic cancers, melanomas, and mesotheliomas (Festuccia, 2007; Myknyoczki, 1999; Florenes, 2004; Davidson, 2004). TrkA is overexpressed in the majority of prostate carcinomas, and is further increased in androgen-independent tumors (Papatsoris, 2007). In prostatic carcinomas, an autocrine loop involving NGF and TrkA is responsible for tumor progression (Djakiew, 1993). An autocrine NGF/TrkA loop and mitogenic role of NGF has been demonstrated in breast cancer cells as well (Chiarenza, 20011; Dolle, 2003). It has also been shown that NGF signaling has angiogenesis-promoting effect (Cantarella, 2002).

TrkB, sometimes in conjunction with its ligand BDNF, is often overexpressed in a variety of human cancers, ranging from neuroblastomas to pancreatic ductal adenocarcinomas, in which it may allow tumor expansion and contribute to resistance to anti-tumor agents. TrkB acts as a potent suppressor of anoikis (detachment-induced apoptosis), which is associated with the acquisition of an aggressive tumorigenic and metastatic phenotype in vivo (Desmet, 2006; Douma, 2004). In summary, Trk family members have been implicated as oncogenes in a number of neoplasms including prostate, thyroid, pancreatic, colon, breast, ovarian cancers, melanomas and some leukemias. For prostate cancer and thyroid carcinomas, TrkA is especially well validated as a drug target.

Strong and diverse experimental evidence suggests that nerve growth factor (NGF), signaling through TrkA pathway, is a mediator of some persistent pain states, including neuropathic and inflammatory pain (Pezet, 2006; Hefti, 2006; Bennet, 2001). Function-neutralizing anti-NGF and anti-TrkA antibodies demonstrated therapeutic effect in models of inflammatory, neuropathic, skeletal and cancer pain (Ugolini, 2007; Koewler, 2007; Sevcik, 2005). In such disease states as prostate cancer with metastatic bone pain and pancreatic cancer with perineural invasion, cancer progression, pain and TrkA signaling has been shown to be all positively correlated (Dang, 2006; Halvorson, 2005) Inhibition of the NGF/TrkA pathway appears to be very well validated for treatment of chronic pain of different natures: (i) inflammatory pain; (ii) neuropathic pain and (iii) cancer pain.

It is noteworthy that in the skin, TrkA receptor mediates the ability of NGF to stimulate keratinocytes proliferation and inhibit keratinocytes apoptosis. NGF is produced by keratinocytes to stimulate their cell proliferation with an autocrine loop and melanocyte proliferation with a paracrine pathway (Di Marco, 1993; Pincelli, 2000). NGF/TrkA signaling also modulates inflammation (Frossard, 2004) and proliferation of terminal cutaneous nerves (Raychaudhury, 2004), components of psoriasis and atopic dermatitis. Murine models for psoriasis and atopic dermatitis have been established and K252a and AG879, both potent non-clinical TrkA inhibitors, were demonstrated to have therapeutic effect [Raychaudhury, 2004; Takano, 2007] in the models. This data indicates that TrkA is a potential drug target in skin disorders characterized by keratinocytes hyperproliferation.

Kelly cell lines are a human neuroblastoma cell line in which a constitutively active mutant (F1174L) ALK promotes cell growth. Various gain-of-function mutations occur in approximately in 8% of primary neuroblastomas and are believed to have a transforming influence. Neuroblastoma most often begins during early childhood, usually in children younger than 5 years. Neuroblastoma often begins in the nerve tissue of the adrenal glands. By the time neuroblastoma is diagnosed, the cancer has usually metastasized (spread), most often to the lymph nodes, bones, bone marrow, liver, and skin. Neuroblastoma, accounts for approximately 15% of all deaths due to childhood cancer. High-risk neuroblastomas are rapidly progressive; even with intensive myeloablative chemotherapy, relapse is common and almost uniformly fatal.

Thus, tyrosine kinases are now widely recognized as attractive proteins for molecularly targeted cancer therapy. Blocking the ALK activity (e.g., inhibition of oncogenic ALK fusion proteins (NPM-ALK or others), gain-of-function ALK mutations (F1174L or others), or aberrant overexpression of wild-type or mutant ALK) represents a rational, targeted approach to therapy of various diseases. As there are several tyrosine kinases that are evolutionary and structurally related to ALK, such as Ret, Ros, Axl, and members of Trk family, there is an opportunity to either identify a multitargeted kinase inhibitor with a potential utility in other types of malignancies not targeted by selective ALK inhibition, or to fine-tune the inhibition selectivity towards a particular kinase of interest by lead optimization.

SUMMARY OF THE INVENTION

Provided herein are selective tyrosine kinase inhibitors, compositions that comprise the compounds, and methods of using the compounds for the treatment or prevention of diseases or conditions that are characterized by ALK activity or expression in mammals.

Provided herein are selective inhibitors of tyrosine kinases evolutionary and structurally related to ALK, such as Ros, and members of Trk family (Trk A, B and C) and are useful for the treatment or prevention of diseases or conditions characterized by aberrant ALK, ROS, and Trk family of tyrosine kinase activity or expression in mammals.

The compounds provided herein are inhibitors of ALK, ROS, and Trk family of tyrosine kinases.

In one embodiment, this invention is directed to Compound (45) or its stereoisomer, tautomer, pharmaceutically acceptable salt, hydrate, or any combination thereof represented by the following structure:

(Compound 45)

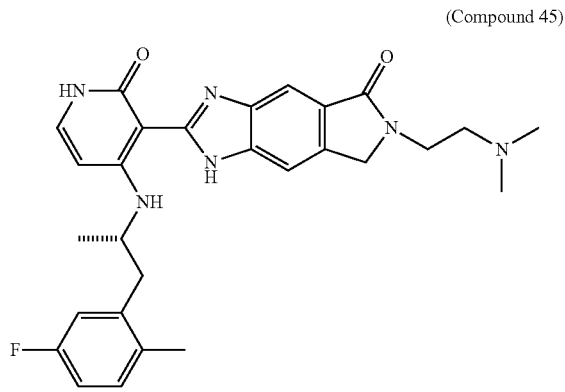 [SMILES: Cc1ccc(F)cc1C[C@H](C)Nc1cc[nH]c(=O)c1-c1nc2cc3c(cc2[nH]1)CN(CCN(C)C)C3=O]

In one embodiment, this invention is directed to a compound represented by the structure of formula (IX) or its stereoisomer, tautomer, pharmaceutically acceptable salt, hydrate, or any combination thereof:

(IX)

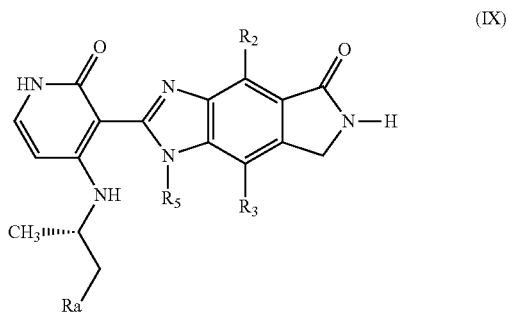

wherein $R^a$ is optionally substituted aryl or heteroaryl;
$R^2$ and $R^3$ are each independently hydrogen, lower alkyl, lower alkoxy, halogen, cyano, lower alkylamino or di-lower alkylamino; and
$R^5$ is hydrogen, lower alkyl, lower alkoxy, halogen, cyano, lower alkylamino or di-lower alkylamino.

In one embodiment, the compounds of this invention are inhibitors of ALK, ROS, and members of Trk family (Trk A, B and C).

In one embodiment, this invention is directed to a pharmaceutical composition comprising the compound of this invention or its stereoisomer, tautomer, pharmaceutically acceptable salt, hydrate, or any combination thereof and one or more pharmaceutically acceptable diluents, excipients or carriers.

In one embodiment, this invention is directed to a method of modulating a tyrosine kinase activity comprising the step of contacting the tyrosine kinase with an amount of a compound of this invention effective to modulate the tyrosine kinase activity. In another embodiment, the tyrosine kinase is selected from the group consisting of Alk, Axl, CSFR, DDR1, DDR2, EphB4, EphA2, EGFR, Flt-1, Flt3, Flt4, FGFR1, FGFR2, FGFR3, FGFR4, HER2, HER3, HER4, IR, IGF1R, IRR, Kit, KDR/Flk-1, Met, Mer, PDGFR.alpha, PDGFR.beta, Ret, Ros, Ron, Tie1, Tie2, TrkA, TrkB and TrkC.

In one embodiment, this invention is directed to a method of treating, suppressing, reducing the incidence, reducing the severity, inhibiting the progression a condition or disorder related to tyrosine kinase activity comprising administering to a subject a compound of this invention. In another embodiment, the condition or disorder is selected from the group consisting of ALK-positive anaplastic large cell lymphoma, an inflammatory myofibroblastic tumor, diffuse large B-cell non-Hodgkin lymphoma, non-small cell lung cancer, esophageal carcinoma, breast cancer, neuroblastoma and glioblastoma.

In one embodiment, this invention is directed to a method of inhibiting a tyrosine kinase activity comprising contacting the tyrosine kinase with a compound of this invention.

In one embodiment, this invention is directed to a method of treating, suppressing, reducing the incidence, reducing the severity, inhibiting the progression of neuroblastoma in a subject comprising administering to a subject a compound of this invention.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 2A: Pharmacokinetics of racemic PF02341066 in rats (10 mg/kg I.V. and P.O.) FIG. 2B: Pharmacokinetics of Compound 1 in rats (10 mg/kg I.V. and P.O.)

FIG. 3A: pharmacokinetics of Compound 1 in guinea pigs (10 mg/kg I.V. and P.O.); FIG. 3B: pharmacokinetics of Compound 1 in beagle dog (1 mg/kg I.V. and 5 mg/kg P.O.); FIG. 3C: pharmacokinetics of Compound 1 in mice (10 mg/kg S.C.); and FIG. 3D: pharmacokinetics of Compound 1 in mice (10 mg/kg I.V.).

FIG. 4A refers to bioavailability of Compound 53; FIG. 4B refers to PF2341066.

FIG. 6A depicts Compound 45 results; FIG. 6B depicts PF2341066 (crizotinib) results.

FIG. 7A depicts Compound 45 results; FIG. 7B depicts PF2341066 (crizotinib) results.

DETAILED DESCRIPTION OF THE INVENTION

Figure 1:
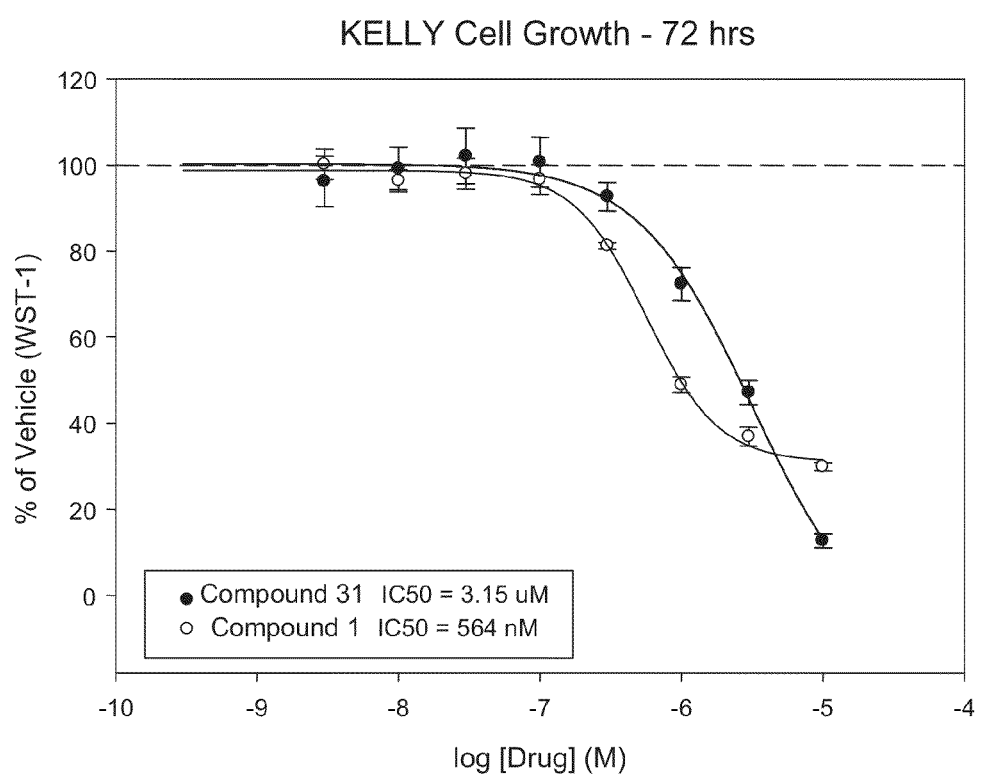
FIG. 1: depicts inhibition of ALK mediated KELLY cell line growth with Compound 1 compared to Compound 31.

In one embodiment, this invention is directed to tyrosine kinase inhibitors, compositions that comprise the compounds, and methods of using the compounds of this invention for the treatment or prevention of diseases or conditions that are characterized by ALK activity or expression in mammals.

In one embodiment, this invention is directed to selective inhibitors of tyrosine kinases which are evolutionary and structurally related to ALK, such as Ret, Ros, Axl- and members of Trk family (Trk A, B and C) and are useful for the treatment or prevention of diseases or conditions characterized by aberrant ALK, RET, ROS, Axl- and Trk family of tyrosine kinase activity or expression in mammals.

The compounds provided herein can be used to treat and/or prevent a mammal affected by a neoplastic disease, in particular ALK-positive anaplastic large cell lymphoma, inflammatory myofibroblastic tumors, diffuse large B-cell non-Hodgkin lymphoma, non-small cell lung cancer, esophageal carcinoma, breast cancer, neuroblastoma and glioblastoma.

Certain compounds provided herein have therapeutic utility in treating various types of neoplasms and other disease states, caused by the aberrant activity of Alk, RET, ROS, AXL and TRK family tyrosine kinases. In particular, provided compounds potently inhibit the catalytic activity of TrkA and/or other Trk family kinases and thereby provide new treatment strategies for patients afflicted with cancer, chronic pain and certain hyperproliferative skin diseases.

The compounds provided herein can be used to treat and/or prevent a mammal affected by tyrosine kinase related disorder such as cancer selected from, but not limited to, astrocytoma, basal or squamous cell carcinoma, brain cancer, gliobastoma, bladder cancer, breast cancer, colorectal cancer, chrondrosarcoma, cervical cancer, adrenal cancer, choriocarcinoma, esophageal cancer, endometrial carcinoma, erythroleukemia, Ewing's sarcoma, gastrointestinal cancer, head and neck cancer, hepatoma, glioma, hepatocellular carcinoma, leukemia, leiomyoma, melanoma, non-small cell lung cancer, neural cancer, ovarian cancer, pancreatic cancer, prostate cancer, renal cell carcinoma, rhabdomyosarcoma, small cell lung cancer, thyoma, thyroid cancer, testicular cancer and osteosarcoma.

The compounds provided herein can be used to treat and/or prevent a mammal affected by tyrosine kinase related disorder such as hyperproliferative skin disease selected from, but not limited to, psoriasis, acne vulgaris, acne rosacea, actinic keratosis, solar keratosis, Bowen's disease, ichthyosis, hyperkeratosis, disorders of keratinization such as Daffier's disease, palmoplanter keratoderma, pityriasis rubra pilaris, epidermal naevoid syndrome, erythrokeratoderma variabilis, epidermolytic hyperkeratosis, non-bullous ichthyosiform erythroderma, cutaneous lupus erythematosus and lichen planus.

In one embodiment, this invention is directed to a method of treating, suppressing, reducing the incidence, reducing the severity, inhibiting the progression of neuroblastoma in a subject comprising administering to a subject a compound of this invention.

In another aspect, provided are compounds of the formula (I) (see paragraph 100761) that are ALK inhibitors, selective especially with respect to IGF1R and/or IRK.

In another aspect, provided are compounds of formula I-XI that are ALK inhibitors, selective especially with respect to Kelly cell cytotoxicity. In another aspect, provided are compounds of formula I-XI that are ALK inhibitors, selective with respect to its ability to inhibit mutant ALK activity and especially those mutant which are present in neuroblastomas.

In another embodiment, provided are pharmaceutical compositions comprising one or more compounds of formula I-XI or a stereoisomer, tautomer, salt, hydrate or prodrug thereof useful for treatment of a disease or condition characterized by Alk activity or expression.

In yet another aspect, provided are pharmaceutical compositions comprising one or more compounds of formula I-XI or a stereoisomer, tautomer, salt, hydrate or prodrug thereof useful for treatment of a disease or condition characterized by Alk, RET, ROS, AXL and TRK family tyrosine kinases activity or expression.

A disease or condition characterized by ALK activity or expression includes but is not limited to ALK-positive anaplastic large cell lymphoma, an inflammatory myofibroblastic tumor, diffuse large B-cell non-Hodgkin lymphoma, non-small cell lung cancer, esophageal carcinoma, breast cancer, neuroblastoma and glioblastoma.

A disease or condition characterized by ALK, RET, ROS, AXL and TRK family tyrosine kinases activity or expression includes but is not limited to cancer, chronic pain and certain hyperproliferative skin diseases.

In yet another aspect, provided are methods for treating a disease or disorder characterized by ALK activity or expression comprising administration of one or more compounds of this invention to a mammal.

In yet another aspect, provided are methods for treating a disease or disorder characterized by ALK, RET, ROS, AXL and TRK family tyrosine kinases activity or expression comprising administration of one or more compounds of this invention to a mammal.

In one embodiment, this invention is directed to methods for modulating the activity of a tyrosine kinase. In one embodiment, the methods comprise the step of contacting the tyrosine kinase with a compound provided herein. The contacting can be in any environ known to those of skill in the art, for instance, in vitro, in vivo, ex vivo or otherwise. In certain embodiments, provided are methods of modulating the activity of a tyrosine kinase in a mammal in need thereof comprising contacting the tyrosine kinase with a compound provided herein. Modulating can refer to the activation or to the inhibition of the tyrosine kinase. The tyrosine kinase can be any tyrosine kinase known to those of skill in the art. In certain embodiments, the tyrosine kinase is a receptor tyrosine kinase or an intracellular tyrosine kinase.

In one embodiment, this invention provides increased potency of Compound 1 in its ability to inhibit ALK promoted KELLY cell growth as presented in Example 8 and FIG. 1.

Figure 5:
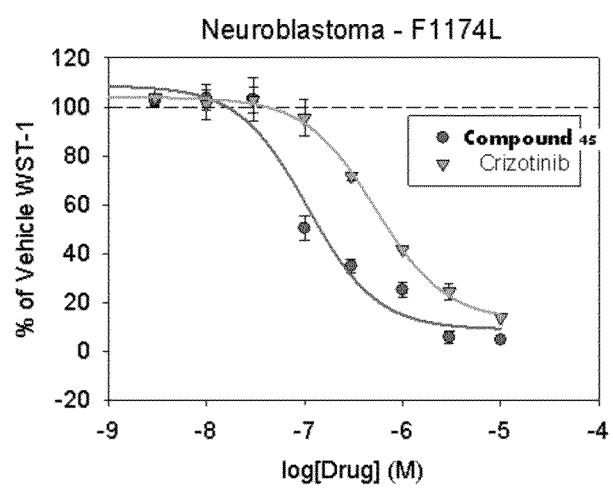
FIG. 5: depicts Compound 45 activity in NB. Kelly NB Cells (Full length ALK; F1174L Activating Point Mutation). F1174L is the most common NB mutation. Potency of Compound 45 is greater than PF2341066 (crizotinib).
Figure 6A:
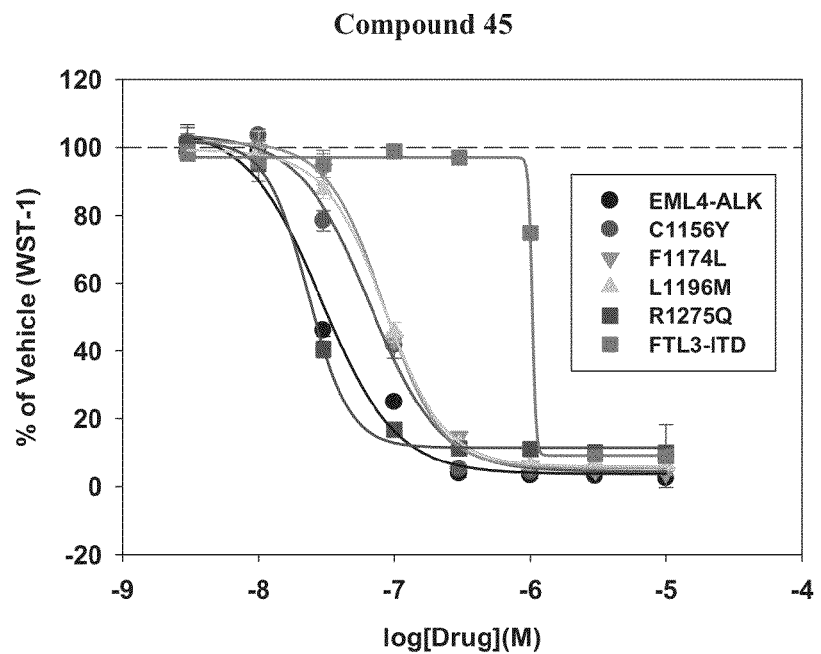
FIGS. 6A and 6B: depict EML4-ALK NSCLC Models.

In one embodiment, this invention provides increased potency of Compound 45 in its ability to inhibit ALK promoted KELLY cell growth as presented in Example 11 and FIG. 5. In another embodiment, this invention provides increased potency of Compound 45 in its ability to inhibit EML4-ALK promoted cell growth in PF2341066-resistant cell lines (FIG. 6A, Example 11).

In one embodiment, this invention provides a compound of this invention having the ability to inhibit ROS1 kinase. In another embodiment, this invention provides an increased potency of Compound 1 in its ability to inhibit ALK mediated ROS1 kinase. ROS1 is an oncogene that is overexpressed in malignant brain tumors including gliomas.

In one embodiment, Compound 1 provides high tyrosine kinase inhibition activity against ALK, TRK (A/B/C) and ROS1 targets.

In certain embodiments, the receptor tyrosine kinase is selected from the group consisting of EGFR, HBER2, HER3, HER4, IR, IGF1R, IRR, PDGFRα, PDGFRβ, TrkA, TrkB, TrkC, HGFR, CSFIR, C-Kit, C-fms, Flk4, KDR/Flk-1, Flt-1, FGF1R, FGF2R, FGF3R and FGF4R.

In certain embodiments, the intracellular tyrosine kinase is selected from the group consisting of Alk, Src, Frk, Btk, Csk, Abl, ZAP70, Fes, Fps, Fak, Jak1, Jak2, Jak3, Jak4, Ack, Yes, Fyn, Lyn, Lck, Blk, Hck, Fgr and Yrk.

In specific embodiments, the intracellular tyrosine kinase is Alk.

In another specific embodiment, the tyrosine kinases are those that are evolutionary and structurally related to ALK, such as Ret, Ros, Axl and members of Trk family (Trk A, B and C).

In another aspect, provided are methods for treating or preventing a tyrosine kinase related disorder in a subject in need thereof. In one embodiment, the methods comprise administering to the subject an amount of a disclosed compound of this invention effective to treat or prevent the disorder. The compound can be in the form of a pharmaceutical composition or a unit dose as described below.

A tyrosine kinase related disorder can be any disorder known to those of skill in the art to be related to tyrosine kinase activity. Such disorders include those related to excessive tyrosine kinase activity, those related to reduced tyrosine kinase activity and to those that can be treated or prevented by modulation of tyrosine kinase activity. Excessive tyrosine kinase activity can arise as the result of, for example: (1) tyrosine kinase expression in cells which normally do not express tyrosine kinases; (2) increased tyrosine kinase expression leading to unwanted cell proliferation, differentiation and/or growth; (3) activating alterations of a tyrosine kinase such as translocation (e.g., NPM-ALK) and gain-of-function mutations (e.g., F1174L ALK) which lead to aberrantly high and/or constitutive active receptor tyrosine kinase activity; or (4) decreased tyrosine kinase expression leading to unwanted reductions in cell proliferation, differentiation and/or growth.

The tyrosine kinase related disorder can be a cancer selected from, but not limited to, astrocytoma, basal or squamous cell carcinoma, brain cancer, gliobastoma, bladder cancer, breast cancer, colorectal cancer, chrondrosarcoma, cervical cancer, adrenal cancer, choriocarcinoma, esophageal cancer, endometrial carcinoma, erythroleukemia, Ewing's sarcoma, gastrointestinal cancer, head and neck cancer, hepatoma, glioma, hepatocellular carcinoma, leukemia, leiomyoma, melanoma, non-small cell lung cancer, neural cancer, ovarian cancer, pancreatic cancer, prostate cancer, renal cell carcinoma, rhabdomyosarcoma, small cell lung cancer, thyoma, thyroid cancer, testicular cancer and osteosarcoma.

The tyrosine kinase related disorder can be an IGFR-related disorder selected from diabetes, an autoimmune disorder, Alzheimer's and other cognitive disorders, a hyperproliferation disorder, aging, cancer, acromegaly, Crohn's disease, endometriosis, diabetic retinopathy, restenosis, fibrosis, psoriasis, osteoarthritis, rheumatoid arthritis, an inflammatory disorder and angiogenesis.

In another embodiment, the tyrosine kinase related disorder is non-small cell lung cancer, non-Hodgkin's lymphoma or neuroblastoma. In another embodiment, this invention provides methods of treating, suppressing, reducing the incidence, reducing the severity, inhibiting the progression of non-small cell lung cancer, nonHodgkin's lymphoma or neuroblastoma in a subject comprising administering to a subject a compound of this invention. In another embodiment, this invention provides methods of treating, suppressing, reducing the incidence, reducing the severity, inhibiting the progression of non-small cell lung cancer, nonHodgkin's lymphoma or neuroblastoma in a subject comprising administering to a subject Compound 1 or its stereoisomer, tautomer, pharmaceutically acceptable salt, hydrate, or any combination thereof. In another embodiment, this invention provides methods of treating, suppressing, reducing the incidence, reducing the severity, inhibiting the progression of non-small cell lung cancer, nonHodgkin's lymphoma or neuroblastoma in a subject comprising administering to a subject Compound 45 or its stereoisomer, tautomer, pharmaceutically acceptable salt, hydrate, or any combination thereof.

In one embodiment, this invention provides methods of treating, suppressing, reducing the incidence, reducing the severity, inhibiting the progression of cancer, or countering chemotherapy resistance, comprising administering to a subject a compound of this invention. In another embodiment, this invention provides methods of treating, suppressing, reducing the incidence, reducing the severity, inhibiting the progression of cancer, or countering chemotherapy resistance, comprising administering to a subject Compound 1 or its stereoisomer, tautomer, pharmaceutically acceptable salt, hydrate, or any combination thereof. In another embodiment, this invention provides methods of treating, suppressing, reducing the incidence, reducing the severity, inhibiting the progression of cancer, or countering chemotherapy resistance, comprising administering to a subject Compound 45 or its stereoisomer, tautomer, pharmaceutically acceptable salt, hydrate, or any combination thereof.

In one embodiment, this invention provides a method of treating, suppressing, reducing the incidence, reducing the severity, inhibiting the progression of neuropathic pain comprising administering a compound of this invention. In another embodiment, this invention provides a method of treating, suppressing, reducing the incidence, reducing the severity, inhibiting the progression of neuropathic pain comprising administering Compound 1 or its stereoisomer, tautomer, pharmaceutically acceptable salt, hydrate, or any combination thereof. In another embodiment, this invention provides a method of treating, suppressing, reducing the incidence, reducing the severity, inhibiting the progression of neuropathic pain comprising administering Compound 45 or its stereoisomer, tautomer, pharmaceutically acceptable salt, hydrate, or any combination thereof.

Other disorders which might be treated with compounds provided herein include, without limitation, immunological and cardiovascular disorders such as atherosclerosis.

A disease or condition characterized by ALK activity or expression includes but is not limited to ALK-positive anaplastic large cell lymphoma, an inflammatory myofibroblastic tumor, diffuse large B-cell non-Hodgkin lymphoma, non-small cell lung cancer, esophageal carcinoma, breast cancer, neuroblastoma and glioblastoma.

In one embodiment, the methods, compositions and tyrosine kinase inhibitors make use of a compound of this invention.

In one embodiment, this invention is directed to a compound represented by the structure of formula (I) or its stereoisomer, tautomer, pharmaceutically acceptable salt, hydrate or combination thereof:

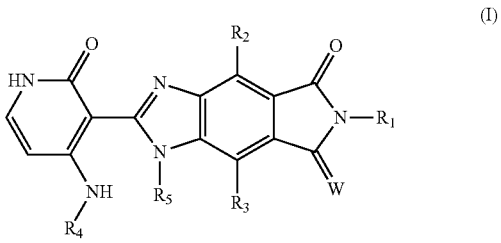

wherein:
R² and R³ are each independently hydrogen, lower alkyl, lower alkoxy, halogen, cyano, lower alkylamino or di-lower alkylamino;
W is O, S, or NR$^e$, wherein
R$^e$ is hydrogen or lower alkyl;
or W represents bonding of two atoms to a carbon atom, forming an optionally substituted methylene group:

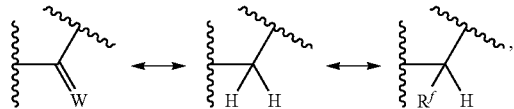

wherein
R$^f$ is hydrogen, OH, alkoxy or lower alkyl;
R⁴ is

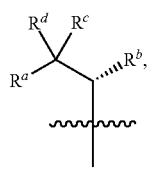

wherein
R$^a$ is optionally substituted aryl or heteroaryl;
R$^b$ is lower alkyl, trifluoromethyl, hydroxymethyl, methoxymethyl, aminomethyl, di-lower alkylaminomethyl or heterocyclylaminomethyl;
R$^c$ is selected from hydrogen, hydroxy, lower alkoxy, or lower alkyl;
R$^d$ is selected from hydrogen, or lower alkyl; and
R⁵ is hydrogen, lower alkyl, lower alkoxy, halogen, cyano, lower alkylamino or di-lower alkylamino;
R¹ is independently selected from hydrogen or optionally substituted alkyl, heterocyclyl, heterocyclylalkyl, heteroaryl, heteroarylalkyl, heterocyclyloxyalkyl, heteroalkyl, heterocyclylaminoalkyl, aminoalkyl, lower alkylaminoalkyl, di-(lower alkyl)-aminoalkyl, aminocycloalkyl, alkylaminocyloalkyl, di-(lower alkyl)-aminocycloalkyl, di-(lower alkyl)-aminocycloalkylalkyl, wherein the substituents are selected from hydrogen, lower alkyl, hydroxy, lower alkoxy, amino, amidino, carboxamido, sulfonamido, cyano, primary, secondary or tertiary amino, halo, azido, lower alkoxyalkyl, cyanoalkyl, azidoalkyl, haloalkyl, hydroxyalkyl, methanesulfonylalkyl, primary, secondary or tertiary amino-alkyl, optionally substituted aryl, heteroaryl, heteroalkyl, heterocyclyl, cycloalkyl, alkenyl and alkynyl.
In another embodiment, R² and R³ are hydrogen or methyl.
In another embodiment, W is

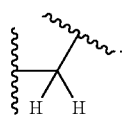

In one embodiment, R$^a$ is optionally substituted thienyl or phenyl wherein the optional substituents are alkyl, alkoxy or halo.
In another embodiment, R$^a$ is optionally substituted thienyl or phenyl wherein the optional substituents are methyl, methoxy or fluoro.

In another embodiment, R$^a$ is thiophene, phenyl, methylthiophene, methylphenyl, fluoromethylphenyl, fluoromethoxyphenyl, trifluorophenyl or tetrafluorophenyl.
In another embodiment, R$^c$ and R$^d$ are hydrogen or hydroxy.
In one embodiment, R$^b$ is alkyl.
In another embodiment, R$^b$ is methyl.
In another embodiment, R¹ includes, but is not limited to:

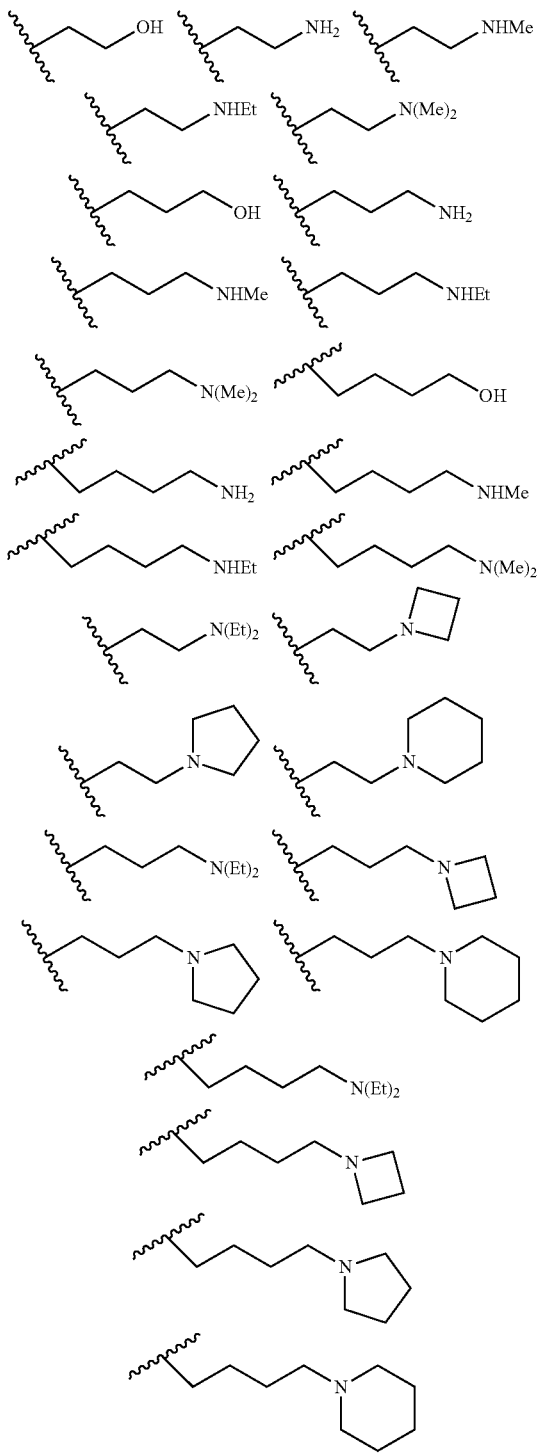

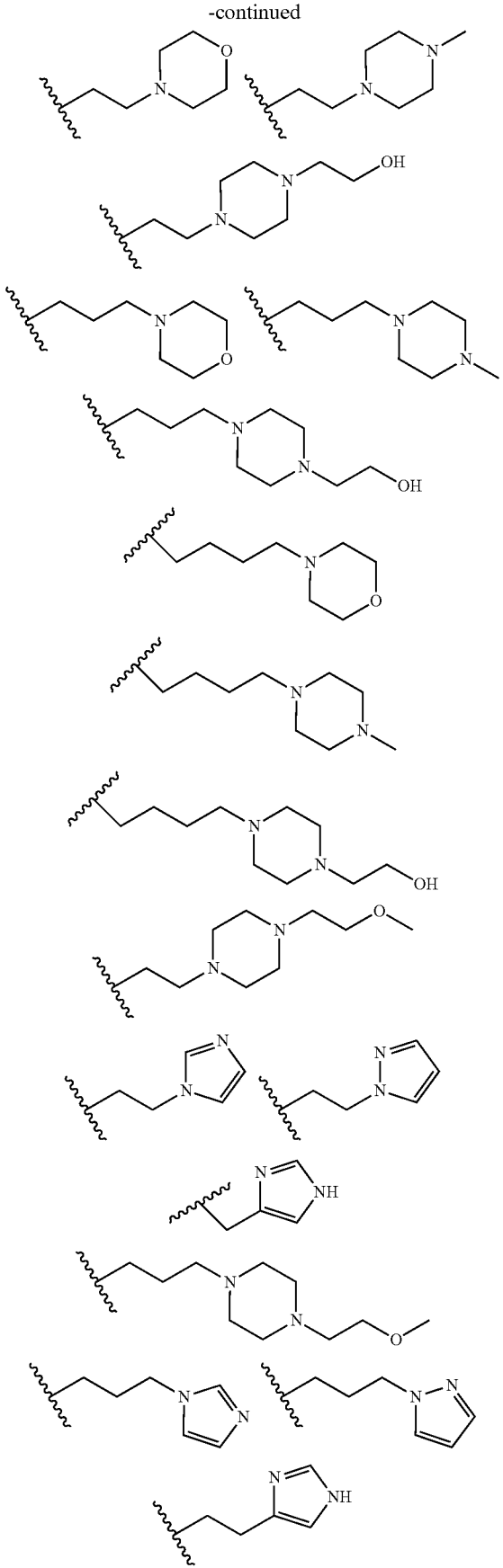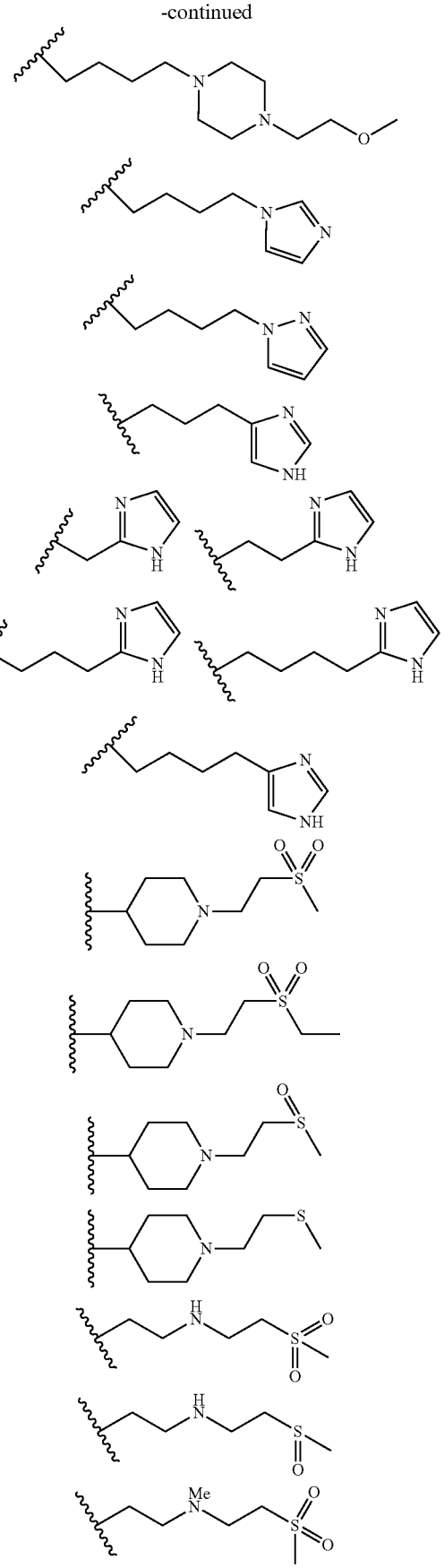

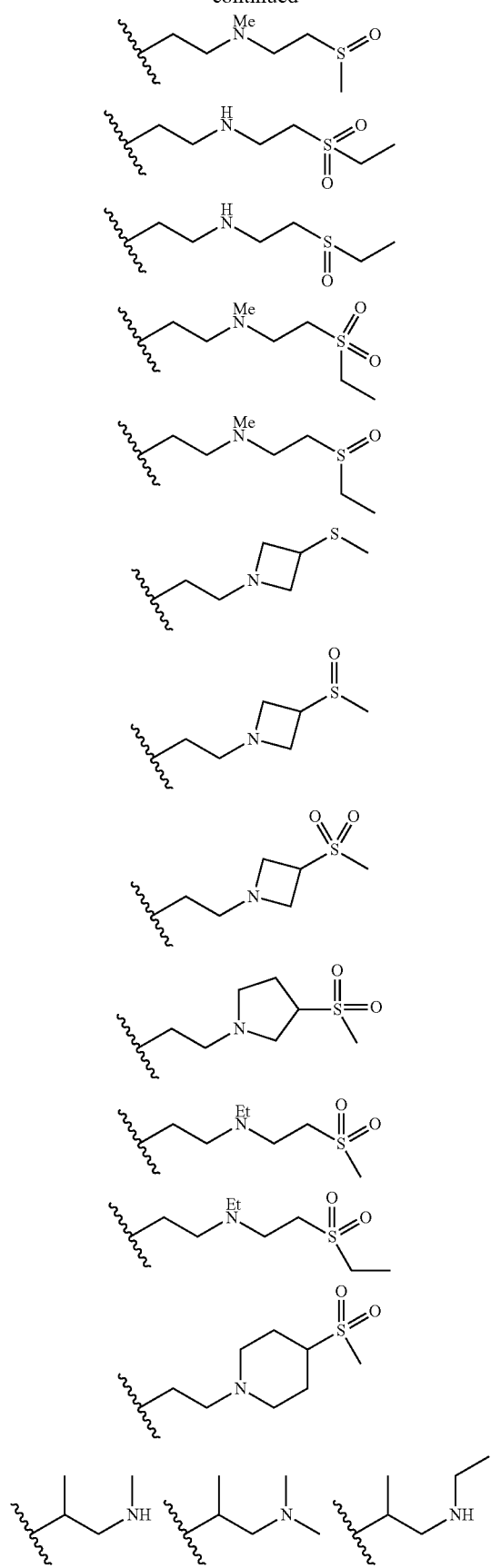

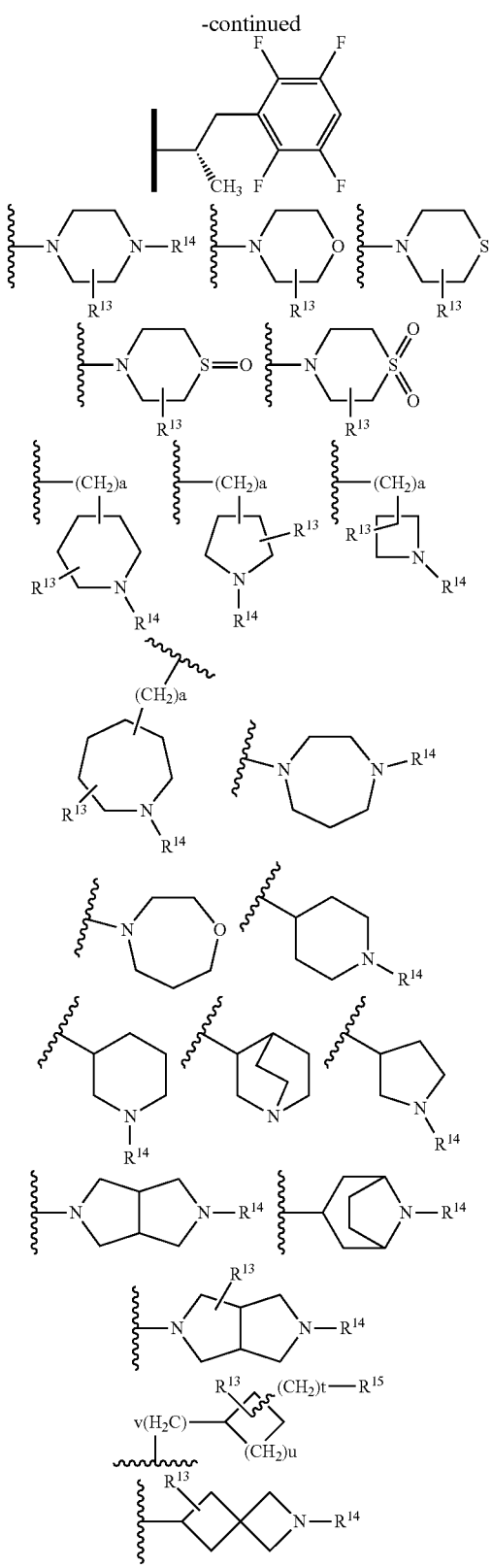

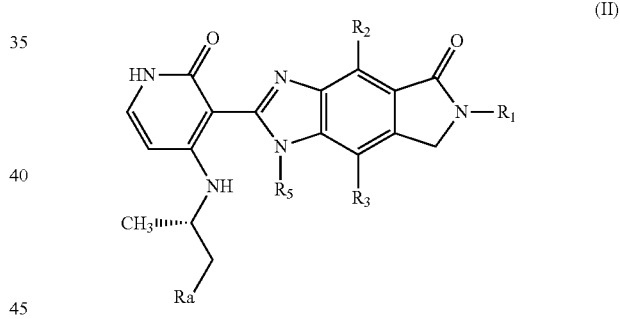

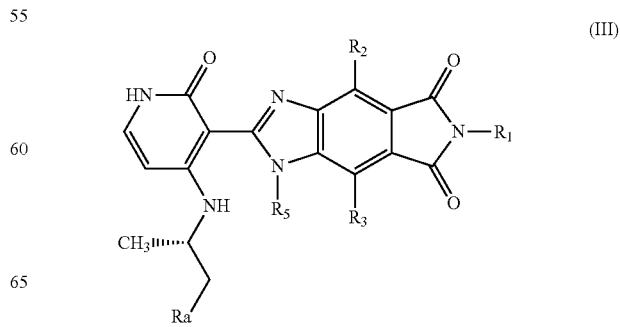

cycloalkyl, heterocycloalkyl, lower alkoxyalkyl, cyanoalkyl, azidoalkyl, nitroalkyl, ketoalkyl, methanesulfonylalkyl, aminoalkyl, lower alkylaminoalkyl, di-(lower alkyl)aminoalkyl, optionally substituted aryl, heteroaryl, arylalkyl, and heteroarylalkyl;

$R^{15}$ is selected from hydrogen, amino, lower alkylamino, di-(lower alkyl)amino, hydroxy, lower alkoxy, heteroalkyl, lower alkoxyalkyl, aminoalkyl, lower alkylaminoalkyl and di-(lower alkyl)aminoalkyl;

a is an integer from 0 to 4; and t, u, v are independent integers from 0 to 5.

It is understood that if any of the integers is (are) 0 (zero), it means a covalent chemical bond.

In certain embodiments, one or more of the $R^1$ methylene chain between the connection and the heteroatom is optionally substituted by one or more hydrogen, lower alkyl, hydroxy, hydroxy-lower alkyl, lower alkoxy, carboxamido or sulfonamido.

In certain embodiments, the $R^1$ methylene groups is optionally substituted by a heteroatom selected from O and S, or NR*, S=O, or S(=O)$_2$, wherein R* is selected from hydrogen, hydroxy, lower alkyl, lower alkoxy, heteroalkyl, hydroxyalkyl, aminoalkyl, lower alkylaminoalkyl and di-(lower alkyl)aminoalkyl.

In one embodiment, $R^1$ is an alkyl. In another embodiment, $R^1$ is a methyl. In another embodiment $R^1$ is a linear or branched alkyl.

In certain embodiments, any $R^1$ ring is optionally substituted by a lower alkyl or heteroalkyl group.

In one embodiment, $R^1$ of formula I is hydrogen.

In one embodiment, this invention is directed to compounds represented by the structure of formula (II) or its stereoisomer, tautomer, pharmaceutically acceptable salt, hydrate or combination thereof:

wherein $R^1$, $R^2$, $R^3$, $R^5$ and $R^a$ are as defined for formula I. In another embodiment, $R^1$ is an alkyl. In another embodiment, $R^1$ is hydrogen.

In one embodiment, this invention is directed to compounds represented by the structure of formula (III) or its stereoisomer, tautomer, pharmaceutically acceptable salt, hydrate or combination thereof:

wherein:

$R^{13}$ is selected from hydrogen, lower alkyl, heteroalkyl, heterocyclyl, cycloalkyl and heterocycloalkyl;

$R^{14}$ is selected from hydrogen, hydroxy, lower alkoxy, di-(lower alkyl)amino, lower alkyl, heteroalkyl, heterocyclyl, wherein $R^1, R^2, R^3, R^5$ and $R^a$ are as defined for formula I. In another embodiment, $R^1$ is an alkyl. In another embodiment, $R^1$ is hydrogen.

In one embodiment, this invention is directed to compounds represented by the structure of formula (IV) or its stereoisomer, tautomer, pharmaceutically acceptable salt, hydrate or combination thereof:

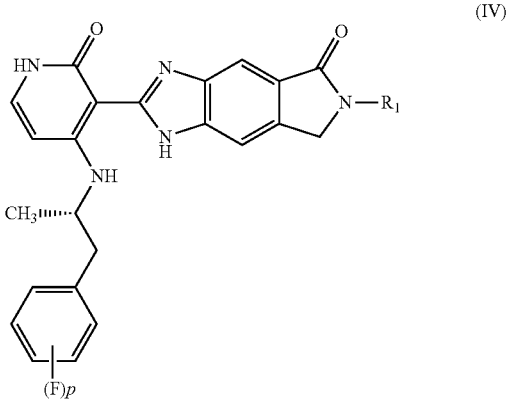

(IV)

wherein $R^1$ is as defined for formula I and p is an integer between 1-5. In another embodiment, $R^1$ is an alkyl. In another embodiment, $R^1$ is hydrogen.

In one embodiment, this invention is directed to compounds represented by the structure of formula (V) or its stereoisomer, tautomer, pharmaceutically acceptable salt, hydrate or combination thereof:

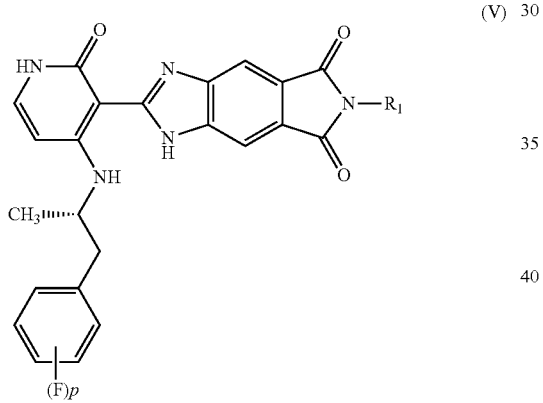

(V)

wherein $R^1$ is as defined for formula I and p is an integer between 1-5. In another embodiment, $R^1$ is an alkyl. In another embodiment, $R^1$ is an hydrogen.

In one embodiment, this invention is directed to compounds represented by the structure of formula (VI) or its stereoisomer, tautomer, pharmaceutically acceptable salt, hydrate or combination thereof:

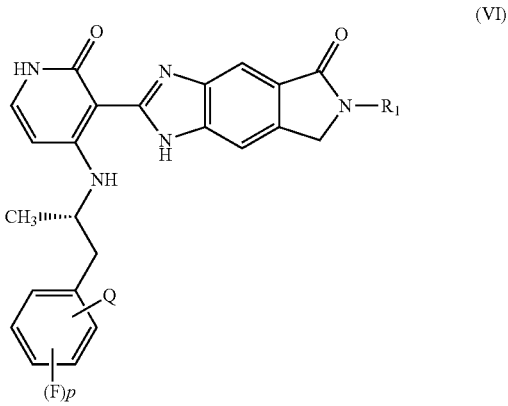

(VI)

wherein $R^1$ is as defined for formula I;

Q is hydrogen, lower alkyl, hydroxy, lower alkoxy, amino, amidino, carboxamido, sulfonamido, cyano, primary, secondary or tertiary amino, halo, azido, lower alkoxyalkyl, cyanoalkyl, azidoalkyl, haloalkyl, hydroxyalkyl, methanesulfonylalkyl, primary, secondary or tertiary amino-alkyl, optionally substituted aryl, heteroaryl, heteroalkyl, heterocyclyl, cycloalkyl, alkenyl and alkynyl; and p is an integer between 1-4.

In another embodiment, $R^1$ of formula VI is substituted or unsubstituted alkyl. In another embodiment $R^1$ is an alkyl and Q is methyl. In another embodiment $R^1$ is an alkyl and Q is hydrogen. In another embodiment, $R^1$ is an hydrogen.

In one embodiment, this invention is directed to compounds represented by the structure of formula (VII) or its stereoisomer, tautomer, pharmaceutically acceptable salt, hydrate or combination thereof:

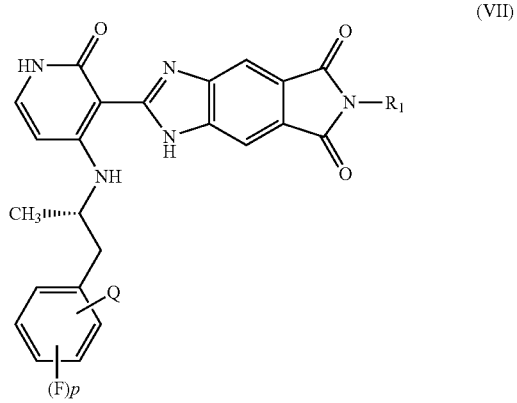

(VII)

wherein $R^1$ is as defined for formula I;

Q is hydrogen, lower alkyl, hydroxy, lower alkoxy, amino, amidino, carboxamido, sulfonamido, cyano, primary, secondary or tertiary amino, halo, azido, lower alkoxyalkyl, cyanoalkyl, azidoalkyl, haloalkyl, hydroxyalkyl, methanesulfonylalkyl, primary, secondary or tertiary amino-alkyl, optionally substituted aryl, heteroaryl, heteroalkyl, heterocyclyl, cycloalkyl, alkenyl and alkynyl; and p is an integer between 1-4.

In another embodiment, $R^1$ of formula VII is substituted or unsubstituted alkyl. In another embodiment $R^1$ is an alkyl and Q is methyl. In another embodiment $R^1$ is an alkyl and Q is hydrogen. In another embodiment, $R^1$ is an hydrogen.

In one embodiment, $R^1$ of formula I-VII is an alkyl. In another embodiment, $R^1$ of formula I-VII is a methyl. In another embodiment $R^1$ of formula I-VII is a linear or branched alkyl substituted by hydroxy, halogen, cyano, nitro or combination thereof. In another embodiment, $R^1$ of formula I-VII is an hydrogen.

In one embodiment, this invention is directed to compounds represented by the structure of formula (VIII) or its stereoisomer, tautomer, pharmaceutically acceptable salt, hydrate or combination thereof:

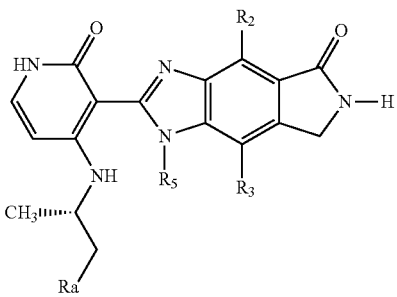

(VIII)

wherein

R$^a$ is optionally substituted aryl or heteroaryl;

R$^2$ and R$^3$ are each independently hydrogen, lower alkyl, lower alkoxy, halogen, cyano, lower alkylamino or di-lower alkylamino; and R$^5$ is hydrogen, lower alkyl, lower alkoxy, halogen, cyano, lower alkylamino or di-lower alkylamino.

In one embodiment, this invention is directed to compounds represented by the structure of formula (IX) or its stereoisomer, tautomer, pharmaceutically acceptable salt, hydrate or combination thereof:

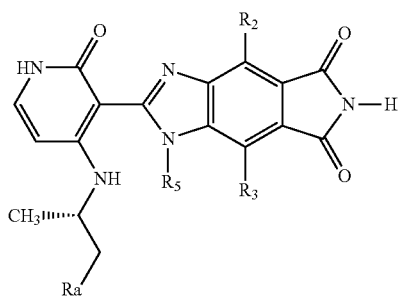

(IX)

wherein

R$^a$ is optionally substituted aryl or heteroaryl;

R$^2$ and R$^3$ are each independently hydrogen, lower alkyl, lower alkoxy, halogen, cyano, lower alkylamino or di-lower alkylamino; and R$^5$ is hydrogen, lower alkyl, lower alkoxy, halogen, cyano, lower alkylamino or di-lower alkylamino.

In one embodiment, R$^a$ of formula VIII-IX is optionally substituted thienyl or phenyl wherein the optional substituents are alkyl, alkoxy or halo.

In another embodiment, R$^a$ of formula VIII-IX is optionally substituted thienyl or phenyl wherein the optional substituents are methyl, methoxy or fluoro.

In another embodiment, R$^a$ of formula VIII-IX is thiophene, phenyl, methylthiophene, methylphenyl, fluoromethylphenyl, fluoromethoxyphenyl, trifluorophenyl or tetrafluorophenyl.

In one embodiment, R$^2$ of formula VIII-IX is a methyl. In another embodiment, R$^2$ of formula VIII-IX is hydrogen.

In one embodiment, R$^3$ of formula VIII-IX is a methyl. In another embodiment, R$^3$ of formula VIII-IX is hydrogen.

In one embodiment, R$^5$ of formula VIII-IX is a methyl. In another embodiment, R$^5$ of formula VIII-IX is hydrogen.

In one embodiment, this invention is directed to compounds represented by the structure of formula (X) or its stereoisomer, tautomer, pharmaceutically acceptable salt, hydrate or combination thereof:

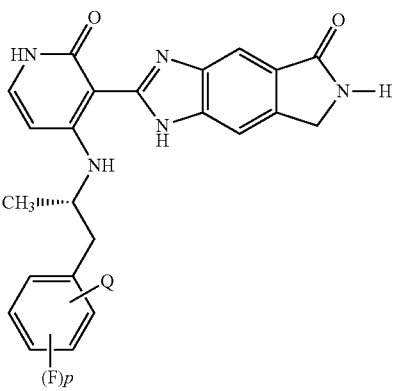

(X)

wherein

Q is hydrogen, lower alkyl, hydroxy, lower alkoxy, amino, amidino, carboxamido, sulfonamido, cyano, primary, secondary or tertiary amino, halo, azido, lower alkoxyalkyl, cyanoalkyl, azidoalkyl, haloalkyl, hydroxyalkyl, methanesulfonylalkyl, primary, secondary or tertiary amino-alkyl, optionally substituted aryl, heteroaryl, heteroalkyl, heterocyclyl, cycloalkyl, alkenyl and alkynyl; and p is an integer between 1-4.

In one embodiment, this invention is directed to compounds represented by the structure of formula (XI) or its stereoisomer, tautomer, pharmaceutically acceptable salt, hydrate or combination thereof:

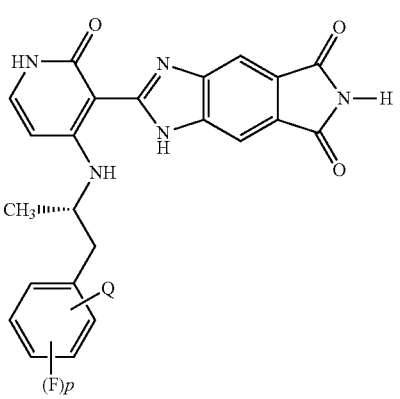

(XI)

wherein

Q is hydrogen, lower alkyl, hydroxy, lower alkoxy, amino, amidino, carboxamido, sulfonamido, cyano, primary, secondary or tertiary amino, halo, azido, lower alkoxyalkyl, cyanoalkyl, azidoalkyl, haloalkyl, hydroxyalkyl, methanesulfonylalkyl, primary, secondary or tertiary amino-alkyl, optionally substituted aryl, heteroaryl, heteroalkyl, heterocyclyl, cycloalkyl, alkenyl and alkynyl; and p is an integer between 1-4.

In one embodiment, this invention is directed to Compound 45 or its stereoisomer, tautomer, pharmaceutically acceptable salt, hydrate or combination thereof represented by the following structure:

Compound 45

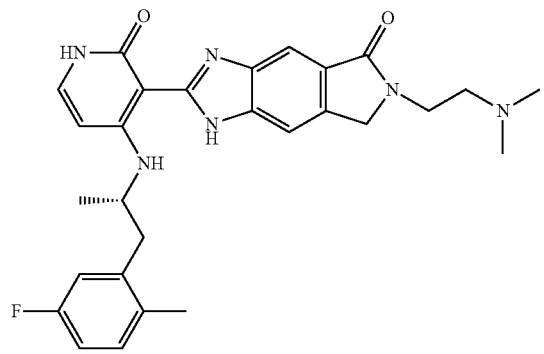

In one embodiment, this invention is directed to Compound 52 or its stereoisomer, tautomer, pharmaceutically acceptable salt, hydrate or combination thereof represented by the following structure:

Compound 52

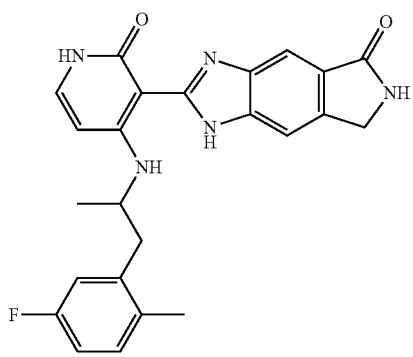

In one embodiment, this invention is directed to Compound 53 or its stereoisomer, tautomer, pharmaceutically acceptable salt, hydrate or combination thereof represented by the following structure:

Compound 53

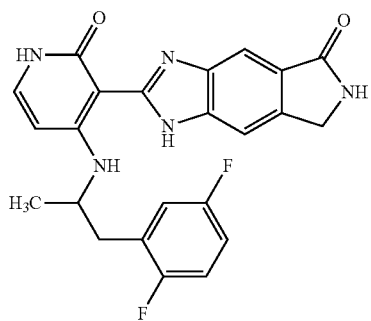

In one embodiment, this invention is directed to the following exemplary compounds or its stereoisomer, tautomer, pharmaceutically acceptable salt, hydrate or combination thereof:

TABLE 1

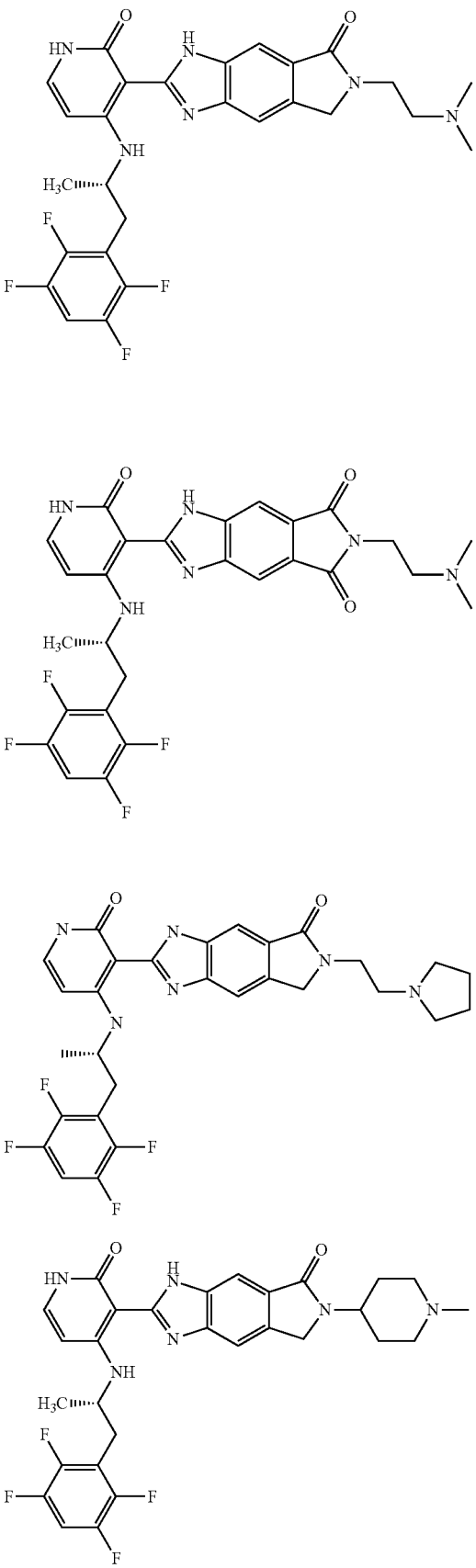

TABLE 1-continued
| 12 | 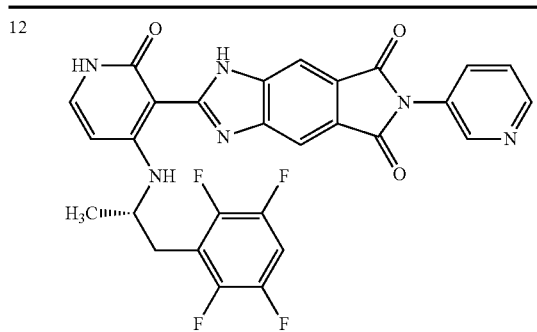 |
|---|---|
| 13 | 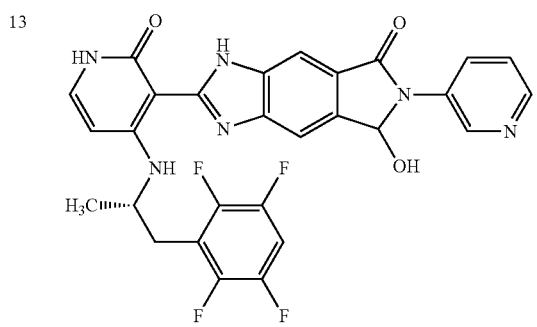 |
| 14 | 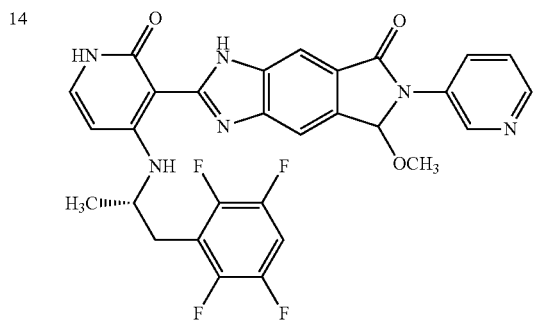 |
| 15 | 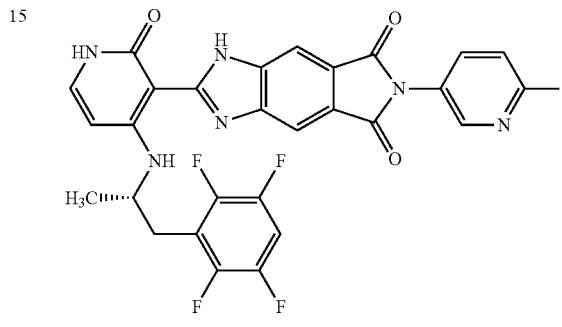 |
| 17 | 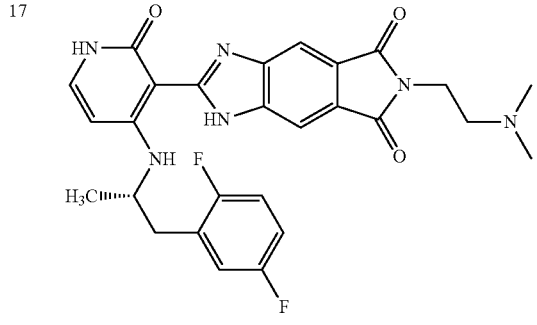 |
| 18 | 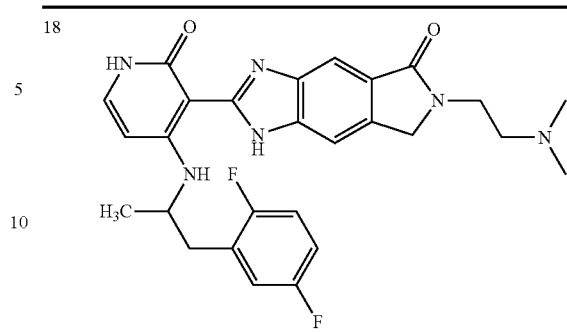 |
| 24 | 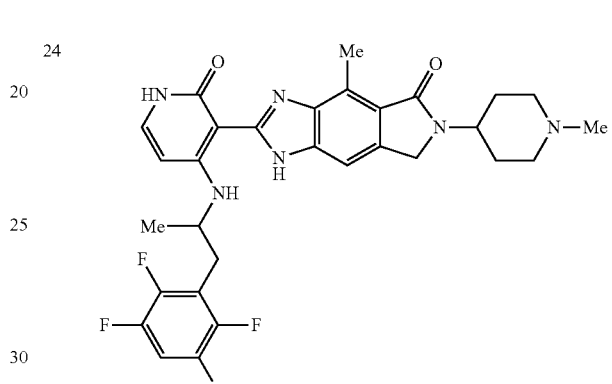 |
| 24a | 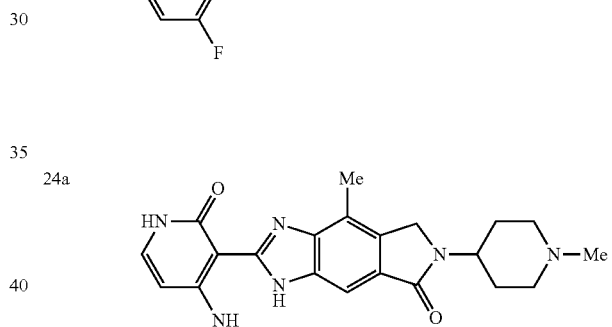 |
| 25 | 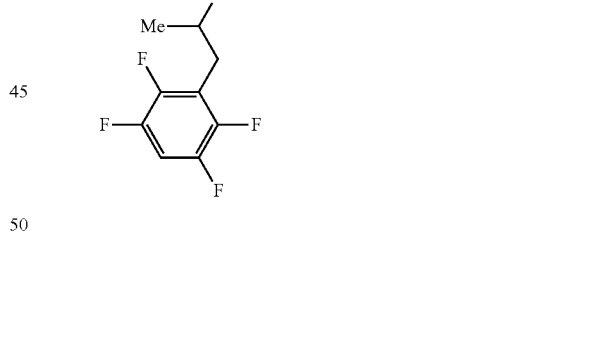 |

TABLE 1-continued
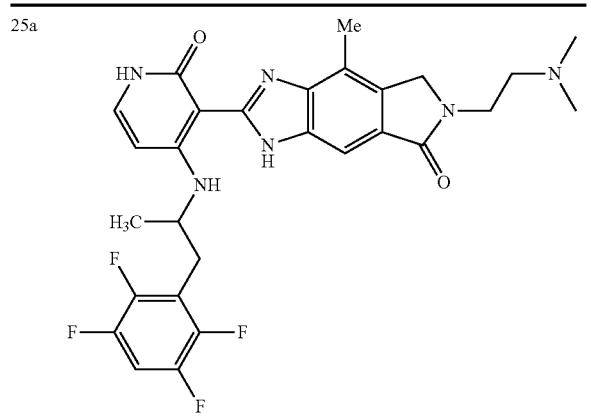
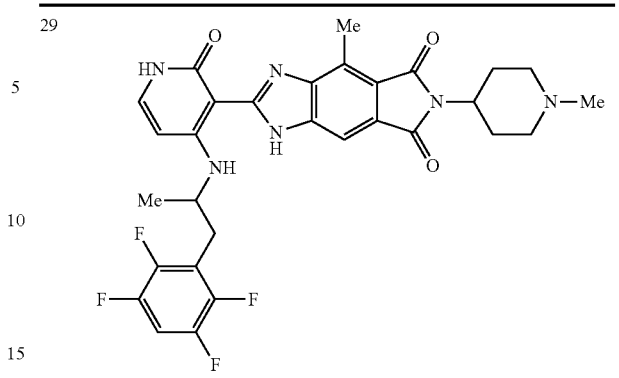
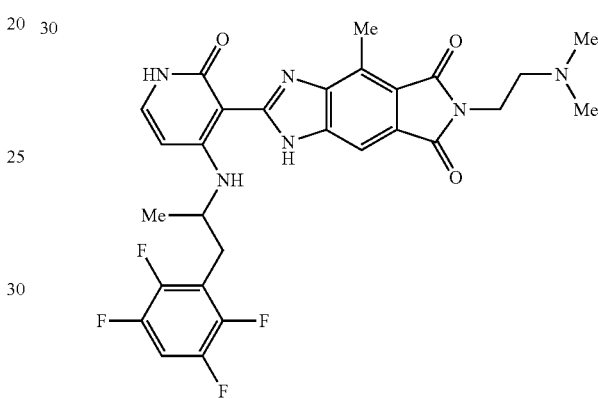
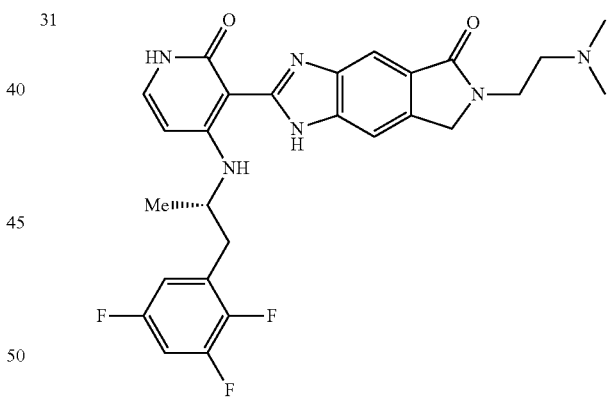
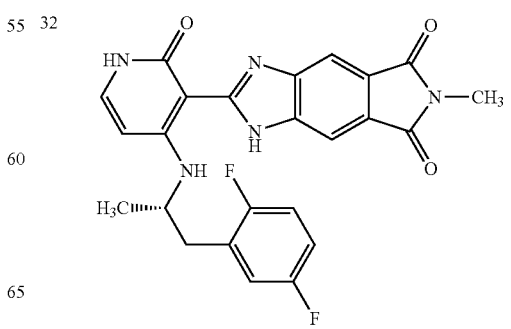

TABLE 1-continued
33 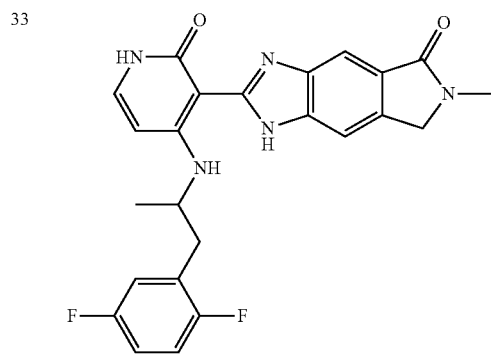
34 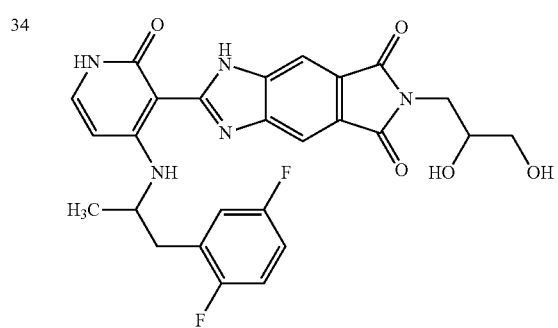
35 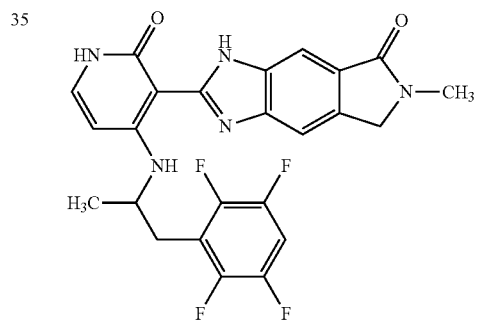
36 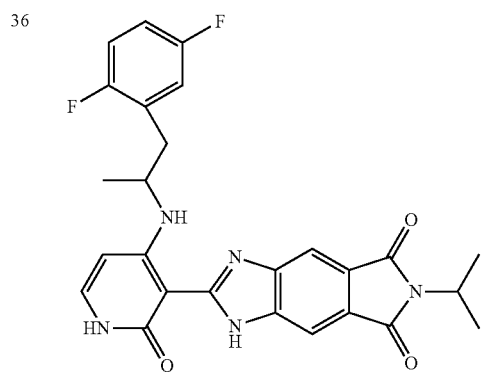
TABLE 1-continued
37 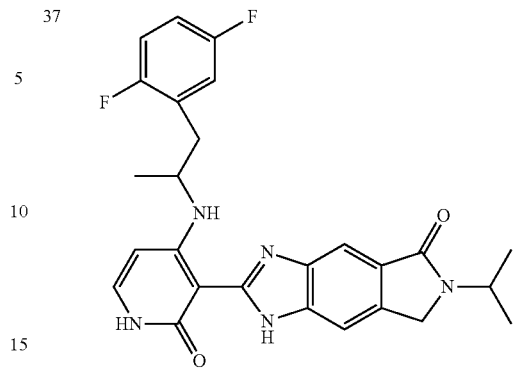
38 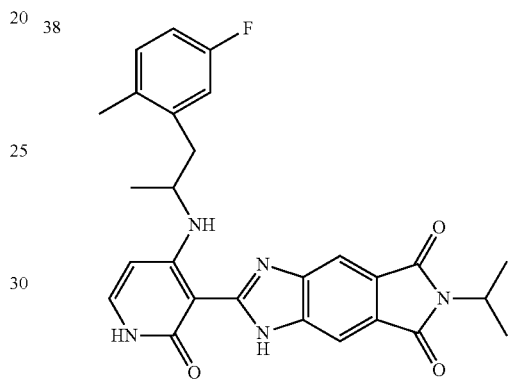
39 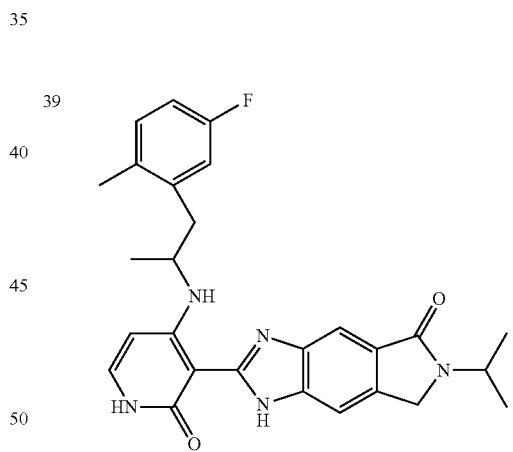
40 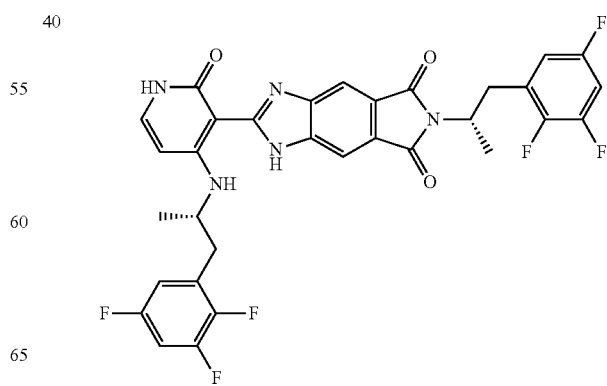

TABLE 1-continued
41
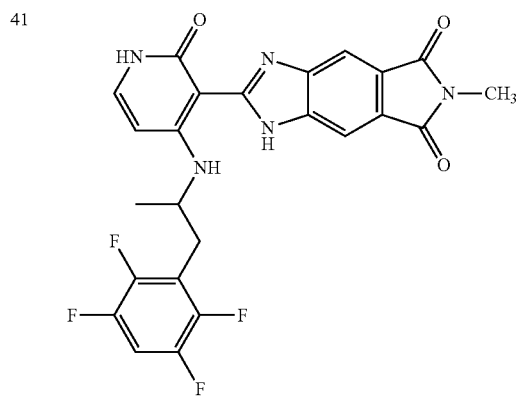
42
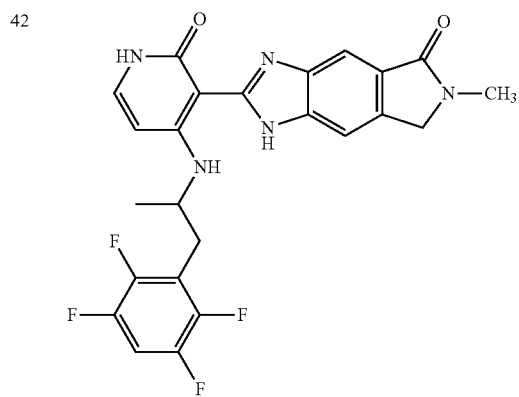
43
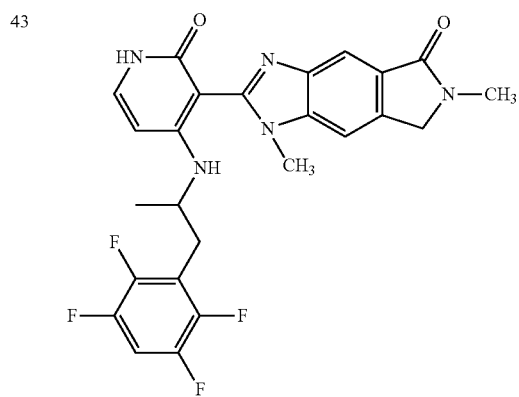
43a
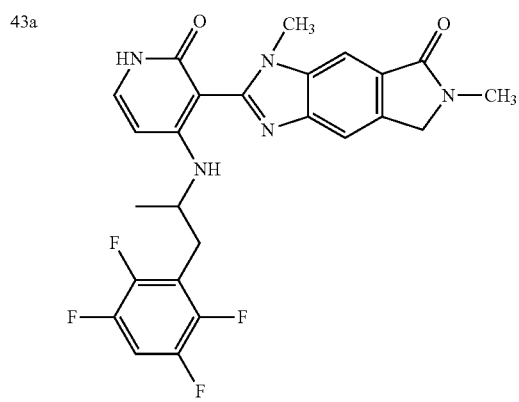
TABLE 1-continued
44
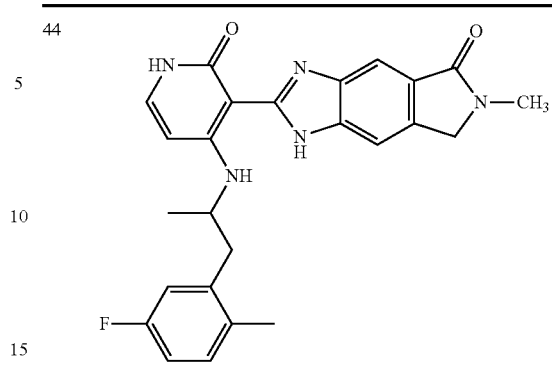
45
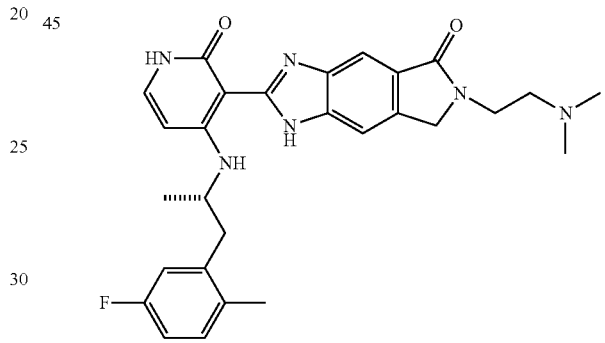
46
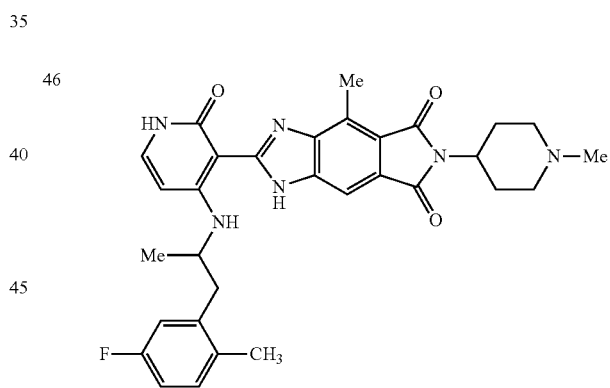
47A
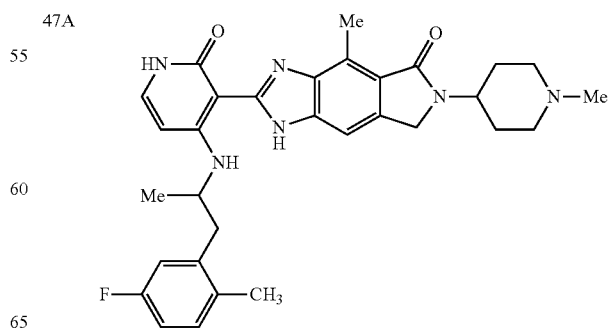

TABLE 1-continued

| | |
|---|---|
| 47B | 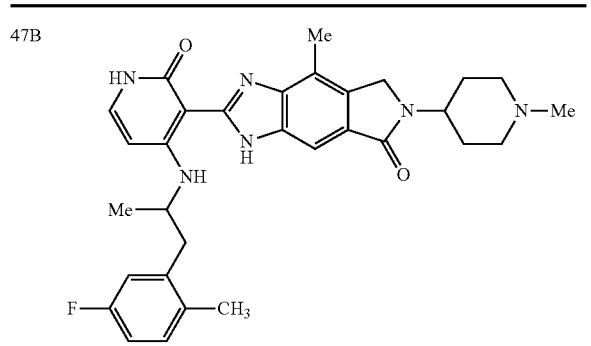 |
| 48 | 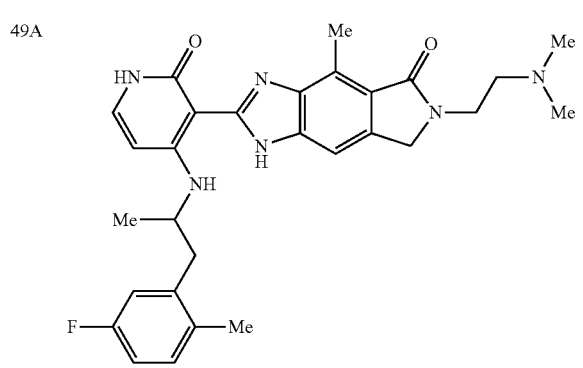 |
| 49A | |
| 49B | |

TABLE 1-continued

| | |
|---|---|
| 50 | 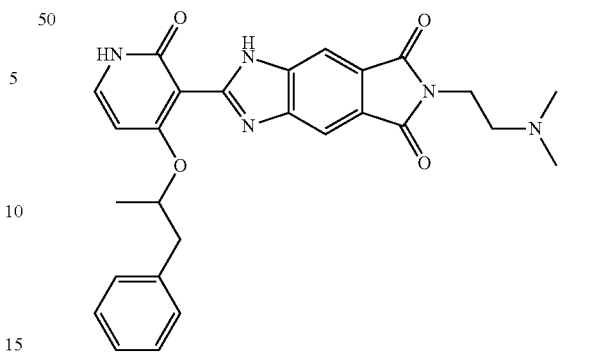 |
| 51 | 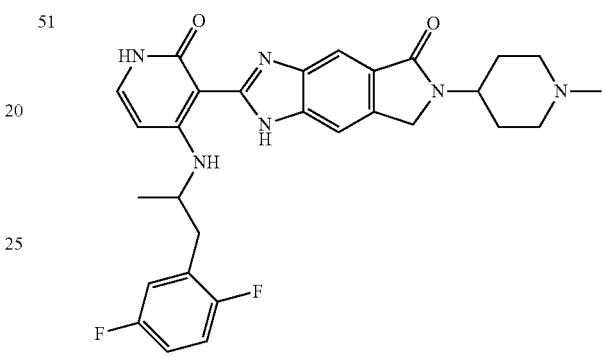 |
| 52 | 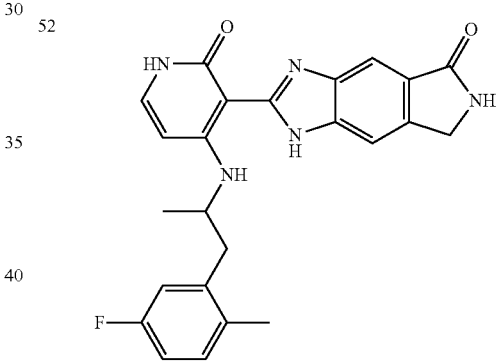 |
| 53 | 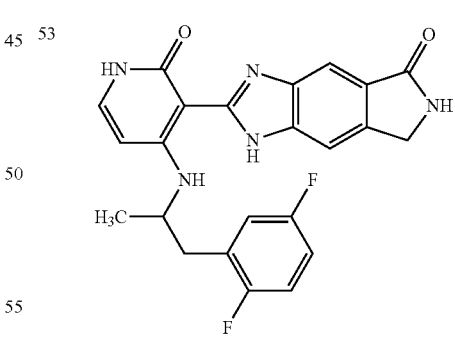 |

When describing the compounds, pharmaceutical compositions containing such compounds, and methods of using such compounds and compositions, the following terms have the following meanings unless otherwise indicated. When two terms referring to chemical groups are combined, the combined term refers to the groups covalently linked in either orientation, unless specified otherwise. For instance, the term "acylamino" can refer to either "—C(O)—N(R)—" or to "—N(R)—C(O)—" unless specified otherwise and similarly sulfonamido or aminosulfonyl can refer to either —S(O)$_2$—N(R)— or —N(R)—S(O)$_2$—.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups, in one embodiment having up to about 11 carbon atoms, in another embodiment, as a lower alkyl, from 1 to 8 carbon atoms, and in yet another embodiment, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyl" as defined below.

"Substituted alkyl" includes those groups recited in the definition of "substituted" herein, and in one embodiment refers to an alkyl group having 1 or more substituents, in another embodiment, from 1 to 5 substituents, and yet in another embodiment, from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, alkylthio, substituted alkylthio, arylthio, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups in one embodiment having up to about 11 carbon atoms and in another embodiment having 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups having in one embodiment up to about 11 carbon atoms, in another embodiment from 2 to 8 carbon atoms, and in yet another embodiment from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Substituted alkenyl" includes those groups recited in the definition of "substituted" herein, and particularly refers to an alkenyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Alkenylene" refers to divalent olefinically unsaturated hydrocarbyl groups particularly having in one embodiment up to about 11 carbon atoms and in another embodiment 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically unsaturated hydrocarbyl groups particularly having in one embodiment up to about 11 carbon atoms and in another embodiment 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Alkanoyl" as used herein, which can include "acyl", refers to the group R—C(O)—, where R is hydrogen or alkyl as defined above.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having in one embodiment 1 or more substituents, in another embodiment from 1 to 5 substituents, and yet in another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Heteroalkyl" refers to an alkyl chain as specified above, having one or more heteroatoms selected from O, S, or N.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, indacene, indacene, indane, indene, naphthalene, octacene, octaphene, octalene, ovalene, penta 2,4 diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted in one embodiment with 1 or more substituents, in another embodiment from 1 to 5 substituents, and in yet another embodiment from 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, alkylthio, substituted alkylthio, arylthio, thiol, alkyl-S(O)—, aryl-S(O)—, alkyl-S(O)$_2$— and aryl-S(O)$_2$—.

"Fused Aryl" refers to an aryl having two of its ring carbons in common with a second aryl ring or with an aliphatic ring. In certain embodiments, a bicyclic compound provided herein comprises a fused aryl.

"Amino" refers to the radical —NH$_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Azido" refers to the radical —N$_3$.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Particular halo groups are either fluoro or chloro.

"Hydroxy" refers to the radical —OH.

"Nitro" refers to the radical —NO$_2$.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" or "heteroaromatic" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, tetrahydroisoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, tetrahydroquinoline, quinolizine, quinoxaline, tetrazole, thiadiazole, thiazole, thiophene, triazole, xanthene, and the like. Particularly, heteroaryl can include other saturated ring systems, and can therefore be derived from indoline, indolizine, tetrahydroquinoline, and tetrahydroisoquinoline. In certain embodiments, the heteroaryl group is between 5-20 membered heteroaryl, with 5-10 membered heteroaryl being useful in certain embodiments. Particular heteroaryl groups are those derived from thiophene, pyrrole, benzothiophene, benzofuran, indole, pyridine, pyrimidine, quinoline, tetrahydroquinoline, isoquinoline, tetrahydroisoquinoline, imidazole, oxazole and pyrazine.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl.

"Sulfanyl" refers to the radical HS—. "Substituted sulfanyl" refers to a radical such as RS— wherein R is any substituent described herein. In certain embodiments, "substituted sulfanyl" refers to a radical —SR where R is an alkyl or cycloalkyl group as defined herein that may be optionally substituted as defined herein. Alkylthio or arylthio refer to the above sulfanyl group. Representative examples include, but are not limited to, methylthio, ethylthio, propylthio, butylthio, phenylthio and the like.

"Sulfinyl" refers to the radical —S(O)H. "Substituted sulfinyl" refers to a radical such as S(O)—R wherein R is any substituent described herein.

"Sulfonyl" refers to the divalent radical —S(O$_2$)—. "Substituted sulfonyl" refers to a radical such as —S(O$_2$)—R wherein R is any substituent described herein. "Aminosulfonyl" or "Sulfonamide" refers to the radical H$_2$N(O$_2$)S—, and "substituted aminosulfonyl" "substituted sulfonamide" refers to a radical such as R$_2$N(O$_2$)S— wherein each R is independently any substituent described herein. In particular embodiments, R is selected from H, lower alkyl, alkyl, aryl and heteroaryl.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms as long as the heteroaromatic ring is chemically feasible and stable.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like. The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations and the like.

"Solvate" refers to a compound provided herein or a salt thereof, that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78:413-447, *Angew. Chem.*, Int. Ed. Engl. 5:385-414 (errata: *Angew. Chem.*, Int. Ed. Engl. 5:511); Prelog and Helmchen, 1982, *Angew. Chem.* 94:614-631, *Angew. Chem.* Internat. Ed. Eng. 21:567-583; Mata and Lobo, 1993, *Tetrahedron*: Asymmetry 4:657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In certain embodiments, the compounds provided herein may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, provided are the stereoisomers of the compounds depicted herein upon use of stereoisomerically pure intermediates in their synthesis, such as pure enantiomers, or diastereomers as building blocks, prepared by chiral synthesis methodologies, or resolution by formation of diastereomeric salts with chiral acid or base and their separation, or separation by means of chromatography, including using chiral stationary phase. The racemic, or diastereomeric mixtures of compounds provided herein can also be separated by means of chromatography, including chiral stationary phase chromatography.

In certain embodiments, the compounds provided herein are "stereochemically pure." A stereochemically pure compound has a level of stereochemical purity that would be recognized as "pure" by those of skill in the art. Of course, this level of purity will be less than 100%. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

As used herein, the terms "disorder" and "disease" are used interchangeably to refer to a condition in a subject. Certain conditions may be characterized as more than one disorder. For example, certain conditions may be characterized as both non-cancerous proliferative disorders and inflammatory disorders.

As used herein, the term "effective amount" refers to the amount of a compound provided herein which is sufficient to reduce or ameliorate the severity, duration of a disorder, cause regression of a disorder, prevent the recurrence, development, or onset of one or more symptoms associated with a disorder, or enhance or improve the prophylactic or therapeutic effect(s) of another therapy.

As used herein, the term "in combination" refers to the use of more than one therapies. The use of the term "in combination" does not restrict the order in which therapies (e.g., prophylactic and/or therapeutic agents) are administered to a subject with a disorder. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with a disorder.

As used herein, the terms "prophylactic agent" and "prophylactic agents" as used refer to any agent(s) which can be used to prevent disorder or one or more symptoms thereof. In certain embodiments, the term "prophylactic agent" refers to a compound provided herein. In certain other embodiments, the term "prophylactic agent" does not refer a compound provided herein. In certain embodiments, a prophylactic agent is an agent which is known to be useful for, or has been or is currently being used to the prevent or impede the onset, development, progression and/or severity of a disorder. Prophylactic agents may be characterized as different agents based upon one or more effects that the agents have in vitro and/or in vivo. For example, an anti-angiogenic agent may also be characterized as an immunomodulatory agent.

As used herein, the terms "prevent," "preventing" and "prevention" refer to the prevention of the recurrence, onset, or development of one or more symptoms of a disorder in a subject resulting from the administration of a therapy, or the administration of a combination of therapies.

As used herein, the phrase "prophylactically effective amount" refers to the amount of a therapy which is sufficient to result in the prevention of the development, recurrence or onset of one or more symptoms associated with a disorder, or to enhance or improve the prophylactic effect(s) of another therapy.

As used herein, the terms "subject" and "patient" are used interchangeably herein. The terms "subject" and "subjects" refer to an animal, in certain embodiments a mammal including a non-primate (e.g., a cow, pig, horse, cat, dog, rat, and mouse) and a primate (e.g., a monkey such as a cynomolgous monkey, a chimpanzee and a human), and more particularly a human. In another embodiment, the subject is a farm animal (e.g., a horse, a cow, a pig, etc.) or a pet (e.g., a dog or a cat). In certain embodiments, the subject is a human.

As used herein, the term "synergistic" refers to a combination of a compound provided herein and another therapy which has been or is currently being used to prevent, manage or treat a disorder, which is more effective than the additive effects of the therapies. A synergistic effect of a combination of therapies permits the use of lower dosages of one or more of the therapies and/or less frequent administration of said therapies to a subject with a disorder. The ability to utilize lower dosages of a therapy and/or to administer said therapy less frequently reduces the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies may avoid or reduce adverse or unwanted side effects associated with the use of either therapy alone.

As used herein, the terms "therapeutic agent" and "therapeutic agents" refer to any agent(s) which can be used in the treatment, management, or amelioration of a disorder or one or more symptoms thereof. In certain embodiments, the term "therapeutic agent" refers to a compound provided herein. In certain other embodiments, the term "therapeutic agent" does not refer to a compound provided herein. In certain embodiments, a therapeutic agent is an agent which is known to be useful for, or has been or is currently being used for the treatment, management, prevention, or amelioration a disorder or one or more symptoms thereof. Therapeutic agents may be characterized as different agents based upon one or more effects the agents have in vivo and/or in vitro, for example, an anti-inflammatory agent may also be characterized as an immunomodulatory agent.

As used herein, the term "therapeutically effective amount" refers to that amount of a therapy sufficient to result in the amelioration of one or more symptoms of a disorder, prevent advancement of a disorder, cause regression of a disorder, or to enhance or improve the therapeutic effect(s) of another therapy. In a specific embodiment, with respect to the treatment of cancer, an effective amount refers to the amount of a therapy that inhibits or reduces the proliferation of cancerous cells, inhibits or reduces the spread of tumor cells (metastasis), inhibits or reduces the onset, development or progression of one or more symptoms associated with cancer, or reduces the size of a tumor. In certain embodiments, a therapeutically effective of a therapy reduces the proliferation of cancerous cells or the size of a tumor by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, relative to a control or placebo such as phosphate buffered saline ("PBS").

As used herein, the terms "therapies" and "therapy" can refer to any protocol(s), method(s), and/or agent(s) that can be used in the prevention, treatment, management, or amelioration of a disorder or one or more symptoms thereof. In certain embodiments, the terms "therapy" and "therapies" refer to chemotherapy, radiation therapy, hormonal therapy, biological therapy, and/or other therapies useful in the prevention, management, treatment or amelioration of a disorder or one or more symptoms thereof known to one of skill in the art (e.g., skilled medical personnel).

As used herein, the terms "treat", "treatment" and "treating" refer to the reduction or amelioration of the progression, severity and/or duration of a disorder, or the amelioration of one or more symptoms thereof resulting from the administration of one or more therapies.

As used herein, the term "modulation" or "modulating" refers to the alteration of the catalytic activity of a tyrosine kinase. In particular, modulating can refer to the activation or to the inhibition of the tyrosine kinase. The tyrosine kinase can be any tyrosine kinase known to those of skill in the art. In certain embodiments, the tyrosine kinase is a receptor tyrosine kinase or an intracellular tyrosine kinase.

As used herein, the term "ALK" refers to anaplastic lymphoma kinase.

The definitions used herein are according to those generally accepted in the pertinent art and those specified herein.

All compounds include tautomeric forms, as exemplified by, but not limited to the following:

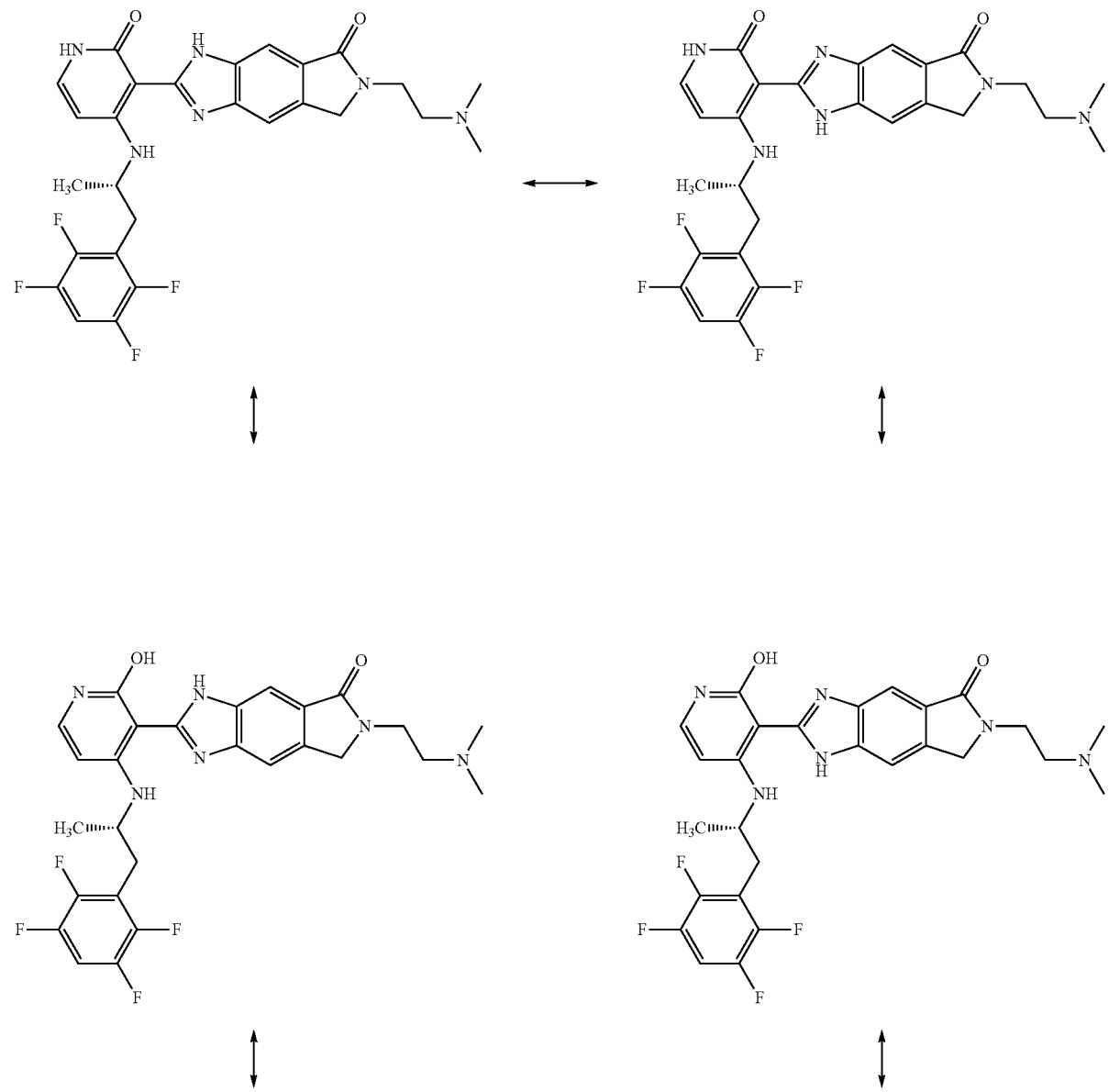

47

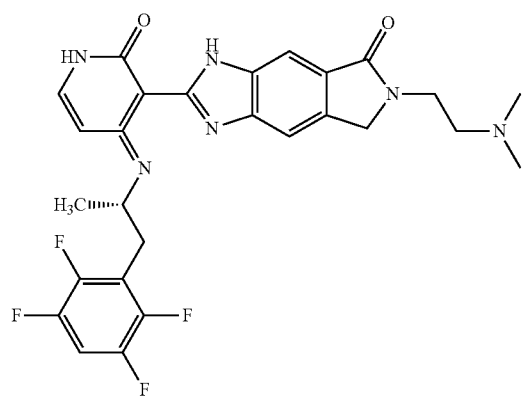 [SMILES: C[C@@H](Cc1c(F)c(F)cc(F)c1F)Nc1cc[nH]c(=O)c1-c1nc2cc3c(cc2[nH]1)C(=O)N(CCN(C)C)C3]

-continued

48

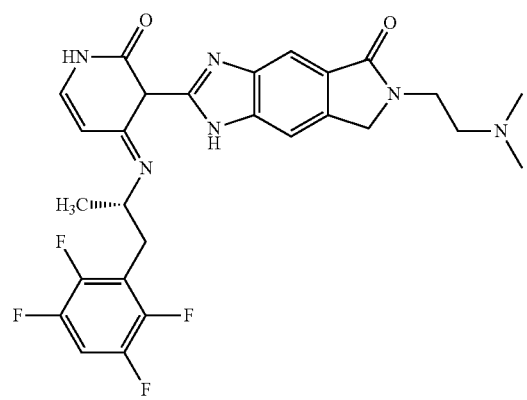

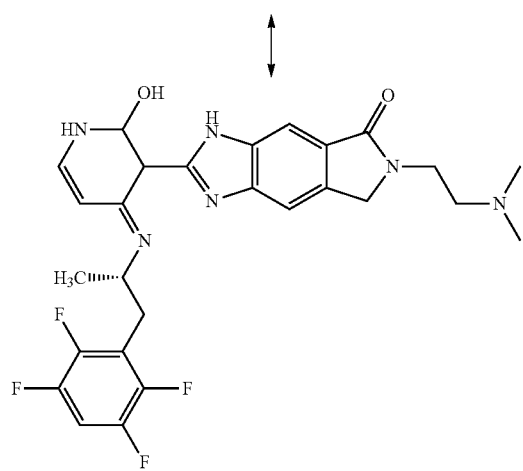

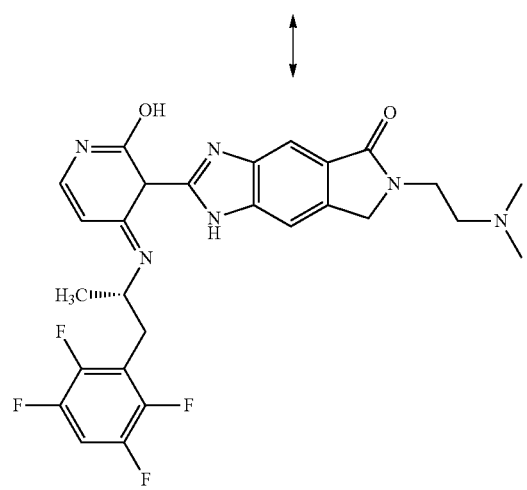

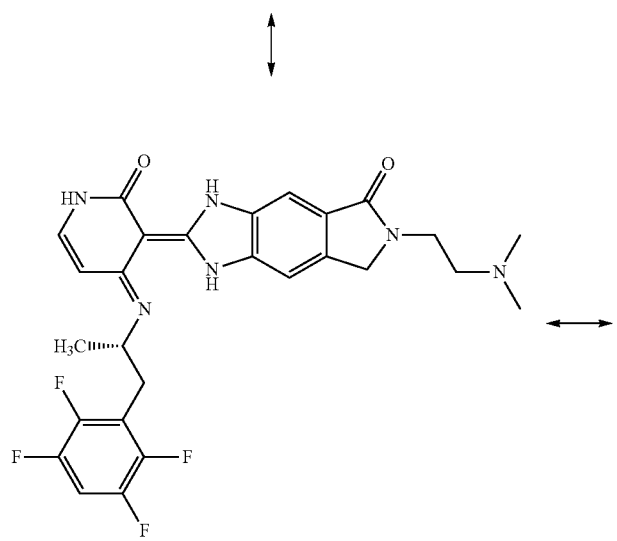

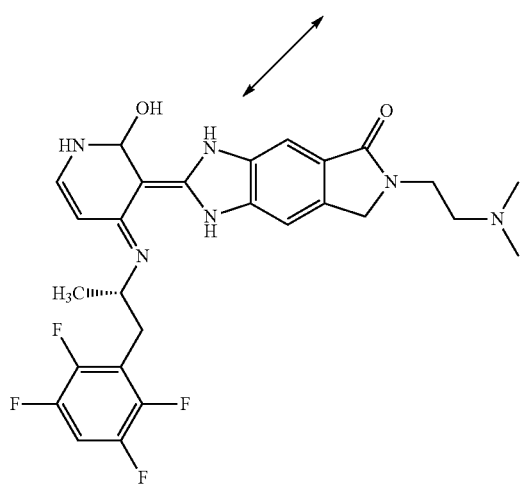

Included are also without limitation their corresponding prodrugs, such as are known in the art. They include esters, such as acetate, propionate and other esters of fatty acids, aminoacids natural and unnatural, such as glycine, valine esters and the like, amides such as acetamides, propionamides and other amides of fatty or aromatic acids, aminoacids, such as glycinamide and other aminonoacids natural or unnatural, ethers, such as methoxy or ethoxy, methoxyethyl, ethoxyethyl, hydroxyethyl, propyleneglycol ethers and/or polyethyleneglycol ethers and/or polypropylene glycol ethers.

Compositions and Methods of Administration

In certain aspects, provided are compostions comprising a compound provided herein. The compositions can be used, for example, in the methods of use described above.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and one or more pharmaceutically acceptable carriers or excipients or diluents. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

On one embodiment, pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose-free compositions provided herein can comprise excipients that are well known in the art and are listed, for example, in the U.S. Pharmacopeia (USP) SP (XXI)/NF (XVI). In one embodiment, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pregelatinized starch, and magnesium stearate.

Provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are in certain embodiments anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are in certain embodiments packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent in certain embodiments in purified form, together with a suitable amount of carrier so as to provide the form for proper administration to the patient. The formulation should suit the mode of administration. In certain embodiments, the pharmaceutical compositions or single unit dosage forms are sterile and in suitable form for administration to a subject, in certain embodiments an animal subject, such as a mammalian subject, particularly a human subject.

A pharmaceutical composition provided herein is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration.

In a specific embodiment, the composition is formulated in accordance with routine procedures as a pharmaceutical composition adapted for intravenous, subcutaneous, intramuscular, oral, intranasal or topical administration to human beings.

In an embodiment, a pharmaceutical composition is formulated in accordance with routine procedures for subcutaneous administration to human beings. In one embodiment, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms provided herein will typically vary depending on their use. For example, a dosage form used in the acute treatment of inflammation or a related disorder may contain larger amounts of one or more of the active ingredients it comprises than a dosage form used in the chronic treatment of the same disease. Also, the therapeutically effective dosage form may vary among different types of cancer. Similarly, a parenteral dosage form may contain smaller amounts of one or more of the active ingredients it comprises than an oral dosage form used to treat the same disease or disorder. These and other ways in which specific dosage forms provided herein will vary from one another will be readily apparent to those skilled in the art. See, e.g., Remington's Pharmaceutical Sciences, 18th ed., Mack Publishing, Easton Pa. (1990).

The ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day. Particular dosage forms have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the compound.

Oral Dosage Forms

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

In certain embodiments, the oral dosage forms are solid and prepared under anhydrous conditions with anhydrous ingredients, as described in detail in the sections above. However, the scope extends beyond anhydrous, solid oral dosage forms. As such, further forms are described herein.

Typical oral dosage forms provided herein are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Controlled Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients. Thus provided are single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are in certain embodiments sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms provided herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients provided herein. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Dosage & Frequency of Administration

The amount of the compound or composition which will be effective in the prevention, treatment, management, or amelioration of a disorder or one or more symptoms thereof will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems.

Exemplary doses of a compound include milligram or microgram amounts of the active peptide per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). In one embodiment, the recommended daily dose range of a compound provided herein for the conditions described herein lie within the range of from about 0.01 mg to about 1000 mg per day, given as a single once-a-day dose in certain embodiments as divided doses throughout a day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the compounds provided herein are also encompassed by the above described dosage amounts and dose frequency schedules. Further, when a patient is administered multiple dosages of a compound provided herein, not all of the dosages need be the same. For example, the dosage administered to the patient may be increased to improve the prophylactic or therapeutic effect of the compound or it may be decreased to reduce one or more side effects that a particular patient is experiencing.

In certain embodiments, administration of the same compound provided herein may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

Compounds according to formula (I) can be prepared according to any method apparent to those skilled in the art. Provided below are exemplary methods for their preparation.

Scheme 1

Synthesis of substituted -6,7-dihydroimidazo[4,5-f]isoindol-5(1H)-ones:

General Approach 1:

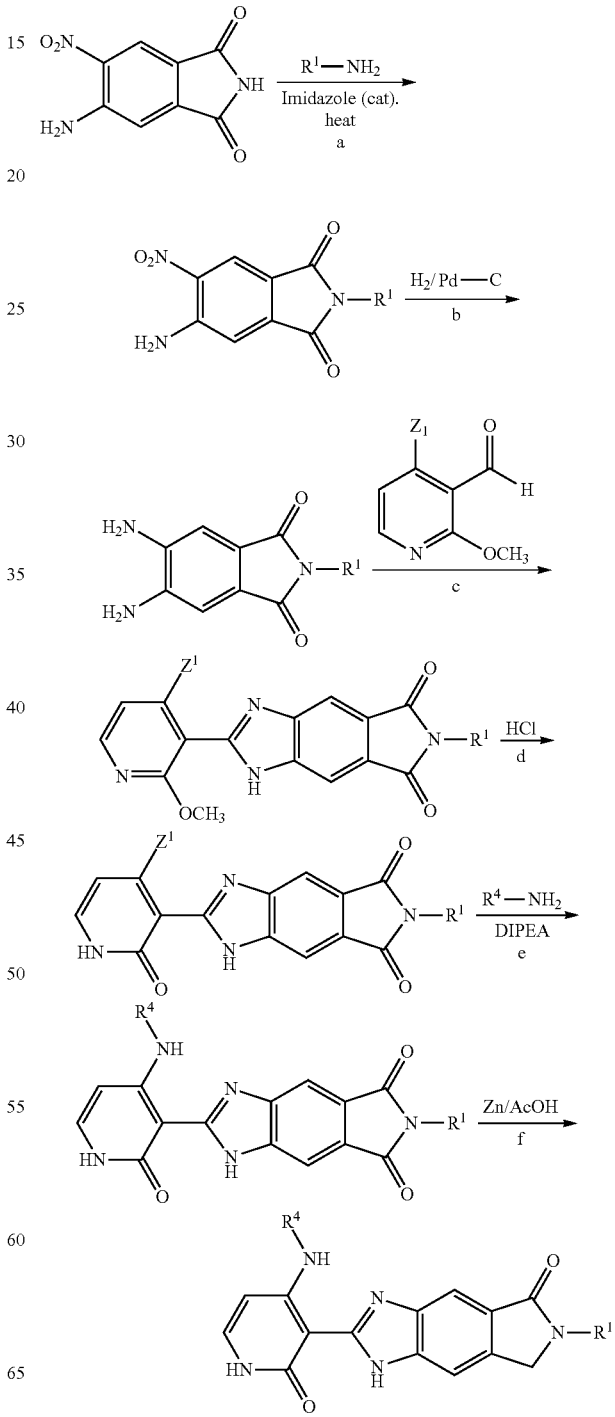

wherein $Z^1$ is Cl or I.

Scheme 2
Synthesis of Amines $R^4$—$NH_2$

General Approach 2:

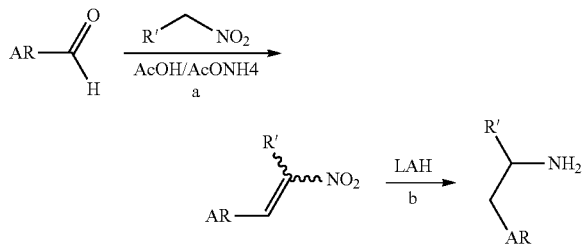

wherein AR is selected from optionally substituted aryl or heteroaryl.

This scheme was described in *J. Med. Chem.* 35 (1992), 280-285. The racemic compounds can be resolved by any of the resolution methods known in the art, including but not limited to chiral chromatography (e.g.: chromatography on a chiral support column), formation of diastereomeric compounds, either ionic, or covalent, such as chiral tartrate salts or salts with any feasible chiral acid, carboxylic, or sulfonic. As an example of covalent compounds the corresponding diastereomeric amides, such as chiral mandelamides, formed by standard non-racemizing amide coupling reactions, followed by separation either by chromatography, or fractional crystallization.

Scheme 3
Synthesis of Amines $R^4$—NH2

General Approach 3:

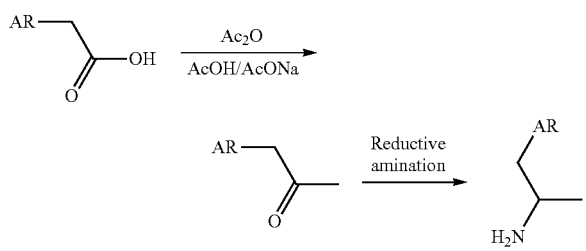

Scheme 4
Synthesis of Chiral Amines $R^4$—$NH_2$

General Approach 4:

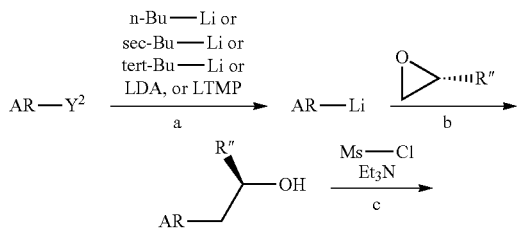

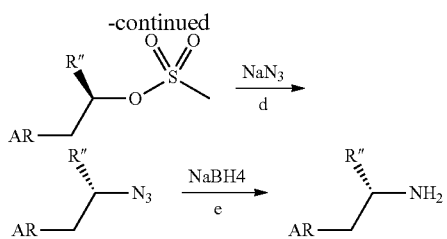

wherein $Y^2$ is selected from hydrogen, bromo or iodo.

The synthesis of the chiral and/or racemic amines is according to the above general scheme and is a modification of the approach described in: Wagner, Jared M.; McElhinny, Charles J.; Lewin, Anita H.; Carroll, F. Ivy. *Tetrahedron: Asymmetry* (2003), 14(15), 2119-2125.

The following examples are presented in order to more fully illustrate the preferred embodiments of the invention. They should in no way, however, be construed as limiting the broad scope of the invention.

EXAMPLES

Example 1

General Procedures for Racemic Amphetamines

Synthesis of 1-(2,5-difluorophenyl)propan-2-amine (A)

The synthesis and procedures of this compound was described in *Bioorganic & Medicinal Chemistry*, 1992, 16, 4661-4669.

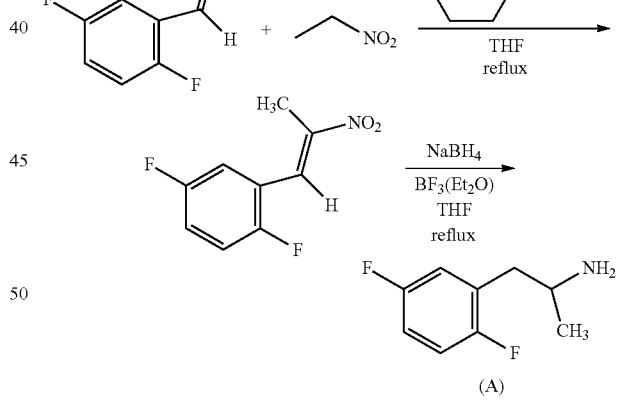

(A)

1-(2,5-Difluorophenyl)-2-nitropropene

A mixture of 2,5-difluorobenzaldehyde (25.0 g, 0.176 mol), nitroethane (26.41 g, 0.352 mol) and cyclohexylamine (17.45 g, 0.176 mol) in 150 mL of acetic acid was stirred at 80° C. overnight. After cooling to rt the solvent was evaporated, the residue was purified by column chromatography (silica-gel, $CH_2Cl_2$/acetone=19/1 v/v) to give a yellow solid product, 28.5 g, 81.3% yield. MS: 197.6 [M–H]$^-$. $^1$H NMR (DMSO-$d_6$, 500 MHz): δ 7.94 (s, 1H), 7.46-7.43 (m, 1H), 7.41-7.35 (m, 2H), 2.31 (s, 3H).

1-(2,5-Difluorophenyl)propan-2-amine (A)

In a dry flask were placed NaBH$_4$ (9.50 g, 0.251 mol) and 300 mL of dry THF. The flask was cooled to 0° C. under argon and 42.76 g of BF$_3$(Et$_2$O) was added via a syringe. After addition, a solution of 10.0 g (50.21 mmol) of 1-(2,5-difluorophenyl)-2-nitropropene was added dropwise via a syringe, and the reaction mixture was heated to reflux for 8 h. The reaction was quenched by carefully pouring the mixture to water, acidified with 2 N HCl and heated to 80° C. for 4 h. The THF was removed under reduced pressure; the residue was washed with ether twice (2×50 mL). The aqueous layer was separated, made strongly alkaline with 10% aqueous NaOH solution and extracted with ether until no product is left in aqueous layer. The extracts were dried over anhydrous MgSO$_4$, filtered, evaporated and purified by column chromatography (silica-gel, CH$_2$Cl$_2$/MeOH=9/1 v/v) to give a colorless oil, 7.65 g, 88.9% yield. MS: 172.0 [M+H]$^+$. $^1$H NMR (DMSO-d$_6$, 500 MHz): δ 7.20-7.13 (m, 1H), 7.10-7.05 (m, 2H), 3.06 (sextet, 1H, J=6.5 Hz), 2.63-2.54 (m, 2H), 0.96 (d, 3H, J=6.0 Hz). Racemate status was confirmed by HPLC using a chiral column as described for compound D below.

Synthesis of 1-(2,3,5,6-tetrafluorophenyl)propan-2-amine (B)

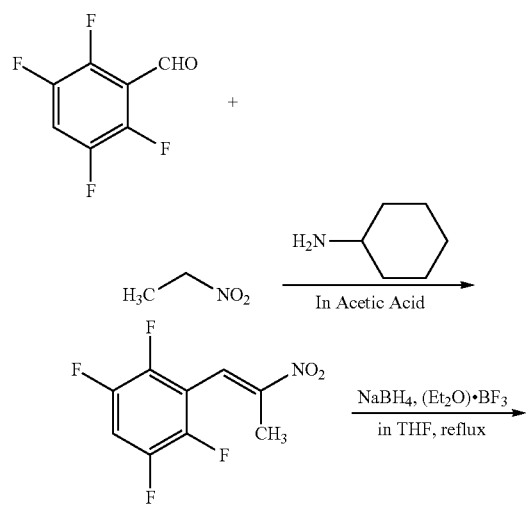

B

1,2,4,5-Tetrafluoro-3-(2-nitroprop-1-enyl)benzene

A mixture of 2,3,5,6-tetrafluorobenzaldehyde (25.0 g, 0.14 mol), nitroethane (21.08 g, 0.28 mol), and cyclohexylamine (13.92 g, 0.14 mol) in 150 mL of acetic acid was heated at 80° C. for 5-6 h under an argon atmosphere. After the end of the reaction was established by TLC, the reaction mixture was cooled to room temperature (rt) and the solvent was removed under vacuum. The residue was diluted with water, extracted with ethyl acetate three times. The combined extracts were dried over anhydrous MgSO$_4$, filtered, and concentrated under vacuum. Product was purified by a silica gel chromatography using ethyl acetate and hexanes (1:6 to 1:4) as eluent to afford 30.0 g (91%) of the designed compound as yellow solid. Mass (ESI, positive) m/z 258.0 [M+Na]$^+$.

1-(2,3,5,6-Tetrafluorophenyl)propan-2-amine (B)

Borontrifluoride diethyletherate (113.17 g, 0.797 mol) was added dropwise through a syringe to a cooled mixture of NaBH$_4$ (24.13 g, 0.638 mol) in 500 mL of anhydrous THF under an argon atmosphere. After addition, the mixture was warmed to rt and continued to stir for 20 minutes. A solution of 1,2,4,5-tetrafluoro-3-(2-nitroprop-1-enyl)benzene (30.0 g, 0.128 mol) in 200 mL of anhydrous THF was added dropwise through an additional funnel to the above mixture. The resulting reaction mixture was stirred for 20 minutes at rt and heated at reflux for 5-6 h under an argon atmosphere. After the end of the reaction was established by TLC, the reaction mixture was cooled to rt, quenched by water, acidified by concentrated HCl, and heated to 80° C. for 2-3 h. The mixture was washed with diethyl ether twice. The aqueous layer was separated, basified with 10% aqueous NaOH solution, and extracted with diethyl ether until no or a little product is left in aqueous layer. The combined extracts were dried over anhydrous MgSO$_4$, filtered, evaporated and purified by a silica gel column chromatography using CH$_2$Cl$_2$ and methanol (85:15 v/v) as eluent to give 8.4 g of the designed compound as yellowish solid. $^1$H NMR (500 MHz, DMSO-d$_6$) δ 7.83-7.76 (m, 1H, ArH), 5.28 (br s, 2H, NH$_2$), 3.25-3.21 (m, 1H, CH), 2.89-2.85 (m, 1H, CH), 2.81-2.76 (m, 1H, CH), 1.06 (d, J=6.5 Hz, 3H, CH$_3$); Mass (APCI, positive) m/z 208.0 [M+H]$^+$. Racemate status was confirmed by HPLC using a chiral column (see FIG. 9A). Samples were diluted with a hexane:EtOH and injected onto a Waters 2695 Separations Module equipped with a Regis Pack C-18 (25 cm×4.6 mm, 5 μm particle size) column. The LC separation is an isocratic elution at a flow rate of 1.50 mL/min using a mobile phase of 97:3 hexane:EtOH 0.10% TFA with UV detection at 254 nm. The injection volume was 2 μL with a run time of 12 minutes.

Synthesis of 1-(5-fluoro-2-methylphenyl)propan-2-amine (C)

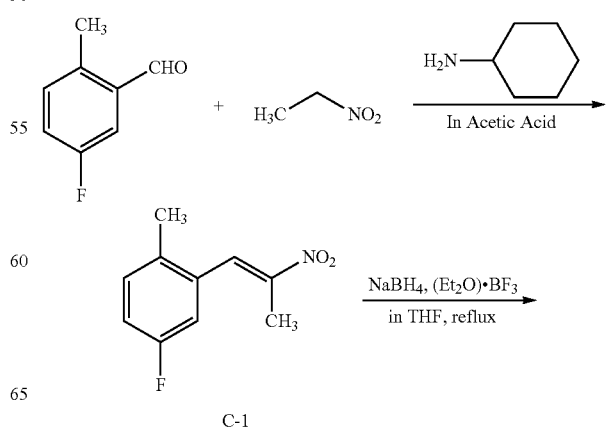

C-1

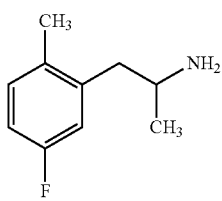

C

4-Fluoro-1-methyl-2-(2-nitroprop-1-enyl)benzene (C-1)

A mixture of 5-fluoro-2-methylbenzaldehyde (50.0 g, 0.382 mol), nitroethane (54.34 g, 0.724 mol), and cyclohexylamine (35.90 g, 0.382 mol) in 300 mL of acetic acid was heated at 80° C. for 5-6 h under an argon atmosphere. After the end of the reaction was established by TLC, the reaction mixture was cooled to rt and the solvent was removed under vacuum. The residue was diluted with water, extracted with ethyl acetate three times. The combined extracts were dried over anhydrous MgSO$_4$, filtered, and concentrated under vacuum. Product was purified by a silica gel chromatography using ethyl acetate and hexanes (1:6 to 1:4) as eluent to afford 62.8 g (89%) of the designed compound as yellow solid. Mass (ESI, positive) m/z 217.9 [M+Na]$^+$.

1-(5-Fluoro-2-methylphenyl)propan-2-amine (C)

Borontrifluoride diethyletherate (272.68 g, 1.921 mol) was added dropwise through an additional funnel to a mixture of NaBH$_4$ (58.14 g, 1.537 mol) in 600 mL of anhydrous THF cooled in a cooling bath under an argon atmosphere. After addition, the mixture was warmed to rt and continued to stir for 30 minutes. A solution of 4-fluoro-1-methyl-2-(2-nitroprop-1-enyl)benzene (60 g, 0.307 mol) in 200 mL of anhydrous THF was added dropwise through an additional funnel to the above mixture. The resulting reaction mixture was heated at reflux for 6-7 h under an argon atmosphere. After the end of the reaction was established by TLC, the reaction mixture was cooled to rt, quenched by water, acidified by concentrated HCl, and heated to 80° C. for 4 h. The mixture was washed with diethyl ether twice. The aqueous layer was separated, basified with 10% aqueous NaOH solution, and extracted with diethyl ether until no or a little product is left in aqueous layer. The combined extracts were dried over anhydrous MgSO$_4$, filtered, evaporated and purified by a silica gel column chromatography using CH$_2$Cl$_2$ and methanol (85:15 v/v) as eluent to give 43.3 g of the designed compound as off-white solid. $^1$H NMR (500 MHz, DMSO-d$_6$) δ 7.89 (br s, 2H, NH$_2$), 7.22-7.20 (m, 1H, ArH), 7.03-6.96 (m, 2H, ArH), 3.40-3.34 (m, 1H, CH), 2.91-2.87 (m, 1H, CH), 2.69-2.65 (m, 1H, CH), 2.24 (s, 3H, CH$_3$), 1.10 (d, J=6.5 Hz, 3H, CH$_3$); Mass (ESI, positive) m/z 168.0 [M+H]$^+$.

General Procedures for Optically Pure Amphetamines

Synthesis of (S)-1-(2,5-difluorophenyl)propan-2-amine (D)

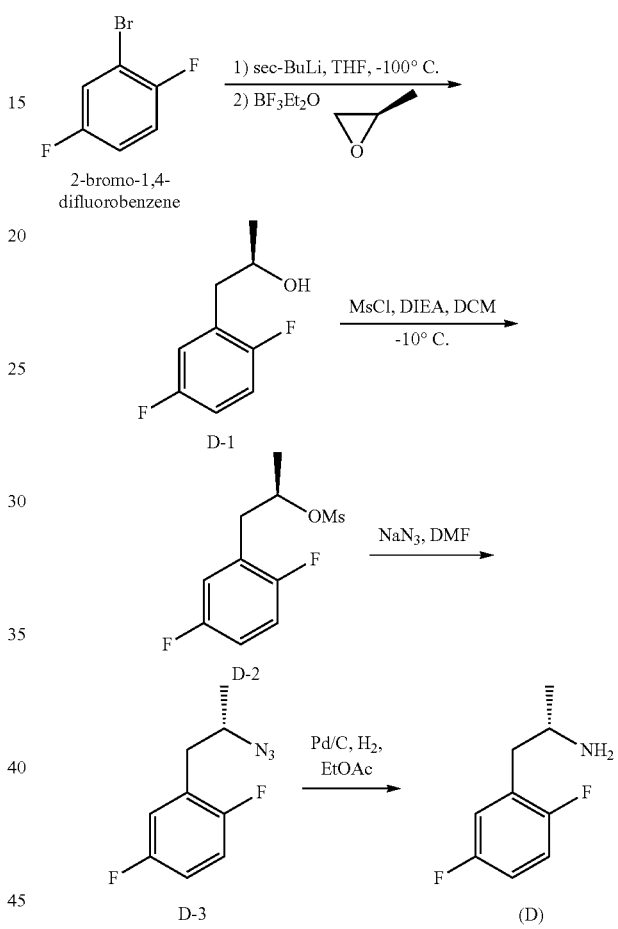

(R)-1-(2,5-Difluorophenyl)propan-2-ol (D-1)

A solution of 2-bromo-1,4-difluorobenzene (3.85 g, 20.0 mmol) in anhydrous THF (100 mL) was stirred to −100° C. (liq. nitrogen/ethanol) under argon gas. Then, 1.6 M solution of sec-BuLi in cyclohexane (14.3 mL, 21.0 mmol) was added dropwise at −100° C.~−90° C. for 10 min, then a solution of R-(+)-propylene (1.14 g, 1.4 mL, 26.0 mmol) in anhydrous THF (15 mL) was added dropwise at −100° C.~−90° C. for 2 h, then the mixture was cooled to −105° C. and a 46.5% solution of BF$_3$ in diethyl ether (4.18 mL, 30 mmol) was added dropwise. The mixture was stirred at −100° C. to −90° C. for 2 h, then the reaction was quenched with 20 mL of sat. aq. NH$_4$Cl at −90° C. The mixture was stirred and warmed to 0° C. overnight. Then, 20 mL of water was added and extracted with EtOAc (2×60 mL), dried over anhydrous MgSO$_4$, evaporated to give crude oil, which was purified by column chromatography (silicagel, EtOAc/hexane=1:9, v/v) to give (R)-1-(2,5-difluorophenyl)propan-2-ol (2.15 g, 62.5%). ¹H NMR (CDCl₃, 500 MHz) δ 6.98 (m, 2H), 6.88 (m, 1H), 4.10 (m, 1H), 4.03 (bs, OH), 2.79 (m, 1H), 2.71 (m, 1H), 1.23 (s, 3H).

(R)-1-(2,5-Difluorophenyl)propan-2-yl methanesulfonate (D-2)

A solution of D-1 (1.27 g, 7.4 mmol) and DIEA (2.6 mL, 14.8 mmol) in 30 mL of anhydrous DCM was cooled to −10° C. Then methanesulfonyl chloride (0.69 mL, 8.88 mmol) was carefully added and the mixture was warmed to rt and stirred for 30 min And then, saturated aq. NaHCO₃ solution (10 mL) was added to the solution and extracted with dichloromethane (DCM) (2×20 mL), dried over anhydrous MgSO₄, concentrated under reduced pressure, and crystallized with DCM/hexane to give white solid (1.79 g, 97%). MS (ESI) m/z 263.9 [M+Na]⁺, ¹H NMR (CDCl₃, 500 MHz) δ 7.02 (m, 1H), 6.96 (m, 2H), 4.97 (m, 1H), 2.99 (m, 2H), 2.75 (s, 3H), 1.47 (d, J=6.5 Hz, 3H).

(S)-1-(2,5-Difluorophenyl)propan-2-amine (D)

A solution of D-2 (1.95 g, 7.8 mmol) was dissolved in anhydrous DMF (10 mL). Then, sodium azide (1.01 g, 15.6 mmol) was added and the mixture was heated at 80° C. for 2 h. Then, the temperature was cooled to rt and 20 mL of water was added, extracted with EtOAc/hexane (20 mL, 1/1, v/v), dried over anhydrous MgSO₄ and evaporated to give crude oil, which was passed through a silica gel pad and evaporated under reduced pressure to give the crude azide (D-3), which was dissolved in 50 mL of EtOAc, then Pd/C (180 mg of 10% Pd/C) was added and the mixture was hydrogenated under hydrogen balloon for 3 h. The catalyst was removed by filtration through celite and purified by column chromatography (MeOH/EtOAc/NH₄OH=5:93:2, v/v/v) to give D (1.1 g, 82.4% through 2 steps). MS (ESI) m/z 172.0 [M+H]⁺; ¹H NMR (CDCl₃, 500 MHz) δ 6.95 (m, 1H), 6.89 (m, 2H), 3.24 (m, 1H), 2.73 (m, 1H), 2.64 (m, 1H), 2.84 (bs, 2H, NH₂), 1.14 (d, J=6.5 Hz, 3H). Chiral purity was monitored by HPLC using a chiral column Samples were diluted with a hexane:IPA and injected onto a Waters 2695 Separations Module equipped with a Regis Pack C-18 (25 cm×4.6 mm, 5 µm particle size) column. The LC separation is an isocratic elution at a flow rate of 1.50 mL/min using a mobile phase of 96:4 hexane:IPA 0.10% TFA with UV detection at 254 nm. The injection volume was 5 µL with a run time of 15 minutes.

Synthesis of (S)-1-(2,3,5,6-tetrafluorophenyl)propan-2-amine (E)

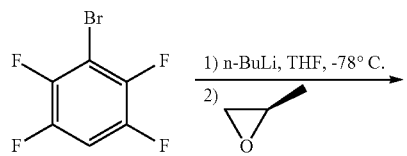

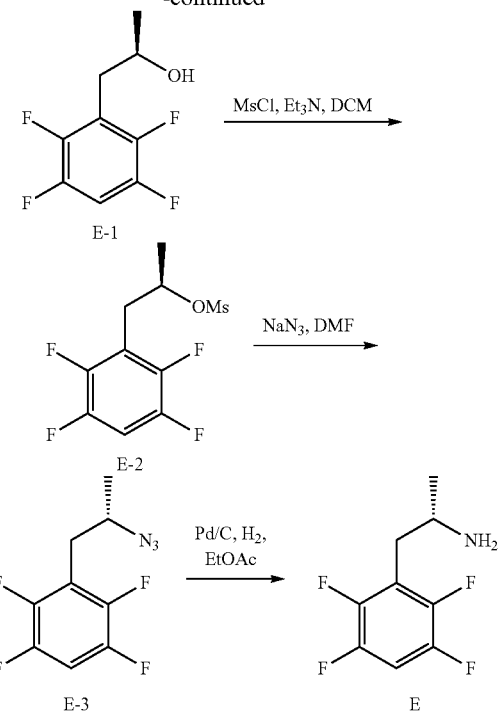

(2R)-1-(2,3,5,6-Tetrafluorophenyl)propan-2-ol (E-1)

A solution of 1-bromo-2,3,5,6-tetrafluorobenzene (4.71 g, 20.57 mmol) in anhydrous THF (100 mL) was stirred in a −78° C. in dry ice/acetone bath under argon gas. After 30 min, 2.5 M n-BuLi in hexane (9.05 mmol, 22.63 mmol) was added dropwise at that temperature for 20 min. After adding, the mixture was stirred at −78° C. in the dry ice/acetone bath for 30 min, and stirred more for 10 min without the bath. And then, the solution was cooled again in the dry ice/acetone to −78° C. and a solution of R-(+)-propylene (1.44 mL, 20.57 mmol) in 10 mL anhydrous THF was added dropwise at the temperature for 10 min and stirred at ambient temperature for overnight. And then, the solution was quenched slowly by sat. NH₄Cl, and stirred more for 2 h. Water (20 mL) was added and extracted with EtOAc, dried over anhydrous MgSO₄, evaporated and purified by column chromatography (DCM/hexane 9/1) to give pale yellow oil (yield 49%~59%). ¹H NMR (CDCl₃, 500 MHz) δ 6.97 (m, 1H), 4.12 (m, 1H), 2.89 (m, 2H), 1.45 (bs, 1H), 1.29 (d, J=6.5 Hz, 3H).

(2R)-1,2,4,5-Tetrafluoro-3-(2-(methylsulfonyl)propyl)benzene (E-2)

A solution of (2R)-1-(2,3,5,6-tetrafluorophenyl)-propan-2-ol (E-1) (1.9 g, 9.13 mmol) and Et₃N (0.85 mL, 10.95 mmol) in 40 mL anhydrous DCM was cooled in ice-water bath. Then methylsulfonyl chloride (0.85 mL, 10.95 mmol) was added slowly and the mixture was stirred for 30 min at rt. And then, saturated NaHCO₃ solution (10 mL) was added to the solution and extracted with DCM, dried over anhydrous MgSO₄ and concentrated, and crystallized with DCM/hexane to give white solid (2.58 g, 99%). MS (ESI) m/z 309.0 [M+Na]⁺, ¹H NMR (CDCl₃, 500 MHz) δ 7.02 (m, 1H), 5.04 (m, 1H), 3.14~3.07 (m, 2H), 2.90 (s, 3H), 1.49 (d, J=6.0 Hz, 3H).

(2S)-3-(2-Azidopropyl)-1,2,4,5-tetrafluorobenzene (E-3)

To a solution of (2R)-1,2,4,5-tetrafluoro-3-(2-(methylsulfonyl)propyl)benzene (2.3 g, 8.03 mmol) in anhydrous DMF (10 mL) was added sodium azide (1.045 g, 16.07 mmol) and the solution was heated to 80° C. and stirred for 2 h. Then, the temperature was cooled to rt and 20 mL of water was added, extracted with EtOAc/hexane (1/1 v/v), dried over anhydrous MgSO₄ and evaporated to give crude oil, which was passed through silica gel pad and evaporated under reduced pressure to give the product. This was used as starting material for next reduction without more purification.

(2S)-1-(2,3,5,6-Tetrafluorophenyl)propan-2-amine (E)

Figure 9A:
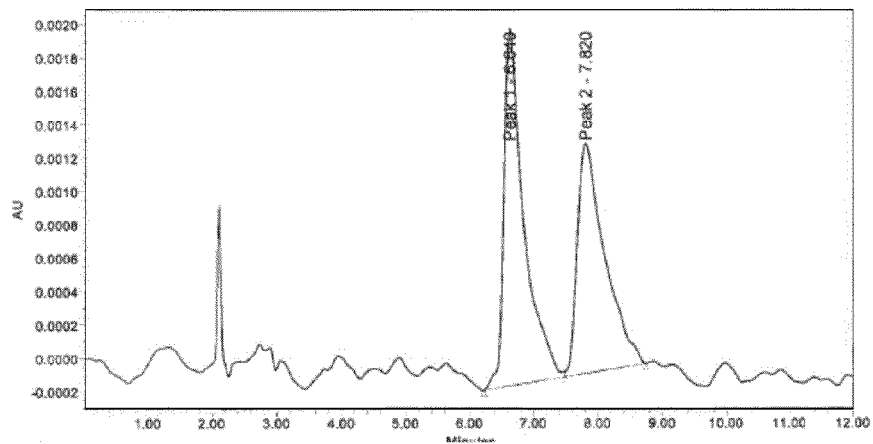
FIGS. 9A and 9B: depict HPLC of 1-(2,3,5,6-Tetrafluorophenyl)propan-2-amine-(Compound B) racemate using a chiral column (FIG. 9A) and the purity of (2S)-1-(2,3,5,6-Tetrafluorophenyl)propan-2-amine-Compound E (FIG. 9B); as described in Example 1.
Figure 9B:
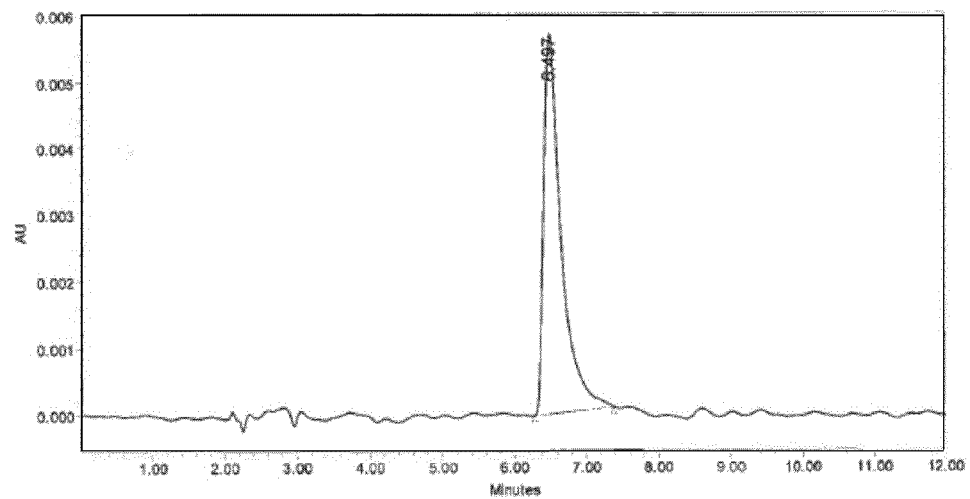

To a solution of (2S)-1-(2,3,5,6-tetrafluorophenyl)propan-2-amine in 60 mL of EtOAc was added Pd/C (300 mg, 10% Pd) and the mixture was hydrogenated under Parr Apparatus (30~40 psi) for 12 h. The catalyst was removed by filtration through celite pad, then purified by column chromatography as an eluent (EtOAc/MeOH/NH₄OH=93/5/2) to give pale yellow solid (1.22 g, 73% through 2 steps). MS (ESI) m/z 208.0 [M+H]⁺; ¹H NMR (CDCl₃, 500 MHz) δ 6.94 (m, 1H), 3.19 (m, 1H), 2.74 (m, 1H), 1.20 (bs, 2H, NH₂), 1.11 (d, J=6.5 Hz, 3H). Chiral purity was determined by HPLC using a chiral column. Samples were diluted with a hexane:EtOH and injected onto a Waters 2695 Separations Module equipped with a Regis Pack C-18 (25 cm×4.6 mm, 5 μm particle size) column. The LC separation is an isocratic elution at a flow rate of 1.50 mL/min using a mobile phase of 97:3 hexane: EtOH 0.10% TFA with UV detection at 254 nm. The injection volume was 2 μL with a run time of 12 minutes. Compare the chromatogram of FIG. 9B to that for racemate compound B above (FIG. 9A). Similar methods were used to track chirality of difluoro-(A and D) and 5-fluoro-2-methyl-(C and E) amphetamines as well.

Synthesis of (S)-1-(5-fluoro-2-methylphenyl)propan-2-amine (F)

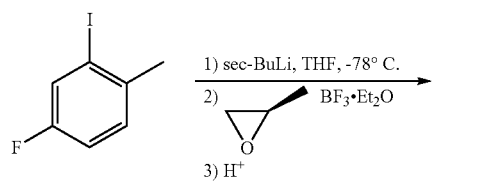

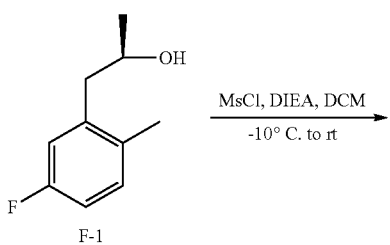

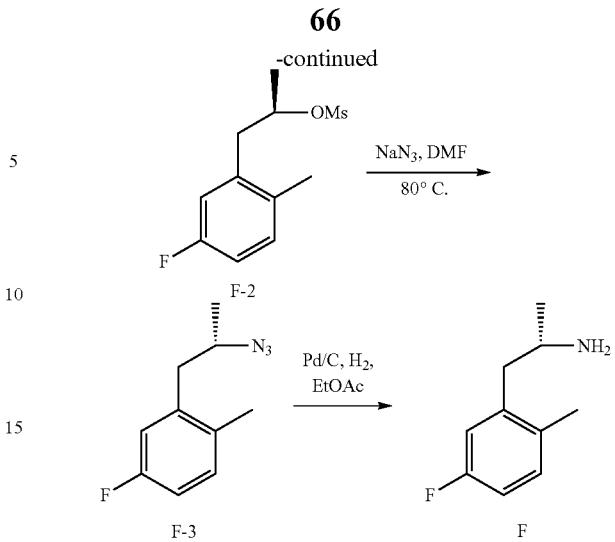

An oven dried 3-necked round bottom flask (rbf), which contained a magnetic stirring bar, was sealed with rubber septum having a thermometer. While cooling to rt, the flask was evacuated and backfilled with argon. This sequence was repeated 3 times. In the flask, a solution of 4-fluoro-2-iodo-1-methylbenzene (25 g, 105.9 mmol) in anhydrous THF (800 mL) was stirred at −78° C. in a dry ice/acetone bath under argon gas. After 30 min, 1.4 M sec-BuLi in hexane (83.2 mL, 116.5 mmol) was added dropwise at that temperature for 20 min. After adding, the mixture was stirred at −78° C. in the dry ice/acetone bath for 30 min, and stirred more for 30 min without the bath. And then, the solution was cooled again in the dry ice/acetone to −78° C. and a solution of R-(+)-propylene (8 g, 137.7 mmol) in 50 mL anhydrous THF was added dropwise at the temperature for 10 min. And then, the mixture was cooled to −105° C. and 46.5% solution of BF₃ in diethyletherate (19.6 mL) was added dropwise. And the mixture was stirred at −78° C. for 2 h, and then quenched slowly by sat. NH₄Cl at −78° C. and stirred at ambient temperature for overnight. Water (20 mL) was added and extracted with EtOAc, dried over anhydrous MgSO₄, evaporated and purified by column chromatography (DCM/hexane 9/1) to give (R)-1-(5-fluoro-2-methylphenyl)propan-2-ol (F-1) as pale yellowish oil.

A solution of (R)-1-(5-fluoro-2-methylphenyl)propan-2-ol (6.1 g, 36.3 mmol) and DIEA (12.6 mL, 72.6 mmol) in 200 mL anhydrous DCM was cooled in ice-water bath. Then methylsulfonyl chloride (3.4 mL, 43.5 mmol) was added slowly and the mixture was stirred for 30 min at rt. And then, saturated NaHCO₃ solution (30 mL) was added to the solution and extracted with DCM, dried over anhydrous MgSO₄, concentrated, passed through silicagel pad to give crude (R)-1-(5-fluoro-2-methylphenyl)propan-2-yl methanesulfonate (F-2).

A solution of (R)-1-(5-fluoro-2-methylphenyl)propan-2-yl methanesulfonate (6.3 g, 2.56 mmol) in anhydrous DMF (30 mL) was added sodium azide (3.32 g, 5.11 mmol) and the solution was heated to 80° C. and stirred for 2 h. Then, the temperature was cooled to rt and 20 mL of water was added, extracted with EtOAc/hexane (1/1, v/v), dried over anhydrous MgSO₄ and evaporated to give crude oil, which was passed through silicagel pad and evaporated under reduced pressure to give (S)-2-(2-azidopropyl)-4-fluoro-1-methylbenzene (F-3), which used as starting material for next reduction without more purification. To the solution of (S)-2-(2-azidopropyl)-4-fluoro-1-methylbenzene in 80 mL of EtOAc was added Pd/C (500 mg, 10% Pd) and the mixture was hydrogenated under Parr Apparatus (30~40 psi) for 2 h. The catalyst was removed by filtration through Celite pad, then purified by column chromatography as an eluent (EtOAc/MeOH/NH$_4$OH=93/5/2) to give (S)-1-(5-fluoro-2-methylphenyl)propan-2-amine (F) as pale yellow oil (total yield=30% through 4 steps). MS (ESI) m/z 168.0 [M+H]$^+$; $^1$H NMR (CDCl$_3$, 500 MHz) δ 7.10 (m, 1H), 6.84 (m, 2H), 3.19 (m, 1H), 2.69 (dd, J=13.5, 6.0 Hz, 1H), 2.56 (dd, J=13.5, 8.0 Hz, 1H), 2.28 (s, 3H), 1.68 (bs, 2H), 1.15 (d, J=6.0 Hz, 3H).

Synthesis of Final Products

Synthesis of Compounds 1 and 2

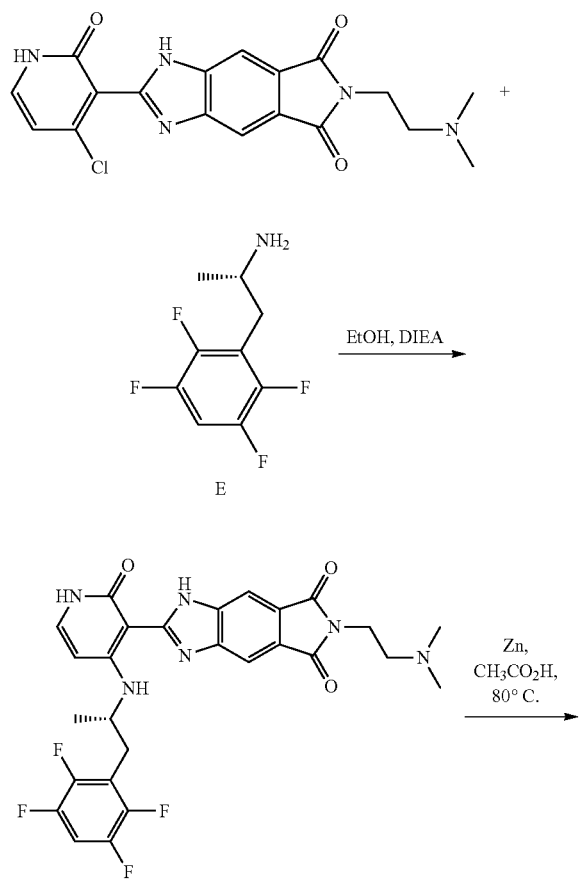

Compound 2

Compound 1

(S)-6-(2-(Dimethylamino)ethyl)-2-(2-oxo-4-((1-(2,3,5,6-tetrafluorophenyl)propan-2-yl)amino)-1,2-dihydropyridin-3-yl)imidazo[4,5-f]isoindole-5,7(1H,6H)-dione (Compound 2)

An oven dried round bottom flask (rbf), which contained a magnetic stirring bar, was sealed with a rubber septum. While cooling to rt, the flask was evacuated and backfilled with argon. This sequence was repeated 3 times. In the flask, a mixture of 2-(4-chloro-2-oxo-1,2-dihydropyridin-3-yl)-6-(2-(dimethylamino)ethyl)imidazo[4,5-f]isoindole-5,7(1H,6H)-dione (126 mg, 0.33 mmol), (S)-1-(2,3,5,6-tetrafluorophenyl)propan-2-amine (E) (45 mg, 0.39 mmol), anhydrous ethanol (4 mL) and DIEA (0.17 mL, 0.98 mmol) was stirred at 100° C. overnight. After cooling to rt, the solvent was evaporated and the residue was purified by crystallization with dichloromethane to gain (S)-6-(2-(dimethylamino)ethyl)-2-(2-oxo-4-((1-(2,3,5,6-tetrafluorophenyl)propan-2-yl)amino)-1,2-dihydropyridin-3-yl)imidazo[4,5-f]isoindole-5,7(1H,6H)-dione (Compound 2) (yield 43%). $^1$H NMR (DMSO-d$_6$, 500 MHz) δ 13.4 (bs, 1H), 10.90 (d, J=8.0 Hz, 1H), 8.12 (s, 1H), 7.89 (s, 1H), 7.68 (m, 1H), 7.38 (d, J=7.5 Hz, 1H), 6.17 (d, J=7.5 Hz, 1H), 4.24 (m, 1H), 3.68 (t, J=6.5 Hz, 2H), 3.32 (s, 3H), 3.13 (t, J=6.5 Hz, 2H), 2.49 (m, 2H), 2.17 (s, 6H), 1.38 (d, J=3.0 Hz, 3H). LC-MS: 557.2 [M+H]$^+$.

(S)-6-(2-(Dimethylamino)ethyl)-2-(2-oxo-4-((1-(2,3,5,6-tetrafluorophenyl)propan-2-yl)amino)-1,2-dihydropyridin-3-yl)-6,7-dihydroimidazo[4,5-f]isoindol-5(3H)-one (Compound 1)

Compound 2 (40 mg, 0.07 mmol), Zn (dust, 129 mg) and acetic acid (5.0 mL) were added and the mixture stirred at 110° C. for 5 h. Solids were removed by filtration, filtrate was evaporated, and the residue was purified by column chromatography to gain (S)-6-(2-(dimethylamino)ethyl)-2-(2-oxo-4-((1-(2,3,5,6-tetrafluorophenyl)propan-2-yl)amino)-1,2-dihydropyridin-3-yl)-6,7-dihydroimidazo[4,5-f]isoindol-5(3H)-one (Compound 1) (yield 25%). $^1$H NMR (DMSO-d$_6$, 500 MHz) δ 13.04 (bs, 1H), 11.30 (bs, 1H), 11.11 (s, 1H), 7.95 (s, 1H), 7.76 (s, 1H), 7.61 (m, 1H), 7.36 (m, 1H), 6.15 (m, 1H), 4.53 (m, 2H), 4.22 (m, 1H), 3.63 (m, 2H), 3.32 (s, 3H), 3.15 (m, 2H), 2.51 (m, 2H), 2.19 (s, 6H), 1.37 (m, 3H). LC-MS: m/z 543.2 [M+H]$^+$; MS (ESI): m/z 543.2 [M+H]$^+$.

Synthesis of Compound 4

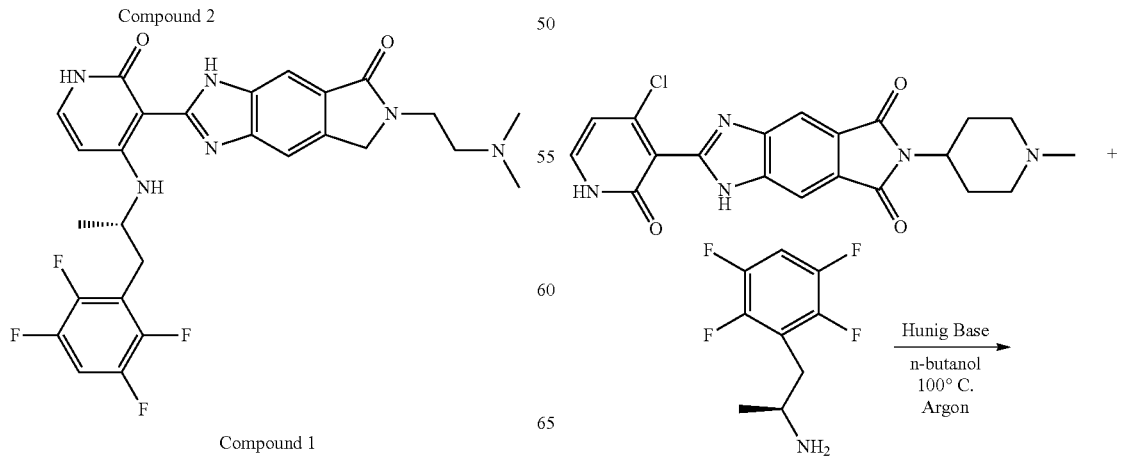

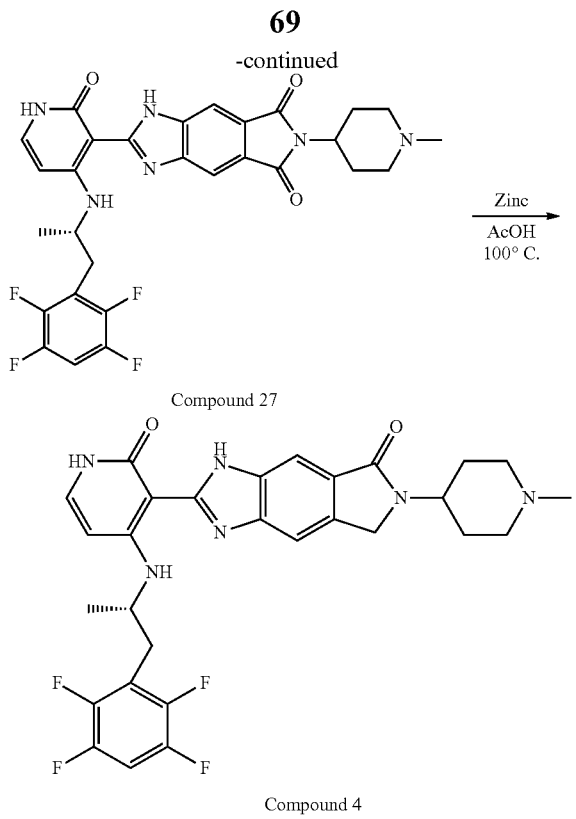

Compound 27

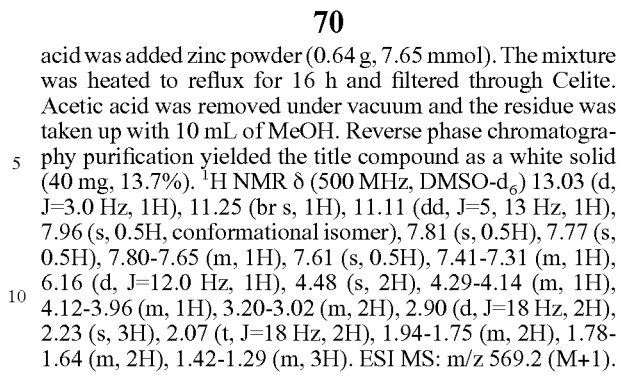

Compound 4

General Procedure A: Coupling amphetamine substituent to 4-chloro-2-methoxypridin-3-yl-imidazo[4,5-f]isoindole-5,7(1H,6H)-dione fragment. A mixture of equal molar amount of substituted amphetamine, 6-substituted 4-chloro-2-oxo-1,2-dihydropyridin-3-yl-imidazo[4,5-f]isoindole-5,7(1H,6H)-dione, and 2 molar equivalents of Hunig base in 25 volume of n-butanol was heated to reflux and maintained for 16 h. TLC was used to monitor reaction progress. Once the reaction reached completion, the solution was allowed to cool to rt. The resulting crystal was filled and washed with MeOH to remove residual n-butanol and Hunig base. The compound was further purified by recrystallization or column chromatography.

(S)-6-(1-Methylpiperidin-4-yl)-2-(2-oxo-4-(1-(2,3,5,6-tetrafluorophenyl)propan-2-ylamino)-1,2-dihydropyridin-3-yl)imidazo[4,5-f]isoindole-5,7(1H,6H)-dione (Compound 27)

(S)-1-(2,3,5,6-Tetrafluorophenyl)propan-2-amine and 2-(4-chloro-2-oxo-1,2-dihydropyridin-3-yl)-6-(1-methylpiperidin-4-yl)imidazo[4,5-f]isoindole-5,7(1H,6H)-dione were submitted to general procedure A. The isolated solid was triturated with water once and MeOH four times to give the title compound as an off-white solid, which was used directly in the next step.

(S)-6-(1-Methylpiperidin-4-yl)-2-(2-oxo-4-(1-(2,3,5,6-tetrafluorophenyl) propan-2-ylamino)-1,2-dihydropyridin-3-yl)-6,7-dihydroimidazo[4,5-f]isoindol-5(3H)-one (Compound 4)

To a solution of (S)-6-(1-methylpiperidin-4-yl)-2-(2-oxo-4-(1-(2,3,5,6-tetrafluorophenyl)propan-2-ylamino)-1,2-dihydropyridin-3-yl)imidazo[4,5-f]isoindole-5,7(1H,6H)-dione (Compound 27) (0.30 g, 0.51 mmol) in 50 mL of acetic acid was added zinc powder (0.64 g, 7.65 mmol). The mixture was heated to reflux for 16 h and filtered through Celite. Acetic acid was removed under vacuum and the residue was taken up with 10 mL of MeOH. Reverse phase chromatography purification yielded the title compound as a white solid (40 mg, 13.7%). $^1$H NMR δ (500 MHz, DMSO-$d_6$) 13.03 (d, J=3.0 Hz, 1H), 11.25 (br s, 1H), 11.11 (dd, J=5, 13 Hz, 1H), 7.96 (s, 0.5H, conformational isomer), 7.81 (s, 0.5H), 7.77 (s, 0.5H), 7.80-7.65 (m, 1H), 7.61 (s, 0.5H), 7.41-7.31 (m, 1H), 6.16 (d, J=12.0 Hz, 1H), 4.48 (s, 2H), 4.29-4.14 (m, 1H), 4.12-3.96 (m, 1H), 3.20-3.02 (m, 2H), 2.90 (d, J=18 Hz, 2H), 2.23 (s, 3H), 2.07 (t, J=18 Hz, 2H), 1.94-1.75 (m, 2H), 1.78-1.64 (m, 2H), 1.42-1.29 (m, 3H). ESI MS: m/z 569.2 (M+1).

Synthesis of Compound 51

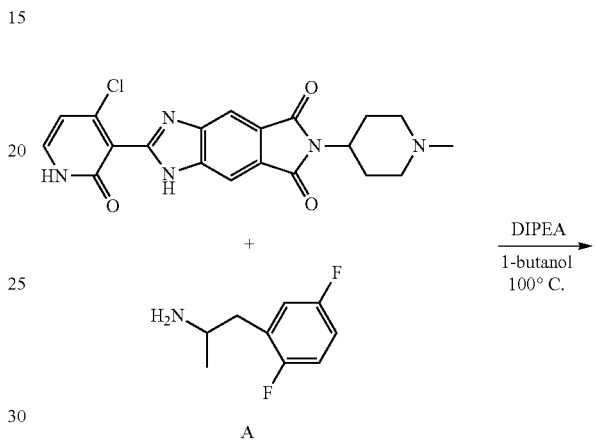

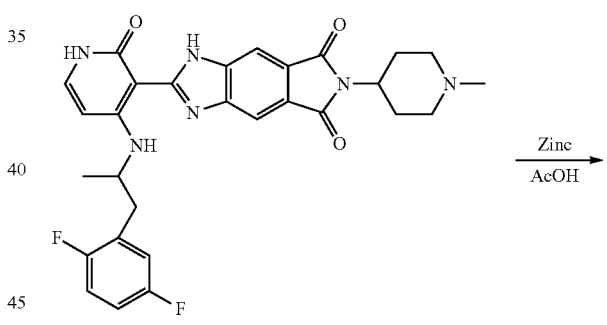

Compound 28

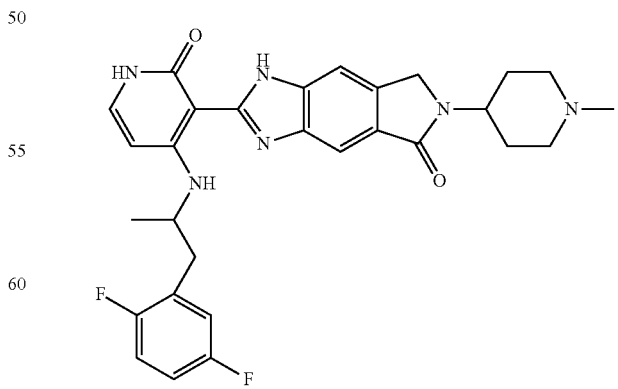

Compound 51

2-(4-(1-(2,5-Difluorophenyl)propan-2-ylamino)-2-oxo-1,2-dihydropyridin-3-yl)-6-(1-methylpiperidin-4-yl)imidazo[4,5-f]isoindole-5,7(1H,6H)-dione (Compound 28)

Racemic 1-(2,5-difluorophenyl)propan-2-amine and 2-(4-chloro-2-oxo-1,2-dihydropyridin-3-yl)-6-(1-methylpiperidin-4-yl)imidazo[4,5-f]isoindole-5,7(1H,6H)-dione were submitted to general procedure A. The isolated solid was triturated with water once and MeOH four times to give the title compound as an off-white solid, which was used directly in the next step.

2-(4-(1-(2,5-Difluorophenyl)propan-2-ylamino)-2-oxo-1,2-dihydropyridin-3-yl)-6-(1-methylpiperidin-4-yl)-6,7-dihydroimidazo[4,5-f]isoindol-5(1H)-one (Compound 51)

To a solution of 2-(4-(1-(2,5-difluorophenyl)propan-2-ylamino)-2-oxo-1,2-dihydropyridin-3-yl)-6-(1-methylpiperidin-4-yl)imidazo[4,5-f]isoindole-5,7(1H,6H)-dione (0.30 g, 0.53 mmol) in 50 mL of acetic acid was added zinc powder (0.64 g, 9.78 mmol). The mixture was heated to reflux for 16 h and filtered through Celite. Acetic acid was removed under vacuum and the residue was taken up with 10 mL of MeOH. Reverse phase chromatography purification yielded the title compound as a white solid (39 mg, 13.8%). $^1$H NMR δ (500 MHz, DMSO-$d_6$) 13.05 (d, J=3.5 Hz, 1H), 11.23 (t, J=6.5 Hz, 1H), 11.10 (d, J=7.5 Hz, 1H), 7.96 (s, 0.5H, conformational isomer), 7.85 (s, 0.5H), 7.81 (s, 0.5H), 7.68 (s, 0.5H), 7.44-7.30 (m, 2H), 7.22-7.14 (m, 1H), 7.11-7.02 (m, 1H), 6.17 (d, J=8.0 Hz, 1H), 4.48 (s, 2H), 4.18-4.08 (m, 1H), 4.08-3.98 (m, 1H), 3.08-3.02 (m, 1H), 3.02-2.94 (m, 1H), 2.91 (d, J=10.5 Hz, 2H), 2.23 (s, 3H), 2.11-2.02 (m, 2H), 1.90-1.78 (m, 2H), 1.74-1.66 (m, 2H), 1.34-1.29 (m, 3H). ESI MS: m/z 533.02 (M+1).

Synthesis of Compounds 12, 13 and 14

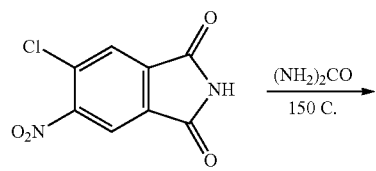

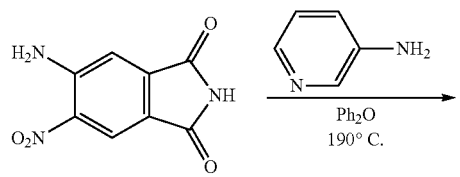

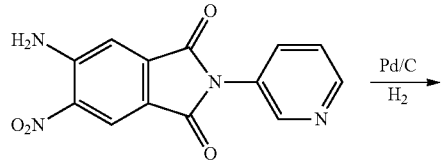

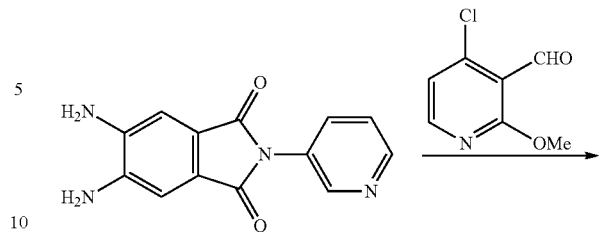

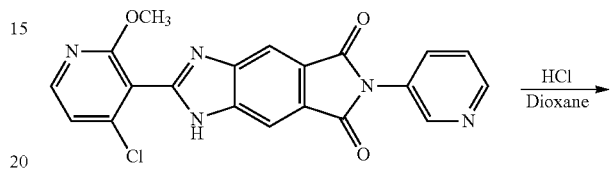

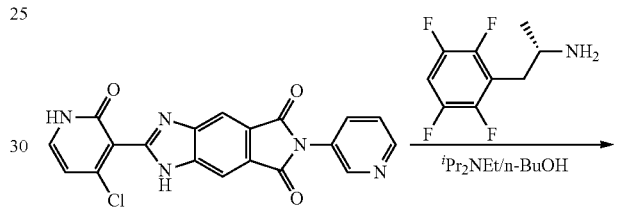

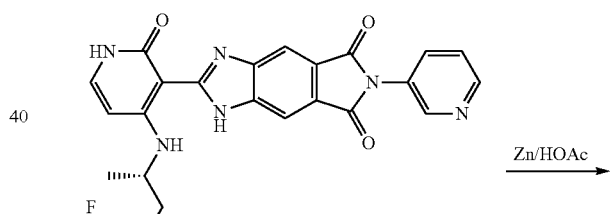

Compound 12

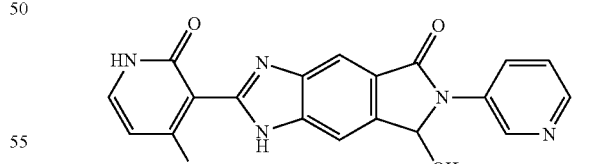

+

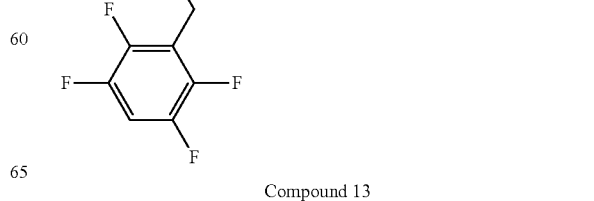

Compound 13

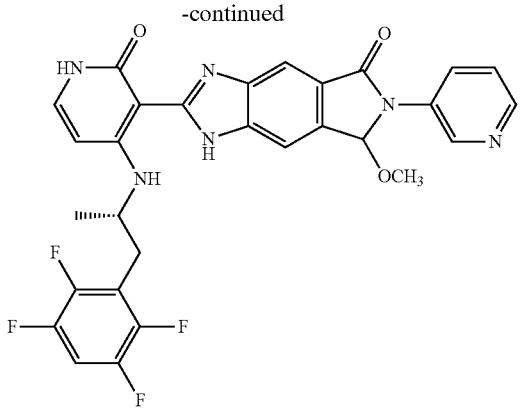

Compound 14

5-Amino-6-nitroisoindoline-1,3-dione

A mixture of 5-chloro-6-nitroisoindoline-1,3-dione (28.0 g, 0.123 mol) and urea (73.8 g, 1.23 mol) was stirred and heated to 150° C. under argon for 6 h. After cooled to rt, the solid was suspended in hot water (100 mL, 80° C.), filtered, washed with hot water (3×50 mL) and dried under vacuum to give a yellow solid product, 23.56 g, 92.5% yield.

5-Amino-6-nitro-2-(pyridine-3-yl)isoindoline-1,3-dione

5-Amino-6-nitroisoindoline-1,3-dione (3.00 g, 14.48 mmol), 3-aminopyridine (5.45 g, 57.92 mmol) and imidazole (3.94 g, 57.92 mmol) were suspended in diphenyl ether (50 mL). The mixture was stirred and heated to 190° C. for 3 days under argon. Then, the solid was filtered, washed with hexanes and purified by column chromatography (silica-gel, $CH_2Cl_2$/Acetone=7/3 v/v) to give a yellow solid product, 2.56 g, 62.2% yield. MS: 282.8 [M–H]⁻. ¹H NMR (DMSO-$d_6$, 500 MHz): δ 8.65 (d, 1H, J=2.0 Hz), 8.62 (dd, 1H, $J_1$=5.0 Hz, $J_2$=1.0 Hz), 8.46 (S, 2H), 8.42 (s, 1H), 7.89 (m, 1H), 7.60-7.58 (m, 1H), 7.55 (s, 1H).

2-(4-Chloro-2-methoxypyridin-3-yl)-6-(pyridine-3-yl)imidazo[4,5-f]isoindole-5,7(1H, 6H)-dione Pd/C (200 mg, 10% on charcoal, 50% wet) was added to a solution of 5-amino-6-nitro-2-(pyridine-3-yl)isoindoline-1,3-dione (0.76 g, 2.67 mmol) in 30 mL of MeOH/HOAc (3/1 v/v) and hydrogenated under $H_2$ (30 psi) for 3 h at rt. Then, the solvent was removed under reduced pressure. The residue was acidified by adding 6 N HCl solution. The aqueous solution was filtered out and its pH was adjusted to 9 by adding $K_2CO_3$. The brown precipitate was filtered, washed with water and dried under vacuum to give diamine product as a brown solid (0.50 g) which was used in the next step reaction without further purification. This brown solid (0.50 g, 1.97 mmol) and 4-chloro-2-methoxynicotinaldehyde (0.34 g, 1.97 mmol) were suspended in MeOH/HOAc (33 mL, 3/1 v/v) at rt under air. The reaction mixture was stirred under air overnight. The solvents were removed. The solid residue was washed with saturated $NaHCO_3$ solution, dried under vacuum and purified by column chromatography (silica-gel, EtOAc) to give a pale-yellow solid, 0.65 g, 81.5% yield. MS: 428.1 [M+Na]⁺. ¹H NMR (DMSO-$d_6$, 500 MHz): δ 13.71 (s, 1H), 8.74 (s, 1H), 8.64 (d, 1H, J=4.5 Hz), 8.38 (d, 1H, J=5.5 Hz), 8.22 (S, 2H), 7.97 (d, 1H, J=8.0 Hz), 7.63-7.58 (m, 1H), 7.41 (d, 1H, J=5.5 Hz), 3.91 (s, 3H).

(S)-2-(2-oxo-4-((1-(2,3,5,6-tetrafluorophenyl)propan-2-yl)amino)-1,2-dihydropyridin-3-yl)-6-(pyridin-3-yl)imidazo[4,5-f]isoindole-5,7(1H,6H)-dione (Compound 12)

2-(4-Chloro-2-methoxypyridin-3-yl)-6-(pyridine-3-yl)imidazo[4,5-f]isoindole-5,7(1H, 6H)-dione (0.60 g, 1.48 mmol) was dissolved in 10 mL of 1,4-dioxane and 5 mL of concentrated HCl at rt. The reaction mixture was stirred at rt overnight. Then, the volatile was removed to give a yellow-brown solid. This solid was mixed with (S)-1-(2,3,5,6-tetrafluorophenyl)propan-2-amine (0.46 g, 2.22 mmol), N,N-diisopropylethylamine (1.32 mL, 7.40 mmol) and n-butanol (30 mL) in a flask. The reaction mixture was stirred and heated to reflux overnight under argon. Then, volatiles were removed under reduced pressure. The residue solid was purified by column chromatography (silica-gel, $CH_2Cl_2$/MeOH=9/1 v/v) to give a yellow-brown solid product, 0.65 g, 78.3% yield. MS: 560.8 [M–H]⁻. ¹H NMR (DMSO-$d_6$, 500 MHz): δ 13.48 (s, 1H), 11.35 (d, 1H, J=4.5 Hz), 10.91 (d, 1H, J=8.0 Hz), 8.73-8.72 (m, 1H), 8.63-8.61 (m, 1H), 8.25 (s, 1H), 8.03 (s, 1H), 7.95 (dd, 1H, $J_1$=8.0 Hz, $J_2$=2.0 Hz), 7.77-7.70 (m, 1H), 7.62-7.58 (m, 1H), 7.41 (t, 1H, J=4.5 Hz), 6.18 (d, 1H, J=7.5 Hz), 4.25 (m, 1H), 3.18-3.10 (m, 2H), 1.93 (d, 3H, J=6.0 Hz).

7-Hydroxy-2-(2-oxo-4-(((S)-1-(2,3,5,6-tetrafluorophenyl)propan-2-yl)amino)-1,2-dihydropyridin-3-yl)-6-(pyridin-3-yl)-6,7-dihydroimidazo[4,5-f]isoindol-5(1H)-one (Compound 13)

Compound (S)-2-(2-oxo-4-((1-(2,3,5,6-tetrafluorophenyl)propan-2-yl)amino)-1,2-dihydropyridin-3-yl)-6-(pyridin-3-yl)imidazo[4,5-f]isoindole-5,7(1H,6H)-dione (0.46 g, 0.82 mmol) and zinc powder (1.23 g, 18.8 mmol) were suspended in acetic acid (30 mL). The reaction mixture was stirred and heated to reflux overnight under argon. Then, the solvent was removed under reduced pressure. The residue solid was stirred in 50 mL of saturated $K_2CO_3$ solution. The white solid was filtered out, dried under vacuum and extracted with $CH_2Cl_2$/MeOH (7/3 v/v) three times (150 mL). The extracts were concentrated to dryness. The residue was purified by column chromatography (silica-gel, $CH_2Cl_2$/MeOH=9/1 v/v) to give a white solid product, 0.15 g, 32.6% yield. MS: 563.0 [M–H]⁻. ¹H NMR (DMSO-$d_6$, 500 MHz): δ 13.21-13.19 (m, 1H), 11.30-11.29 (m, 1H), 11.13-11.09 (m, 1H), 9.08 (s, 1H), 8.41 (d, 1H, J=3.5 Hz), 8.26 (d, 1H, J=7.0 Hz), 8.11 (s, 0.5H), 7.98 (s, 0.5H), 7.90 (s, 0.5 Hz), 7.78-7.73 (m, 1.5H), 7.52-7.50 (m, 1H), 7.41-7.38 (m, 1H), 6.93-6.90 (m, 1H), 6.67-6.64 (m, 1H), 6.20-6.17 (m, 1H), 4.26-4.25 (m, 1H), 3.19-3.14 (m, 2H), 1.41 (d, 3H, J=5.0 Hz).

7-Methoxy-2-(2-oxo-4-(((S)-1-(2,3,5,6-tetrafluorophenyl)propan-2-yl)amino)-1,2-dihydropyridin-3-yl)-6-(pyridin-3-yl)-6,7-dihydroimidazo[4,5-f]isoindol-5(1H)-one (Compound 14)

Compound was isolated in the above reaction as a white solid product, 0.20 g, 42.6% yield. MS: 576.8 [M–H]⁻. ¹H NMR (DMSO-$d_6$, 500 MHz): δ 13.25-13.22 (m, 1H), 11.31-11.28 (m, 1H), 11.08-11.03 (m, 1H), 9.06 (d, 1H, J=2.0 Hz), 8.43 (d, 1H, J=4.0 Hz), 8.24-8.23 (m, 1H), 8.15 (d, 0.5H, J=2.0 Hz), 7.96 (s, 0.5H), 7.94 (s, 0.5 Hz), 7.77-7.72 (m, 1.5H), 7.53-7.51 (m, 1H), 7.40-7.37 (m, 1H), 6.90-6.87 (m, 1H), 6.17 (d, 1H, J=7.5 Hz), 4.25 (m, 1H), 3.18-3.09 (m, 2H), 2.88-2.84 (m, 3H), 1.38 (d, 3H, J=6.0 Hz).

Synthesis of Compound 15

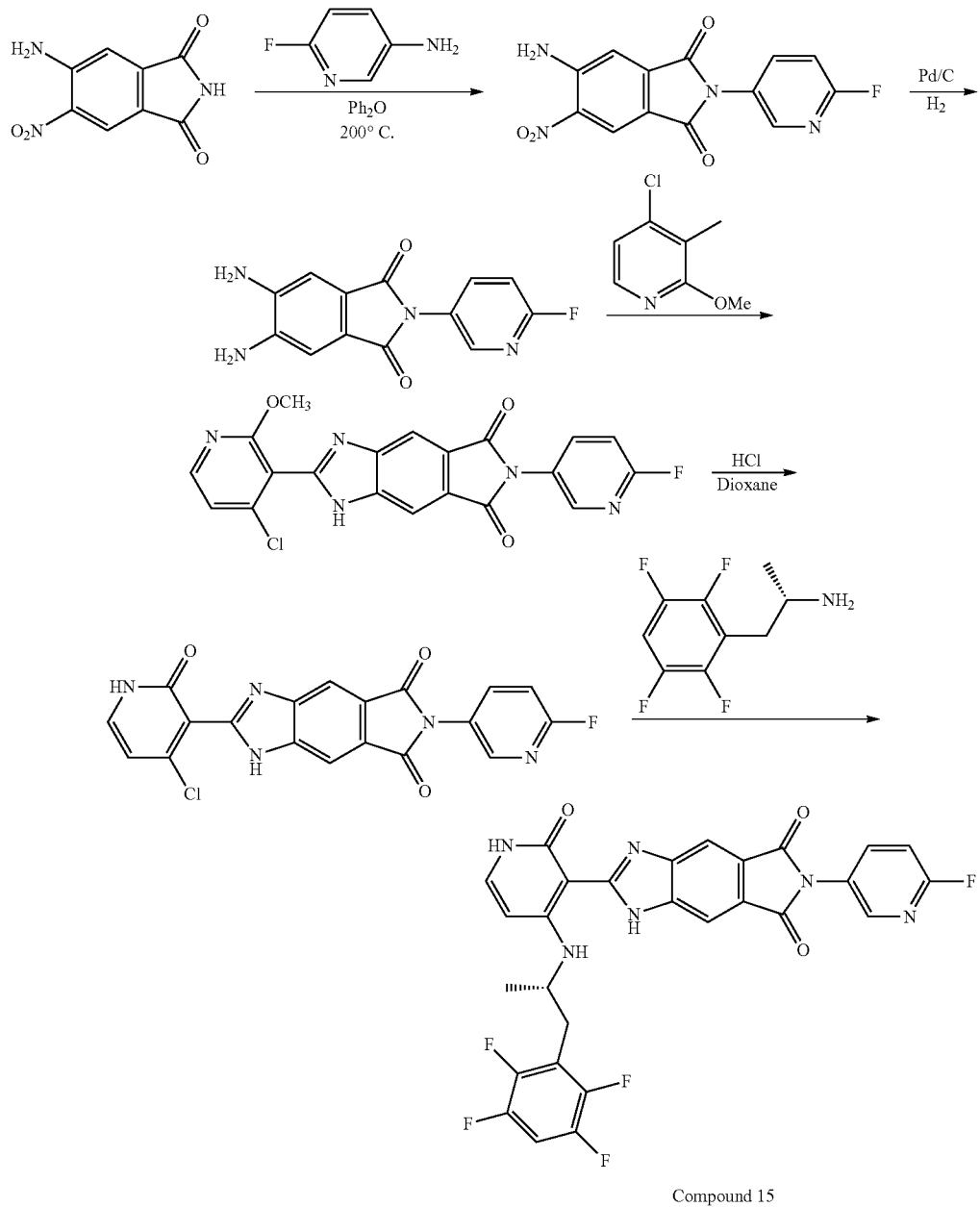

Compound 15

5-Amino-2-(6-fluoropyridin-3-yl)-6-nitroisoindoline-1,3-dione

5-Amino-6-nitroisoindoline-1,3-dione (2.00 g, 9.66 mmol), 6-fluoropyridin-3-amine (3.25 g, 28.98 mmol) and imidazole (1.32 g, 19.32 mmol) were suspended in diphenyl ether (50 mL). The mixture was stirred and heated to 200° C. for 24 h under argon. Then, the solid was filtered, washed with hexanes and purified by column chromatography (silica-gel, $CH_2Cl_2$/Acetone=7/3 v/v) to give a yellow solid product, 0.37 g, 12.7% yield. MS: 300.8 [M−H]−. $^1$H NMR (DMSO-$d_6$, 500 MHz): δ 8.47 (s, 2H), 8.45 (s, 1H), 8.13-8.06 (m, 1H), 8.34 (d, 1H, J=2.1 Hz), 7.56 (s, 1H), 7.41 (dd, 1H, $J_1$=8.7 Hz, $J_2$=3.0 Hz).

2-(4-Chloro-2-methoxypyridin-3-yl)-6-(6-fluoropyridine-3-yl)imidazo[4,5-f]isoindole-5,7(1H, 6H)-dione Pd/C (100 mg, 10% on charcoal, 50% wet) was added to a solution of 5-amino-2-(6-fluoropyridine-3-yl)-6-nitroisoindoline-1,3-dione (0.30 g, 0.99 mmol) in 40 mL of MeOH/HOAc (3/1 v/v) and hydrogenated under $H_2$ (30 psi) for 3 h at rt. Then, the solvent was removed under reduced pressure.

The residue was acidified by adding 6 N HCl solution. The aqueous solution was filtered out and its pH was adjusted to 9 by adding $K_2CO_3$. The brown precipitate was filtered, washed with water and dried under vacuum to give the diamine product as a brown solid (0.27 g) which was used in next step reaction without further purification. This brown solid (0.27 g, 0.99 mmol) and 4-chloro-2-methoxynicotinaldehyde (0.17 g, 0.99 mmol) were suspended in MeOH/HOAc (40 mL, 3/1 v/v) at rt under air. The reaction mixture was stirred under air overnight. The solvents were removed. The solid residue was washed with saturated $NaHCO_3$ solution, dried under vacuum and purified by column chromatography (silica-gel, EtOAc) to give a pale-yellow solid, 0.15 g, 35.7% yield. MS: 424.1 $[M+H]^+$. $^1H$ NMR (DMSO-$d_6$, 500 MHz): δ 13.72 (s, 1H), 8.43-8.39 (m, 2H), 8.31-8.16 (m, 3H), 7.45-7.42 (m, 2H), 3.92 (s, 3H).

(S)-6-(6-Fluoropyridin-3-yl)-2-(2-oxo-4-((1-(2,3,5,6-tetrafluorophenyl)propan-2-yl)amino)-1,2-dihydropyridin-3-yl)imidazo[4,5-f]isoindole-5,7(1H,6H)-dione (Compound 15)

2-(4-Chloro-2-methoxypyridin-3-yl)-6-(6-fluoropyridine-3-yl)imidazo[4,5-f]isoindole-5,7(1H, 6H)-dione (0.15 g, 0.35 mmol) was dissolved in 10 mL of 1,4-dioxane and 5 mL of concentrated HCl at rt. The reaction mixture was stirred at rt overnight. Then, the volatile was removed to give a yellow-brown solid. This solid was mixed with (S)-1-(2,3,5,6-tetrafluorophenyl)propan-2-amine (55 mg, 0.26 mmol), N,N-diisopropylethylamine (1 mL) and n-butanol (20 mL) in a flask. The reaction mixture was stirred and heated to reflux overnight under argon. Then, volatiles were removed under reduced pressure. The residue solid was purified by column chromatography (silica-gel, $CH_2Cl_2$/MeOH=9/1 v/v) to give a yellow-brown solid product, 80 mg, 63.0% yield. MS: 578.8 $[M-H]^-$. $^1H$ NMR (DMSO-$d_6$, 500 MHz): δ 13.48 (s, 1H), 11.35 (d, 1H, J=6.0 Hz), 10.91 (d, 1H, J=8.5 Hz), 8.40 (d, 1H, J=2.0 Hz), 8.26 (s, 1H), 8.18-8.14 (m, 1H), 8.04 (s, 1H), 7.77-7.70 (m, 1H), 7.42-7.39 (m, 2H), 6.19 (d, 1H, J=7.5 Hz), 4.27-4.24 (m, 1H), 3.18-3.10 (m, 2H), 1.39 (d, 3H, J=6.0 Hz).

Synthesis of Compounds 17 and 18

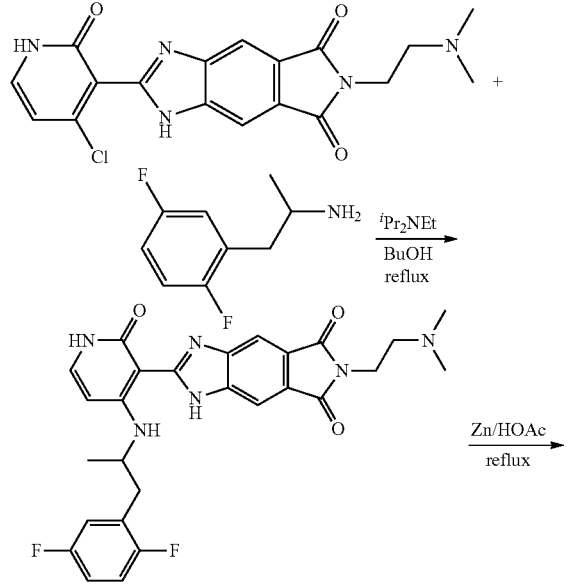

Compound 17

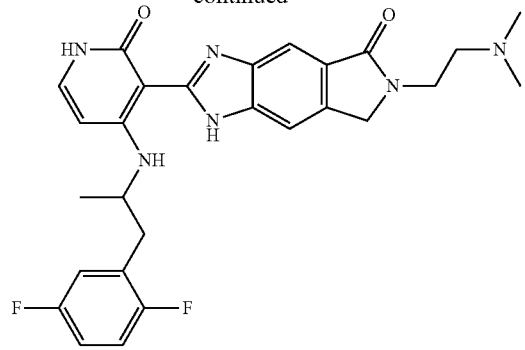

Compound 18

2-(4-(1-(2,5-Difluorophenyl)propan-2-ylamino)-2-oxo-1,2-dihydropyridin-3-yl)-6-(2-(dimethylamino)ethyl)imidazo[4,5-f]isoindole-5,7(1H,6H)-dione (Compound 17)

2-(4-Chloro-2-oxo-1,2-dihydropyridin-3-yl)-6-(2-(dimethylamino)ethyl)imidazo[4,5-f]isoindole-5,7(1H,6H)-dione (1.00 g, 2.59 mmol), 1-(2,5-difluorophenyl)propan-2-amine (0.44 g, 2.59 mmol), n-butanol (50 mL) and N,N-diisopropylethylamine (10 mL) were mixed together in a flask. The reaction mixture was stirred and heated to reflux overnight under argon. Solvents were removed under reduced pressure. The residue solid was purified by column chromatography (silica-gel, $CH_2Cl_2$/MeOH=9/1 v/v) to give a brown solid product, 1.15 g, 85.2% yield. MS: 521.2 $[M+H]^+$. $^1H$ NMR (DMSO-$d_6$, 300 MHz): δ 13.43 (s, 1H), 11.31 (d, 1H, J=6.0 Hz), 10.98 (d, 1H, J=7.5 Hz), 8.16 (s, 1H), 8.01 (s, 1H), 7.42-7.35 (m, 2H), 7.20-7.13 (m, 1H), 7.10-7.02 (m, 1H), 6.18 (d, 1H, J=7.2 Hz), 4.16 (m, 1H), 3.95 (t, 2H, J=6.0 Hz), 3.33 (m, 2H), 3.10-2.96 (m, 2H), 2.81 (s, 6H), 1.33 (d, 3H, J=6.3 Hz).

2-(4-(1-(2,5-Difluorophenyl)propan-2-ylamino)-2-oxo-1,2-dihydropyridin-3-yl)-6-(2-(dimethylamino)ethyl)-6,7-dihydroimidazo[4,5-f]isoindole-5(1H)-one (Compound 18)

Compound 2-(4-(1-(2,5-difluorophenyl)propan-2-ylamino)-2-oxo-1,2-dihydropyridin-3-yl)-6-(2-(dimethylamino)ethyl)imidazo[4,5-f]isoindole-5,7(1H,6H)-dione (1.00 g, 1.92 mmol) and zinc powder (3.12 g, 24.85 mmol) were suspended in acetic acid (50 mL). The reaction mixture was stirred and heated to reflux overnight under argon. Then, the solvent was removed under reduced pressure. The residue solid was stirred in 100 mL of saturated $K_2CO_3$ solution. The white solid was filtered out, dried under vacuum and extracted with $CH_2Cl_2$/MeOH (7/3 v/v) three times (300 mL). The extracts were concentrated to dryness. The residue was purified by column chromatography (silica-gel, $CH_2Cl_2$/MeOH=9/1 v/v) to give a white solid product, 0.75 g, 77.3% yield. MS: 505.0 $[M-H]^-$. $^1H$ NMR (DMSO-$d_6$, 300 MHz): δ 13.06 (s, 1H), 11.21 (s, 1H), 11.12-11.08 (m, 1H), 7.96 (s, 0.5H), 7.84 (s, 0.5H), 7.80 (s, 0.5H), 7.68 (s, 0.5H), 7.40-7.33 (m, 2H), 7.23-7.13 (m, 1H), 7.11-7.01 (m, 1H), 6.17 (d, 1H, J=7.5 Hz), 4.54 (s, 2H), 4.18-4.10 (m, 1H), 3.64 (t, 2H, J=6.0 Hz), 3.10-2.91 (m, 2H), 2.52-2.48 (m, 2H), 2.18 (s, 6H), 1.34-1.31 (m, 3H).

Synthesis of Compounds 24 and 24A

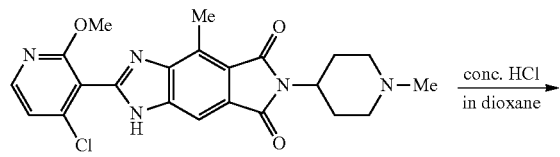

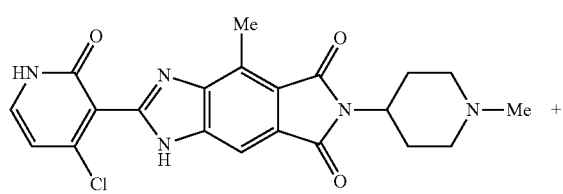

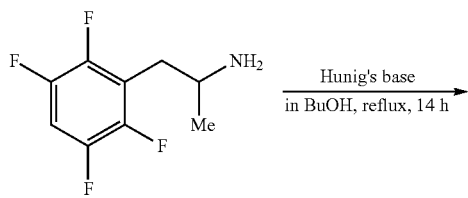

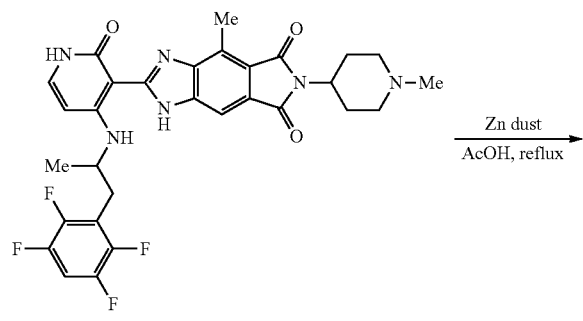

Compound 29

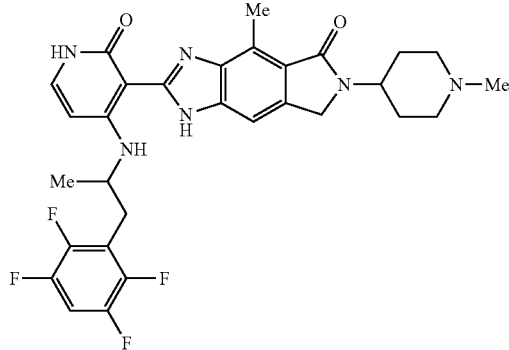 [SMILES: Cc1c2c(cc3[nH]c(-c4c(NC(C)Cc5c(F)c(F)cc(F)c5F)cc[nH]c4=O)nc13)CN(C1CCN(C)CC1)C2=O]

Compound 24

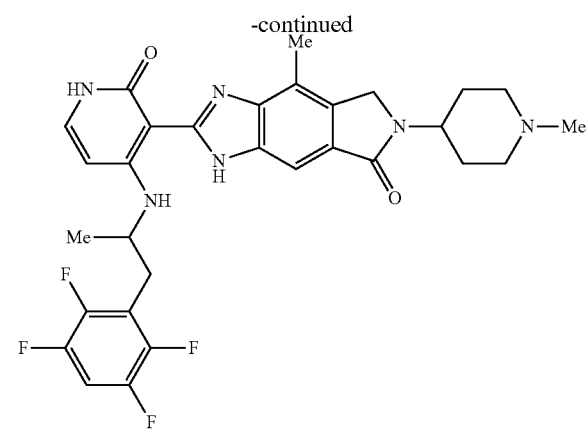

Compound 24A 2-(4-Chloro-2-oxo-1,2-dihydropyridin-3-yl)-4-methyl-6-(1-methylpiperidin-4-yl)imidazo[4,5-f]isoindole-5,7(1H,6H)-dione A solution of 2-(4-chloro-2-methoxypyridin-3-yl)-4-methyl-6-(1-methylpiperidin-4-yl)imidazo[4,5-f]isoindole-5,7 (1H,6H)-dione in a mixture of 1,4-dioxane and concentrated HCl was heated at 45-50° C. for 14 h. After the end of reaction was established by TLC, the reaction mixture was concentrated under vacuum to afford a crude product as a yellow solid, which was used for the next step without further purification. $^1$H NMR (500 MHz, DMSO-$d_6$) δ 12.60 (s, 1H, NH), 9.90 (s, 1H, NH), 7.90 (s, 1H, ArH), 7.70 (d, J=7.0 Hz, 1H, ArH), 6.58 (d, J=7.5 Hz, 1H, ArH), 4.34-4.29 (m, 1H, CH), 3.53-3.50 (m, 2H, CH$_2$), 3.20-3.13 (m, 2H, CH$_2$), 2.87 (s, 3H, CH$_3$), 2.76 (d, J=4.5 Hz, 3H, CH$_3$), 2.66-2.59 (m, 2H, CH$_2$), 1.96-1.93 (m, 2H, CH$_2$); Mass (ESI, positive) m/z 426.1 [M+H]$^+$.

4-Methyl-6-(1-methylpiperidin-4-yl)-2-(2-oxo-4-(1-(2,3,5,6-tetrafluorophenyl)propan-2-ylamino)-1,2-dihydropyridin-3-yl)imidazo[4,5-f]isoindole-5,7(1H, 6H)-dione (Compound 29)

A mixture of 2-(4-chloro-2-oxo-1,2-dihydropyridin-3-yl)-4-methyl-6-(1-methylpiperidin-4-yl)imidazo[4,5-f]isoindole-5,7(1H,6H)-dione (1.00 g, 2.35 mmol), 1-(2,3,5,6-tetrafluorophenyl)propan-2-amine (0.54 g, 2.58 mmol), Hunig,s base (1.52 g, 0.011 mol), and 20 mL of anhydrous 1-butanol was heated at reflux for 14-15 h under an argon atmosphere. Product was purified by a silica gel column using methylene chloride and methanol (9:1 v/v) as eluent to afford 1.10 g of the designed compound as yellowish solid. $^1$H NMR (500 MHz, DMSO-$d_6$) δ 13.35 (s, 1H, NH), 11.35 (d, J=6.0 Hz, 1H, NH), 11.02 (d, J=8.5 Hz, 1H, NH), 7.93 (s, 1H, ArH), 7.81-7.77 (m, 1H, ArH), 7.42 (t, J=7.0 Hz, 1H, ArH), 6.22 (d, J=8.0 Hz, 1H, ArH), 4.34-4.29 (m, 1H, CH), 4.12 (m, 1H, CH), 3.17 (m, 2H, CH$_2$), 3.08 (d, J=5.5 Hz, 2H, CH$_2$), 2.72 (s, 3H, CH$_3$), 2.48 (s, 3H, CH$_3$), 1.77-1.76 (m, 2H, CH$_2$), 1.37 (d, J=6.5 Hz, 3H, CH$_3$), 1.29-1.24 (m, 6H, 2×CH$_2$); Mass (ESI, positive) m/z 597.2 [M+H]$^+$.

4-Methyl-6-(1-methylpiperidin-4-yl)-2-(2-oxo-4-(1-(2,3,5,6-tetrafluorophenyl)propan-2-ylamino)-1,2-dihydropyridin-3-yl)-6,7-dihydroimidazo[4,5-f]isoindol-5(1H)-one (compound 24)

A mixture of 4-methyl-6-(1-methylpiperidin-4-yl)-2-(2-oxo-4-(1-(2,3,5,6-tetrafluorophenyl)propan-2-ylamino)-1,2- dihydropyridin-3-yl)imidazo[4,5-f]isoindole-5,7(1H,6H)-dione (0.93 g, 1.65 mmol), zinc dust (1.02 g, 15.6 mmol), and 30 mL of acetic acid was heated at reflux for 14 h under an argon atmosphere. Product was separated by a silica gel column using methylene chloride and methanol (85:15 v/v) as eluent to afford 0.33 g (36.3%) of the designed compound as yellowish solid. $^1$H NMR (500 MHz, DMSO-$d_6$) δ 12.95 (s, 1H, NH), 11.32 (d, J=8.5 Hz, 1H, NH), 11.25 (d, J=4.1 Hz, 1H, NH), 7.80 (s, 1H, ArH), 7.77-7.75 (m, 1H, ArH), 7.63 (t, J=7.0 Hz, 1H, ArH), 6.19 (d, J=7.5 Hz, 1H, ArH), 4.41 (d, J=3.5 Hz, 2H, CH$_2$), 4.29-4.21 (m, 1H, CH), 4.06-4.01 (m, 1H, CH), 3.07-3.06 (m, 2H, CH$_2$), 2.92-2.90 (m, 2H, CH$_2$), 2.43 (s, 3H, CH$_3$), 2.24 (s, 3H, CH$_3$), 2.09 (m, 2H, CH$_2$), 1.91-1.83 (m, 2H, CH$_2$), 1.72-1.69 (m, 2H, CH$_2$), 1.36 (d, J=6.5 Hz, 3H, CH$_3$); Mass (ESI, positive) m/z 583.2 [M+H]$^+$.

8-Methyl-6-(1-methylpiperidin-4-yl)-2-(2-oxo-4-(1-(2,3,5,6-tetrafluorophenyl)propan-2-ylamino)-1,2-dihydropyridin-3-yl)-6,7-dihydroimidazo[4,5-f]isoindol-5(3H)-one (compound 24A)

A mixture of 4-methyl-6-(1-methylpiperidin-4-yl)-2-(2-oxo-4-(1-(2,3,5,6-tetrafluorophenyl)propan-2-ylamino)-1,2-dihydropyridin-3-yl)imidazo[4,5-f]isoindole-5,7(1H,6H)-dione (0.93 g, 1.65 mmol), zinc dust (1.02 g, 15.6 mmol), and 30 mL of acetic acid was heated at reflux for 14 h under an argon atmosphere. Product was separated by a silica gel column using methylene chloride and methanol (85:15 v/v) as eluent to afford 0.10 g (11.0%) of the designed compound as yellowish solid. $^1$H NMR (500 MHz, DMSO-$d_6$) δ 12.93 (s, 1H, NH), 11.28 (d, J=8.5 Hz, 1H, NH), 11.23 (d, J=4.1 Hz, 1H, NH), 7.75 (m, 1H, ArH), 7.60 (s, 1H, ArH), 7.36 (m, 1H, ArH), 6.19 (d, J=8.0 Hz, 1H, ArH), 4.40 (s, 2H, CH2), 4.28 (m, 1H, CH), 3.99 (m, 1H, CH), 3.07 (m, 2H, CH$_2$), 2.88-2.84 (m, 2H, CH$_2$), 2.74 (s, 3H, CH$_3$), 2.20 (s, 3H, CH$_3$), 2.02-1.98 (m, 2H, CH$_2$), 1.82-1.80 (m, 2H, CH$_2$), 1.67 (m, 2H, CH$_2$), 1.36 (d, J=6.0 Hz, 3H, CH$_3$); Mass (ESI, positive) m/z 583.2 [M+H]$^+$.

Synthesis of Compounds 25 and 25A

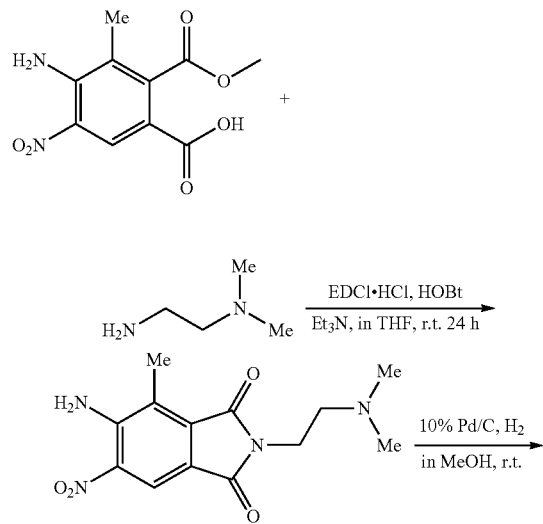

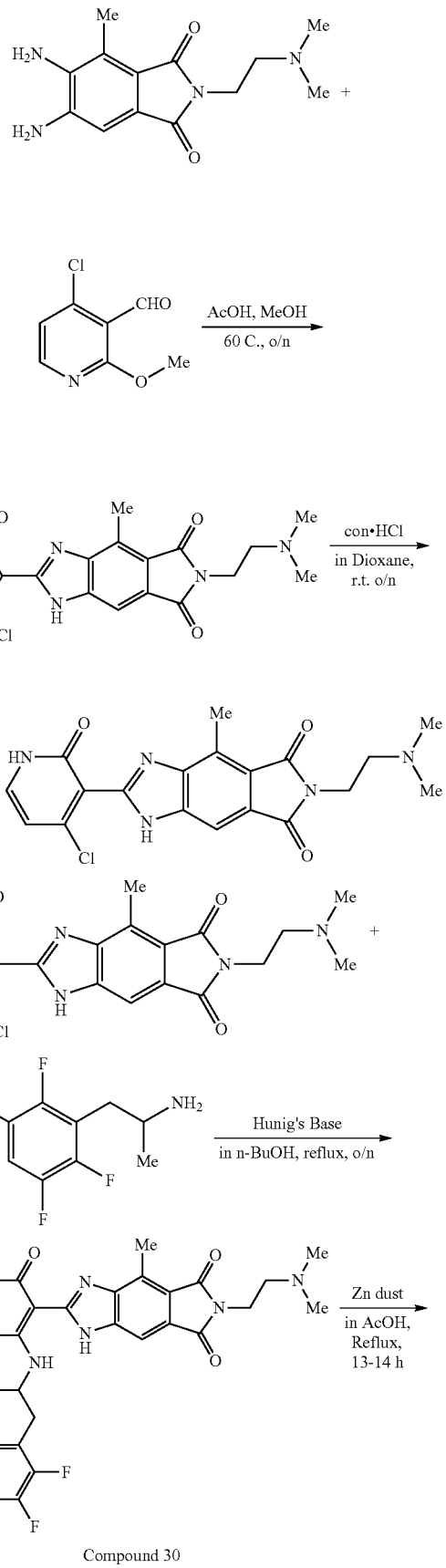

Compound 30

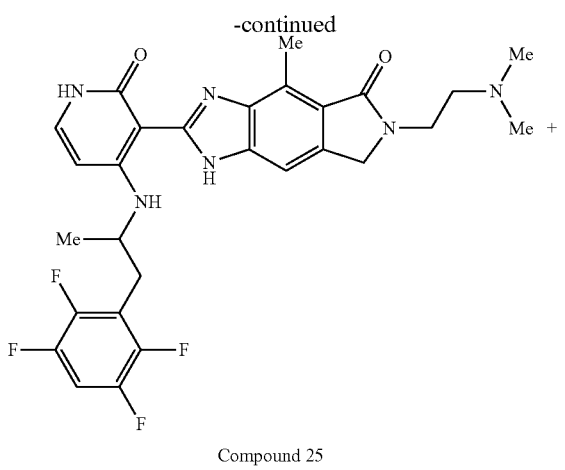

Compound 25

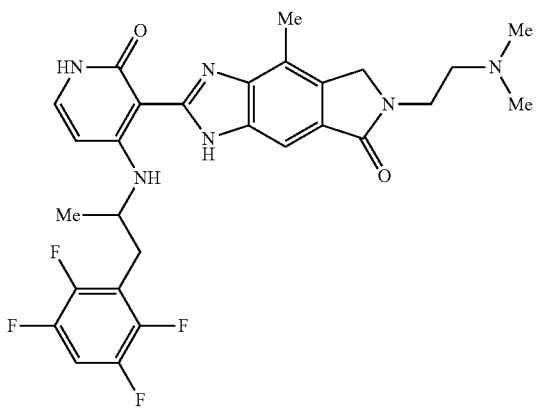 [SMILES: Cc1c2c(cc3[nH]c(-c4c(NC(C)Cc5c(F)c(F)cc(F)c5F)cc[nH]c4=O)nc13)C(=O)N(CCN(C)C)C2=O]

Compound 25A

5-Amino-2-(2-(dimethylamino)ethyl)-4-methyl-6-nitroisoindoline-1,3-dione

To a solution of 4-amino-2-(methoxycarbonyl)-3-methyl-5-nitrobenzoic acid (0.43 g, 1.69 mmol), EDCI hydrochloride (0.36 g, 1.86 mmol), and HOBt (0.23 g, 1.69 mmol) in 22 mL of anhydrous THF was added 1.18 mL of triethylamine and stirred for 10 min at rt under an argon atmosphere. $N^1,N^1$-dimethylethane-1,2-diamine (0.16 g, 1.86 mmol) was added into above mixture and the reaction mixture was heated at reflux for 14 h under an argon atmosphere. Product was purified by a silica gel column using methylene chloride and methanol (9:1 v/v) as eluent to afford 0.44 g (90%) of the designed compound as yellow solid. $^1$H NMR (500 MHz, DMSO-$d_6$) δ 8.21 (s, ArH), 8.12 (br s, 2H, NH$_2$), 3.64 (t, J=6.5 Hz, 2H, CH$_2$), 2.57 (s, 3H, CH$_3$), 2.45 (t, J=6.5 Hz, 2H, CH$_2$), 2.15 (S, 6H, 2×CH$_3$); Mass (ESI, positive) m/z 293.0 [M+H]$^+$.

5,6-Diamino-2-(2-(dimethylamino)ethyl)-4-methyl-isoindoline-1,3-dione

To a solution of 5-amino-2-(2-(dimethylamino)ethyl)-4-methyl-6-nitroisoindoline-1,3-dione (0.40 g, 1.37 mmol) in the mixture of methanol (8 mL) and acetic acid (0.4 mL) was added Pd/C (20 mg), and the resulting reaction mixture was hydrogenated for 2-3 h at 20-25 psi of hydrogen at rt. The reaction mixture was filtered through a pad of Celite and washed with methanol. The combined solvents were concentrated under vacuum to dryness. The crude product was used for the next step reaction without further purification. Mass (ESI, positive) m/z 263.0 [M+H]$^+$.

2-(4-Chloro-2-methoxypyridin-3-yl)-6-(2-(dimethylamino)ethyl)-4-methylimidazo[4,5-f]isoindole-5,7(1H,6H)-dione A mixture of 5,6-diamino-2-(2-(dimethylamino)ethyl)-4-methylisoindoline-1,3-dione (0.36 g, 1.37 mmol) and 4-chloro-2-methoxynicotinaldehyde (0.26 g, 1.51 mmol) in a mixture of methanol (8 mL) and acetic acid (0.4 mL) was heated at 50° C. for 14 h. After the end of reaction was established by TLC, the reaction mixture was concentrated under vacuum to dryness, and the crude product was subjected to the next step without further purification. Mass (ESI, positive) m/z 414.1 [M+H]$^+$.

2-(4-Chloro-2-oxo-1,2-dihydropyridin-3-yl)-6-(2-(dimethylamino)ethyl)-4-methylimidazo[4,5-f]isoindole-5,7(1H,6H)-dione A solution of 2-(4-chloro-2-methoxypyridin-3-yl)-6-(2-(dimethylamino)ethyl)-4-methylimidazo[4,5-f]isoindole-5,7(1H,6H)-dione in a mixture of 1,4-dioxane (14 mL) and concentrated HCl (2.5 mL) was heated at 45-50° C. for 14 h. After the end of reaction was established by TLC, the reaction mixture was concentrated under vacuum to afford a crude product as a yellow solid, which was used for the next step without further purification. Mass (ESI, positive) m/z 400.1 [M+H]$^+$.

6-(2-(Dimethylamino)ethyl)-4-methyl-2-(2-oxo-4-(1-(2,3,5,6-tetrafluorophenyl)propan-2-ylamino)-1,2-dihydropyridin-3-yl)imidazo[4,5-f]isoindole-5,7(1H,6H)-dione (Compound 30)

A mixture of 2-(4-chloro-2-oxo-1,2-dihydropyridin-3-yl)-6-(2-(dimethylamino)ethyl)-4-methylimidazo[4,5-f]isoindole-5,7(1H,6H)-dione (0.54 g, 1.35 mmol), 1-(2,3,5,6-tetrafluorophenyl)propan-2-amine (0.34 g, 1.62 mmol), Hunig,s base (0.87 g, 6.75 mmol), and 12 mL of anhydrous 1-butanol was heated at reflux for 13-14 h under an argon atmosphere. Product was purified by a silica gel column using methylene chloride and methanol (9:1 v/v) as eluent to afford 0.33 g of the designed compound as yellow solid. $^1$H NMR (300 MHz, DMSO-$d_6$) δ 13.33 (s, 1H, NH), 11.29 (br s, 1H, NH), 11.00 (d, J=5.7 Hz, 1H, NH), 7.97 (s, ArH), 7.73-7.70 (m, 1H, ArH), 7.40 (d, J=7.6 Hz, 1H, ArH), 6.21 (d, J=7.6 Hz, 1H, ArH), 4.32-4.28 (m, 1H, CH), 3.65 (t, J=6.3 Hz, 2H, CH$_2$), 3.08 (d, J=5.1 Hz, 2H, CH$_2$), 2.72 (s, 3H, CH$_3$), 2.19 (S, 6H, 2×CH$_3$); 1.36 (d, J=6.3 Hz, 3H, CH$_3$), 1.11 (t, J=6.3 Hz, 2H, CH$_2$); Mass (ESI, negative) m/z 568.8 [M−H]$^−$.

6-(2-(Dimethylamino)ethyl)-4-methyl-2-(2-oxo-4-(1-(2,3,5,6-tetrafluorophenyl)propan-2-ylamino)-1,2-dihydropyridin-3-yl)-6,7-dihydroimidazo[4,5-f]isoindol-5(1H)-one (compound 25)

A mixture of 6-(2-(dimethylamino)ethyl)-4-methyl-2-(2-oxo-4-(1-(2,3,5,6-tetrafluorophenyl)propan-2-ylamino)-1,2-dihydropyridin-3-yl)imidazo[4,5-f]isoindole-5,7(1H,6H)- dione (0.25 g, 0.44 mmol), zinc dust (0.29 g, 4.38 mmol), and 7.5 mL of acetic acid was heated at reflux for 13-14 h under an argon atmosphere. Product was separated by a silica gel column using methylene chloride and methanol (85:15 v/v) as eluent to afford 0.20 g of the designed compound as yellowish solid. $^1$H NMR (500 MHz, DMSO-d$_6$) δ 12.96 (s, 1H, NH), 11.32 (d, J=8.5 Hz, 1H, NH), 11.27 (s, 1H, NH), 7.80 (s, 1H, ArH), 7.77-7.72 (m, 1H, ArH), 7.37 (d, J=8.0 Hz, 1H, ArH), 6.19 (d, J=7.5 Hz, 1H, ArH), 4.46 (d, J=4.0 Hz, 2H, CH$_2$), 4.30-4.24 (m, 1H, CH), 3.67-3.62 (m, 2H, CH$_2$), 3.08 (m, 2H, CH$_2$), 2.52 (m, 2H, CH$_2$), 2.41 (s, 3H, CH$_3$), 2.19 (s, 6H, 2×CH$_3$), 1.36 (d, J=6.0 Hz, 3H, CH$_3$); Mass (ESI, positive) m/z 557.2 [M+H]$^+$.

6-(2-(Dimethylamino)ethyl)-8-methyl-2-(2-oxo-4-(1-(2,3,5,6-tetrafluorophenyl)propan-2-ylamino)-1,2-dihydropyridin-3-yl)-6,7-dihydroimidazo[4,5-f]isoindol-5(3H)-one (compound 25A)

A mixture of 6-(2-(dimethylamino)ethyl)-4-methyl-2-(2-oxo-4-(1-(2,3,5,6-tetrafluorophenyl)propan-2-ylamino)-1,2-dihydropyridin-3-yl)imidazo[4,5-f]isoindole-5,7(1H,6H)-dione (0.25 g, 0.44 mmol), zinc dust (0.29 g, 4.38 mmol), and 7.5 mL of acetic acid was heated at reflux for 13-14 h under an argon atmosphere. Product was separated by a silica gel column using methylene chloride and methanol (85:15 v/v) as eluent to afford 30 mg of the designed compound as yellowish solid. $^1$H NMR (500 MHz, DMSO-d$_6$) δ 12.93 (s, 1H, NH), 11.28 (d, J=8.5 Hz, 1H, NH), 11.27 (s, 1H, NH), 7.78-7.74 (m, 1H, ArH), 7.59 (s, 1H, ArH), 7.37 (d, J=7.5 Hz, 1H, ArH), 6.20 (d, J=7.5 Hz, 1H, ArH), 4.46 (s, 2H, CH$_2$), 4.30-4.27 (m, 1H, CH), 3.60-3.57 (m, 2H, CH$_2$), 3.08-3.06 (m, 2H, CH$_2$), 2.48 (m, 2H, CH$_2$), 2.19 (s, 6H, 2×CH$_3$), 1.83 (s, 3H, CH$_3$), 1.36 (d, J=6.5 Hz, 3H, CH$_3$); Mass (ESI, positive) m/z 557.2 [M+H]$^+$.

Example 2

In Vitro Kinase Activity

In Vitro Kinase Activity Assay

Compounds to be tested were dissolved in 100% DMSO in a range of concentrations from $10^{-8}$ to $10^{-3}$ M including negative control (DMSO), then diluted with Kinase Buffer (50 mM HEPES, pH 7.5, 1 mM EGTA, 10 mM MgCl$_2$, 0.01% Tween-20, and 2 mM DTT, added fresh) to 4× the final concentration. The final curve included 11 concentrations ($10^{-11}$ to $10^{-5}$ M) plus negative control DMSO tested in triplicate.

Kinase and ATP concentrations necessary for optimal activity were determined in separate experiments (Table 2). Briefly, increasing concentrations of kinase were incubated in a fixed concentration of ATP (200 μM) in Kinase Buffer to determine maximal activity at various time points (30-120 min) The concentration of kinase that resulted in maximal activity with the shortest incubation time was then incubated in Kinase Buffer with increasing concentrations of ATP. The concentration of ATP that resulted in 50% maximal stimulation (EC$_{50}$) was chosen for enzyme inhibitor experiments.

Kinase assays were performed in a final volume of 10 μL in 384-well plates, with 2.5 μL of test compound in triplicate at each concentration, 2.5 μL of kinase, and 5 μL of ATP and peptide substrate (LANCE® Ultra Ulight™ poly-GT, PerkinElmer) mix. Reactions were incubated at room temperature (rt), in the dark, for 30-120 min Following incubation, reactions were stopped with the addition of 40 mM EDTA in 1×LANCE® buffer (PerkinElmer) (5 μL), and incubated at rt for 5 min. LANCE® Eu-W1024 anti-phosphotyrosine antibody PT66 (5 μL) in 1×LANCE® buffer was added to the wells at a final concentration of 1.25 nM and incubated for 1 h at rt. The relative amount of phosphorylated substrated was measured with the VICTOR™ Multilabel Plate Reader using the LANCE™ protocol for time-resolved fluorescence resonance energy transfer.

The concentration of test compound required to decrease the fluorescence signal (665 nm) by 50%, IC$_{50}$ value, was determined by computer-fitting the data with SigmaPlot and non-linear regression with the standard curve four parameter logistic curve.

TABLE 2

Kinase assay conditions.

| | Specific Activity* (nmol P/min/mg) | Kinase (ng/mL) | ATP (μM) | Incubation time (min) |
|---|---|---|---|---|
| ALK | 1976 | 25 | 5 | 30 |
| INSR | 3700 | 50 | 3 | 45 |
| IGF1R | 514 | 200 | 4 | 90 |
| TrkA | 503 | 50 | 25 | 45 |
| TrkB | 451 | 100 | 25 | 45 |
| TrkC | 2034 | 50 | 1 | 45 |
| EGFR | 345 | 50 | 5-10 | 30-60 |
| cMET | 488 | 50 | 6 | 120 |
| ROS | 5277 | 12.5 | 12.5 | 30 |
| RET | 2641 | 1.56 | 1.25 | 30 |

*Specific Activity as provided by manufacturer (Invitrogen)

Results:

TABLE 3 presents the pharmacological data (IC$_{50}$ values) for specific kinases showing the relative degree of potency of inhibition of their activity.

| Name | Structure | ALK (nM) | IGF-1R (nM) | InsR (nM) | TrkA (nM) | TrkB (nM) | TrkC (nM) | EGFR (nM) | ROS (nM) | RET (nM) | cMET (nM) |
|---|---|---|---|---|---|---|---|---|---|---|---|
| Staurosporine | | 1.361 | 71.53 | 36.35 | 1.405 | 1.182 | 0.525 | | 0.248 | 2.195 | 107.4 |
| [4] | 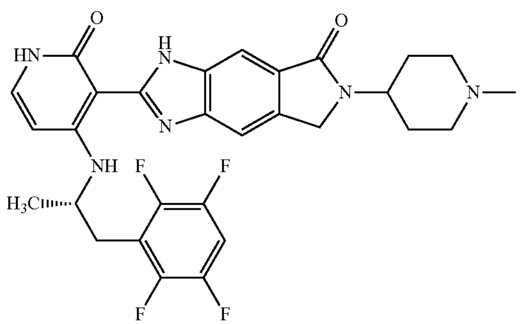 [SMILES: C[C@@H](Cc1c(F)c(F)cc(F)c1F)Nc1cc[nH]c(=O)c1-c1nc2cc3c(cc2[nH]1)C(=O)N(C1CCN(C)CC1)C3] | 9.812 | NT | NT | 5.001 | 3.483 | 2.601 | NT | 0.300 | 5.977 | NT |

TABLE 3-continued presents the pharmacological data (IC$_{50}$ values) for specific kinases showing the relative degree of potency of inhibition of their activity.

| Name | Structure | ALK (nM) | IGF-1R (nM) | InsR (nM) | TrkA (nM) | TrkB (nM) | TrkC (nM) | EGFR (nM) | ROS (nM) | RET (nM) | cMET (nM) |
|---|---|---|---|---|---|---|---|---|---|---|---|
| [2] | 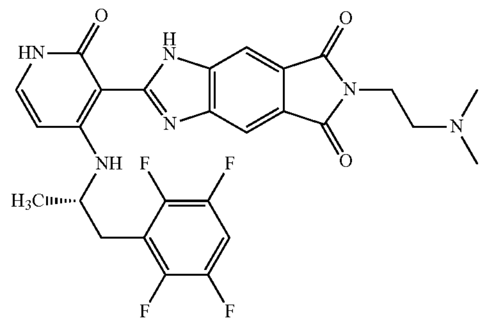 [SMILES: C[C@@H](Cc1c(F)c(F)cc(F)c1F)Nc1cc[nH]c(=O)c1-c1nc2cc3c(cc2[nH]1)C(=O)N(CCN(C)C)C3=O] | 14.03 | NT | NT | 12.24 | NT | NT | NT | 0.436 | 25.82 | 14.03 |
| [1] | 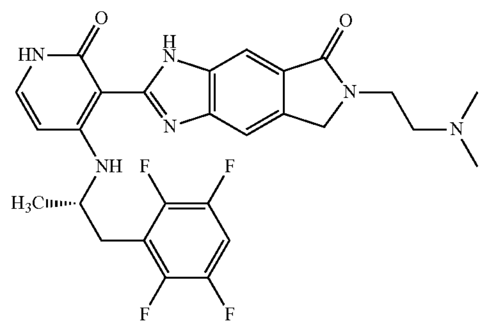 [SMILES: C[C@@H](Cc1c(F)c(F)cc(F)c1F)Nc1cc[nH]c(=O)c1-c1nc2cc3c(cc2[nH]1)C(=O)N(CCN(C)C)C3] | 4.701 | NT | NT | 1.141 | 2.064 | 1.585 | NT | 0.205 | 3.527 | NT |
| [28] | 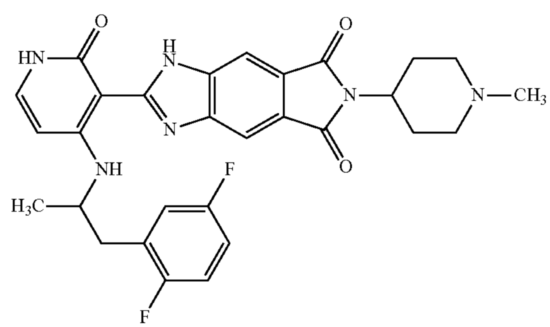 [SMILES: CC(Cc1cc(F)ccc1F)Nc1cc[nH]c(=O)c1-c1nc2cc3c(cc2[nH]1)C(=O)N(C1CCN(C)CC1)C3=O] | 15.11 | NT | NT | 6.353 | NT | NT | NT | NT | NT | NT |

TABLE 3-continued presents the pharmacological data (IC$_{50}$ values) for specific kinases showing the relative degree of potency of inhibition of their activity.

| Name | Structure | ALK (nM) | IGF-1R (nM) | InsR (nM) | TrkA (nM) | TrkB (nM) | TrkC (nM) | EGFR (nM) | ROS (nM) | RET (nM) | cMET (nM) |
|---|---|---|---|---|---|---|---|---|---|---|---|
| [12] | 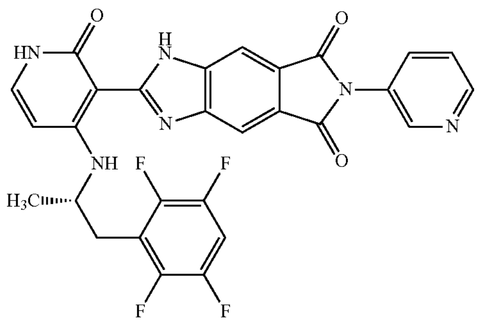 [SMILES: C[C@@H](Cc1c(F)c(F)cc(F)c1F)Nc1cc[nH]c(=O)c1-c1nc2cc3c(cc2[nH]1)C(=O)N(c1cccnc1)C3=O] | 47.30 | NT | NT | 20.41 | NT | NT | NT | NT | NT | >10000 |
| [13] | 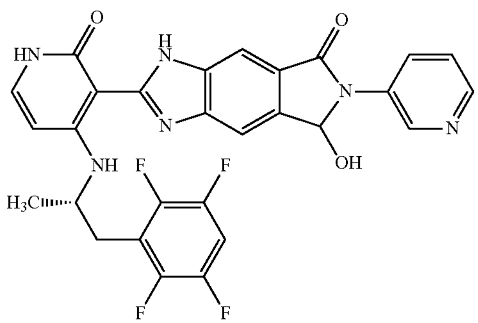 [SMILES: C[C@@H](Cc1c(F)c(F)cc(F)c1F)Nc1cc[nH]c(=O)c1-c1nc2cc3c(cc2[nH]1)C(=O)N(c1cccnc1)C3O] | 15.18 | NT | NT | 6.357 | NT | NT | NT | NT | NT | >10000 |
| [14] | 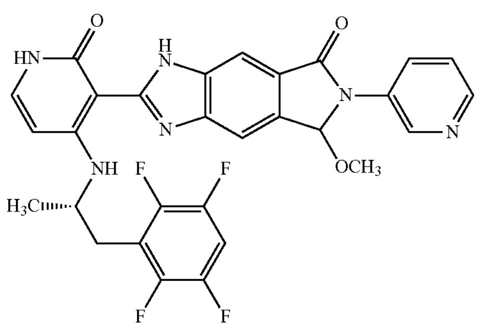 | 174.4 | NT | NT | 41.61 | NT | NT | NT | NT | NT | >10000 |

TABLE 3-continued presents the pharmacological data (IC$_{50}$ values) for specific kinases showing the relative degree of potency of inhibition of their activity.

| Name | Structure | ALK (nM) | IGF-1R (nM) | InsR (nM) | TrkA (nM) | TrkB (nM) | TrkC (nM) | EGFR (nM) | ROS (nM) | RET (nM) | cMET (nM) |
|---|---|---|---|---|---|---|---|---|---|---|---|
| [15] | 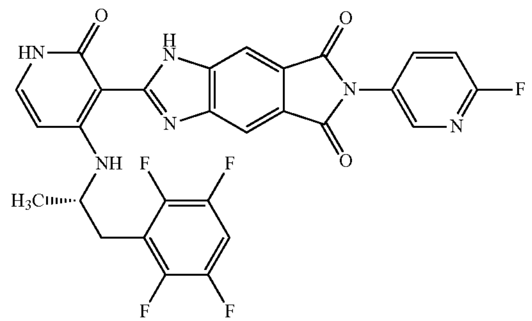 [SMILES: C[C@@H](Cc1c(F)c(F)cc(F)c1F)Nc1cc[nH]c(=O)c1-c1nc2cc3c(cc2[nH]1)C(=O)N(c1ccc(F)nc1)C3=O] | >10000 | NT | NT | >10000 | NT | NT | NT | NT | NT | >10000 |
| [17] | 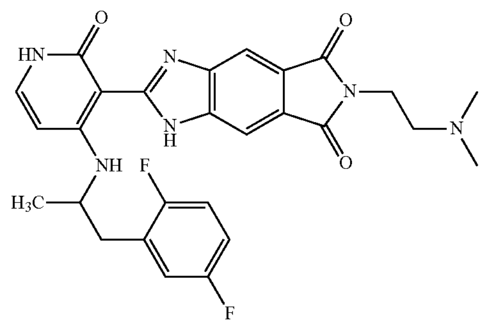 [SMILES: CC(Cc1cc(F)ccc1F)Nc1cc[nH]c(=O)c1-c1nc2cc3c(cc2[nH]1)C(=O)N(CCN(C)C)C3=O] | 38.86 | NT | NT | 17.48 | NT | NT | NT | NT | NT | NT |
| [18] | 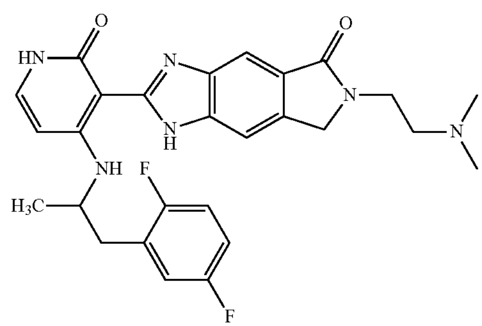 [SMILES: CC(Cc1cc(F)ccc1F)Nc1cc[nH]c(=O)c1-c1nc2cc3c(cc2[nH]1)CN(CCN(C)C)C3=O] | 9.157 | NT | NT | 4.334 | NT | NT | NT | 0.688 | 13.07 | 1000-3000 |

TABLE 3-continued presents the pharmacological data (IC$_{50}$ values) for specific kinases showing the relative degree of potency of inhibition of their activity.

| Name | Structure | ALK (nM) | IGF-1R (nM) | InsR (nM) | TrkA (nM) | TrkB (nM) | TrkC (nM) | EGFR (nM) | ROS (nM) | RET (nM) | cMET (nM) |
|---|---|---|---|---|---|---|---|---|---|---|---|
| [24] | 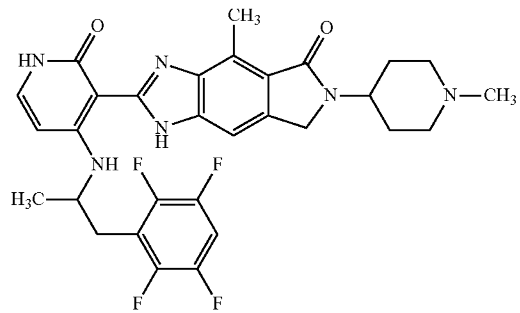 [SMILES: Cc1c2c(cc3[nH]c(-c4c(NC(C)Cc5c(F)c(F)cc(F)c5F)cc[nH]c4=O)nc13)CN(C1CCN(C)CC1)C2=O] | 23.70 | NT | NT | 10.37 | NT | NT | NT | NT | NT | NT |
| [24A] | 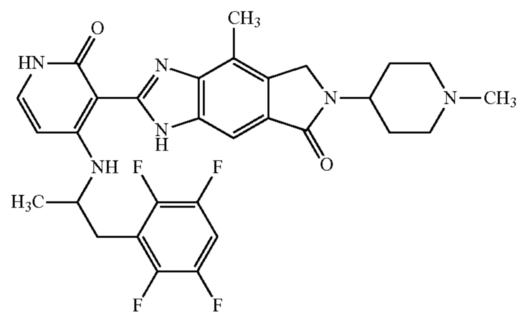 [SMILES: Cc1c2c(cc3[nH]c(-c4c(NC(C)Cc5c(F)c(F)cc(F)c5F)cc[nH]c4=O)nc13)C(=O)N(C1CCN(C)CC1)C2] | 14.59 | NT | NT | 5.992 | NT | NT | NT | 2.365 | 11.15 | NT |
| [29] | 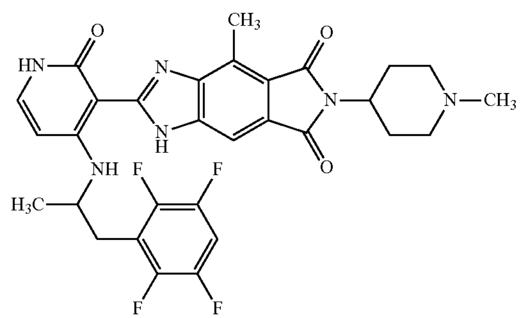 [SMILES: Cc1c2c(cc3[nH]c(-c4c(NC(C)Cc5c(F)c(F)cc(F)c5F)cc[nH]c4=O)nc13)C(=O)N(C1CCN(C)CC1)C2=O] | 231.3 | NT | NT | 164.9 | NT | NT | NT | NT | NT | NT |

NT refers to Not Tested.

Example 3

Cellular Assays Using the Compounds of this Invention

Methods

Commercially available lymphoma (K299, U937, SUDHL-1) or neuroblastoma cells (NB-1) in log-phase growth were plated using RPMI (MediaTech) and 10% fetal bovine serum (HighClone) in 96-well plates at a density of 3,000-5,000 cells per well. An equal volume of RPMI (no FBS) containing drug solution (0.1%) was added. Concentrations ranging from $10^{-10}$ to $10^{-5}$ M were evaluated at half-log intervals in triplicate. The cells were allowed to proliferate for 3 days at the end of which cell viability was determined using WST-1 (Roche) reagent according to the manufacturer's instructions. The resulting absorbance values were represented as a percentage of untreated control and fit using a four parameter logistic model in Sigma Plot© (Systat Software) to determine $IC_{50}$ values. The results are presented in the following Tables 4, 4a, 4b, and 4c.

TABLE 4

| # | STRUCTURE (completely hydrogen suppressed graphs) | | ALK $IC_{50}$ (μM) | IRK $IC_{50}$ (μM) | IGF1R $IC_{50}$ (μM) | TrKA $IC_{50}$ (μM) | K299 $IC_{50}$ (μM) | U937 $IC_{50}$ (μM) | SUDHL-1 $IC_{50}$ (μM) | NB-1 $IC_{50}$ (μM) | hERG inhib. $IC_{50}$ (μM) |
|---|---|---|---|---|---|---|---|---|---|---|---|
| [2] | 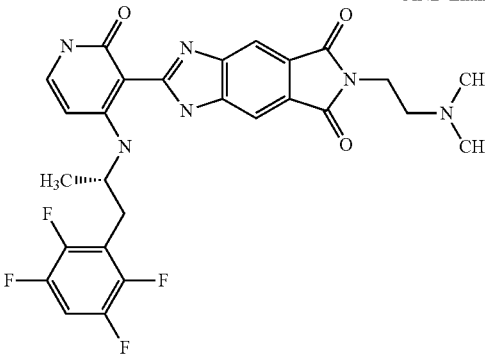 | AND Enantiomer | 0.014 | | 0.012 | 1.917 | >10 | | 2.74 | 0.666 | >30 |
| [1] | 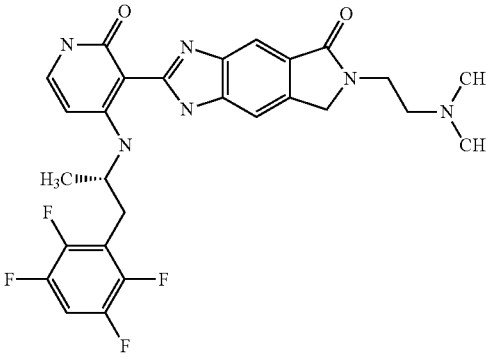 | AND Enantiomer | 0.005 | | 0.001 | 0.076 | 1.6 | 0.102 | | 0.177 | 6.254 |
| [4] | 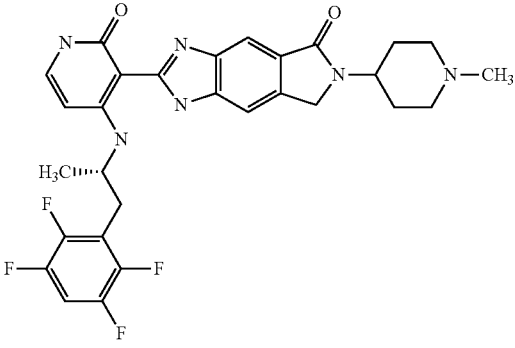 | AND Enantiomer | 0.01 | | 0.005 | 0.099 | 1.18 | 0.093 | | 0.257 | 2.723 |

TABLE 4-continued
| # | STRUCTURE (completely hydrogen suppressed graphs) | ALK IC$_{50}$ (μM) | IRK IC$_{50}$ (μM) | IGF1R IC$_{50}$ (μM) | TrKA IC$_{50}$ (μM) | K299 IC$_{50}$ (μM) | U937 IC$_{50}$ (μM) | SUDHL-1 IC$_{50}$ (μM) | NB-1 IC$_{50}$ (μM) | hERG inhib. IC$_{50}$ (μM) |
|---|---|---|---|---|---|---|---|---|---|---|
| PPP | AND Enantiomer  | >10 | >10 | | | 0.196 | 0.138 | | | |
| Stauros porine | AND Enantiomer 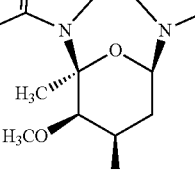 | 0.002 | 0.042 | 0.095 | 0.001 | 0.029 | 0.03 | 0.116 | 0.024 | |
| racemic PF0234 1066 | 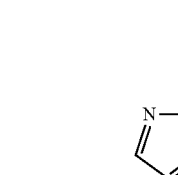 | 0.011 | 0.6 | 0.403 | 0.085 | 1.67 | 0.132 | 0.167 | | |

TABLE 4-continued

| # | STRUCTURE (completely hydrogen suppressed graphs) | ALK IC$_{50}$ (μM) | IRK IC$_{50}$ (μM) | IGF1R IC$_{50}$ (μM) | TrKA IC$_{50}$ (μM) | K299 IC$_{50}$ (μM) | U937 IC$_{50}$ (μM) | SUDHL-1 IC$_{50}$ (μM) | NB-1 IC$_{50}$ (μM) | hERG inhib. IC$_{50}$ (μM) |
|---|---|---|---|---|---|---|---|---|---|---|
| [12] | AND Enantiomer | 0.047 | | | 0.02 | >10 | | | | >3 |
| [13] | AND Enantiomer | 0.015 | | | 0.006 | 0.787 | | | | >3 |
| [14] | AND Enantiomer | 0.174 | | | 0.042 | | | | | |

TABLE 4-continued
| # | STRUCTURE (completely hydrogen suppressed graphs) | | ALK IC$_{50}$ (μM) | IRK IC$_{50}$ (μM) | IGF1R IC$_{50}$ (μM) | TrKA IC$_{50}$ (μM) | K299 IC$_{50}$ (μM) | U937 IC$_{50}$ (μM) | SUDHL-1 IC$_{50}$ (μM) | NB-1 IC$_{50}$ (μM) | hERG inhib. IC$_{50}$ (μM) |
|---|---|---|---|---|---|---|---|---|---|---|---|
| [15] | 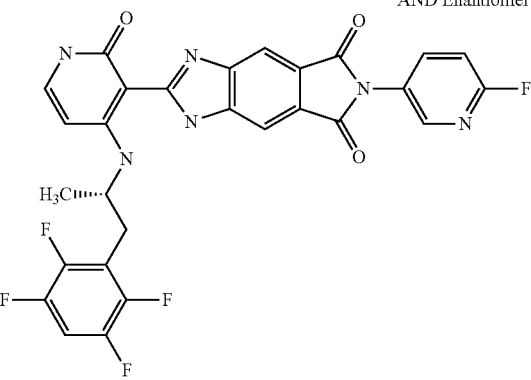 | AND Enantiomer | >10 | | | >10 | >10 | | | | |
| [18] | 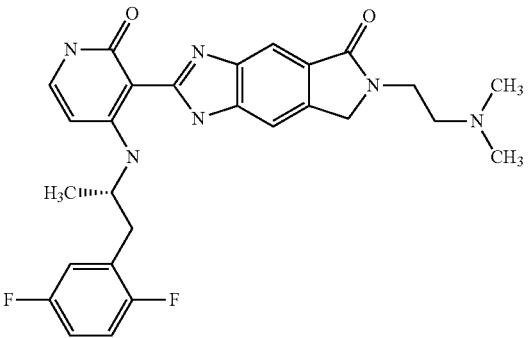 | AND Enantiomer | 0.009 | | 0.004 | 0.265 | >3 | | 0.172 | | 5.417 |
TABLE 4a
| | | ALK | | | | | | | | | |
|---|---|---|---|---|---|---|---|---|---|---|---|
| Name | Structure | ALK (nM) | IGF-1R (nM) | InsR (nM) | TrkA (nM) | TrkB (nM) | TrkC (nM) | EGFR (nM) | ROS (nM) | RET (nM) | cMET (nM) |
| Stauro-sporine | 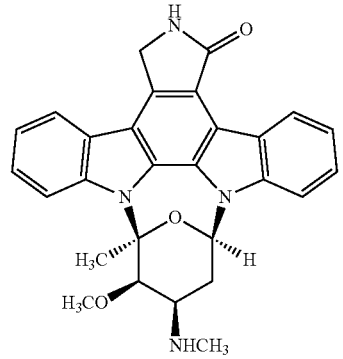 [SMILES: CN[C@@H]1C[C@H]2O[C@@](C)([C@@H]1OC)n1c3ccccc3c3c4c(c5c6ccccc6n2c5c31)C(=O)NC4] | 1.817 0.714 0.254 1.361 2.249 2.393 4.179 3.435 5.192 6.072 3.674 4.600 6.176 3.533 | 95.51 43.58 71.53 53.10 104.4 | 24.03 36.35 42.61 42.13 32.02 31.50 | 0.928 1.035 1.130 1.180 1.405 1.208 1.950 1.031 1.652 1.564 0.871 | 1.182 1.431 | 0.773 0.525 | | 0.248 0.162 0.508 | 2.497 1.527 2.195 | 107.4 101.9 |

TABLE 4a-continued

| | | ALK | | | | | | | | | |
|---|---|---|---|---|---|---|---|---|---|---|---|
| Name | Structure | ALK (nM) | IGF-1R (nM) | InsR (nM) | TrkA (nM) | TrkB (nM) | TrkC (nM) | EGFR (nM) | ROS (nM) | RET (nM) | cMET (nM) |
| [34] | | 13.84 4.709 | | | 6.969 3.705 | | | | | | |
| [40] | | >10000 | | | >10000 | | | | | | |
| [32] | | >300 | | | 30-100 | | | | | | |
| [33] | | 24.70 | | | 5.126 | | | | 0.740 | 17.72 | |
| [53] | | 34.06 | | | 7.805 | | | | 1.877 | 16.85 | |

TABLE 4a-continued

| Name | Structure | ALK (nM) | IGF-1R (nM) | InsR (nM) | TrkA (nM) | TrkB (nM) | TrkC (nM) | EGFR (nM) | ROS (nM) | RET (nM) | cMET (nM) |
|---|---|---|---|---|---|---|---|---|---|---|---|
| [41] | 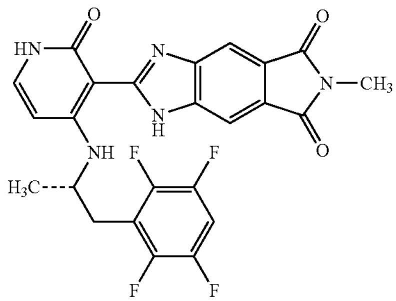 [SMILES: C[C@@H](Cc1c(F)c(F)cc(F)c1F)Nc1cc[nH]c(=O)c1-c1nc2cc3c(cc2[nH]1)C(=O)N(C)C3=O] | >10000 | | | >10000 | | | | 4.531 | >10000 | |
| [42] | 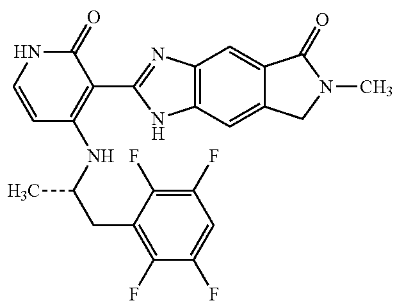 [SMILES: C[C@@H](Cc1c(F)c(F)cc(F)c1F)Nc1cc[nH]c(=O)c1-c1nc2cc3c(cc2[nH]1)CN(C)C3=O] | 17.49 | | | 7.270 | | | | | | |
| [43] | 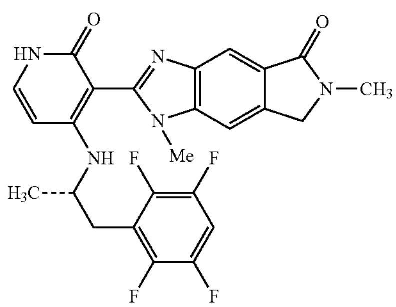 [SMILES: C[C@@H](Cc1c(F)c(F)cc(F)c1F)Nc1cc[nH]c(=O)c1-c1nc2cc3c(cc2n1C)CN(C)C3=O] | >10000 | | | 9495 | | | | | | |
| [43A] | 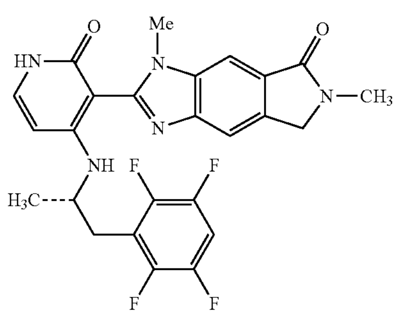 [SMILES: C[C@@H](Cc1c(F)c(F)cc(F)c1F)Nc1cc[nH]c(=O)c1-c1nc2cc3c(cc2n1C)C(=O)N(C)C3] | >10000 | | | 6505 | | | | 1199 | >10000 | |

TABLE 4b

| CRLID | GTx-ALK IC50(uM) | GTx-IRK IC50(uM) | GTx-IGF1R IC50(uM) | GTx-TrKA IC50(uM) | GTx-TrKB IC50(uM) | GTx-TrKC IC50(uM) | GTx-ROS IC50(uM) | GTx-RET IC50(uM) | GTx-cMET IC50(uM) | GTx-K299 IC50(uM) |
|---|---|---|---|---|---|---|---|---|---|---|
| [36] | | | | | | | | | | 1.83 |
| [38] | | | | | | | | | | >3 |
| [37] | | | | | | | | | | 1.83 |
| [39] | | | | | | | | | | >3 |
| Staurosporine | 0.002 | 0.042 | 0.095 | 0.001 | 0.001 | 0.001 | 5E-04 | 0.002 | 0.107 | 0.029 |

TABLE 4b-continued

| CRLID | | | | | | | | | | |
|---|---|---|---|---|---|---|---|---|---|---|
| Pfizer | 0.011 | | 0.6 | 0.403 | 0.058 | 0.021 | | | 0.002 | 0.085 |
| [40] | | | | | | | | | | >10 |
| [32] | >0.300 | | | >0.030 | | | | | | 0.784 |
| [33] | 0.025 | | | 0.005 | | | 7E-04 | 0.018 | | 0.532 |
| [41] | >10 | | | >10 | | | 0.005 | >10 | | |
| [42] | 0.018 | | | 0.007 | | | | | | >10 |
| [43] | >10 | | | 9.5 | | | | | | >10 |
| [43a] | >10 | | | 6.505 | | | 1.12 | >10 | | |
| [44] | 0.037 | | | 0.004 | 0.004 | 0.001 | | | | 0.798 |

| CRLID | GTx-SUDHL-1 IC50(uM) | GTx-U937 IC50(uM) | GTx-KELLY IC50(uM) | GTx-NB-1 IC50(uM) | IV_AUC0-1440 Rat 10 mpk (min*ug/ml) | PO_AUC0-1440 Rat 10 mpk (min*ug/ml) | Rat F % | Human LM-P1 Half-life (min) | Human LM-P1 CL(ul/min/mg) | Rat LM-P1 Half-life (min) |
|---|---|---|---|---|---|---|---|---|---|---|
| [36] | 2.77 | >3 | | | | | | | | |
| [38] | 2.8 | >3 | | | | | | | | |
| [37] | 2.77 | >3 | | | | | | | | |
| [39] | 2.8 | >3 | | | | | | | | |
| Staurosporine | 0.116 | 0.03 | 0.009 | 0.024 | | | | | | |
| Pfizer | 0.132 | 1.67 | 0.528 | 0.167 | 1236 | 33.2 | 2.68 | 54.24 | 12.78 | 94.56 |
| [40] | >10 | >10 | | | | | | | | |
| [32] | 0.957 | >3 | | | | | | 88.72 | 7.813 | |
| [33] | 0.867 | >10 | 0.651 | | | | | 26.59 | 26.07 | 7.135 |
| [41] | | | | | | | | | | |
| [42] | >10 | >10 | >10 | | 232 | 5.48 | 2.36 | | | |
| [43] | >10 | >10 | | | | | | | | |
| [43a] | | | | | | | | | | |
| [44] | 0.829 | >3 | | | | | | | | |

| CRLID | Rat LM-P1 CL(ul/min/mg) | Rat LM-P1 Half-life (min) | Mouse LM-P1 CL(ul/min/mg) | hERG Inhib. IC50(uM) | Papp (10-6 cm/sec) A to B | Papp (10-6 cm/sec) B to A | Efflux Ratio | Qpp Caco |
|---|---|---|---|---|---|---|---|---|
| [36] | | | | | | | | |
| [38] | | | | | | | | |
| [37] | | | | | | | | |
| [39] | | | | | | | | |
| Staurosporine | | | | | | | | |
| Pfizer | 7.331 | 55 | 12.7 | | <0.2 | 50.7 | >253 | |
| [40] | | | | | | | | |
| [32] | | | | | <0.2 | 0.1 | >0.5 | |
| [33] | 97.15 | 54.06 | 12.82 | >10 | 1.7 | 1.4 | 0.8 | |
| [41] | | | | | | | | |
| [42] | | | | | 0.24 | 0.24 | 1 | |
| [43] | | | | | | | | |
| [43a] | | | | | | | | |
| [44] | | | | | | | | |

TABLE 4c

| CRLID | GTx-ALK IC50(uM) | GTx-IRK IC50(uM) | GTx-IGF1R IC50(uM) | GTx-TrKA IC50(uM) | GTx-K299 IC50(uM) | GTx-U937 IC50(uM) | GTx-SUDHL-1 IC50(uM) | GTx-KELLY IC50(uM) | GTx-NB-1 IC50(uM) | Human LM-P1 CL (ul/min/mg) |
|---|---|---|---|---|---|---|---|---|---|---|
| [34] | 0.014 | | | 0.007 | >10 | >10 | >10 | | | 9.159 |
| PPP | >10 | >10 | | | 0.196 | 0.138 | | | | |
| Staurosporine | 0.002 | 0.042 | 0.095 | 0.001 | 0.029 | 0.03 | 0.116 | 0.009 | 0.024 | |
| Pfizer | 0.011 | | 0.6 | 0.403 | 0.085 | 1.67 | 0.132 | 0.528 | 0.167 | 12.78 |
| [087] | | | | | >10 | >10 | >10 | | | |
| [32] | >0.300 | | | >0.030 | 0.784 | >3 | 0.957 | | | 7.813 |
| [33] | 0.025 | | | 0.005 | 0.532 | >10 | 0.867 | 0.651 | | 26.07 |

| CRLID | Human LM-P1 Half-life (min) | Mouse LM-P1 CL(ul/min/mg) | Mouse LM-P1 Half-life (min) | Rat LM-P1 CL(ul/min/mg) | Rat LM-P1 Half-life (min) | hERG Inhib. IC50(uM) | Papp (10−6 cm/sec) A to B | Papp (10−6 cm/sec) B to A | Efflux Ratio |
|---|---|---|---|---|---|---|---|---|---|
| [34] | 75.68 | | | 20.61 | 33.64 | | >0.2 | 1.17 | >5.9 |
| PPP | | | | | | | | | |
| Staurosporine | | | | | | | | | |
| Pfizer | 54.24 | | | 7.331 | 94.56 | | >0.2 | 50.7 | >253 |
| [087] | | | | | | | | | |
| [32] | 88.72 | | | | | | >0.2 | 0.1 | >0.5 |
| [33] | 26.59 | 12.82 | 54.06 | 97.15 | 7.135 | >10 | 1.7 | 1.4 | 0.8 |

Example 4

Metabolic Stability

Materials and Methods

1. Materials and Reagents

Human, monkey, dog, rat, and mouse liver microsomes were purchased from Xenotech, LLC. Solution 'A' and 'B' for NADPH regenerating system (NRS) solution were obtained from BD Biosciences (Waltham, Mass.). Hepatocyte incubation media and supplemented DMEM with and without Percoll were purchased from Xenotech. Verapamil and other chemical reagents were purchased from Sigma-Aldrich.

2. Phase I Microsome Reactions

Test compound stock solutions were prepared in 50% acetonitrile/50% water at 50 µM. The stock solutions were added in incubation mixtures to obtain the final drug concentration of 0.5 µM, containing 0.5% acetonitrile. Verapamil was used as a positive control. Human, monkey, dog, rat, mouse microsomes were all utilized at a final concentration of 1.0 mg/ml. Duplicate wells were used for each time point (0, 5, 10, 30 and 60 minutes). Incubation was conducted at 37° C. in a shaking water bath. The final volume for each reaction was 200 µl, composed of: 66 µl of 0.2 M $KPO_4$ buffer, (pH 7.4); 72 µl of $H_2O$, 10 µl of 20 mg/ml microsome stock; 2 µl of compound stock solution, and 50 µl of NRS solution. The NRS solution consisted of glucose 6-phosphate dehydrogenase, NADP+, $MgCl_2$, and glucose 6-phosphate, and was prepared as described in manufacturer's instructions. At the end of incubation, the reaction was quenched by mixing with same volume of cold acetonitrile containing internal standard ((R)-2-(4-((3-(2,4-dimethylphenoxy)-2-hydroxypropyl) amino)-2-oxo-1,2-dihydropyridin-3-yl)-6-(1-(2-(methylsulfonyl)ethyl)piperidin-4-yl)-6,7-dihydroimidazo[4,5-f]isoindol-5(3H)-one, 200 nM). Samples were then centrifuged at 3,000 rpm for 10 minutes at 4° C. to precipitate protein. Approximately 150 µl of supernantant was subsequently transferred to a new sample block for LC/MS/MS analysis.

3. LC-MS/MS Analysis:

The analysis of the compounds under investigation was performed using LC-MS/MS system consisting of Agilent 1100 HPLC with an MDS/Sciex 4000 Q-Trap™ mass spectrometer. The separation was achieved using a C18 analytical column (Alltima™, 2.1×100 mm, 3 µm) protected by a C18 guard column (SecurityGuard™ 4.0×2.0 mm ID, Phenomenex). Mobile phase consisted of channel A (95% acetonitrile+5% water+0.1% formic acid) and channel B (95% water+5% acetonitrile+0.1% formic acid) and was delivered at a flow rate of 0.3 mL/min. The volume ratio of acetonitrile and water was optimized for each of the analytes. Multiple reaction monitoring (MRM) scans were made with curtain gas at 30, collision gas at high, nebulizer gas at 30, auxiliary gas at 40, and source temperature at 500° C. Molecular ions were formed using an ion spray voltage of 5500 V (positive mode) and −4500 V (negative mode). Declustering potential, entrance potential, collision energy, product ion mass, and cell exit potential were optimized for each compound. The results are summarized in Table 5.

TABLE 5

| | | ALK metabolic stability | |
|---|---|---|---|
| | | Phase I only Human LM | |
| Compound | Structure | Half life (min) | Clearance (ul/min/mg) |
| [4] | | >120 | <5.8 |
| [18] | | >120 | <5.8 |
| [1] | | 118.1 | 5.869 |
| [13] | | 79.08 | 8.765 |

TABLE 5-continued
ALK metabolic stability
| [14] | 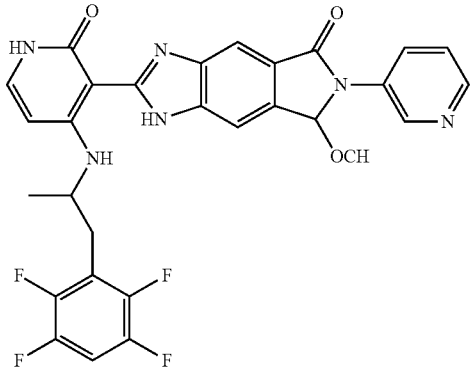 | >120 | <5.8 |
| [12] | 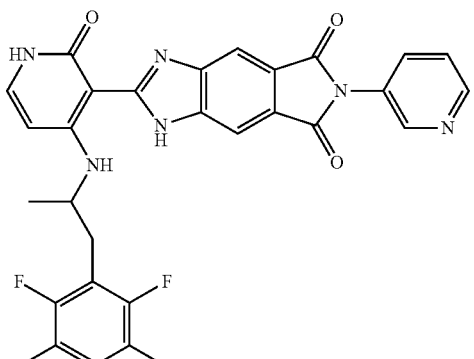 | >120 | <5.8 |
| [52] | 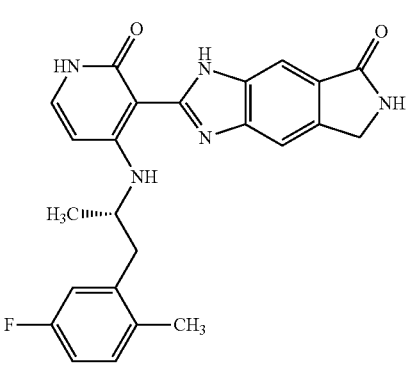 [SMILES: Cc1ccc(F)cc1C[C@H](C)Nc1cc[nH]c(=O)c1-c1nc2cc3c(cc2[nH]1)C(=O)NC3] | 5.169 | 134.1 |
| Pfizer (PF2341066) | 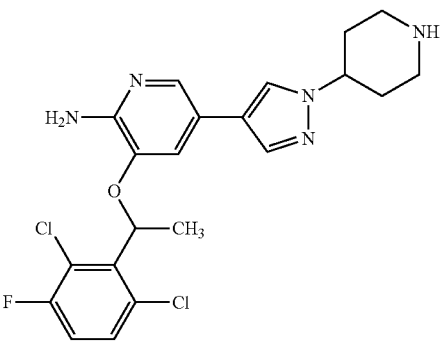 [SMILES: CC(Oc1cc(-c2cnn(C3CCNCC3)c2)cnc1N)c1c(Cl)ccc(F)c1Cl] | 54.24 | 12.78 |

TABLE 5-continued

ALK metabolic stability

| | Compound | | |
|---|---|---|---|
| [32] | (structure) | 88.72 | 7.813 |
| [33] | (structure) | 26.59 | 26.07 |
| [53] | (structure) | 27.4 | 25.3 |
| [34] | (structure) | 75.68 | 9.159 |

TABLE 5-continued

ALK metabolic stability

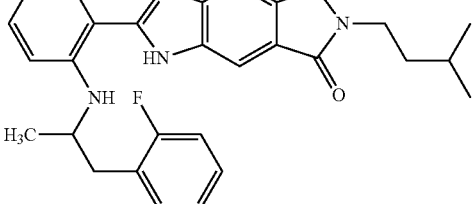

| | | | |
|---|---|---|---|
| [17] | | 79.06 | 8.768 |
| Verapamil | N/A | 9.761 | 71.61 |

| | Phase I only | | | | | | | |
|---|---|---|---|---|---|---|---|---|
| | Rat LM | | Mouse LM | | Monkey LM | | Dog LM | |
| Compound | Half life (min) | Clearance (ul/min/mg) | Half life (min) | Clearance (ul/min/mg) | Half life (min) | Clearance (ul/min/mg) | Half life (min) | Clearance (ul/min/mg) |
| [4] | >120 | <5.8 | | | | | | |
| [18] | 20.57 | 33.31, 33.7 | 23.57 | 29.41 | | | | |
| [1] | 8.429 | 82.23 | | | | | | |
| [13] | 37.76 | 18.36 | 87.83 | 7.892 | | | | |
| [14] | 102.6 | 6.76 | >120 | <5.8 | | | | |
| [12] | >120 | <5.8 | >120 | <5.8 | | | | |
| [52] | 2.512 | 275.9 | | | | | | |
| Pfizer (PF2341066) | 94.56 | 7.331 | | | | | | |
| [32] | >120 | <5.0 | >120 | <5.8 | | | | |
| [33] | 7.135 | 97.15 | 12.82 | 54.06 | | | | |
| [53] | 8.882 | 78.04 | | | | | | |
| [34] | 33.64 | 20.61 | | | | | | |
| [17] | 25.53 | 27.08 | | | | | | |
| Verapamil | 9.914 | 69.92 | | | | | | |

Example 5

Caco-2 Cell Study

Materials and Methods

1. Caco-2 Cell Permeation Study

Caco-2 cells were routinely maintained in T-75 flasks at 37° C. in an atmosphere of 7% $CO_2$ in DMEM supplemented with 20% fetal bovine serum (FBS), 1 mM sodium pyruvate, 2 mM L-glutamine, 100 U/mL penicillin, 100 µg/mL streptomycin, 20 ug/ml gentamicin, and 2 ug/ml Amphotericin B. Confluent cell monolayers were subcultured weekly by treatment with 0.25% trypsin, counted using a haemocytometer and diluted to $2 \times 10^6$ cells and grown in a new T75 flask. For transport studies, cells were seeded onto a 24-well, high density PET transwell membrane inserts, (1.0 µm pore size, 0.31 $cm^2$ surface area) at a density of 40,000 cells/$cm^2$ Caco-2 monolayers were fed with fresh medium 24 h after seeding and then 3 times per week. Caco-2 monolayers were cultured for 21-28 days before use. Prior to all experiments, each monolayer was washed twice with the transport buffer followed by the trans-epithelial electrical resistance (TEER) value measurement to ensure the integrity of the monolayers. Lucifer yellow (0.2 mg/ml) and atenolol (50 µM) were co-treated with test compound/positive control to ensure the integrity of monolayers. The positive control compounds (propranolol, 10 µM) were used to assess the suitability of a batch of cells. The apical buffer (Buffer A) consisted of Hanks Balanced Salt Solution, 10 mM D-glucose monohydrate, 20 mM MES Biological Buffer, 1 mM $CaCl_2$, 1 mM $MgCl_2$ (pH 6.5). The basolateral buffer (Buffer B) consisted of Hanks Balanced Salt Solution, 10 mM D-glucose monohydrate, 20 mM HEPES Biological Buffer, 1 mM $CaCl_2$, 1 mM $MgCl_2$ (pH 7.4). Permeability experiments were performed in the apical-to basolateral (A to B) and the basolateral-to-apical (B to A) directions in triplicate at 37° C. with shaking (100 rpm) for 2 h. Compounds were tested at 10 µM in Buffer A (HBSS-Mes, pH 6.5) for A to B permeability study, and Buffer B (HBSS-Hepes, pH 7.4) for B to A permeability study. Samples for analysis were taken from the basolateral side and mixed with the same volume of ice-cold acetonitrile. The concentrations of the test compounds were analyzed by the following LC/MS/MS method.

2. LC-MS/MS Analysis:

The analysis of the compounds under investigation was performed using LC-MS/MS system consisting of Agilent 1100 HPLC with an MDS/Sciex 4000 Q-Trap™ mass spectrometer. The separation was achieved using a C18 analytical column (Alltima™, 2.1×100 mm, 3 µm) protected by a C18 guard column (SecurityGuard™ 4.0×2.0 mm ID, Phenomenex). Mobile phase was consisting of channel A (95% acetonitrile+5% water+0.1% formic acid) and channel B (95% water+5% acetonitrile+0.1% formic acid) and was delivered at a flow rate of 0.3 mL/min. The volume ratio of acetonitrile and water was optimized for each of the analytes. Multiple reaction monitoring (MRM) scans were made with curtain gas at 30, collision gas at high, nebulizer gas at 30, auxiliary gas at 40, and source temperature at 500° C. Molecular ions were formed using an ion spray voltage of 5500 V (positive mode) and −4500 V (negative mode). Declustering potential, entrance potential, collision energy, product ion mass, and cell exit potential were optimized for each compound.

TABLE 6

| Compound | Structure | Papp (10⁻⁶ cm/sec) A to B | Papp (10⁻⁶ cm/sec) B to A | Efflux ratio | Pos Ctrl (Papp) |
|---|---|---|---|---|---|
| [15] | 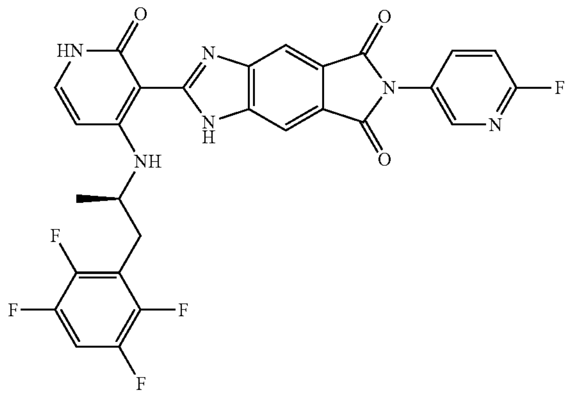 [SMILES: C[C@H](Cc1c(F)c(F)cc(F)c1F)Nc1cc[nH]c(=O)c1-c1nc2cc3c(cc2[nH]1)C(=O)N(c1ccc(F)nc1)C3=O] | <0.2 | <0.2 | N/A | Propranolol (Papp = 11.8, Recovery = 26%) |
| [12] | 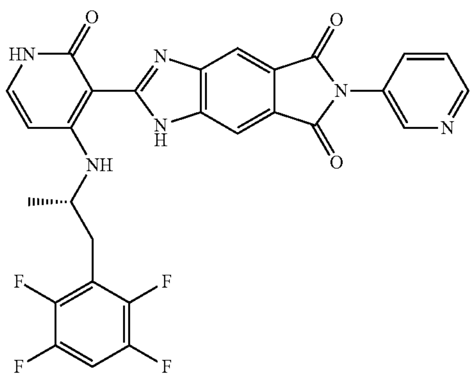 [SMILES: C[C@@H](Cc1c(F)c(F)cc(F)c1F)Nc1cc[nH]c(=O)c1-c1nc2cc3c(cc2[nH]1)C(=O)N(c1cccnc1)C3=O] | <0.2 | <0.2 | N/A | Propranolol (Papp = 14, Recovery = 54%) |
| [1] | 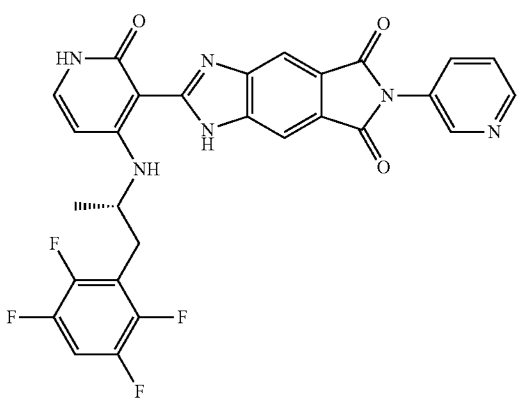 [SMILES: C[C@@H](Cc1c(F)c(F)cc(F)c1F)Nc1cc[nH]c(=O)c1-c1nc2cc3c(cc2[nH]1)C(=O)N(c1cccnc1)C3=O] | <0.2 | 19.9 | >99.5 | Propranolol (Papp = 12.09, Recovery = 63%) |
| [2] | 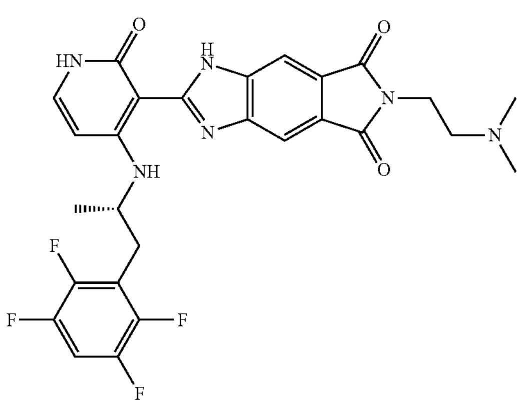 [SMILES: C[C@@H](Cc1c(F)c(F)cc(F)c1F)Nc1cc[nH]c(=O)c1-c1nc2cc3c(cc2[nH]1)C(=O)N(CCN(C)C)C3=O] | <0.2 | 3.6 | >17.75 | Propranolol (Papp = 11, Recovery = 80%) |

TABLE 6-continued
| Compound | Structure | Papp (10⁻⁶ cm/sec) A to B | Papp (10⁻⁶ cm/sec) B to A | Efflux ratio | Pos Ctrl (Papp) |
|---|---|---|---|---|---|
| [4] | 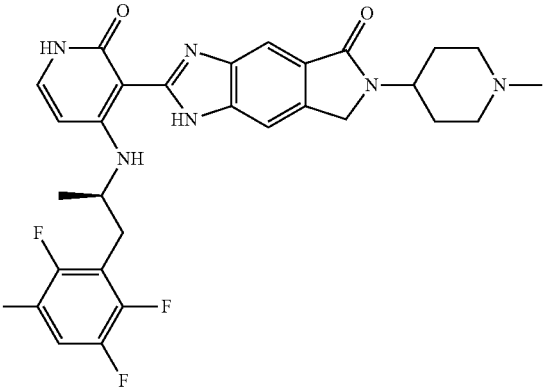 | <0.2 | 20 | >100 | Propranolol (Papp = 10.3, Recovery = 63%) |
| [13] | 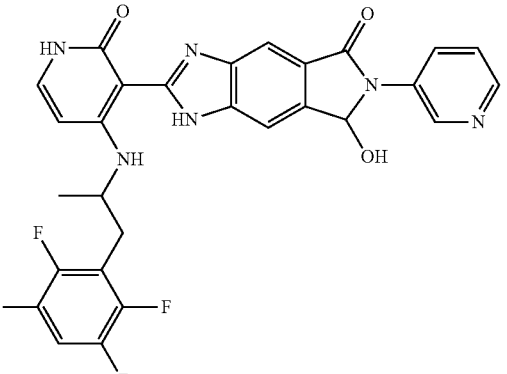 | <0.2 | 1.9 | >9.5 | Propranolol (Papp = 10.3, Recovery = 63%) |
| [52] | 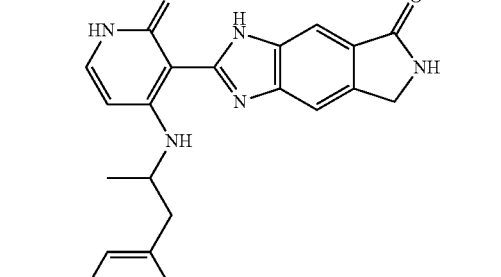 | 9.3 | 7.4 | 0.8 | Propranolol (Papp = 11.8, Recovery = 26%) |
|  |  | 5.0 | 10.2 | 2.1 | Propranolol (Papp = 9.62, Recovery = 36%) |
|  |  | 8.9 | 5.2 | 0.58 | Propranolol (Papp = 6.43, Recovery = 44%) |

TABLE 6-continued

| Compound | Structure | Papp (10⁻⁶ cm/sec) A to B | Papp (10⁻⁶ cm/sec) B to A | Efflux ratio | Pos Ctrl (Papp) |
|---|---|---|---|---|---|
| Pfizer (PF2341066) | 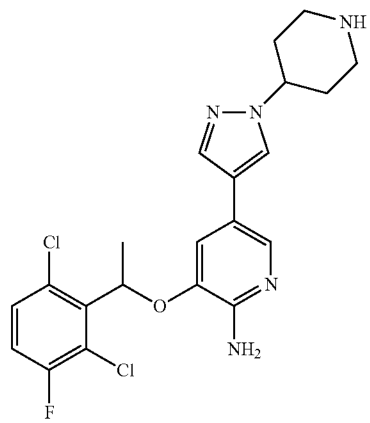 [SMILES: CC(Oc1cc(-c2cnn(C3CCNCC3)c2)cnc1N)c1c(Cl)ccc(F)c1Cl] | <0.2 | 50.7 | >253 | Propranolol (Papp = 9.3, Recovery = 28%) |
| [32] | 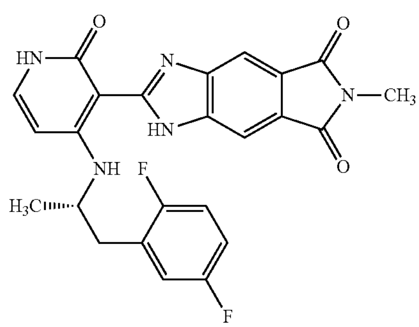 [SMILES: C[C@@H](Cc1cc(F)ccc1F)Nc1cc[nH]c(=O)c1-c1nc2cc3c(cc2[nH]1)C(=O)N(C)C3=O] | <0.2 | 15 | >75 | Propranolol (Papp = 13.7, Recovery = 63%) |
| [34] | 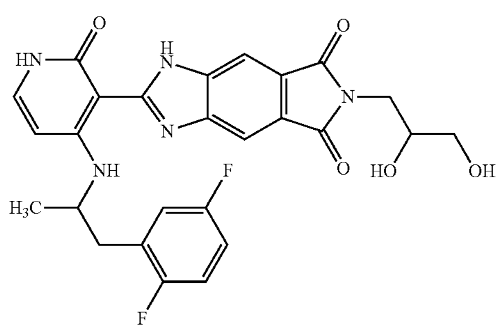 [SMILES: CC(Cc1cc(F)ccc1F)Nc1cc[nH]c(=O)c1-c1nc2cc3c(cc2[nH]1)C(=O)N(CC(O)CO)C3=O] | <0.2 | 1.17 | >5.9 | Propranolol (Papp = 14.3, Recovery = 58%) |
| [35] | 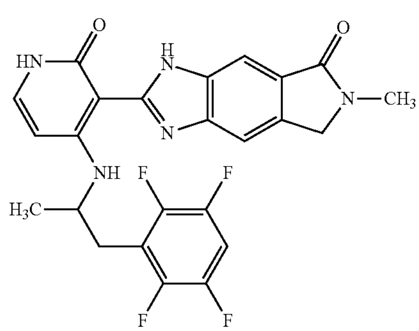 [SMILES: CC(Cc1c(F)c(F)cc(F)c1F)Nc1cc[nH]c(=O)c1-c1nc2cc3c(cc2[nH]1)C(=O)N(C)C3] | 0.24 | 0.24 | 1 | Propranolol (Papp = 17.0, Recovery = 85%) |

TABLE 6-continued

| Compound | Structure | Papp (10⁻⁶ cm/sec) A to B | Papp (10⁻⁶ cm/sec) B to A | Efflux ratio | Pos Ctrl (Papp) |
|---|---|---|---|---|---|
| [33] | 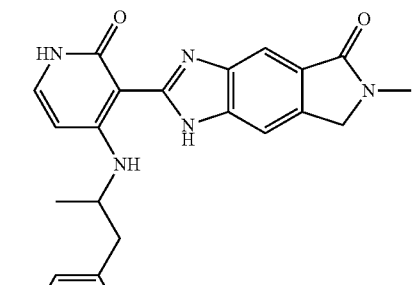 | 1.7<br>5.4<br>6.4 | 1.4<br><br>3.4 | 0.8<br><br>0.5 | Propranolol (Papp = 13.7, Recovery = 63%)<br>Propranolol (Papp = 12.8, Recovery = 95%)<br>Propranolol (Papp = 13.9, Recovery = 63%) |
| [53] | 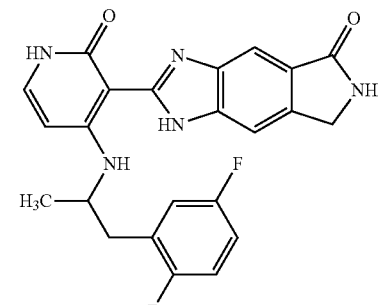 | 1.25<br>0.76 | 8.24<br>7.41 | 6.6<br>10.1 | Propranolol (Papp = 14.3, Recovery = 56%)<br>Propranolol (Papp = 14, Recovery = 63%) |

Example 6

In Vitro Enzyme Inhibition of Compound 31 and Compound 1 to Tyrosine Kinase Inhibitors

TABLE 7

| STRUCTURE (completely hydrogen suppressed graphs) | | ALK IC$_{50}$ (μM) | IRK IC$_{50}$ (μM) | IGF1R IC$_{50}$ (μM) | TrKA IC$_{50}$ (μM) | K299 IC$_{50}$ (μM) | SUDH L-1 IC$_{50}$ (μM) | U937 IC$_{50}$ (μM) | NB-1 IC$_{50}$ (μM) |
|---|---|---|---|---|---|---|---|---|---|
| Compound 31 | 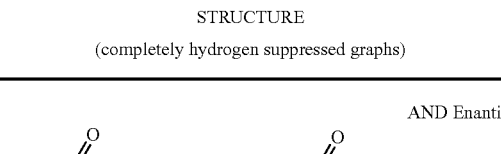 AND Enantiomer | 0.001 | 0.578 | 0.299 | 0.004 | 0.154 | 0.095 | 2.196 | |

TABLE 7-continued

| STRUCTURE (completely hydrogen suppressed graphs) | | ALK IC$_{50}$ (μM) | IRK IC$_{50}$ (μM) | IGF1R IC$_{50}$ (μM) | TrKA IC$_{50}$ (μM) | K299 IC$_{50}$ (μM) | SUDH L-1 IC$_{50}$ (μM) | U937 IC$_{50}$ (μM) | NB-1 IC$_{50}$ (μM) |
|---|---|---|---|---|---|---|---|---|---|
| Compound 1 | AND Enantiomer | 0.005 | | | 0.001 | 0.073 | 0.022 | 1.6 | 0.177 |

Example 7

Metabolite Stability of Compound 1 and Compound 31

TABLE 8

| STRUCTURE (completely hydrogen suppressed graphs) | | Human LM - P1 Half-life (min) | Human LM - P1 CL (ul/min/mg) | Rat LM - P1 Half-life (min) | Rat LM- P1 CL (ul/min/mg) | Mouse LM - P1 Half-life (min) |
|---|---|---|---|---|---|---|
| Compound 31 | AND Enantiomer | >120 | <5.8 | 8.7 | 79.89 | 29.03 |

TABLE 8-continued

| STRUCTURE (completely hydrogen suppresed graphs) | | Human LM - P1 Half-life (min) | Human LM - P1 CL (ul/min/mg) | Rat LM - P1 Half-life (min) | Rat LM- P1 CL (ul/min/mg) | Mouse LM - P1 Half-life (min) |
|---|---|---|---|---|---|---|
| Compound 1 | AND Enantiomer | >120 | <5.8 | 6.993 | 99.97 | 8.4 |

Example 8

Activity of Compound 1 Vs. Compound 31 on KELLY CELLS

Introduction

Recently several activating ALK mutations have been characterized in neuroblastoma. [George et al. Activating mutations in ALK provide a therapeutic target in neuroblastoma. Nature 455:975, 2008.] F1174L, the most common mutation found in primary tumors is also present in the neuroblastoma cell line KELLY (ATCC)[Janoueix-Lerosey et al. Molecular pathogenesis of peripheral neuroblastic tumors. Oncogene 29:1566, 2010.] When ALK expression is abrogated in KELLY cells using siRNA methods their growth rate is significantly reduced. Also the addition of F1174L-ALK to the mouse B-cell line BaF3 renders them IL-3 independent indicating the transformative capacity of this mutation. When taken together these data suggest KELLY cell growth is ALK dependent. To test the ligands ability to inhibit ALK mediated growth in KELLY cells we performed a 3 day growth study in the presence of increasing concentrations of ligand.

Methods

KELLY cells in log-phase growth were plated using full growth media (RPMI, 10% FBS) in 96-well plates at a density of 3,000 cells per well. An equal volume of RPMI (no FBS) with double the indicated concentration of ligand was also added. Each concentration was performed in triplicate. The cells were allowed to proliferate for 3 days at the end of which cell viability was determined using WST-1 reagent (Roche). The resulting absorbance values were represented as a percentage of untreated control and fit using SigmaPlot to determine $IC_{50}$ values.

Results

Compound 1 demonstrated increased potency over 31 in its ability to inhibit ALK mediated KELLY growth. The $IC_{50}$ for Compound 31 (trifluoro-amphetamine) was determined to be 3.15 µM whereas the $IC_{50}$ for Compound 1 (tetrafluoro-amphetamine) 564 nM (FIG. 1).

Example 9

Bioavailability of Compound 1

Study Design

The Animal Care and Use Committee (ACUC) of the University of Tennessee approved the study. Male Sprague-Dawley rats, weighing approximately 250 g, were purchased from Harlan (Indianapolis, Ind., USA). Animals (n=5 per group) were assigned to receive test compound. Intravenous (I.V.) and oral (P.O.) doses were administered at the following dose levels 10 mg/kg. Eighteen h before dosing, the animals were catheterized in the right jugular vein. The animals were provided food (Harlan Teklad 22/5 rodent diet) and water ad libitum. Body weights were determined at the time of catheter placement.

Dosing Vehicles

Doses were administered in a volume of 1 ml/kg. I.v. Doses were administered via the jugular catheter and the catheter was flushed with 3x the dosing volume of heparinized saline. P.o. Doses were administered via gavage. For racemic PF02341066, the dosing vehicle consisted of a 25:75 mixture of dimethylsulfoxide (dmso) and polyethylene glycol 300 (peg 300). For Compound 1 the dosing vehicle consisted of a 10:90 mixture of dimethylsulfoxide (DMSO) and polyethylene glycol 300 (peg 300).

Blood Sampling

Two hundred fifty (250) µL blood samples were drawn from the jugular vein at 0, 10, 20, 30, 60, 120, 240, 480, 720, 1440, and 2880 min following the I.V. dose and 0, 30, 60, 90, 120, 150, 180, 210, 240, 480, 720, 1440, and 2880 min following the P.O. dose. Whole blood samples were collected in sodium heparinized tubes and placed on ice until plasma was separated by centrifugation at 1800 g for 15 min. Plasma was stored at −80° C. until analysis.

Analytical Methods

Non-GLP study sample analysis was performed for rat plasma samples collected below. The study samples were analyzed using a non validated LC-MS/MS testing method.

Pharmacokinetic Data Analysis

The plasma concentration-time data were analyzed by non-compartmental methods using WinNonlin (Phoenix Version 6.0, Pharsight Corporation, Mountain View, Calif., USA).

The area under the plasma concentration-time curve from time zero to infinity (AUC) was calculated by the trapezoidal rule with extrapolation to time infinity. The terminal half-life ($T_{1/2}$) was calculated as $0.693\lambda_z^{-1}$, where $\lambda_z$ was the terminal phase rate constant. The plasma clearance (CL) was calculated as $CL = dose_{i.v.} AUC_{i.v.}^{-1}$, where $dose_{i.v.}$ and $AUC_{i.v.}$ are the i.v. dose and corresponding area under the curve from time 0 to infinity, respectively. The maximal plasma concentration ($C_{max}$) and time at which it occurred ($T_{max}$) for the p.o. doses were determined by visual inspection of the concentration-time profiles. The apparent volume of distribution at equilibrium ($V_{ss}$) was calculated using: $V_{ss} = dose*AUMC_{0\to\infty}(AUC_{0\to\infty})^{-2}$ where $AUMC_{0\to\infty}$ is the area under the first moment of the plasma concentration-time curve extrapolated to infinity. The mean residence time (MRT) was calculated using: $MRT = AUMC_{0\to\infty}(AUC_{0\to\infty})^{-1}$ Oral bioavailability (F) for each dose was calculated using: $F = AUC_{p.o.} dose_{i.v.} (AUC_{i.v.} dose_{p.o.})^{-1}$ where $dose_{p.o.}$, $dose_{i.v.}$, $AUC_{i.v.}$ and $AUC_{p.o.}$ are the mean oral dose, mean i.v. dose, and the corresponding mean areas under the curve from time 0 to 1440 min, respectively.

Results

TABLE 9

Figure 2A:
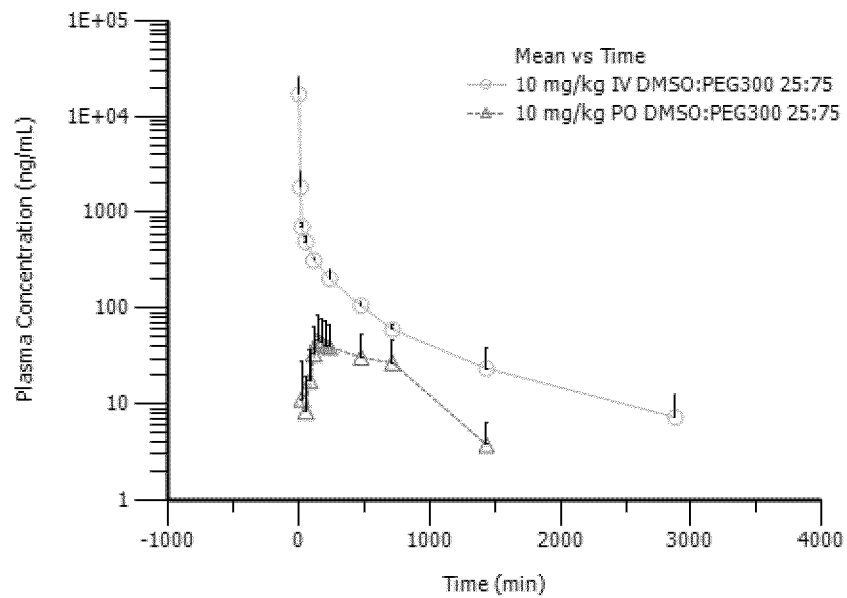
FIGS. 2A and 2B: depict pharmacokinetics of Compound 1 compared with standard agent PF2341066 (see structure in Example 3, Table 4).
Figure 2B:
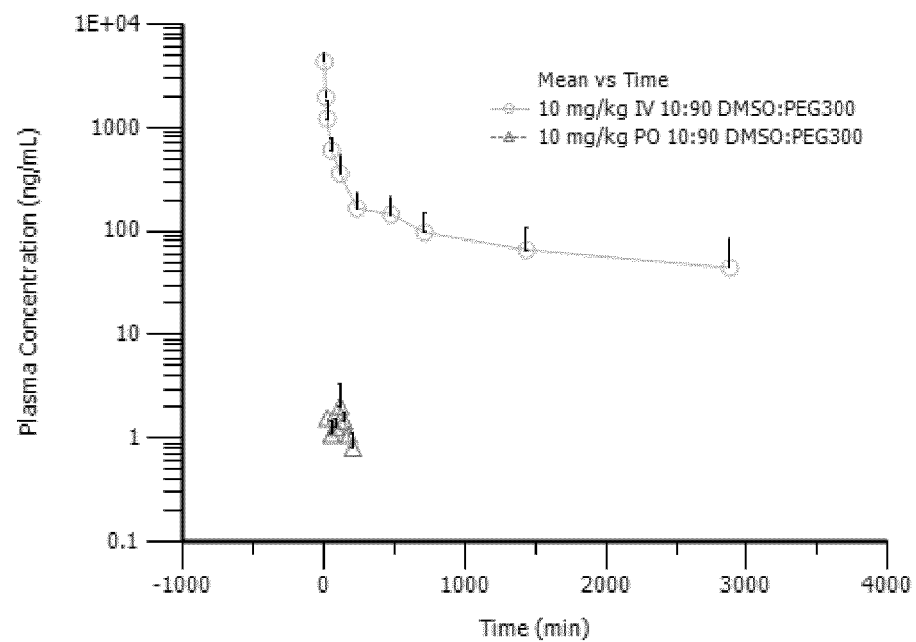
Figure 3A:
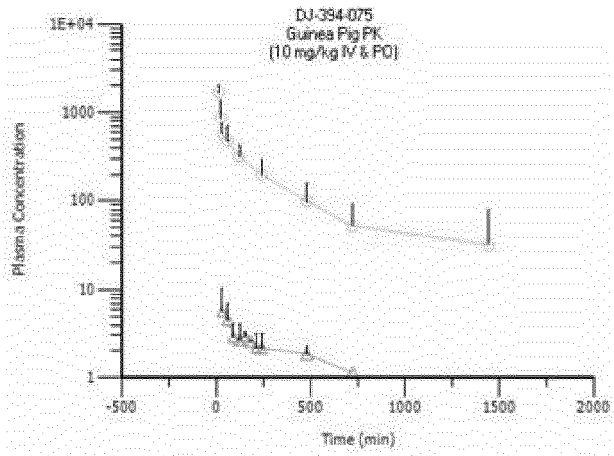
FIGS. 3A-3D: depict pharmacokinetics of Compound 1 in guinea pigs, beagle dogs, and mice.
Figure 3B:
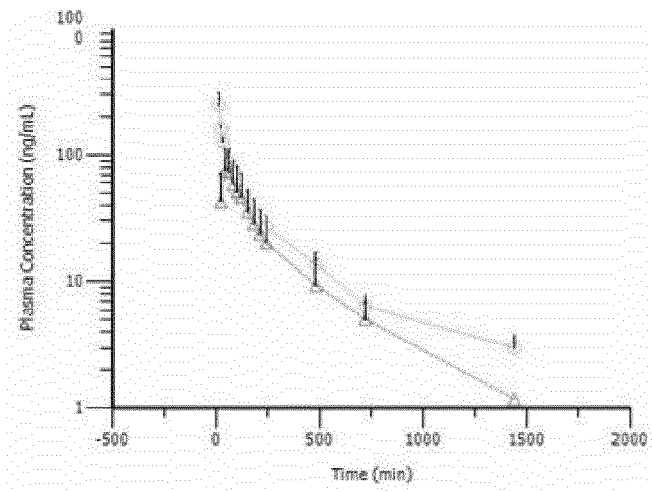
Figure 3C:
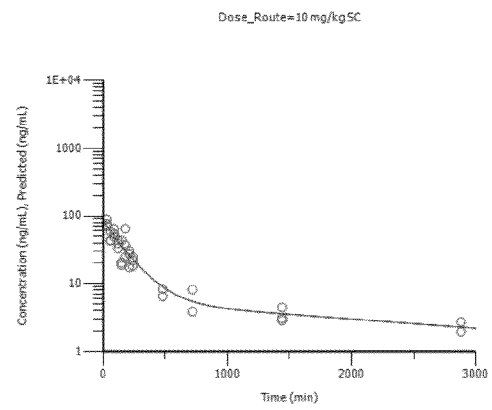
Figure 3D:
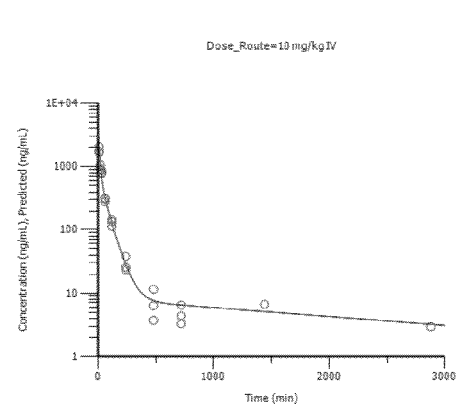

Non-compartmental analysis of 10 mg/kg I.V. doses of racemic PF02341066 and Compound 1 in rats. (See FIG. 2)

| | PF02341066 | | Compound 1 | |
|---|---|---|---|---|
| Parameter | Mean | S.D. | Mean | S.D. |
| $AUC_{0-1440}$ (min*ug/mL) | 1236 | 706 | 329 | 108 |
| CL (mL/min/kg) | 10.5 | 5.87 | 25.5 | 18.3 |
| $T_{1/2}$ (min) | 604 | 246 | 1323 | 705 |
| $V_{ss}$ (L/kg) | 1.33 | 1.05 | 23.9 | 8.20 |
| MRT (min) | 113 | 42.9 | 1362 | 1030 |

TABLE 10

Non-compartmental analysis of 10 mg/kg P.O. doses of racemic PF02341066 and Compound 1 in rats. (See FIG. 2)

| | PF02341066 | | Compound 1 | |
|---|---|---|---|---|
| Parameter | Mean | S.D. | Mean | S.D. |
| $AUC_{0-1440}$ (min*ug/mL) | 33.2 | 21.2 | 0.943 | ND |
| $T_{max}$ (min) | 315 | 273 | 113 | 37.7 |
| $C_{max}$ (ng/mL) | 58.3 | 27.0 | 2.21 | 1.17 |
| F (%) | 2.68 | | 0.287 | |

TABLE 11

(See FIG. 3)

Guinea Pig Pharmacokinetics

| Compound | Parameter | Dose_Route | Units | | SD |
|---|---|---|---|---|---|
| Compound 1 | $AUC_{0-1440}$ | 10 mg/kg IV | min*ug/mL | 214 | 118 |
| Compound 1 | $AUC_{0-1440}$ | 10 mg/kg PO | min*ug/mL | 2.23 | 0.491 |
| Compound 1 | F | 10 mg/kg PO | % | 1% | |

Mouse Pharmacokinetics

| Compound | Parameter | Dose_Route | Units | | |
|---|---|---|---|---|---|
| Compound 1 | AUC | 10 mg/kg IV | min*ug/mL | 106 | |
| Compound 1 | AUC | 10 mg/kg SC | min*ug/mL | 31.3 | |
| Compound 1 | F | 10 mg/kg SC | % | 30% | |

TABLE 11-continued (See FIG. 3)

Dog Pharmacokinetics

| Compound | Parameter | Dose_Route | Units | | SD |
|---|---|---|---|---|---|
| Compound 1 | $AUC_{0-1440}$ | 1 mg/kg IV | min*ug/mL | 29 | 5 |
| Compound 1 | Compound 1 | 5 mg/kg PO | min*ug/mL | 17.2 | 9.1 |
| Compound 1 | F | 5 mg/kg PO | % | 12% | |

Similar studies in mouse and dog suggested substantially improved oral bioavailability in these species for compound 1.

Example 10 hERG Activity

1)

Compound 3

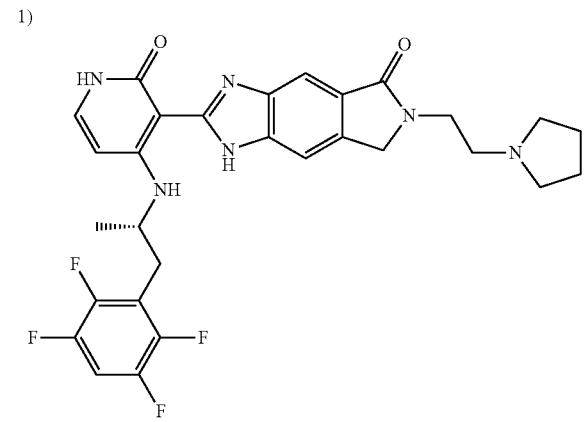

hERG $IC_{50}$ = 3.18 μM

2)

Compound 1

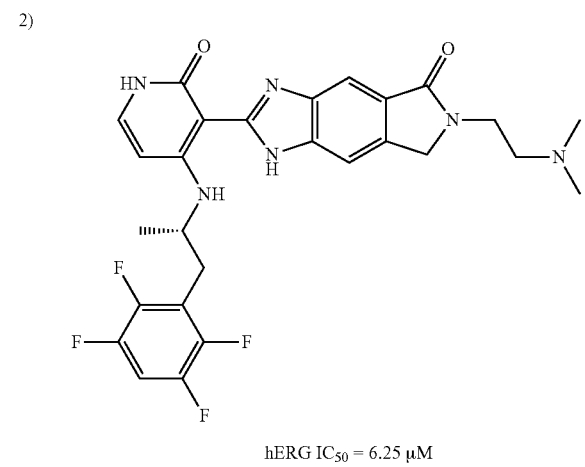

hERG $IC_{50}$ = 6.25 μM

The in vitro effects of Compound 3 and Compound 1 on the hERG (human ether-a-go-go related gene) potassium channel current (a surrogate for $I_{Kr}$, the rapidly activating, delayed rectifier cardiac potassium current) expressed in HEK293 cells were evaluated at rt using the PatchXpress 7000A (Molecular Devices), an automatic parallel patch clamp system.

Each compound was evaluated at 0.3, 3, 10 and 30 μM with each concentration level tested in two cells (n=2). The duration of exposure for each compound concentration was 5 minutes. Results show that compound Compound 3 induced a dose-dependent inhibition of the hERG tail current with a calculated IC$_{50}$ of 3.175 μM; whereas the IC$_{50}$ for compound Compound 1 was 2-fold higher at 6.254 μM. The positive control inhibitor E-4031 caused a mean 97.8% inhibition of the hERG current at 0.5 μM, confirming the sensitivity of the assay system to hERG inhibition.

TABLE 12

| Compound ID | IC$_{50}$ (μM) | Conc. (μM) | Mean % hERG Inhibition | Standard Deviation | n | Individual Data Points (% Inhibition) |
|---|---|---|---|---|---|---|
| Compound 3 | 3.175 | 0.3 | 12.2 | 1.4 | 2 | 13.2 |
|  |  |  |  |  |  | 11.2 |
|  |  | 3 | 49.4 | 0.4 | 2 | 49.7 |
|  |  |  |  |  |  | 49.1 |
|  |  | 10 | 73.3 | 3.5 | 2 | 75.7 |
|  |  |  |  |  |  | 70.8 |
|  |  | 30* | 84.4 | 3.8 | 2 | 87.2 |
|  |  |  |  |  |  | 81.7 |
| Compound 1 | 6.254 | 0.3 | 5.5 | 0.6 | 2 | 5.9 |
|  |  |  |  |  |  | 5.0 |
|  |  | 3 | 39.9 | 5.2 | 2 | 43.6 |
|  |  |  |  |  |  | 36.3 |
|  |  | 10 | 54.4 | 7.0 | 2 | 59.4 |
|  |  |  |  |  |  | 49.4 |
|  |  | 30* | 66.9 | 6.0 | 2 | 71.1 |
|  |  |  |  |  |  | 62.7 |
| E4031 (positive control) | n/a | 0.5 | 97.8 | 0.8 | 3 | 98.4 |
|  |  |  |  |  |  | 97.0 |
|  |  |  |  |  |  | 98.0 |

*low solubility at this concentration for this compound.

Example 11

Activities Against ALK Mutants Conferring PF2341066 (Crizotinib) Resistance Methods NPM-ALK was cloned from KARPAS-299 cells and further subcloned into the mammalian expression construct pCR3.1 (Invitrogen). An EML4-ALK construct was synthesized (Genscript) using the reference sequence (NM_019063.3, transcript variant 1 E13;A20) and subcloned into pCR3.1. Site-directed mutagenesis (QuickChange, Qiagen) was performed on each construct at a single nucleotide whereby upon translation C1156→Y, or F1174→L, or L1196→M, or R1275→Q. All of these mutants except R1275Q have been found in tumor biopsies of patients refractory to PF2341066 (crizotinib) therapy (Sakamoto H, Tsukaguchi T, Hiroshima S, Kodama T, Kobayashi T, Fukami T A, Oikawa N, Tsukuda T, Ishii N, Aoki Y CH5424802, a selective ALK inhibitor capable of blocking the resistant gatekeeper mutant. *Cancer Cell* (2011) 19:679-90). FLT3-ITD was cloned from the MRV411 cell line and further subcloned into pCR3.1. All constructs were stably transfected into the mouse pre-B cell line BaF3 by electroporation (Amaxa). Transformed clones were selected positively by the presence of G418 sulfate (Invitrogen) in the media and negatively by the absence of the otherwise required growth factor, IL-3 (R&D Systems).

Stable clones in log-phase growth were plated using RPMI (MediaTech) and 10% fetal bovine serum (HighClone) in 96-well plates at a density of 3,000 cells per well. An equal volume of RPMI (no FBS) containing drug solution (0.1%) was added. Concentrations ranging from $10^{-10}$ to $10^{-5}$M were evaluated at half-log intervals in triplicate. The cells were allowed to proliferate for 3 days at the end of which cell viability was determined using WST-1 (Roche) reagent according to the manufacturer's instructions. The resulting absorbance values were represented as a percentage of untreated control and fit using a four parameter logic model in Sigma Plot© (Systat Software) to determine IC$_{50}$ values.

Results

TABLE 13

EML4-ALK NSCLC Models

| CMPD | STRUCTURE | GTx-ALK IC50 (nM) | BaF3 Stables IC50 nM ± SEE | | | | |
|---|---|---|---|---|---|---|---|
|  |  |  | EML-4 ALK | C1156Y | F1174L | L1196M | R1275Q | FLT3-ITD |
| Crizotinib | 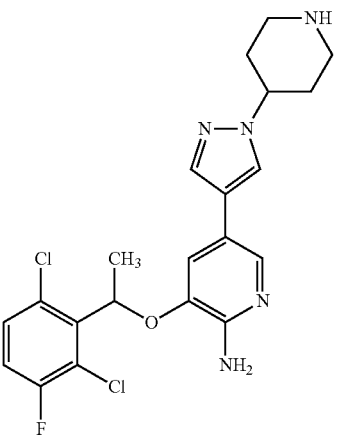 [SMILES: CC(Oc1cc(-c2cnn(C3CCNCC3)c2)cnc1N)c1c(Cl)ccc(F)c1Cl] | 11 | 70 ± 6.7 | 219 ± 11 | 264 ± 9.2 | 265 ± 19 | 85 ± 4.1 | 1.222 ± 88 |

TABLE 13-continued

EML4-ALK NSCLC Models

| CMPD | STRUCTURE | GTx-ALK IC50 (nM) | BaF3 Stables IC50 nM ± SEE | | | | | |
|------|-----------|-------------------|---------|---------|---------|---------|---------|----------|
| | | | EML-4 ALK | C1156Y | F1174L | L1196M | R1275Q | FLT3-ITD |
| Compound 1 | 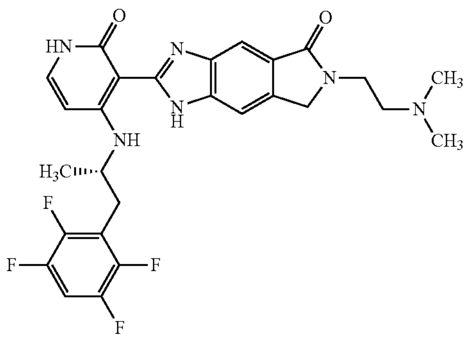 | 5 | 86 ± 14 | 251 ± 8.7 | 548 ± 22 | 355 ± 23 | 126 ± 14 | >3,000 |
| Compound 45 | 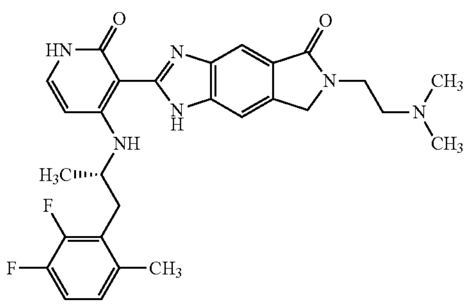 [SMILES: Cc1ccc(F)c(F)c1C[C@H](C)Nc1cc[nH]c(=O)c1-c1nc2cc3c(cc2[nH]1)CN(CCN(C)C)C3=O] | 7 | 66 ± 2.7 | 90 ± 3.2 | 95 ± 10 | 118 ± 8.8 | ~90 | >1,000 |
| Compound 4 | 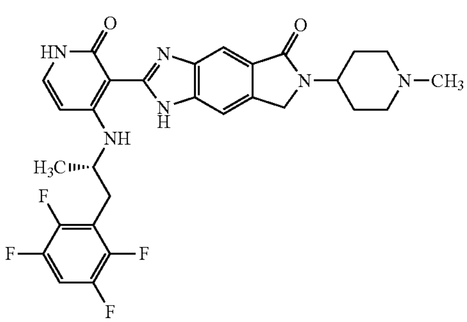 [SMILES: C[C@@H](Cc1c(F)c(F)cc(F)c1F)Nc1cc[nH]c(=O)c1-c1nc2cc3c(cc2[nH]1)CN(C1CCN(C)CC1)C3=O] | 10 | 143 ± 6 | 283 ± 43 | 1,037 ± 17 | 863 ± 190 | 2885 ± 20 | 1,341 ± 143 |

Figure 6B:
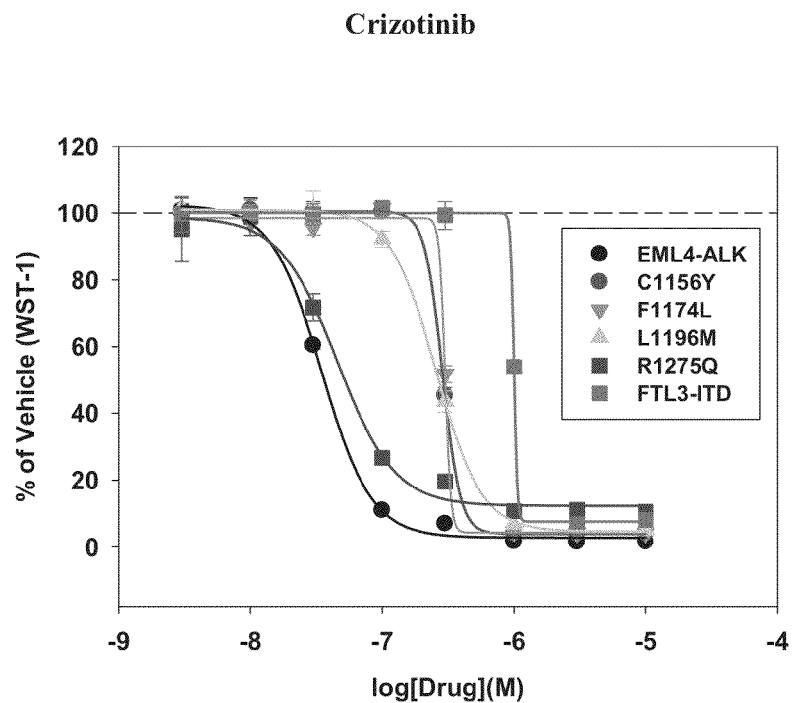

In the EML4-ALK construct the C1156Y, F1174L and L1196M mutations resulted in 3.1-, 3.7- and 3.8-fold reduced potency compared to the EM4-ALK parent construct following treatment with PF2341066 (crizotinib). No resistance was apparent in the R1275Q mutant and PF2341066 (crizotinib) demonstrated ALK selectivity by requiring 1.2 µM to inhibit FLT3-ITD BaF3 cell growth by fifty percent. Compound 1 and Compound 4 were similarly affected with corresponding reduced potencies of 2.9- and 2.0-fold, 6.4- and 7.3-fold, and 4.1- and 6.3-fold, respectively. However Compound 45, (FIG. 6) was only minimally affected demonstrating reduced potencies of only 1.3-, 1.4-, and 1.8-fold in the corresponding mutants.

TABLE 14

NPM-ALK ALCL Models

| CRLID | STRUCTURE | GTx-ALK IC50 (nM) | BaF3 Stables IC50 nM ± SEE | | | | | |
|---|---|---|---|---|---|---|---|---|
| | | | NPM-ALK | C1156Y | F1174L | L1196M | R1275Q | FLT3-ITD |
| Crizotinib | (structure) | 11 | 75 ± 8.0 | 225 ± 43 | 150 ± 15 | 480 ± 35 | 78 ± 8.3 | >1,000 |
| Compound 1 | (structure) | 5 | 78 ± 10 | 195 ± 63 | >2,000 | 745 ± 85 | 279 ± 21 | >3,000 |
| Compound 45 | (structure) | 14 | 46 ± 2.0 | 72 ± 1.2 | 90 ± 14 | 108 ± 11 | 81 ± 4.2 | >1,000 |

Figure 7A:
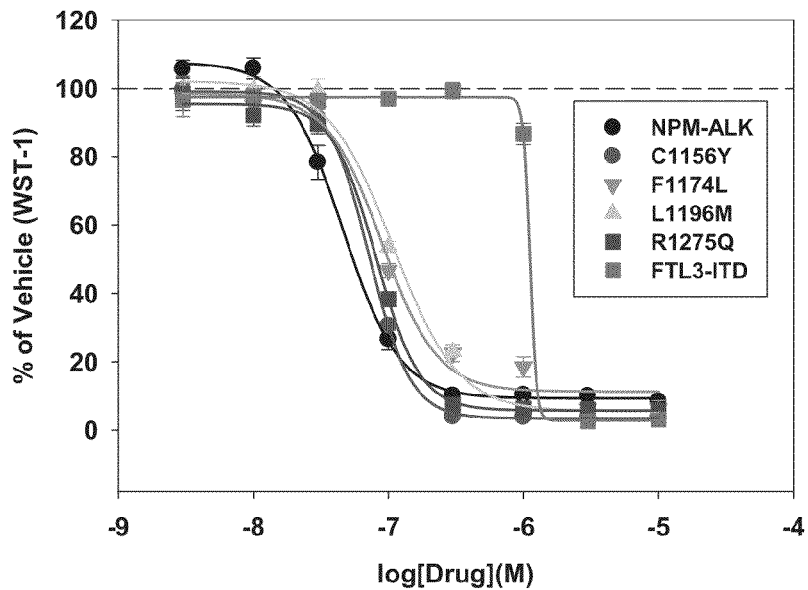
FIGS. 7A and 7B: depict NPM-ALK ALCL Models.
Figure 7B:
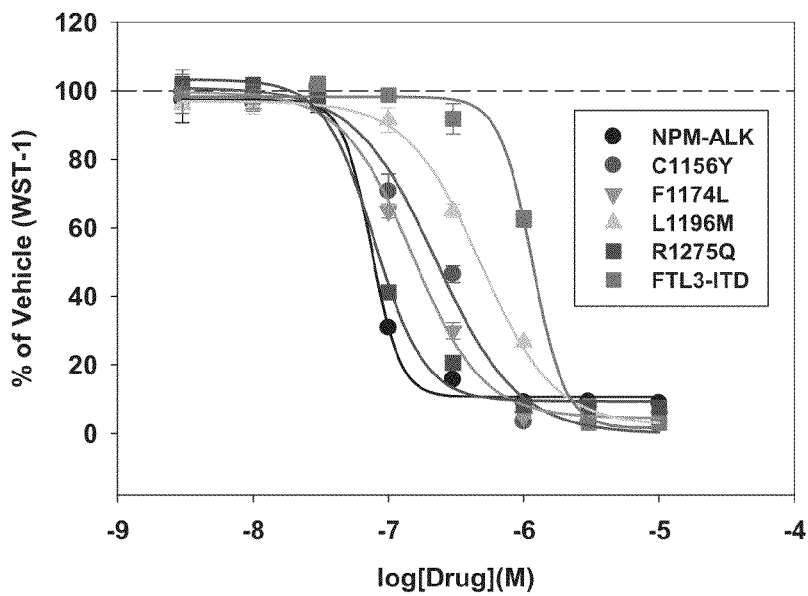

In the NPM-ALK construct the C1156Y, F1174L and L1196M mutations resulted in 3.0-, 2.0- and 6.4-fold reduced potency compared to the NPM-ALK parent construct following treatment with PF2341066 (crizotinib). No resistance was apparent in the R1275Q mutant and PF2341066 (crizotinib) demonstrated ALK selectivity by requiring >1.0 μM to inhibit FLT3-ITD BaF3 cell growth by fifty percent. Compound 1 was similarly affected with corresponding reduced potencies of 2.5-, >25- and 9.6-fold. However Compound 45 (FIG. 7) was only minimally affected demonstrating reduced potencies of only 1.6-, 2.0-, and 2.3-fold in the corresponding mutants.

TABLE 15

| | | Cell Free Data | | | | | | | |
|---|---|---|---|---|---|---|---|---|---|
| | | Cell Free IC50 (nM) | | | | Cellular - BaF3 Stables IC50 (nM) | | | |
| CRLID | STRUCTURE | ALK (WT) | F1174L | L1196M | R1275Q | EML4-ALK | F1174L | L1196M | R1275Q |
| Staurosporine | | 7.1 | 8.1 | 4.5 | 27.4 | — | — | — | — |
| Pfizer | | 15.4 | 20 | 137 | 38 | 70 | 264 | 265 | 85 |
| Compound 45 S isomer | | 3.3 | 36.1 | 7.7 | 16.8 | 66 | 95 | 119 | 90 |

TABLE 15-continued

| | | Cell Free Data | | | | | | | |
|---|---|---|---|---|---|---|---|---|---|
| | | Cell Free IC50 (nM) | | | | Cellular - BaF3 Stables IC50 (nM) | | | |
| CRLID | STRUCTURE | ALK (WT) | F1174L | L1196M | R1275Q | EML4-ALK | F1174L | L1196M | R1275Q |
| Compound 1 S isomer | | 2.8 | 24.1 | 6.2 | 11.6 | 86 | 251 | 355 | 126 |
| Compound 1 R isomer | | 784 | >10.000 | 1413 | 4882 | 1.060 | — | — | — |

Figure 8:
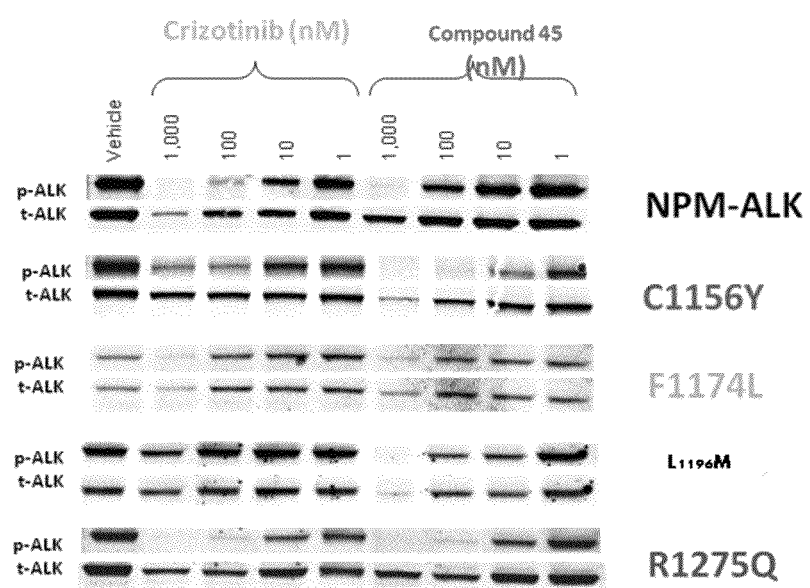
FIG. 8: depicts p-ALK in NPM-BaF3 Mutants.

Carna Biosciences kinases consist of the entire cytoplasmic domain. Most ALK translocations are thought to be cytomplasmic and include a normally cytoplasmic N-terminal partner and the intracellular kinase domain of ALK (FIG. 8). For PF-02341066, the F1174L resistance requires N-terminal fusion partner in the cellular context as no resistance is seen in cell-free assays (Table 15). By comparison Compound 45 demonstrated 10-fold cell free resistance in F1174L mutant which was not reflected in EML4-ALK BaF3 cells and 2-fold L1196M resistance (similar to cellular models) which is an improvement over the 9×L1196M resistance observed for PF-02341066. Compound 45 had 4-fold R1275Q resistance compared to 2-fold for PF-02341066. Compound 1 (S-isomer) demonstrated nearly identical cell free activities to Compound 45, consistent with small changes to amphetamine ring which is not expected to interact directly with F1174 and R1275. Also, the N-terminal fusion partner and the cellular context were required to observe F1174L and L1196M resistance for compound 1.

Compound 1 (R-isomer) was inactive, consistent with the cellular data.

Compound 45 further demonstrated activity in Neuroblastoma (NB-1)-F1174L as demonstrated in FIG. 5. It would be unexpected to observe that the minor structural differences between 1 and 45 would cause a change in sensitivity to PF-02341066 crizotinib resistance.

Example 12

Synthesis of Compounds of this Invention ($R^1$ being Alkyl or Substituted Alkyl)

Synthesis of (Compound 34)

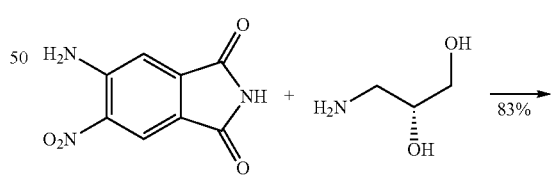

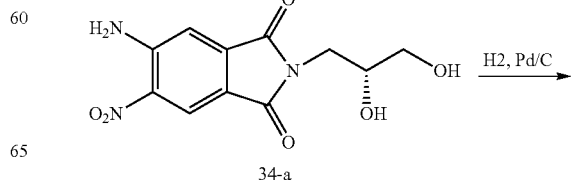

34-a

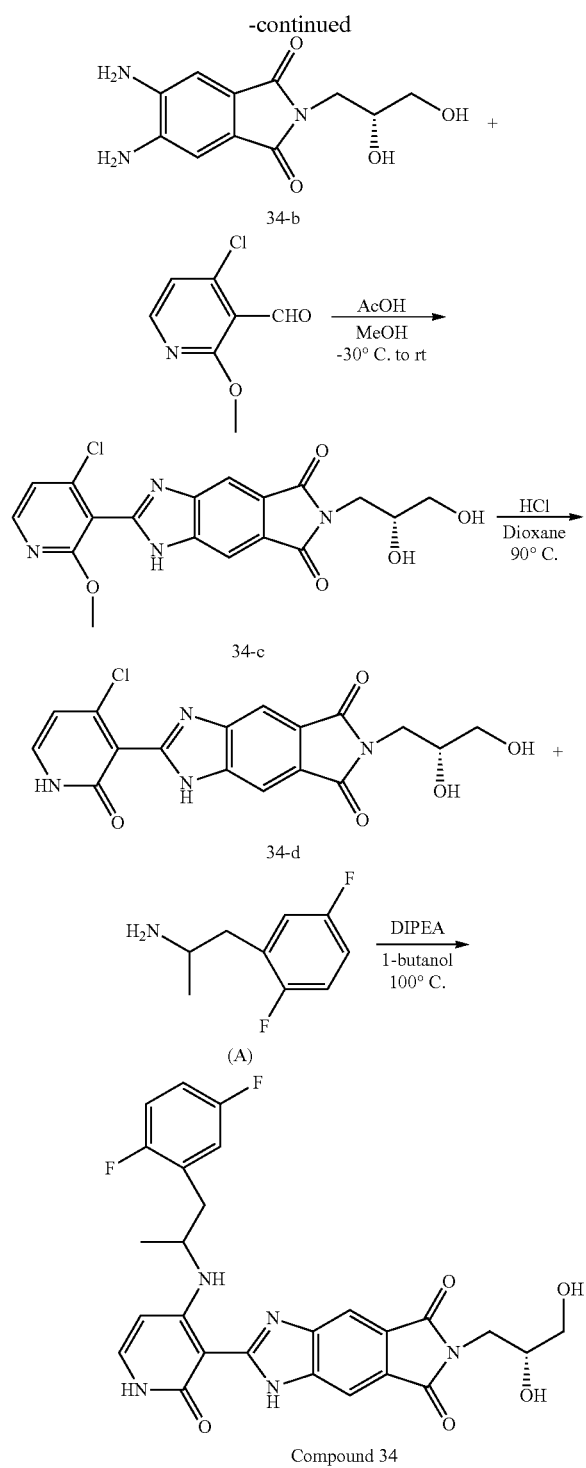

(R)-5-Amino-2-(2,3-dihydroxypropyl)-6-nitroisoindoline-1,3-dione (34-a)

A mixture of 5-amino-6-nitroisoindoline-1,3-dione (2.27 g, 10.98 mmol), (R)-3-aminopropane-1,2-diol (1.0 g, 10.98 mmol), and imidazole (0.75 g, 10.98 mmol) in 100 mL of pentanol was heated to reflux and maintained for 8 h and allowed to cool down to rt. The precipitate was filtered and washed with heptanes and dried to give a yellow crystalline solid (2.57 g, 9.14 mmol, 83%). $^1$H NMR (500 MHz, DMSO-$d_6$) δ 8.38 (s, 2H), 8.31 (s, 1H), 7.45 (1, 1H), 4.90 (d, J=5.0 Hz, 1H), 4.66 (t, J=5.5 Hz, 1H), 3.82-3.74 (m, 1H), 3.55 (d, J=6.5 Hz, 2H), 3.42-3.18 (m, 2H). ESI MS: m/z 279.8 (M−1).

(R)-2-(4-Chloro-2-methoxypyridin-3-yl)-6-(2,3-dihydroxypropyl)imidazo[4,5-f]isoindole-5,7(1H, 6H)-dione (34-c)

To a suspension of (R)-5-amino-2-(2,3-dihydroxypropyl)-6-nitroisoindoline-1,3-dione (0.50 g, 1.78 mmol) in 100 mL of MeOH was added 5 mL of AcOH. The resulting solution was degassed with Argon and then charged with 10% Pd/C (0.19 g, 50% wet, 0.089 mmol) and hydrogenated at 40 psi of hydrogen for 16 h. Another 5 mL of AcOH was added to the mixture and then solids were filtered off. The filtrate was cooled to −30° C. and a solution of 4-chloro-2-methoxynicotinaldehyde (0.31 g, 1.78 mmol) in 50 mL of MeOH was added dropwise under inert atmosphere. The resulting red clear solution was allowed to warm up to rt and stirred for 16 h. Solvent was evaporated and the oily residue was purified by column chromatography (7.5% MeOH in dichloromethane) to give title compound as a yellow solid (0.21 g, 29.3%). $^1$H NMR (500 MHz, DMSO-$d_6$) δ 8.37 (d, J=5.5 Hz, 1H), 8.07 (s, 2H), 7.40 (d, J=5.5 Hz, 1H), 4.92 (d, J=5.0 Hz, 1H), 4.67 (br s, 1H), 4.20-4.14 (br s, 1H), 3.90 (s, 3H), 3.90-3.80 (m, 1H), 3.64-3.60 (m, 2H), 3.42-3.36 (m, 2H). ESI MS: m/z 403.1 (M+1).

(R)-2-(4-chloro-2-oxo-1,2-dihydropyridin-3-yl)-6-(2,3-dihydroxypropyl)imidazo[4,5-f]isoindole-5,7(1H, 6H)-dione (34-d)

To a solution of (R)-2-(4-chloro-2-methoxypyridin-3-yl)-6-(2,3-dihydroxypropyl)imidazo[4,5-f]isoindole-5,7(1H, 6H)-dione (380 mg, 0.95 mmol) in 50 mL of dioxane was added 1 mL of conc. HCl. The mixture was heated to reflux and maintained for 3 h. The solvent was removed by rotary evaporation and the solid residue was triturated with n-butanol three times to give a white solid which was used directly in the next step. APCI MS: m/z 389.0 (M+1).

General Procedure A: Coupling amphetamine substituent to 4-chloro-2-methoxypridin-3-yl-imidazo[4,5-f]isoindole-5,7(1H,6H)-dione fragment A mixture of equal molar amount of substituted amphetamine, 6-substituted 4-chloro-2-oxo-1,2-dihydropyridin-3-yl-imidazo[4,5-f]isoindole-5,7(1H,6H)-dione, and 2 molar equivalents of Hunig base in 25 volume of n-butanol was heated to reflux and maintain for 16 h. TLC was used to monitor reaction progress. Once the reaction reached completion, the solution was allowed to cool to rt. The resulting crystal was filled and washed with MeOH to remove residual n-butanol and Hunig base. The compound was further purified by recrystallization or column chromatography.

2-(4-(1-(2,5-Difluorophenyl)propan-2-ylamino)-2-oxo-1,2-dihydropyridin-3-yl)-6-(R)-2,3-dihydroxypropyl)imidazo[4,5-f]isoindole-5,7(1H,6H)-dione (Compound 34)

Racemic 1-(2,5-difluorophenyl)propan-2-amine (0.16 g, 0.95 mmol) and (R)-2-(4-chloro-2-oxo-1,2-dihydropyridin-3-yl)-6-(2,3-dihydroxypropyl)imidazo[4,5-f]isoindole-5,7 (1H,6H)-dione (380 mg, 0.95 mmol) were submitted to general procedure A to give the title compound as a brown solid. $^1$H NMR (500 MHz, DMSO-$d_6$) δ 13.40 (s, 1H), 11.31 (d, J=6.0 Hz, 1H), 10.91 (d, J=7.5 Hz, 1H), 8.13 (s, 1H), 7.99 (s, 1H), 7.44-7.34 (m, 2H), 7.14-7.12 (m, 1H), 7.10-7.02 (m, 1H), 6.18 (d, J=7.0 Hz, 1H), 4.93 (br s, 1H), 4.66 (br s, 1H), 4.22-4.12 (m, 1H), 3.83 (t, J=6.0 Hz, 1H), 3.64-3.54 (m, 2H), 3.42-3.26 (m, 2H), 2.31-2.98 (m, 2H), 1.33 (d, J=6.5 Hz, 3H). APCI MS: m/z 524.2 (M+1).

Synthesis of Compounds 36-39
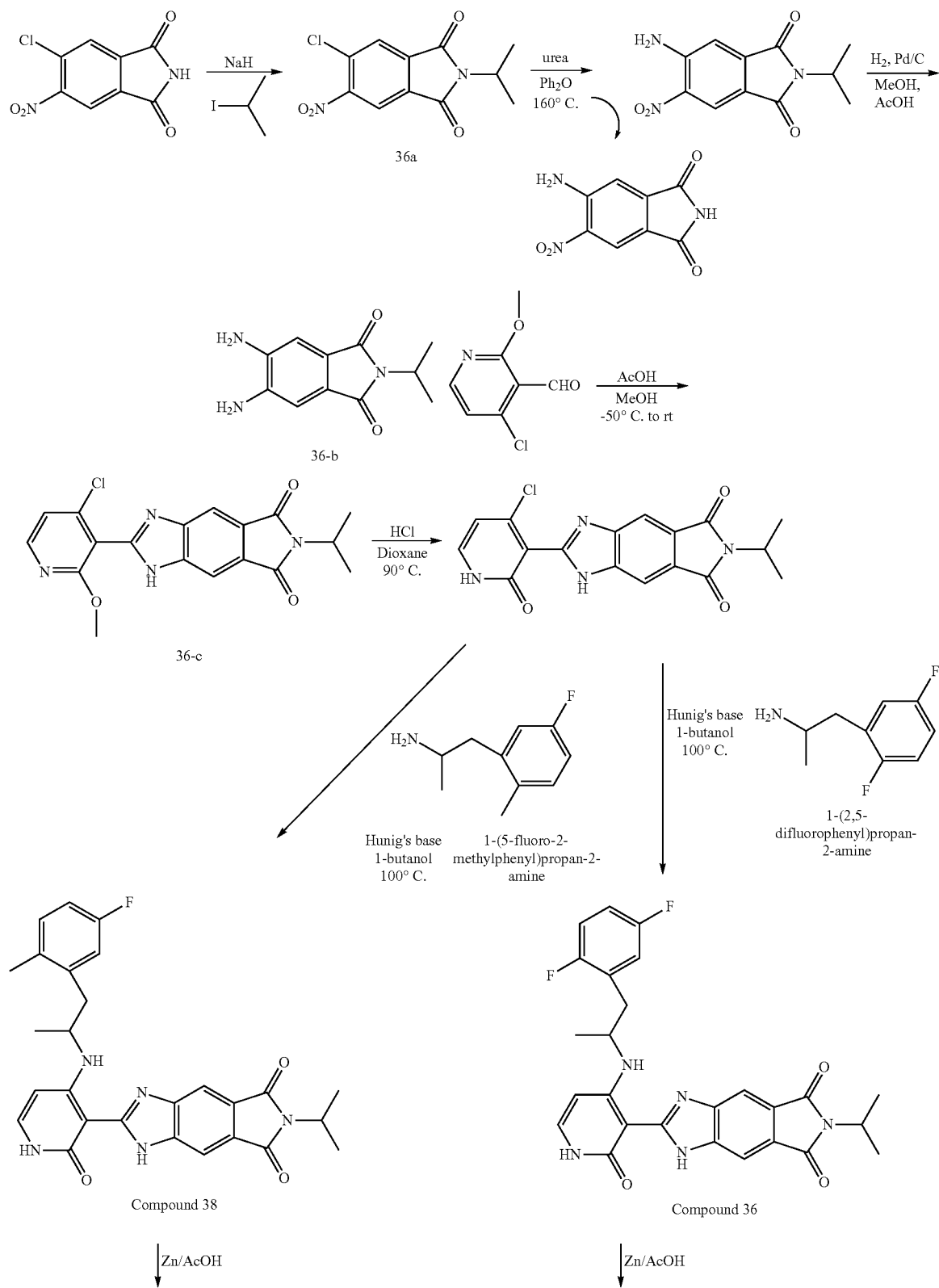

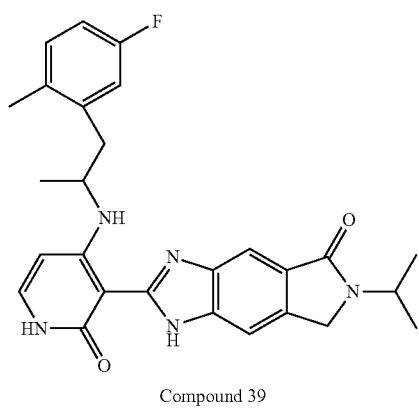

Compound 39

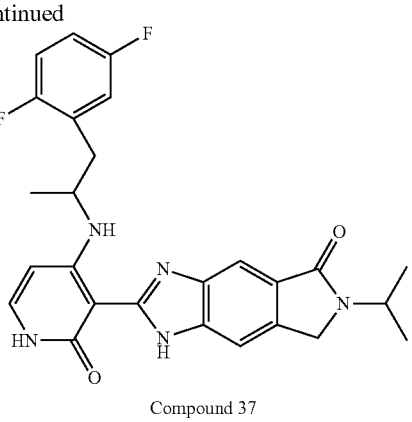

Compound 37

5-Chloro-2-isopropyl-6-nitroisoindoline-1,3-dione (36-a)

NaH (5.30 g, 0.132 mol) was added in portions to a solution of 5-chloro-6-nitroisoindoline-1,3-dione (20.0 g, 88.27 mmol) in 100 mL of anhydrous DMF at 0° C. under argon. The reaction mixture was then stirred at rt for 3 h. 2-Iodopropane (15.0 g, 106 mol) was added dropwise via a syringe at rt under argon. The resulted mixture was stirred for 6 h at rt, hydrolyzed by adding 200 mL of water. The precipitate was isolated, washed with water and dried under vacuum. The solid was purified by column chromatography (silica-gel, $CH_2Cl_2$/Acetone=19/1 v/v) to give a solid product.

5-Amino-2-isopropyl-6-nitroisoindoline-1,3-dione

5-Chloro-2-isopropyl-6-nitroisoindoline-1,3-dione (14.40 g, 59.85 mmol) and urea (35.95 g, 599 mmol) were mixed together under argon. The mixture was stirred and heated to 150° C. for 3 h and cooled to rt. The solid was washed with 200 mL of hot water (90° C.) and filtered to remove the remaining urea. The isolated yellow solid was washed twice with hot water, dried under vacuum and purified by column chromatography (silica-gel $CH_2Cl_2$/acetone=19/1 v/v) to give a solid product.

2-(4-Chloro-2-methoxypyridin-3-yl)-6-isopropylimidazo[4,5-f]isoindole-5,7(1H,6H)-dione (36-c)

To a suspension of 5-amino-2-isopropyl-6-nitroisoindoline-1,3-dione (0.37 g) in 250 mL of MeOH was added 5 mL of AcOH. The resulting solution was degassed with argon and then charged with 10% Pd/C (0.12 g, 50% wet) and hydrogenated at 40 psi of hydrogen for 16 h. Another 2 mL of AcOH was added to the mixture and then solids were filtered off. The filtrate was cooled to −50° C. and a solution of 4-chloro-2-methoxynicotinaldehyde (0.31 g, 1.78 mmol) in 200 mL of MeOH was added dropwise under inert atmosphere. The resulting solution was allowed to warm up to rt and stirred for 16 h. Solvent was evaporated and the oily residue was purified by column chromatography (7.5% MeOH in dichloromethane) to give title compound as a solid (0.23 g, 29.3%). $^1$H NMR (500 MHz, CDCl$_3$) δ58.18 (s, 1H), 8.12 (d, 1H), 8.03 (s, 1H), 7.90 (d, 1H), 6.92 (d, 1H), 6.75 (d, 1H), 5.39 (s, 2H), 4.56 (p, 1H), 3.72 (s, 3H), 3.61 (s, 3H), 1.50 (d, 6H). ESI MS: m/z 371.1 (M+1).

2-(4-Chloro-2-oxo-1,2-dihydropyridin-3-yl)-6-isopropylimidazo[4,5-f]isoindole-5,7(1H,6H)-dione To a solution of (2-(4-chloro-2-methoxypyridin-3-yl)-6-isopropylimidazo[4,5-f]isoindole-5,7(1H,6H)-dione (220 mg) in 50 mL of dioxane was added 1 mL of conc. (12 N) HCl. The mixture was heated to reflux and maintained for 3 h. The solvent was removed by rotary evaporation and the solid residue was triturated with n-butanol three times to give a white solid which was used directly in the next step.

General Procedure A: Coupling amphetamine substituent to 4-chloro-2-methoxypridin-3-yl-imidazo[4,5-f]isoindole-5,7(1H,6H)-dione fragment A mixture of equal molar amount of substituted amphetamine, 6-substituted 4-chloro-2-oxo-1,2-dihydropyridin-3-yl-imidazo[4,5-f]isoindole-5,7(1H,6H)-dione, and 2 molar equivalents of Hunig base in 25 volumes of n-butanol was heated to reflux and maintain for 16 h. TLC was used to monitor reaction progress. Once the reaction reached completion, the solution was allowed to cool to rt. The resulting crystal was filled and washed with MeOH to remove residual n-butanol and Hunig base. The compound was further purified by recrystallization or column chromatography.

2-(4-((1-(5-Fluoro-2-methylphenyl)propan-2-yl)amino)-2-oxo-1,2-dihydropyridin-3-yl)-6-isopropylimidazo[4,5-f]isoindole-5,7(1H,6H)-dione (Compound 38)

Racemic 1-(5-fluoro-2-methylphenyl)propan-2-amine (0.13 g) and 2-(4-chloro-2-oxo-1,2-dihydropyridin-3-yl)-6-isopropylimidazo[4,5-f]isoindole-5,7(1H,6H)-dione (0.2965 mmol) were submitted to general procedure A to give 0.184 g the title compound. $^1$H NMR (500 MHz, CDCl$_3$) δ513.07 (s, 1H), 11.14 (d, 1H), 10.09 (s, 1H), 8.07 (s, 1H), 7.87 (s, 1H), 7.16-7.14 (m, 1H), 7.10-7.06 (m, 1H), 6.97 (d, 1H), 6.89-6.77 (m, 2H), 5.95 (d, 1H), 4.93 (br s, 1H), 4.57 (br s, 1H), 4.02 (br s, 1H), 3.14-3.04 (m, 1H), 3.04-2.94 (m, 1H), 2.36 (s, 3H), 1.54 (d, 6H), 1.48 (d, 3H). APCI MS: m/z 485.9 (M+1).

2-(4-((1-(2,5-Difluorophenyl)propan-2-yl)amino)-2-oxo-1,2-dihydropyridin-3-yl)-6-isopropylimidazo[4,5-f]isoindole-5,7(1H,6H)-dione (Compound 36)

Racemic 1-(2,5-difluorophenyl)propan-2-amine (0.051 g) and 2-(4-chloro-2-oxo-1,2-dihydropyridin-3-yl)-6-isopropylimidazo[4,5-f]isoindole-5,7(1H,6H)-dione (0.2965 mmol) were submitted to general procedure A to give 0.144 g the title compound. $^1$H NMR (500 MHz, DMSO-d$_6$) δ13.04 (s, 1H), 11.20 (d, 1H), 11.10 (d, 1H), 8.13 (s, 1H), 7.82 (t, 2H), 7.36-7.31 (m, 2H), 7.22-7.14 (m, 1H), 7.09-7.03 (m, 1H), 6.17 (d, 1H), 4.51-4.42 (m, 3H), 4.18-4.10 (m, 1H), 3.09-2.93 (m, 2H), 1.32 (d, 3H), 1.25 (d, 6H). APCI MS: m/z 489.9 (M+1).

2-(4-((1-(5-Fluoro-2-methylphenyl)propan-2-yl)amino)-2-oxo-1,2-dihydropyridin-3-yl)-6-isopropyl-6,7-dihydroimidazo[4,5-f]isoindol-5(1H)-one (Compound 39)

2-(4-((1-(5-Fluoro-2-methylphenyl)propan-2-yl)amino)-2-oxo-1,2-dihydropyridin-3-yl)-6-isopropylimidazo[4,5-f]isoindole-5,7(1H,6H)-dione (0.138 g) and zinc powder (0.4 g) were suspended in acetic acid (10 mL). The reaction mixture was stirred and heated to reflux overnight under argon. Then, the solvent was removed under reduced pressure. The residue solid was stirred in 100 mL of saturated $K_2CO_3$ solution. The white solid was filtered out, dried under vacuum and extracted with $CH_2Cl_2$/MeOH (7/3 v/v) three times (300 mL). The extracts were concentrated to dryness. The residue was purified by column chromatography (silica-gel, $CH_2Cl_2$/MeOH=9/1 v/v) to give an off-white solid product, 0.086 g. MS: 473.9 [M+1]. $^1$H NMR (DMSO-$d_6$, 500 MHz): δ 13.06 (s, 1H), 11.15 (s, 1H), 11.01-11.00 (d, 1H), 7.95 (s, 0.5H), 7.84-7.82 (d, 0.5H), 7.70 (s, 0.5H), 7.30-7.10 (m, 3H), 6.91-6.84 (m, 1H), 6.15-6.11 (dd, 1H), 4.51-4.42 (m, 3H), 4.18-4.13 (m, 1H), 3.32 (s, 1H), 2.99-2.97 (m, 2H), 2.36 (d, 3H), 1.34 (d, 3H), 1.23 (d, 6H).

2-(4-((1-(2,5-Difluorophenyl)propan-2-yl)amino)-2-oxo-1,2-dihydropyridin-3-yl)-6-isopropyl-6,7-dihydroimidazo[4,5-f]isoindol-5(1H)-one (Compound 37)

2-(4-((1-(2,5-Difluorophenyl)propan-2-yl)amino)-2-oxo-1,2-dihydropyridin-3-yl)-6-isopropylimidazo[4,5-f]isoindole-5,7(1H,6H)-dione (0.115 g) and zinc powder (0.290 g) were suspended in acetic acid (10 mL). The reaction mixture was stirred and heated to reflux overnight under argon. Then, the solvent was removed under reduced pressure. The residue solid was stirred in 100 mL of saturated $K_2CO_3$ solution. The white solid was filtered out, dried under vacuum and extracted with $CH_2Cl_2$/MeOH (7/3 v/v) three times (300 mL). The extracts were concentrated to dryness. The residue was purified by column chromatography (silica-gel, $CH_2Cl_2$/MeOH=9/1 v/v) to give an off-white solid product, 0.055 g. MS: 475.9 [M+1]. $^1$H NMR (CDCl$_3$, 500 MHz): δ 12.79 (s, 1H), 12.73 (s, 1H), 11.57 (d, 1H), 11.40 (d, 1H), 11.38 (d, 1H), 11.07 (d, 1H), 8.16 (s, 1H), 7.96 (s, 1H), 7.70 (s, 1H), 7.50 (s, 1H), 7.30 (t, 1H), 7.26 (t, 1H), 7.06-6.97 (m, 5H), 6.91-6.86 (m, 2H), 6.13 (d, 2H), 4.77-4.71 (m, 2H), 4.43 (d, 5H), 4.07-4.00 (m, 2H), 3.18-3.13 (m, 2H), 2.93-2.89 (q, 2H), 1.74 (s, 6H), 1.44 (d, 8H), 1.34-1.23 (m, 16H).

Synthesis of Compound 40

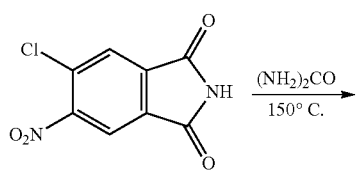

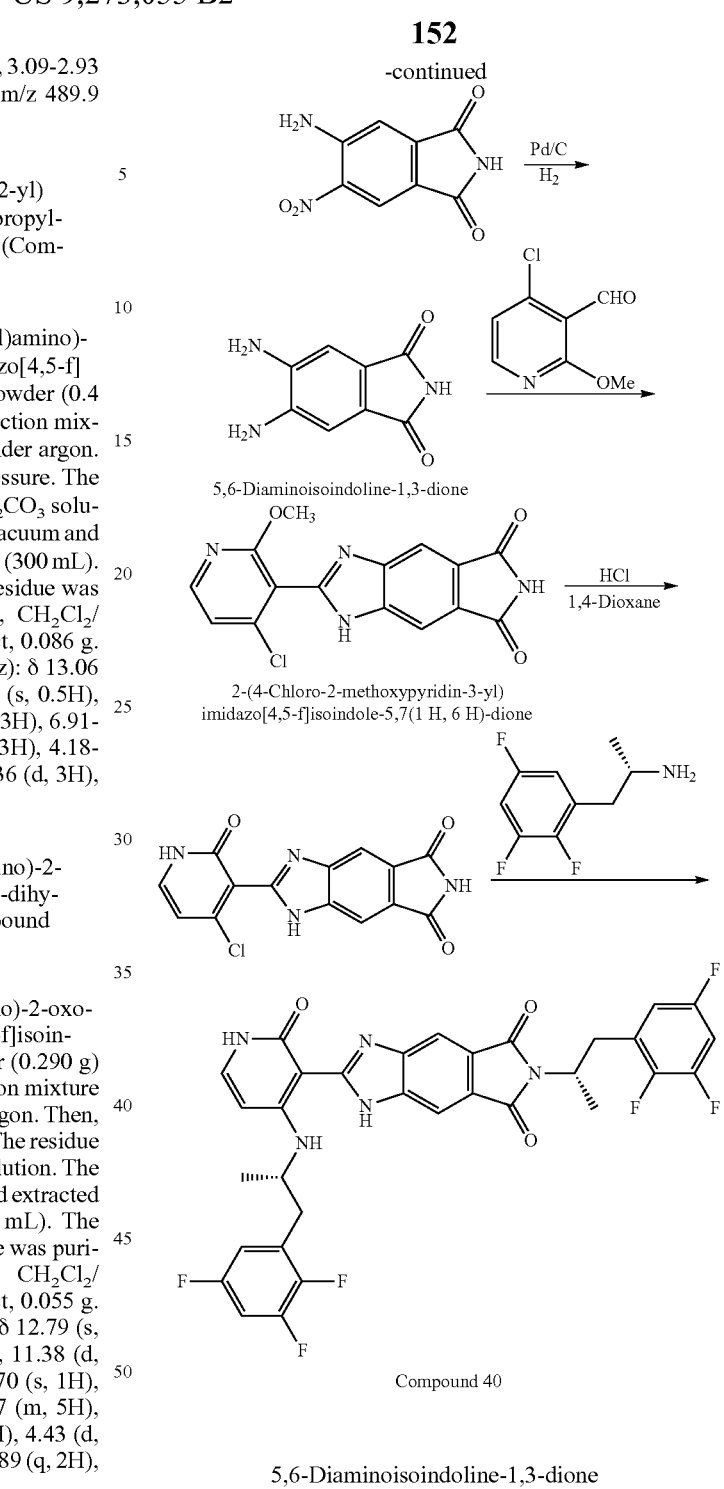

Compound 40

5,6-Diaminoisoindoline-1,3-dione

Pd/C (3.0 g, 10% on charcoal, 50% wet) was added to a solution of 5-amino-6-nitroisoindoline-1,3-dione (5.0 g, 24.14 mmol) in 100 mL of MeOH/HOAc (3/1 v/v) and hydrogenated under $H_2$ (30 psi) for 3 h at rt. Then, the solvent was removed under reduced pressure. The residue was acidified by adding 6 N HCl solution. The aqueous solution was filtered out and its pH was adjusted to 9 by adding $K_2CO_3$. The orange-brown precipitate was filtered, washed with water and dried under vacuum to give a diamine product as an orange solid, 3.60 g, 84.2% yield. MS: 200.0 [M+Na]$^+$. $^1$H NMR (DMSO-$d_6$, 500 MHz) δ 10.26 (s, 1H), 6.80 (s, 2H), 5.52 (s, 4H).

2-(4-Chloro-2-methoxypyridin-3-yl)imidazo[4,5-f]isoindole-5,7(1H, 6H)-dione 5,6-Diaminoisoindoline-1,3-dione (2.88 g, 16.26 mmol) and 4-chloro-2-methoxynicotinaldehyde (2.79 g, 16.26 mmol) were suspended in MeOH/HOAc (200 mL, 3/1 v/v) at rt under air. The reaction mixture was stirred under air overnight and diluted with 200 mL of water. The solid was filtered, washed with acetone and recrystallized from hot EtOAc to give a pale-yellow solid product, 4.67 g, 87.5% yield. MS: 329.0 [M+H]$^+$. $^1$H NMR (DMSO-d$_6$, 500 MHz): δ 13.23 (s, 1H), 8.36 (d, 1H, J=5.5 Hz), 8.02 (S, 2H), 7.39 (d, 1H, J=6.0 Hz), 3.89 (s, 3H).

2-(2-oxo-4-(1-(2,3,5-trifluorophenyl)propan-2-ylamino)-1,2-dihydropyridin-3-yl)-6-(1-(2,3,5-trifluorophenyl)propan-2-yl)imidazo[4,5-f]isoindole-5,7(1H,6H)-dione (Compound 40)

2-(4-Chloro-2-methoxypyridin-3-yl)imidazo[4,5-f]isoindole-5,7(1H, 6H)-dione (0.522 g, 1.59 mmol) was dissolved in 10 mL of 1,4-dioxane and 5 mL of concentrated HCl at rt. The reaction mixture was stirred at rt overnight. Then, the volatile was removed to give a yellow-brown solid. This solid was mixed with 1-(2,3,5-trifluorophenyl)propan-2-amine (0.30 g, 1.59 mmol), N,N-diisopropylethylamine (1.10 g, 9.54 mmol) and n-butanol (20 mL) in a flask. The reaction mixture was stirred and heated to reflux overnight under argon. Then, volatiles were removed under reduced pressure. The residue solid was purified by column chromatography (silica-gel, CH$_2$Cl$_2$/MeOH=9/1 v/v) to give a yellow-brown solid product, 0.78 g, 76.5% yield. MS: 640.2 [M+H]$^+$. $^1$H NMR (DMSO-d$_6$, 500 MHz): δ 13.38 (s, 1H), 11.32-11.29 (m, 1H), 10.94-10.91 (m, 1H), 8.06 (s, 1H), 7.84 (s, 1H), 7.64-7.60 (m, 1H), 7.37-7.34 (m, 1H), 7.08-6.99 (m, 2H), 6.14 (d, 1H, J=7.5 Hz), 4.50 (m, 1H), 4.18 (m, 1H), 3.37-3.32 (m, 1H), 3.15-3.01 (m, 3H), 1.57 (d, 3H, J=7.0 Hz), 1.35 (d, 3H, J=6.5 Hz).

Synthesis of Compound 32 and Compound 33

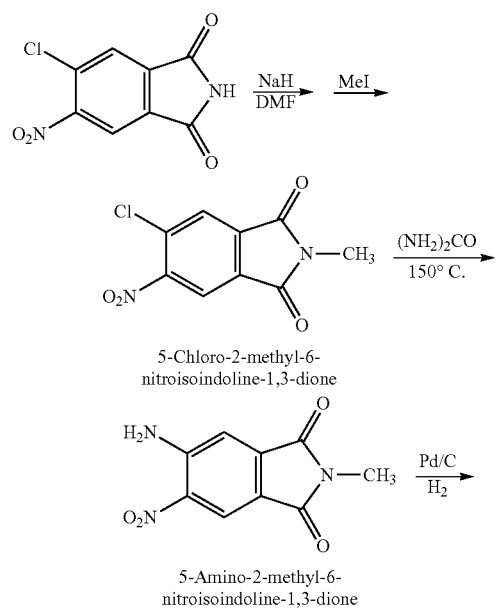

5-Chloro-2-methyl-6-nitroisoindoline-1,3-dione

5-Amino-2-methyl-6-nitroisoindoline-1,3-dione

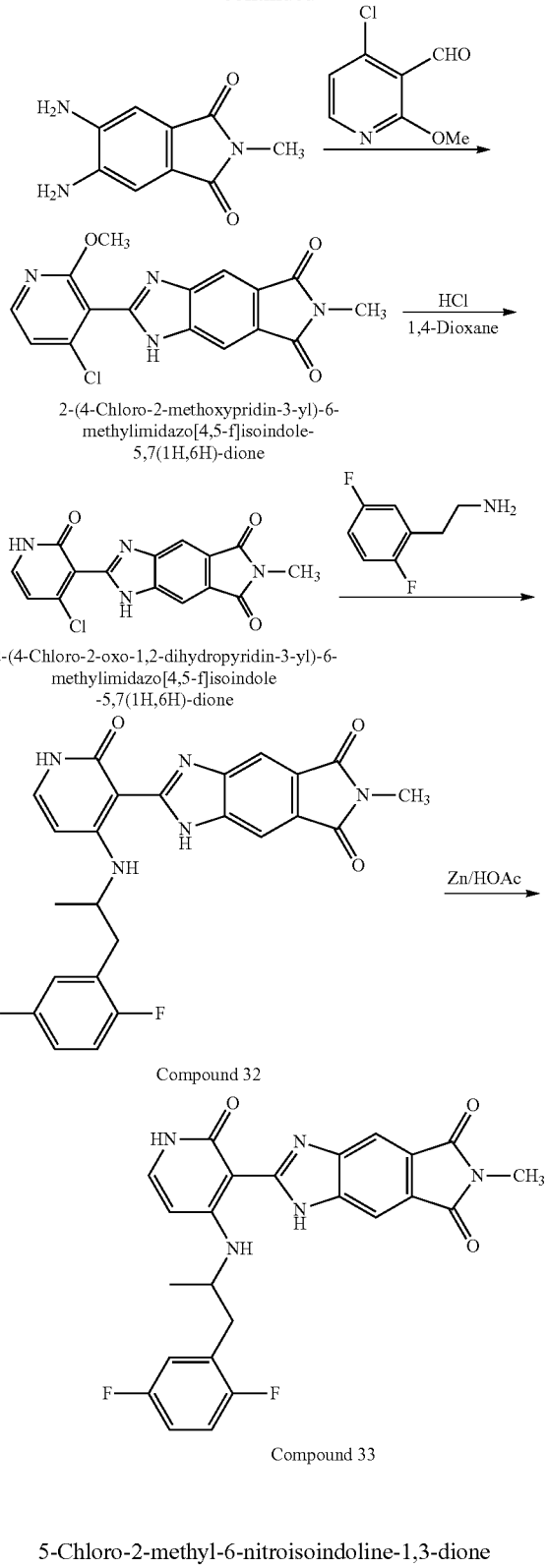

2-(4-Chloro-2-methoxypyridin-3-yl)-6-methylimidazo[4,5-f]isoindole-5,7(1H,6H)-dione 2-(4-Chloro-2-oxo-1,2-dihydropyridin-3-yl)-6-methylimidazo[4,5-f]isoindole-5,7(1H,6H)-dione Compound 32

Compound 33

5-Chloro-2-methyl-6-nitroisoindoline-1,3-dione

NaH (5.30 g, 0.132 mol) was added in portions to a solution of 5-chloro-6-nitroisoindoline-1,3-dione (20.0 g, 88.27 mmol) in 100 mL of anhydrous DMF at 0° C. under argon. The reaction mixture was then stirred at rt for 3 h. MeI (15.0 g, 106 mol) was added dropwise via a syringe at rt under argon. The resulted mixture was stirred for 6 h at rt, hydrolyzed by adding 200 mL of water. The brown precipitate was isolated, washed with water and dried under vacuum. The solid was purified by column chromatography (silica-gel, CH$_2$Cl$_2$/Acetone=19/1 v/v) to give a yellow solid product, 15.6 g, 73.6% yield. MS: 239.2 [M–H]$^-$. $^1$H NMR (DMSO-d$_6$, 500 MHz): δ 8.54 (s, 1H), 8.32 (s, 1H), 3.07 (s, 3H).

5-Amino-2-methyl-6-nitroisoindoline-1,3-dione

5-Chloro-2-methyl-6-nitroisoindoline-1,3-dione (14.40 g, 59.85 mmol) and urea (35.95 g, 599 mmol) were mixed together under argon. The mixture was stirred and heated to 150° C. for 3 h and cooled to rt. The solid was washed with 200 mL of hot water (90° C.) and filtered to remove the remaining urea. The isolated yellow solid was washed twice with hot water, dried under vacuum and purified by column chromatography (silica-gel CH$_2$Cl$_2$/acetone=19/1 v/v) to give a yellow solid product, 8.75 g, 66.1% yield. MS: 219.6 [M–H]$^-$. $^1$H NMR (DMSO-d$_6$, 500 MHz): δ 8.39 (s, 2H), 8.26 (s, 1H), 7.40 (s, 1H), 2.99 (s, 3H).

2-(4-Chloro-2-methoxypyridin-3-yl)-6-methylimidazo[4,5-f]isoindole-5,7(1H,6H)-dione Pd/C (2.0 mg, 10% on charcoal, 50% wet) was added to a solution of 5-amino-2-methyl-6-nitroisoindoline-1,3-dione (6.50 g, 29.39 mmol) in 130 mL of MeOH/HOAc (3/1 v/v) and hydrogenated under H$_2$ (50 psi) for 4 h at rt. Then, the solvent was removed under reduced pressure. The residue was extracted with MeOH. The solvent was removed and residue solid was dried under vacuum to give diamine product as a yellow-orange solid (4.05 g, 72.1% yield) which was used in next step reaction without further purification. Diamine (0.30 g, 1.57 mmol) and 4-chloro-2-methoxynicotinaldehyde (0.26 g, 1.57 mmol) were suspended in MeOH/HOAc (40 mL, 3/1 v/v) at rt under air. The reaction mixture was stirred under air overnight. The pale-yellow precipitate was isolated, washed with EtOAc, and dried under vacuum to give a pale-yellow solid, 0.44 g, 81.8% yield. MS: 340.9 [M+Na]$^+$. $^1$H NMR (DMSO-d$_6$, 500 MHz): δ 13.61 (s, 1H), 8.38 (d, 1H, J=5.5 Hz), 8.12 (s, 2H), 8.01 (s, 1H), 7.40 (d, 1H, J=6.0 Hz), 3.89 (s, 3H), 3.07 (s, 3H).

2-(4-Chloro-2-oxo-1,2-dihydropyridin-3-yl)-6-methylimidazo[4,5-f]isoindole-5,7(1H,6H)-dione 2-(4-Chloro-2-methoxypyridin-3-yl)-6-methylimidazo[4,5-f]isoindole-5,7(1H,6H)-dione (2.0 g, 5.84 mmol) was suspended in 50 mL of 1,4-dioxane at rt. Concentrated HCl (10 mL) was added. The reaction mixture was stirred and heated to reflux for 6 h. Then, it was evaporated to dryness to afford a pale-yellow solid product as a HCl salt. MS: 327.9 [M–H]$^-$. $^1$H NMR (DMSO-d$_6$, 500 MHz): δ 8.11 (s, 2H), 8.01 (s, 1H), 7.77 (d, 1H, J=7.0 Hz), 6.63 (d, 1H, J=7.0 Hz), 3.06 (s, 3H).

2-(4-(1-(2,5-Difluorophenyl)propan-2-ylamino)-2-oxo-1,2-dihydropyridin-3-yl)-6-methylimidazo[4,5-f]isoindole-5,7(1H,6H)-dione (Compound 32)

2-(4-Chloro-2-oxo-1,2-dihydropyridin-3-yl)-6-methylimidazo[4,5-f]isoindole-5,7(1H,6H)-dione (0.44 g, 1.34 mmol), 1-(2,5-difluorophenyl)propan-2-amine (0.27 g, 1.61 mmol), n-butanol (30 mL) and N,N-diisopropylethylamine (5 mL) were mixed together in a flask. The reaction mixture was stirred and heated to reflux overnight under argon. Solvents were removed under reduced pressure. The residue solid was purified by column chromatography (silica-gel, CH$_2$Cl$_2$/MeOH=9/1 v/v) to give a brown solid product, 0.38 g, 61.3% yield. MS: 461.9 [M–H]$^-$. $^1$H NMR (DMSO-d$_6$, 500 MHz): δ 13.40 (s, 1H), 11.31 (s, 1H), 10.92 (d, 1H, J=8.0 Hz), 8.13 (s, 1H), 8.00 (s, 1H), 7.42-7.37 (m, 2H), 7.20-7.18 (m, 1H), 7.09-7.04 (m, 1H), 6.18 (d, 1H, J=8.0 Hz), 4.19-4.14 (m, 1H), 3.06 (s, 3H), 3.04-2.98 (m, 2H), 1.33 (d, 3H, J=6.0 Hz).

2-(4-(1-(2,5-Difluorophenyl)propan-2-ylamino)-2-oxo-1,2-dihydropyridin-3-yl)-6-methyl-6,7-dihydroimidazo[4,5-f]isoindol-5(1H)-one (Compound 33)

2-(4-(1-(2,5-Difluorophenyl)propan-2-ylamino)-2-oxo-1,2-dihydropyridin-3-yl)-6-methylimidazo[4,5-f]isoindole-5,7(1H,6H)-dione (0.33 g, 0.71 mmol) and zinc powder (1.12 g, 17.09 mmol) were suspended in acetic acid (30 mL). The reaction mixture was stirred and heated to reflux overnight under argon. Then, the solvent was removed under reduced pressure. The residue solid was stirred in 100 mL of saturated K$_2$CO$_3$ solution. The white solid was filtered out, dried under vacuum and extracted with CH$_2$Cl$_2$/MeOH (7/3 v/v) three times (100 mL). The extracts were concentrated to dryness. The residue was purified by column chromatography (silica-gel, CH$_2$Cl$_2$/MeOH=9/1 v/v) to give a pale-yellow solid product, 0.20 g, 62.7% yield. MS: 448.0 [M–H]$^-$. $^1$H NMR (DMSO-d$_6$, 500 MHz): δ 13.04 (s, 1H), 11.23 (s, 1H), 11.14-11.11 (m, 1H), 7.96 (s, 0.5H), 7.84 (s, 0.5H), 7.79 (s, 0.5H), 7.68 (s, 0.5H), 7.41-7.34 (m, 2H), 7.22-7.16 (m, 1H), 7.11-7.05 (m, 1H), 4.49 (s, 2H), 4.16-4.13 (m, 1H), 3.10 (s, 3H), 3.07-2.94 (m, 2H), 1.34-1.31 (m, 3H).

Synthesis of Compounds 41 and 42

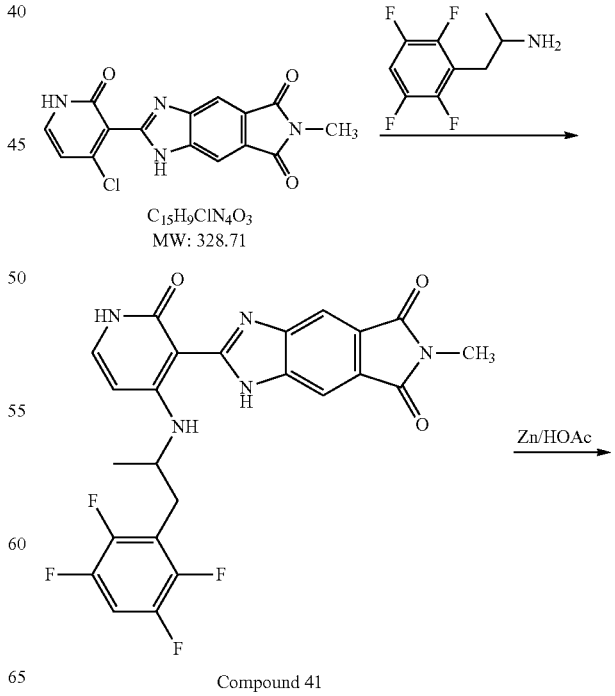

Compound 41

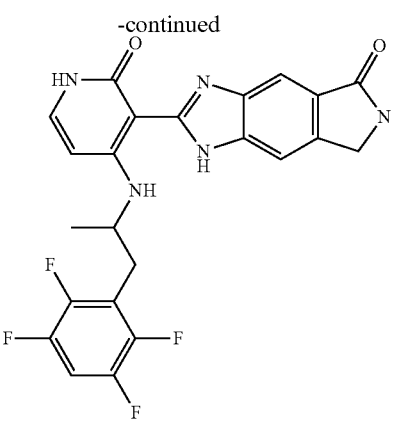

Compound 42

2-(4-(1-(2,3,5,6-Tetrafluorophenyl)propan-2-ylamino)-2-oxo-1,2-dihydropyridin-3-yl)-6-methylimidazo[4,5-f]isoindole-5,7(1H,6H)-dione (Compound 41)

2-(4-Chloro-2-oxo-1,2-dihydropyridin-3-yl)-6-methylimidazo[4,5-f]isoindole-5,7(1H,6H)-dione (0.58 g, 1.75 mmol), 1-(2,3,5,6-tetrafluorophenyl)propan-2-amine (0.36 g, 1.75 mmol), n-butanol (30 mL) and N,N-diisopropylethylamine (5 mL) were mixed together in a flask. The reaction mixture was stirred and heated to reflux overnight under argon. Solvents were removed under reduced pressure. The residue solid was purified by column chromatography (silica-gel, $CH_2Cl_2$/MeOH=9/1 v/v) to give a yellow solid product, 0.66 g, 75.9% yield. MS: 497.8 [M–H]⁻. $^1$H NMR (DMSO-$d_6$, 500 MHz): δ 13.44 (s, 1H), 10.90 (d, 1H, J=7.0 Hz), 8.12 (s, 1H), 7.93-7.90 (m, 2H), 7.73-7.71 (m, 1H), 7.40 (d, 1H, J=7.0 Hz), 6.16 (d, 1H, J=7.5 Hz), 4.23 (m, 1H), 3.38 (m, 2H), 3.05 (s, 3H), 1.38 (d, 3H, J=6.0 Hz).

6-Methyl-2-(2-oxo-4-(1-(2,3,5,6-tetrafluorophenyl)propan-2-ylamino)-1,2-dihydropyridin-3-yl)-6,7-dihydroimidazo[4,5-f]isoindole-5(1H)-one (Compound 42)

2-(4-(1-(2,3,5,6-Tetrafluorophenyl)propan-2-ylamino)-2-oxo-1,2-dihydropyridin-3-yl)-6-methylimidazo[4,5-f]isoindole-5,7(1H,6H)-dione (0.51 g, 1.02 mmol) and zinc powder (1.60 g, 24.51 mmol) were suspended in acetic acid (30 mL). The reaction mixture was stirred and heated to reflux overnight under argon. Then, the solvent was removed under reduced pressure. The residue solid was stirred in 100 mL of saturated $K_2CO_3$ solution. The white solid was filtered out, dried under vacuum and extracted with $CH_2Cl_2$/MeOH (7/3 v/v) three times (300 mL). The extracts were concentrated to dryness. The residue was purified by column chromatography (silica-gel, $CH_2Cl_2$/MeOH=9/1 v/v) to give a pale-yellow solid product, 0.31 g, 62.6% yield. MS: 508.0 [M+Na]⁺. $^1$H NMR (DMSO-$d_6$, 500 MHz): δ 13.03 (s, 1H), 11.24 (s, 1H), 11.14-11.11 (m, 1H), 7.95 (s, 0.5H), 7.78-7.74 (m, 2H), 7.61 (s, 0.5H), 7.35 (s, 1H), 6.15 (s, 1H), 4.48 (s, 2H), 4.22 (m, 1H), 3.17-3.10 (m, 2H), 3.09 (s, 3H), 1.37 (m, 3H).

Synthesis of Compound 43 and Compound 43a

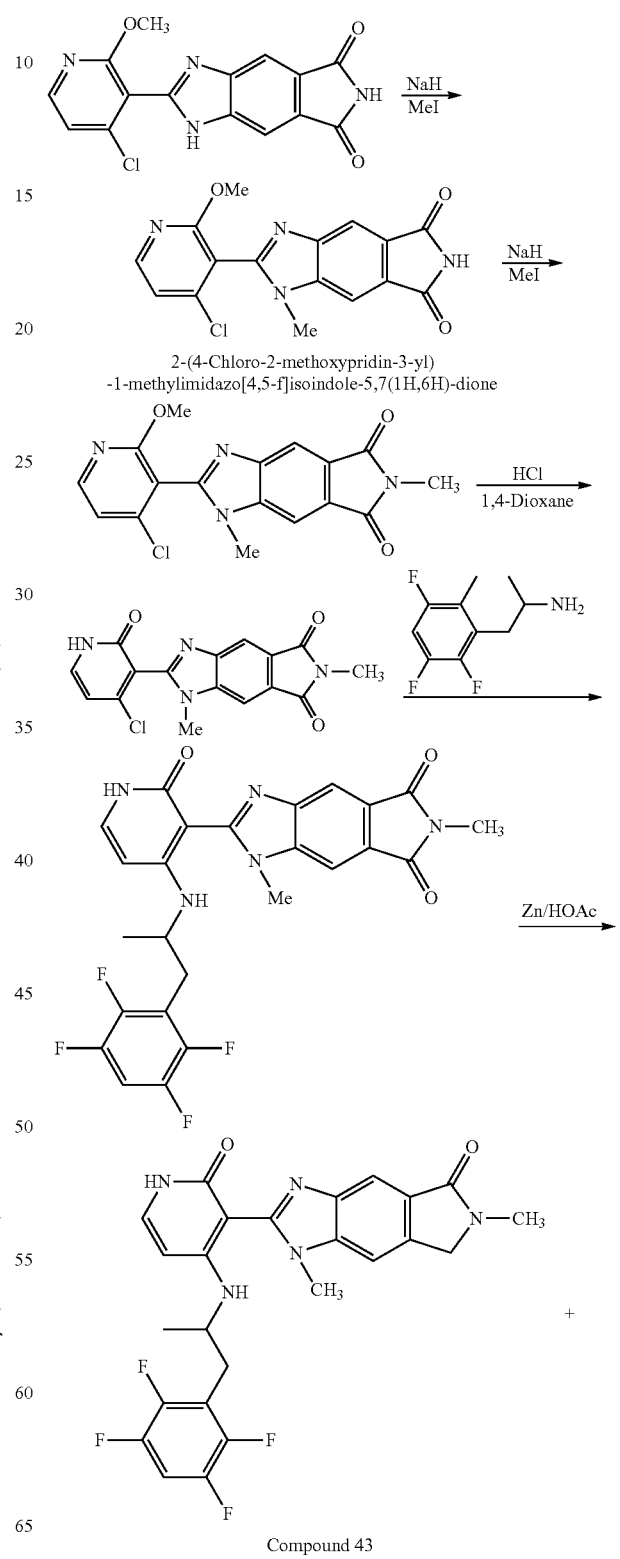

2-(4-Chloro-2-methoxypridin-3-yl)-1-methylimidazo[4,5-f]isoindole-5,7(1H,6H)-dione Compound 43

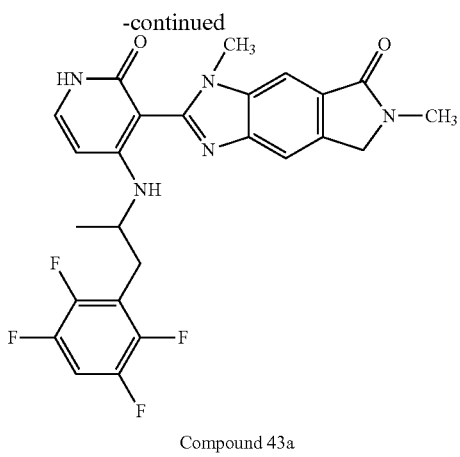

Compound 43a

2-(4-Chloro-2-methoxypyridin-3-yl)-1-methylimidazo[4,5-f]isoindole-5,7(1H,6H)-dione NaH (0.12 g, 3.04 mmol) was added in portions to a solution of 2-(4-chloro-2-methoxypyridin-3-yl)imidazo[4,5-f]isoindole-5,7(1H,6H)-dione (1.0 g, 3.04 mmol) in 30 mL of anhydrous DMF at 0° C. under argon. The reaction mixture was then stirred at rt for 3 h. MeI (2.16 g, 15.2 mmol) was added dropwise via a syringe at rt under argon. The resulted mixture was stirred for 6 h at rt, hydrolyzed by adding 100 mL of water. The brown precipitate was isolated, washed with water and dried under vacuum. The solid was purified by column chromatography (silica-gel, $CH_2Cl_2$/MeOH=49/1 v/v) to give a white solid product, 0.68 g, 65.4% yield. MS: 343.0 [M−H]$^-$. $^1$H NMR (DMSO-d$_6$, 500 MHz): δ 11.27 (s, 1H), 8.42 (d, 1H, J=5.5 Hz), 8.23 (s, 1H), 8.08 (s, 1H), 7.43 (d, 1H, J=5.5 Hz), 3.89 (s, 3H), 3.75 (s, 3H).

Trans-1,6-Dimethyl-2(2-oxo-4-(1-(2,3,5,6-tetrafluorophenyl)propan-2-ylamino)-1,2-dihydropyridin-3-yl)-6,7-dihydroimidazo[4,5-f]isoindol-5(1H)-one (Compound 43)

NaH (53 mg, 2.19 mmol) was added in portions to a solution of 2-(4-chloro-2-methoxypyridin-3-yl)-1-methylimidazo[4,5-f]isoindole-5,7(1H,6H)-dione (0.50 g, 1.46 mmol) in 30 mL of anhydrous DMF at 0° C. under argon. The reaction mixture was then stirred at rt for 3 h. MeI (0.32 g, 2.19 mmol) was added dropwise via a syringe at rt under argon. The resulted mixture was stirred for 6 h at rt, hydrolyzed by adding 100 mL of water. The brown precipitate was isolated, washed with water and dried under vacuum. The solid was purified by column chromatography (silica-gel, $CH_2Cl_2$/MeOH=49/1 v/v) to give a white solid product (0.30 g, 57.7% yield). This product was dissolved in 30 mL of 1,4-dioxane and 5 mL of concentrated HCl at rt. The reaction mixture was stirred at rt overnight. Then, the volatile was removed to give a yellow-brown solid. The solid was mixed with 1-(2,3,5,6-tetrafluorophenyl)propan-2-amine (0.17 g, 0.84 mmol), N,N-diisopropylethylamine (5 mL) and n-butanol (30 mL) in a flask. The reaction mixture was stirred and heated to reflux overnight under argon. Then, volatiles were removed under reduced pressure. The residue solid was purified by column chromatography (silica-gel, $CH_2Cl_2$/MeOH=9/1 v/v) to give a white solid product (0.12 g, 27.9% yield). The product (0.12 g, 0.234 mmol) and zinc powder (0.30 g, 4.67 mmol) were suspended in acetic acid (20 mL).

The reaction mixture was stirred and heated to reflux overnight under argon. Then, the solvent was removed under reduced pressure. The residue solid was stirred in 100 mL of saturated $K_2CO_3$ solution. The white solid was filtered out, dried under vacuum, and extracted with $CH_2Cl_2$/MeOH (7/3 v/v) three times (100 mL). The extracts were concentrated to dryness. The residue was purified by column chromatography (silica-gel, $CH_2Cl_2$/MeOH=9/1 v/v) to give a pale-yellow solid product, 20 mg, 17.1% yield. MS: 500.1 [M+H]$^+$. $^1$H NMR (DMSO-d$_6$, 500 MHz): δ 10.97 (s, 1H), 7.81 (s, 1H), 7.75-7.65 (m, 2H), 7.33-7.28 (m, 2H), 6.00 (d, 1H, J=7.5 Hz), 4.54 (s, 2H), 4.02 (m, 1H), 3.63 (s, 3H), 3.12 (s, 3H), 2.95-2.80 (m, 2H), 1.20 (d, 3H, J=6.3 Hz).

Cis-1,6-Dimethyl-2(2-oxo-4-(1-(2,3,5,6-tetrafluorophenyl)propan-2-ylamino)-1,2-dihydropyridin-3-yl)-6,7-dihydroimidazo[4,5-f]isoindol-5(1H)-one (Compound 43a)

Compound was isolated from the above reaction as a pale-yellow solid (40 mg, 34.2% yield). MS: 500.1 [M+H]$^+$. $^1$H NMR (DMSO-d$_6$, 500 MHz): δ 10.99 (s, 1H), 7.88 (s, 1H), 7.77-7.65 (m, 2H), 7.36-7.27 (m, 2H), 6.00 (d, 1H, J=7.5 Hz), 4.52 (s, 2H), 4.03 (m, 1H), 3.66 (s, 3H), 3.12 (s, 3H), 2.89-2.80 (m, 2H), 1.19 (d, 3H, J=6.3 Hz).

Synthesis of Compound 44

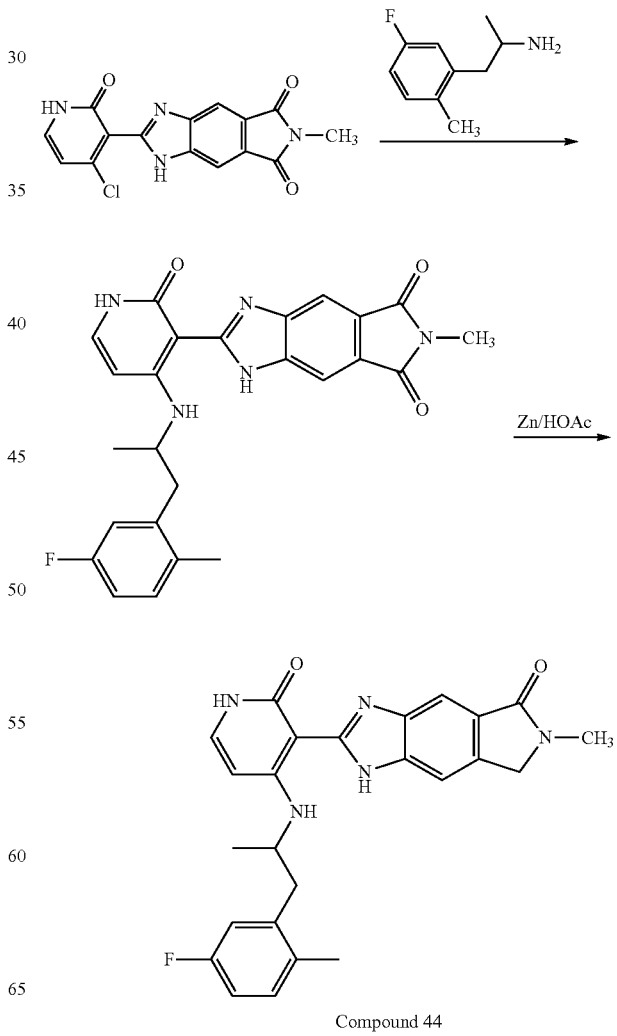

Compound 44

2-(4-(1-5-Fluoro-2-methylphenyl)propan-2-yl) amino)-2-oxo-1,2-dihydropyridin-3-yl)-6-methylimidazo[4,5-f]isoindole-5,7(1H,6H)-dione 2-(4-Chloro-2-oxo-1,2-dihydropyridin-3-yl)-6-methylimidazo[4,5-f]isoindole-5,7(1H,6H)-dione (0.60 g, 1.83 mmol), 1-(5-fluoro-2-methylphenyl)propan-2-amine (0.31 g, 1.83 mmol), n-butanol (40 mL) and N,N-diisopropylethylamine (10 mL) were mixed together in a flask. The reaction mixture was stirred and heated to reflux overnight under argon. Solvents were removed under reduced pressure. The residue solid was purified by column chromatography (silica-gel, $CH_2Cl_2$/MeOH=9/1 v/v) to give a brown solid product, 0.62 g, 74% yield. MS: 457.9 [M−H]⁻. ¹H-NMR (DMSO-$d_6$, 500 MHz): δ 13.40 (s, 1H), 11.2 (d, 1H, J=6.0 Hz), 10.88 (d, 1H, J=8.0 Hz), 8.12 (s, 1H), 8.01 (s, 1H), 7.32-7.30 (m, 1H), 7.24-7.21 (m, 1H), 7.14-7.11 (m, 1H), 6.89-6.85 (m, 1H), 6.14 (d, 1H, J=8.0 Hz), 4.20-4.14 (m, 1H), 3.05 (s, 3H), 3.01-2.99 (m, 2H), 2.35 (s, 3H), 1.33 (d, 3H, J=6.0 Hz).

2-(4-(1-(5-Fluoro-2-methylphenyl)propan-2-ylamino)-2-oxo-1,2-dihydropyridin-3-yl)-6-methyl-6,7-dihydroimidazo[4,5-f]isoindol-5(1H)-one (Compound 44)

2-(4-(1-(5-Fluoro-2-methylphenyl)propan-2-ylamino)-2-oxo-1,2-dihydropyridin-3-yl)-6-methylimidazo[4,5-f]isoindole-5,7(1H,6H)-dione (0.35 g, 0.76 mmol) and zinc powder (1.20 g, 18.28 mmol) were suspended in acetic acid (30 mL). The reaction mixture was stirred and heated to reflux overnight under argon. Then, the solvent was removed under reduced pressure. The residue solid was stirred in 100 mL of saturated $K_2CO_3$ solution. The white solid was filtered out, dried under vacuum and extracted with $CH_2Cl_2$/MeOH (7/3 v/v) three times (100 mL). The extracts were concentrated to dryness. The residue was purified by column chromatography (silica-gel, $CH_2Cl_2$/MeOH=9/1 v/v) to give a pale-yellow solid product, 0.28 g, 82.8% yield. MS: 444.0 [M−H]⁻. ¹H-NMR (DMSO-$d_6$, 300 MHz): δ 13.06 (s, 1H), 11.16 (s, 1H), 11.09-11.06 (m, 1H), 7.95 (s, 0.5H), 7.85 (s, 0.5H), 7.78 (s, 0.5H), 7.69 (s, 0.5H), 7.30-7.10 (m, 3H), 6.91-6.83 (m, 1H), 6.14-6.10 (m, 1H), 4.48 (s, 2H), 4.17-4.13 (m, 1H), 3.10 (s, 3H), 3.03-2.96 (m, 2H), 2.35 (d, 3H, J=4.9 Hz), 1.34-1.32 (m, 3H).

Synthesis of Compound 45

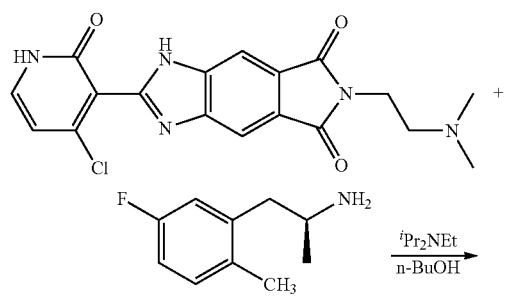

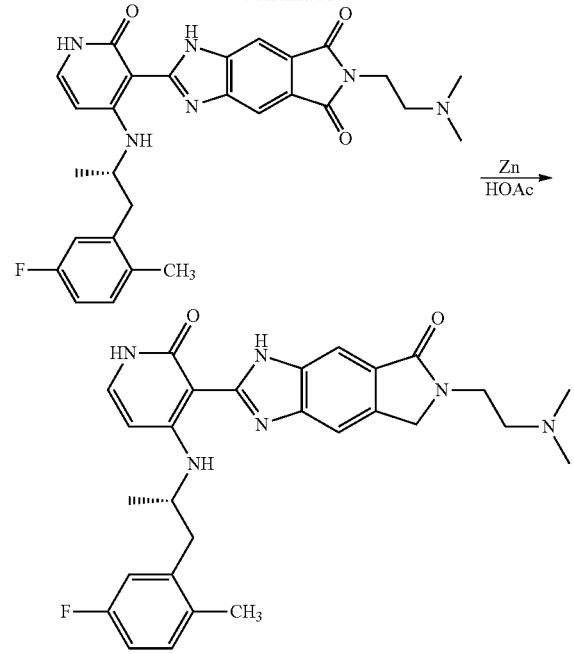

2-(4-(1-(5-Fluoro-2-methylphenyl)propan-2-ylamino)-2-oxo-1,2-dihydropyridin-3-yl)-6-(2-(dimethylamino)ethyl)imidazo[4,5-f]isoindole-5,7(1H,6H)-dione 2-(4-Chloro-2-oxo-1,2-dihydropyridin-3-yl)-6-(2-(dimethylamino)ethyl)imidazo[4,5-f]isoindole-5,7(1H,6H)-dione (1.05 g, 2.72 mmol), (S)-1-(5-fluoro-2-methylphenyl)propan-2-amine (0.55 g, 3.26 mmol), n-butanol (50 mL) and N,N-diisopropylethylamine (5 mL) were mixed together in a flask. The reaction mixture was stirred and heated to reflux overnight under argon. Solvents were removed under reduced pressure. The residue solid was purified by column chromatography (silica-gel, $CH_2Cl_2$/MeOH=9/1 v/v) to give a brown solid product, 1.18 g, 84.3% yield. MS: 517.2 [M+H]⁺. ¹H NMR (DMSO-$d_6$, 300 MHz): δ 13.42 (s, 1H), 11.23 (s, 1H), 10.86 (d, 1H, J=8.1 Hz), 8.13 (s, 1H), 8.00 (s, 1H), 7.31-7.10 (m, 3H), 6.90-6.83 (m, 1H), 6.14 (d, 1H, J=7.5 Hz), 4.22-4.13 (m, 1H), 3.68 (t, 2H, J=6.5 Hz), 3.00 (d, 2H, J=6.9 Hz), 2.51-2.47 (m, 2H), 2.42 (s, 3H), 2.18 (s, 6H), 1.34 (d, 3H, J=6.3 Hz).

2-(4-(1-(5-Fluoro-2-methylphenyl)propan-2-ylamino)-2-oxo-1,2-dihydropyridin-3-yl)-6-(2-(dimethylamino)ethyl)-6,7-dihydroimidazo[4,5-f]isoindole-5(1H)-one (Compound 45)

Compound 2-(4-(1-(5-fluorophenyl)propan-2-ylamino)-2-oxo-1,2-dihydropyridin-3-yl)-6-(2-(dimethylamino)ethyl)imidazo[4,5-f]isoindole-5,7(1H,6H)-dione (1.32 g, 2.56 mmol) and zinc powder (4.01 g, 61.32 mmol) were suspended in acetic acid (60 mL). The reaction mixture was stirred and heated to reflux overnight under argon. Then, the solvent was removed under reduced pressure. The residue solid was stirred in 100 mL of saturated $K_2CO_3$ solution. The white solid was filtered out, dried under vacuum and extracted with $CH_2Cl_2$/MeOH (7/3 v/v) three times (300 mL). The extracts were concentrated to dryness. The residue was purified by column chromatography (silica-gel, $CH_2Cl_2$/MeOH=9/1 v/v) to give a white solid product, 0.85 g, 74% yield. MS: 503.1 [M+H]$^+$. $^1$H NMR (DMSO-d$_6$, 300 MHz): δ 13.07 (s, 1H), 11.17 (s, 1H), 11.09-11.05 (m, 1H), 7.97 (s, 0.5H), 7.86 (s, 0.5H), 7.80 (s, 0.5H), 7.70 (s, 0.5H), 7.30-7.10 (m, 3H), 6.92-6.84 (m, 1H), 6.15-6.11 (m, 1H), 4.54 (s, 2H), 4.18-4.14 (m, 1H), 3.64 (t, 2H, J=6.0 Hz), 3.02-2.97 (m, 2H), 2.53-2.49 (m, 2H), 2.36 (d, 3H, J=3.9 Hz), 2.20 (s, 6H), 1.35-1.33 (m, 3H).

Example 13

Synthesis of Compounds of this Invention

R$^1$ being Alkylamine or Heterocycles

Synthesis of Compounds 46, 47A and 47B

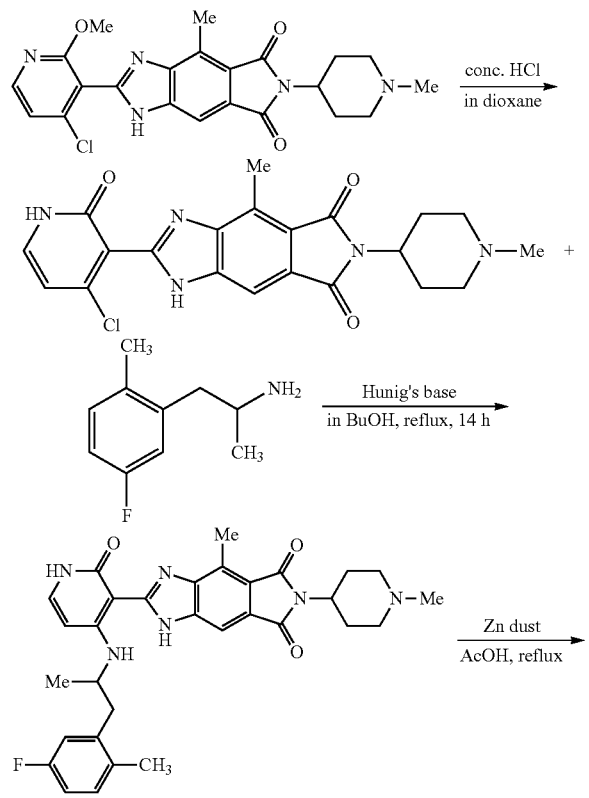

Compound 46

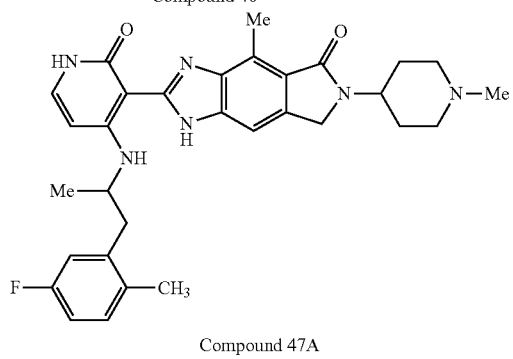

Compound 47A

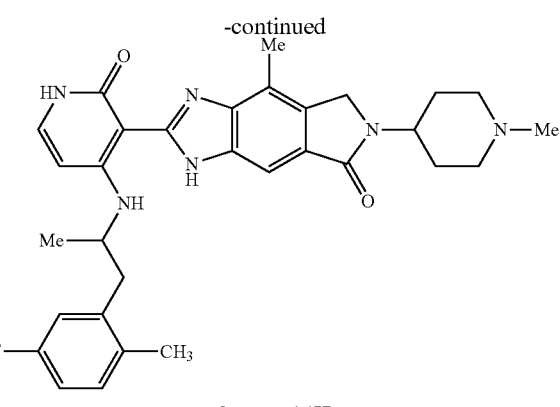

Compound 47B 2-(4-(1-(5-Fluoro-2-methylphenyl)propan-2-ylamino)-2-oxo-1,2-dihydropyridin-3-yl)-4-methyl-6-(1-methylpiperidin-4-yl)imidazo[4,5-f]isoindole-5,7(1H,6H)-dione (Compound 46)

A mixture of 2-(4-chloro-2-oxo-1,2-dihydropyridin-3-yl)-4-methyl-6-(1-methylpiperidin-4-yl)imidazo[4,5-f]isoindole-5,7(1H,6H)-dione (1.00 g, 2.35 mmol), 1-(5-fluoro-2-methylphenyl)propan-2-amine (0.47 g, 2.82 mmol), Hunig's base (1.52 g, 0.011 mol), and 20 mL of anhydrous 1-butanol was heated at reflux for 14-15 h under an argon atmosphere. Product was purified by a silica gel column using methylene chloride and methanol (9:1 v/v) as eluent to afford 1.31 g (99%) of the designed compound as yellowish solid. $^1$H NMR (300 MHz, DMSO-d$_6$) δ 13.37 (s, 1H, NH), 11.25 (d, J=6.3 Hz, 1H, NH), 11.02 (d, J=8.1 Hz, 1H, NH), 7.98 (s, 1H, ArH), 7.32 (t, J=7.2 Hz, 1H, ArH), 7.16-7.07 (m, 2H, ArH), 6.92-6.86 (m, 1H, ArH), 6.17 (d, J=7.5 Hz, 1H, ArH), 4.34-4.19 (m, 2H, 2×CH), 3.51-3.47 (m, 2H, CH$_2$), 3.18-3.11 (m, 2H, CH$_2$), 2.97 (d, J=6.3 Hz, 2H, CH$_2$), 2.83 (s, 3H, CH$_3$), 2.76 (s, 3H, CH$_3$), 2.69-2.61 (m, 2H, CH$_2$), 2.27 (s, 3H, CH$_3$), 1.95-1.91 (m, 2H, CH$_2$), 1.34 (d, J=6.3 Hz, 3H, CH$_3$); Mass (ESI, positive) m/z 557.2 [M+H]$^+$.

2-(4-(1-(5-Fluoro-2-methylphenyl)propan-2-ylamino)-2-oxo-1,2-dihydropyridin-3-yl)-4-methyl-6-(1-methylpiperidin-4-yl)-6,7-dihydroimidazo[4,5-f]isoindol-5(1H)-one (Compound 47A)

A mixture of 2-(4-(1-(5-fluoro-2-methylphenyl)propan-2-ylamino)-2-oxo-1,2-dihydropyridin-3-yl)-4-methyl-6-(1-methylpiperidin-4-yl)imidazo[4,5-f]isoindole-5,7(1H,6H)-dione (0.81 g, 1.46 mmol), zinc dust (0.95 g, 14.55 mmol), and 25 mL of acetic acid was heated at reflux for 13-14 h under an argon atmosphere. Product was separated by a silica gel column using methylene chloride and methanol (85:15 v/v) as eluent to afford 0.12 g of the designed compound as yellowish solid. $^1$H NMR (500 MHz, DMSO-d$_6$) δ 12.98 (s, 1H, NH), 11.32 (d, J=8.0 Hz, 1H, NH), 11.16 (d, J=4.5 Hz, 1H, NH), 7.80 (s, 1H, ArH), 7.29-7.26 (m, 1H, ArH), 7.15-7.12 (2H, ArH), 6.91-6.85 (m, 1H, ArH), 6.14 (d, J=7.5 Hz, 1H, ArH), 4.43 (s, 2H, CH$_2$), 4.21-4.15 (m, 1H, CH), 4.04-3.99 (m, 1H, CH), 2.97 (d, J=6.5 Hz, 2H, CH$_2$), 2.89-2.87 (m, 2H, CH$_2$), 2.54 (s, 2H, CH$_2$), 2.28 (s, 3H, CH$_3$), 2.21 (s, 3H, CH$_3$), 2.04-1.99 (m, 2H, CH$_2$), 1.89 (s, 3H, CH$_3$), 1.89-1.82 (m, 2H, CH$_2$), 1.70-1.67 (m, 2H, CH$_2$), 1.34 (d, J=6.0 Hz, 3H, CH$_3$); Mass (ESI, positive) m/z 543.2 [M+H]$^+$, 565.2 [M+Na]$^+$.

2-(4-(1-(5-Fluoro-2-methylphenyl)propan-2-ylamino)-2-oxo-1,2-dihydropyridin-3-yl)-8-methyl-6-(1-methylpiperidin-4-yl)-6,7-dihydroimidazo[4,5-f]isoindol-5(3H)-one (Compound 47B)

A mixture of 2-(4-(1-(5-fluoro-2-methylphenyl)propan-2-ylamino)-2-oxo-1,2-dihydropyridin-3-yl)-4-methyl-6-(1-methylpiperidin-4-yl)imidazo[4,5-f]isoindole-5,7(1H,6H)-dione (0.81 g, 1.46 mmol), zinc dust (0.95 g, 14.55 mmol), and 25 mL of acetic acid was heated at reflux for 13-14 h under an argon atmosphere. Product was separated by a silica gel column using methylene chloride and methanol (85:15 v/v) as eluent to afford 30 mg of the designed compound as yellowish solid. $^1$H NMR (500 MHz, DMSO-d$_6$) δ; Mass (ESI, positive) m/z 543.2 [M+H]$^+$, 565.2 [M+Na]$^+$.

Synthesis of Compounds 48, 49A and 49B

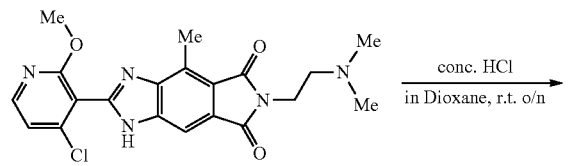

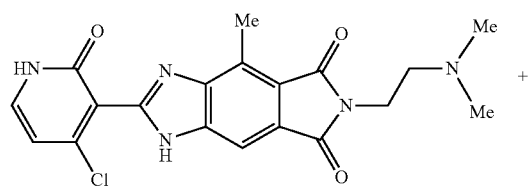

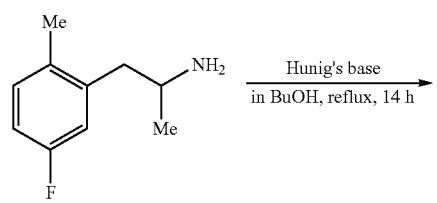

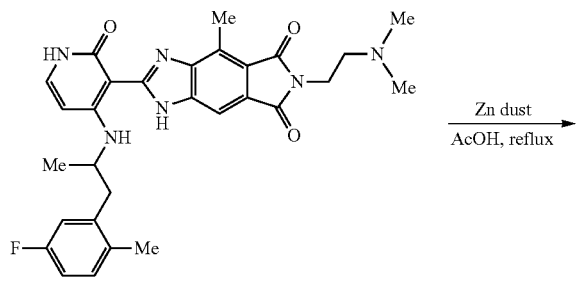

Compound 48

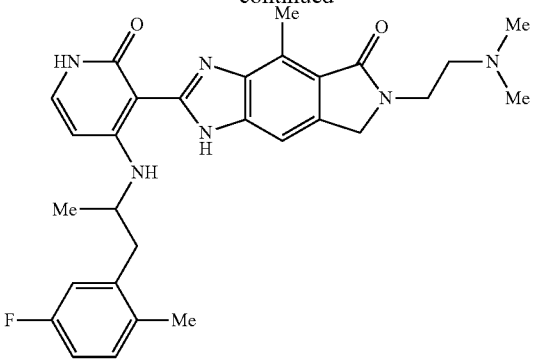

Compound 49A

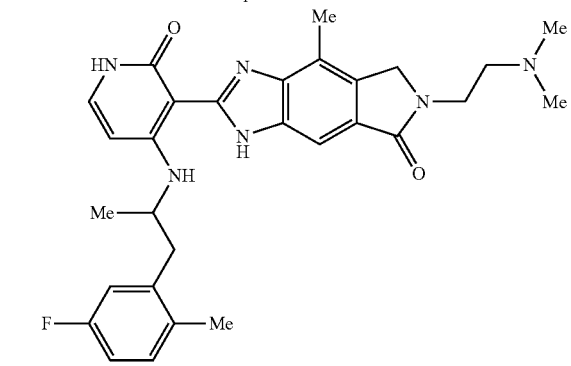

Compound 49B

6-(2-(Dimethylamino)ethyl)-2-(4-(1-(5-fluoro-2-methylphenyl)propan-2-ylamino)-2-oxo-1,2-dihydropyridin-3-yl)-4-methylimidazo[4,5-f]isoindole-5,7(1H,6H)-dione (Compound 48)

A mixture of 2-(4-chloro-2-oxo-1,2-dihydropyridin-3-yl)-6-(2-(dimethylamino)ethyl)-4-methylimidazo[4,5-f]isoindole-5,7(1H,6H)-dione (0.48 g, 1.20 mmol), 1-(5-fluoro-2-methylphenyl)propan-2-amine (0.24 g, 1.44 mmol), Hunig,s base (0.78 g, 6.00 mmol), and 10 mL of anhydrous 1-butanol was heated at reflux for 12-13 h under an argon atmosphere. Product was purified by a silica gel column using methylene chloride and methanol (9:1 v/v) as eluent to afford 0.35 g of the designed compound as yellow solid. $^1$H NMR (500 MHz, DMSO-d$_6$) δ 13.36 (s, 1H, NH), 11.24 (d, J=6.0 Hz, 1H, NH), 11.02 (d, J=8.5 Hz, 1H, NH), 7.99 (s, 1H, ArH), 7.32 (t, J=6.5 Hz, 1H, ArH), 7.15-7.08 (m, 2H, ArH), 6.91-6.87 (m, 1H, ArH), 6.16 (d, J=7.5 Hz, 1H, ArH), 4.22-4.18 (m, 1H, CH), 3.73-3.71 (m, 2H, CH$_2$), 2.97-2.96 (m, 2H, CH$_2$), 2.86 (s, 3H, CH$_3$), 2.72-2.68 (m, 2H, CH$_2$), 2.36 (s, 6H, 2×CH$_3$), 2.27 (s, 3H, CH$_3$), 1.34 (d, J=6.5 Hz, 3H, CH$_3$); Mass (ESI, negative) m/z 529.0 [M−H]$^-$.

6-(2-(Dimethylamino)ethyl)-2-(4-(1-(5-fluoro-2-methylphenyl)propan-2-ylamino)-2-oxo-1,2-dihydropyridin-3-yl)-4-methyl-6,7-dihydroimidazo[4,5-f]isoindol-5(1H)-one (Compound 49A)

A mixture of 6-(2-(dimethylamino)ethyl)-2-(4-(1-(5-fluoro-2-methylphenyl)propan-2-ylamino)-2-oxo-1,2-dihydropyridin-3-yl)-4-methyl-6,7-dihydroimidazo[4,5-f]isoindol-5(1H)-one (0.27 g, 0.51 mmol), zinc dust (0.33 g, 5.09 mmol), and 8.5 mL of acetic acid was heated at reflux for 13-14 h under an argon atmosphere. Product was separated by a silica gel column using methylene chloride and methanol (85:15 v/v) as eluent to afford 0.11 g of the designed compound as yellowish solid. $^1$H NMR (500 MHz, DMSO-$d_6$) δ 12.99 (s, 1H, NH), 11.31 (d, J=8.0 Hz, 1H, NH), 11.17 (br s, 1H, NH), 7.81 (s, 1H, ArH), 7.28 (d, J=7.5 Hz, 1H, ArH), 7.15-7.12 (m, 2H, ArH), 6.96-6.85 (m, 1H, ArH), 6.14 (d, J=7.0 Hz, ArH), 4.47 (s, 2H, $CH_2$), 4.21-1.16 (m, 1H, CH), 3.64 (t, J=6.5 Hz, 2H, $CH_2$), 2.97 (d, J=7.0 Hz, 2H, $CH_2$), 2.53 (m, 2H, $CH_2$), 2.81 (s, 3H, $CH_3$), 2.19 (s, 6H, 2×$CH_3$), 1.89 (s, 3H, $CH_3$), 1.34 (d, J=6.0 Hz, 3H, $CH_3$); Mass (ESI, positive) m/z 517.3 [M+H]$^+$, 539.1 [M+Na]$^+$.

6-(2-(Dimethylamino)ethyl)-2-(4-(1-(5-fluoro-2-methylphenyl)propan-2-ylamino)-2-oxo-1,2-dihydropyridin-3-yl)-8-methyl-6,7-dihydroimidazo[4,5-f]isoindol-5(3H)-one (Compound 49B)

A mixture of 6-(2-(dimethylamino)ethyl)-2-(4-(1-(5-fluoro-2-methylphenyl)propan-2-ylamino)-2-oxo-1,2-dihydropyridin-3-yl)-4-methyl-6,7-dihydroimidazo[4,5-f]isoindol-5(1H)-one (0.27 g, 0.51 mmol), zinc dust (0.33 g, 5.09 mmol), and 8.5 mL of acetic acid was heated at reflux for 13-14 h under an argon atmosphere. Product was separated by a silica gel column using methylene chloride and methanol (85:15 v/v) as eluent to afford 30 mg of the designed compound as yellowish solid. $^1$H NMR (500 MHz, DMSO-$d_6$) δ; Mass (ESI, positive) m/z 517.2 [M+H]$^+$, 539.2 [M+Na]$^+$.

Synthesis of Compound 50

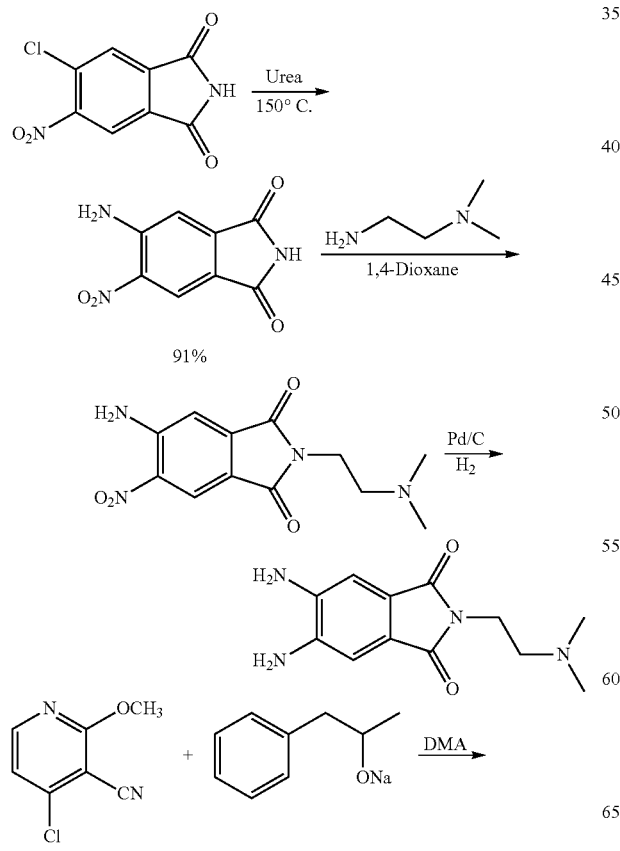

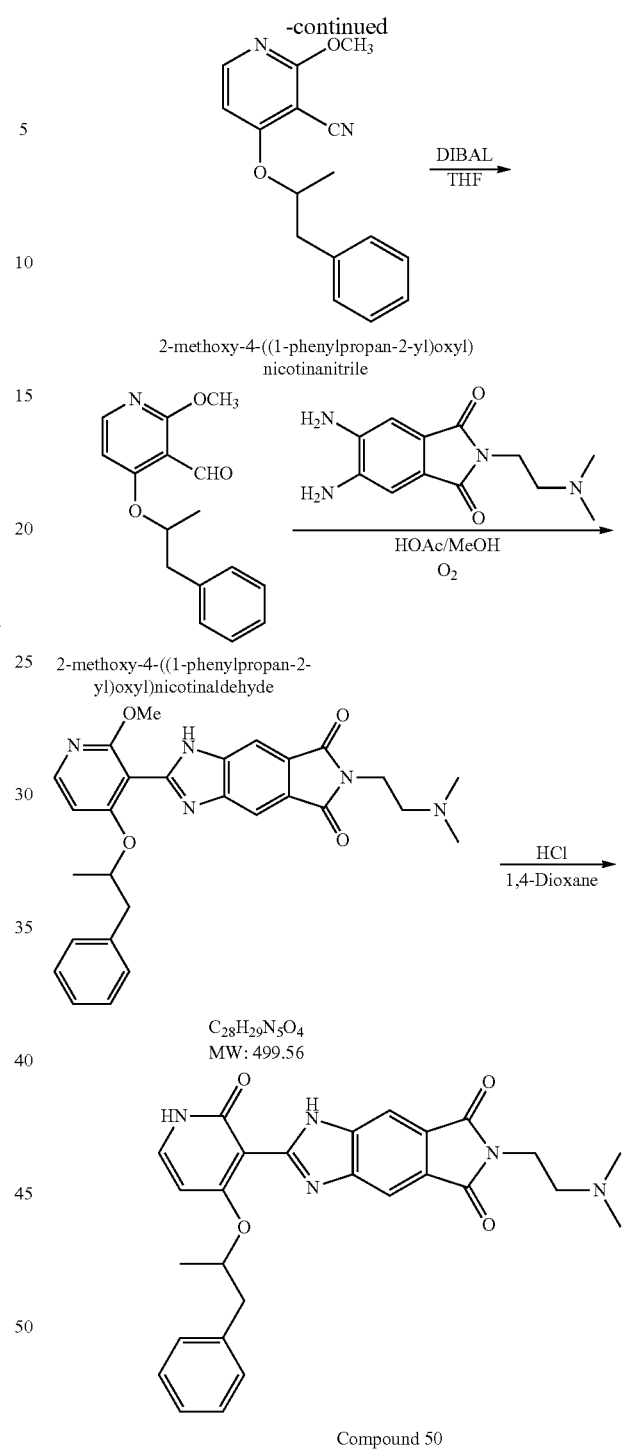

Compound 50

2-Methoxy-4-((1-phenylpropan-2-yl)oxy)nicotinanitrile

1-Phenyl-2-propanol (8.10 g, 59.48 mmol) was dissolved in 100 mL of anhydrous dimethylacetamide at rt under dry argon. The solution was cooled to 0° C. in an ice-bath. NaH (2.38 g, 59.48 mmol) was added in portions at 0° C. under argon. The reaction mixture was slowly warmed to rt and stirred for 3 h. Then, 4-chloro-2-methoxynicotinonitrile (5.01 g, 29.74 mmol) and Bu$_4$NCl were added at rt. After heated to 100° C. overnight, the reaction mixture was diluted with 100 mL of water. The solution was extracted with ethyl acetate (EtOAc). The organic layer was separated, dried over MgSO$_4$ and concentrated to dryness under reduced pressure. The residue was subjected to column chromatography (silica-gel, CH$_2$Cl$_2$) to give a colorless oil product, 1.20 g, 15.0% yield. MS: 269.8 [M+H]$^+$. $^1$H-NMR (DMSO-d$_6$, 500 MHz): δ 8.21 (d, 1H, J=6.0 Hz), 7.31-7.26 (m, 4H), 7.22-7.19 (m, 1H), 6.97 (d, 1H, J=6.0 Hz), 5.01-4.97 (m, 1H), 3.93 (s, 3H), 3.02-2.94 (m, 2H), 1.29 (d, 3H, J=6.0 Hz).

2-Methoxy-4-((1-phenylpropan-2-yl)oxy)nicotinaldehyde

2-Methoxy-4-((1-phenylpropan-2-yl)oxy)nicotinanitrile (1.30 g, 4.85 mmol) was dissolved in anhydrous THF (30 mL) at rt under argon. The solution was cooled to −78° C. Diisobutylaluminum hydride (3.88 mL of 1.5 M in toluene) was added drop wise via a syringe under argon. The reaction solution was gradually warmed to rt and heated to reflux for 3 h. The reaction was quenched by adding 50 mL of saturated NH$_4$Cl solution. Then, the volatiles were removed under reduced pressure. The residue was extracted with ethyl acetate (3×50 mL). The organic layers were combined, dried over anhydrous MgSO$_4$, filtered and concentrated to dryness. The residue was purified by column chromatography (silica-gel, CH$_2$Cl$_2$/acetone=19/1 v/v) to give a pale-yellow solid product, 0.85 g, 64.6% yield. MS: 272.1 [M+H]$^+$. $^1$H-NMR (DMSO-d$_6$, 500 MHz): δ 10.28 (s, 1H), 8.18 (d, 1H, J=6.0 Hz), 7.31-7.25 (m, 5H), 7.21-7.18 (m, 1H), 6.92 (d, 1H, J=6.0 Hz), 4.96-4.92 (m, 1H), 3.89 (s, 3H), 3.32 (s, 1H), 3.03-2.95 (m, 2H), 1.29 (d, 3H, J=6.0 Hz).

6-(2-(Dimethylamino)ethyl)-2-(2-methoxy-4-((1-phenylpropan-2-yl)oxy)pyridine-3-yl)imidazo[4,5-f]isoindole-5,7(1H,6H)-dione 5,6-Diamino-2-(2-(dimethylamino)ethyl)isoindoline-1,3-dione (0.47 g, 1.88 mmol) was dissolved in MeOH (30 mL) and acetic acid (10 mL). 2-Methoxy-4-((1-phenylpropan-2-yl)oxy)nicotinaldehyde (0.51 g, 1.88 mmol) was added under air at rt. The reaction mixture was stirred at rt under air overnight. The volatile was removed. The residue was subjected to column chromatography (silica-gel, CH$_2$Cl$_2$/MeOH=17/3 v/v) to give a white solid product, 0.65 g, 69.2% yield. MS: 500.3 [M+H]$^+$. $^1$H-NMR (DMSO-d$_6$, 500 MHz): δ 13.23 (s, 1H), 8.20 (d, 1H, J=6.0 Hz), 8.12 (s, 1H), 7.95 (s, 1H), 7.09-7.07 (m, 1H), 7.11-7.95 (m, 5H), 4.84-4.81 (m, 1H), 3.82 (s, 3H), 3.72 (t, 2H, J=6.5 Hz), 2.78 (d, 2H, J=6.0 Hz), 2.53 (t, 2H, J=6.5 Hz), 2.19 (s, 6H), 1.17 (d, 3H, J=6.0 Hz).

6-(2-(Dimethylamino)ethyl)-2-(2-oxo-4-((1-phenylpropan-2-yl)oxy)-1,2-dihydropyridine-3-yl)imidazo[4,5-f]isoindole-5,7(1H,6H)-dione (Compound 50)

6-(2-(Dimethylamino)ethyl)-2-(2-methoxy-4-((1-phenylpropan-2-yl)oxy)pyridine-3-yl)imidazo[4,5-f]isoindole-5,7 (1H,6H)-dione (0.52 g, 1.04 mmol) was dissolved in 30 mL of 1,4-dioxane at rt. 5 mL of concentrated HCl was added. The reaction mixture was stirred at rt for 12 h. The volatile was removed under reduced pressure. The residue was washed with 20 mL of saturated K$_2$CO$_3$ solution. The pale-yellow precipitate was purified by column chromatography (silica-gel, CH$_2$Cl$_2$/MeOH=7/3 v/v) to give a pale-yellow solid product, 0.38 g, 75.2% yield. MS: 486.8 [M+H]$^+$. $^1$H-NMR (DMSO-d$_6$, 500 MHz): δ 13.24 (s, 1H), 11.98 (s, 1H), 8.03 (s, 2H), 7.60 (d, 1H, J=7.0 Hz), 7.34-7.32 (m, 2H), 7.12-7.09 (m, 3H), 6.46 (d, 1H, J=7.5 Hz), 4.93-4.87 (m, 1H), 3.70 (t, 2H, J=7.0 Hz), 3.03-2.91 (m, 2H), 2.52 (t, 2H, J=7.0 Hz), 2.19 (s, 6H), 1.27 (d, 3H, J=6.0 Hz).

Synthesis of Compound 51

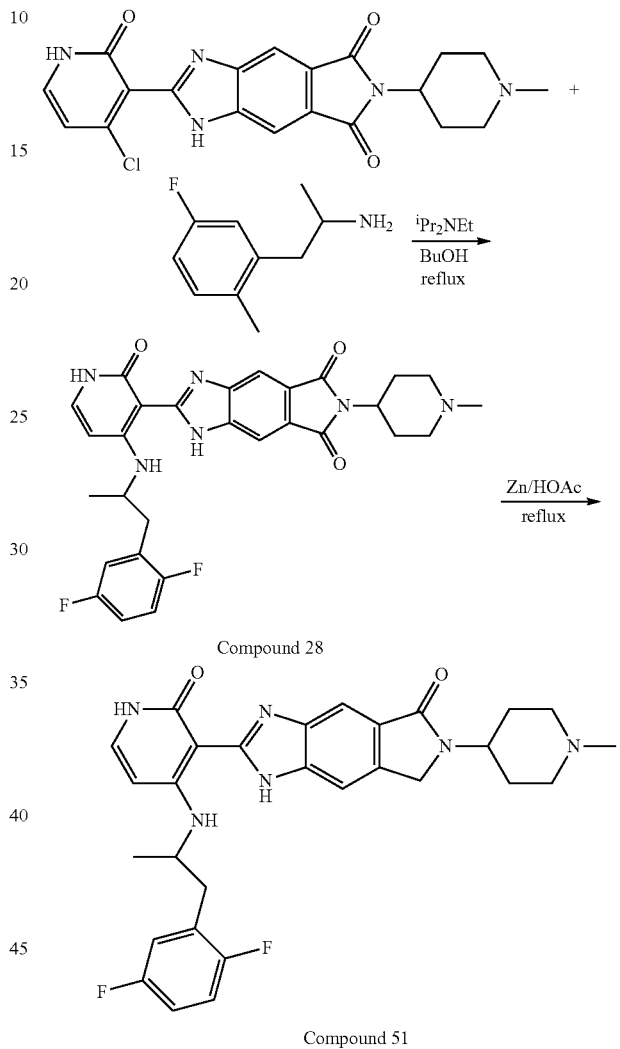

Compound 51

2-(4-((1-(2,5-Difluorophenyl)propan-2-yl)amino)-2-oxo-1,2-dihydropyridin-3-yl)-6-(1-methylpiperidin-4-yl)imidazo[4,5-f]isoindole-5,7(1H,6H)-dione (Compound 28)

2-(4-Chloro-2-oxo-1,2-dihydropyridin-3-yl)-6-(1-methylpiperidin-4-yl)-imidazo[4,5-f]isoindole-5,7(1H,6H)-dione (0.59 g, 1.43 mmol), 1-(2,5-difluorophenyl)propan-2-amine (0.29 g, 1.72 mmol), n-butanol (50 mL) and N,N-diisopropylethylamine (5 mL) were mixed together in a flask. The reaction mixture was stirred and heated to reflux overnight under argon. Solvents were removed under reduced pressure. The residue solid was purified by column chromatography (silica-gel, CH$_2$Cl$_2$/MeOH=9/1 v/v) to give a brown solid product, 0.65 g, 83.8% yield. MS: 540.8 [M−H]$^−$. $^1$H-NMR (DMSO-d$_6$, 300 MHz): δ 13.42 (s, 1H), 11.26 (s, 1 Hz), 10.86 (d, 1H, J=8.0 Hz), 8.12 (s, 1H), 8.01 (s, 1H), 7.32-7.31 (m, 1H), 7.24-7.21 (m, 1H), 7.13-7.11 (m, 1H), 6.88-6.84 (m, 1H), 6.14 (d, 1H, J=7.5 Hz), 4.19-4.14 (m, 2H), 3.37-3.33 (m, 3H), 3.15 (m, 2H), 3.01-2.99 (m, 2H), 2.49 (s, 3H), 2.34 (s, 3H), 1.78-1.77 (m, 2H), 1.33 (d, 3H, J=6.5 Hz).

2-(4-((1-(2,5-Difluorophenyl)propan-2-yl)amino)-2-oxo-1,2-dihydropyridin-3-yl)-6-(1-methylpiperidin-4-yl)-6,7-dihydroimidazo[4,5-f]isoindol-5(1H)-one (Compound 51)

2-(4-((1-(2,5-Difluorophenyl)propan-2-yl)amino)-2-oxo-1,2-dihydropyridin-3-yl)-6-(1-methylpiperidin-4-yl)imidazo[4,5-f]isoindole-5,7(1H,6H)-dione (0.40 g, 0.74 mmol) and zinc powder (1.16 g, 17.7 mmol) were suspended in acetic acid (30 mL). The reaction mixture was stirred and heated to reflux overnight under argon. Then, the solvent was removed under reduced pressure. The residue solid was stirred in 100 mL of saturated $K_2CO_3$ solution. The white solid was filtered out, dried under vacuum and extracted with $CH_2Cl_2$/MeOH (7/3 v/v) three times (300 mL). The extracts were concentrated to dryness. The residue was purified by column chromatography (silica-gel, $CH_2Cl_2$/MeOH=9/1 v/v) to give a white solid product, 0.29 g, 74.6% yield. MS: 527 [M−H]−. $^1$H-NMR (DMSO-$d_6$, 300 MHz): δ 13.06 (s, 1H), 11.18 (s, 1H), 11.06-11.05 (m, 1H), 7.96 (s, 0.5H), 7.86 (s, 0.5H), 7.81 (s, 0.5H), 7.70 (s, 0.5H), 7.29-7.28 (m, 1H), 7.23-7.19 (m, 1H), 7.14-7.12 (m, 1H), 6.89-6.85 (m, 1H), 6.14-6.11 (m, 1H), 4.48 (s, 2H), 4.17-4.13 (m, 1H), 4.03-3.99 (m, 1H), 3.01-2.98 (m, 2H), 2.88-2.85 (m, 2H), 2.35 (d, 3H, J=4.5 Hz), 2.20 (s, 3H), 2.03-1.99 (m, 2H), 1.86-1.83 (m, 3H), 1.70-1.68 (m, 2H), 1.33 (d, 3H, J=6.5 Hz).

Example 14

Synthesis of Compounds of this Invention $R^1$ being Hydrogen

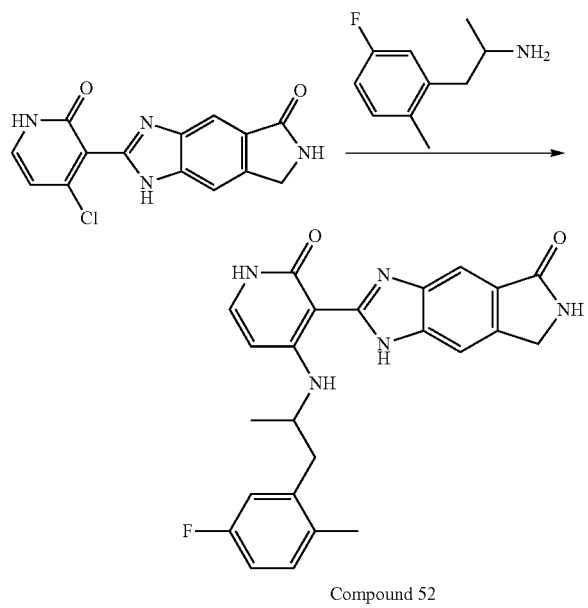

Compound 52

2-(4-((1-(5-Fluoro-2-methylphenyl)propan-2-ylamino)-oxo-1,2-dihydropyridin-3-yl)-6,7-dihydroimidazo[4,5-f]isoindo-5(1H)-one. (Compound 52)

2-(4-Chloro-2-methoxypyridin-3-yl)-6,7-dihydroimidazo[4,5-f]isoindo-5(1H)-one (0.73 g, 2.43 mmol) was dissolved in 30 mL of 1,4-dioxane and 5 mL of concentrated HCl at rt. The reaction mixture was stirred at rt overnight. Then, the volatile was removed to give a yellow-brown solid. This solid was mixed with 1-(5-fluoro-2-methylphenyl)propan-2-amine (0.49 g, 2.91 mmol), N,N-diisopropylethylamine (5 mL) and n-butanol (30 mL) in a flask. The reaction mixture was stirred and heated to reflux overnight under argon. Then, volatiles were removed under reduced pressure. The residue solid was purified by column chromatography (silica-gel, $CH_2Cl_2$/MeOH=9/1 v/v) to give a white solid product, 0.76 g, 72.4% yield. MS: 429.9 [M−H]−. $^1$H-NMR (DMSO-$d_6$, 500 MHz): δ 13.05 (s, 1H), 11.17-11.14 (m, 1H), 11.09-11.06 (m, 1H), 8.35 (d, 1H, J=6.0 Hz), 7.96 (s, 0.5H), 7.85 (s, 0.5H), 7.79 (s, 0.5H), 7.68 (s, 0.5H), 7.29-7.27 (m, 1H), 7.24-7.18 (m, 1H), 7.14-7.11 (m, 1H), 6.90-6.85 (m, 1H), 4.41 (m, 2H), 4.17-4.14 (m, 1H), 3.16-3.11 (m, 1H), 3.04-2.97 (m, 1H), 2.35 (d, 3H, J=8.0 Hz), 1.35-1.33 (m, 3H).

Example 15

Bioavailability of Compound 53

Figure 4A:
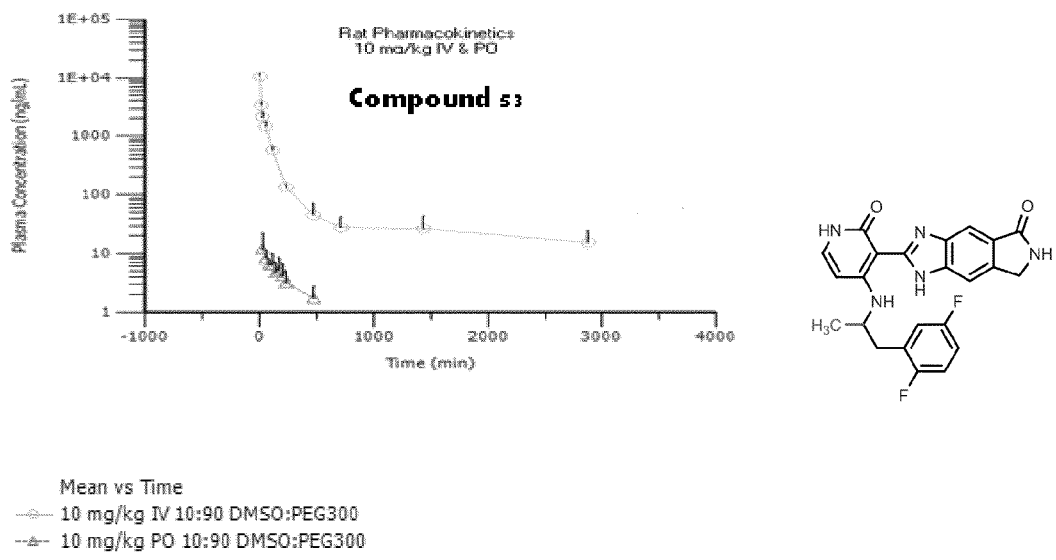
FIGS. 4A and 4B: Bioavailability of Compound 53 in comparison to compound PF2341066.
Figure 4B:
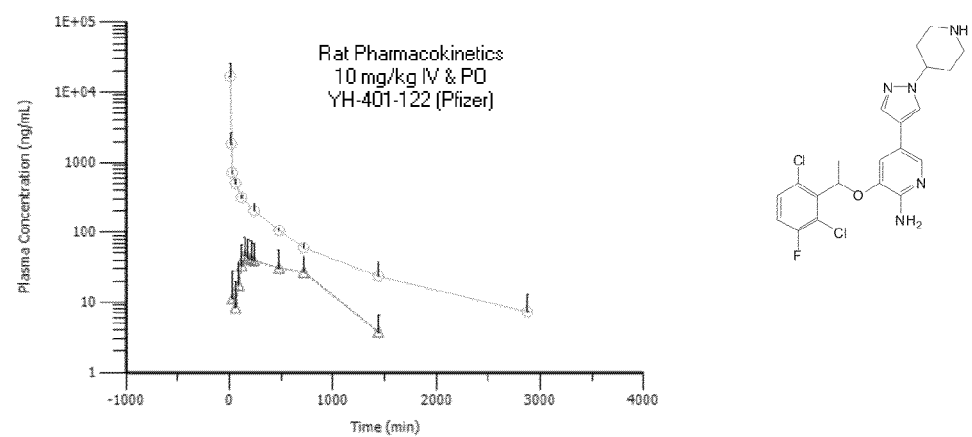

The pharmacokinetics of Compound 53 was measured in rats and compared with the pharmacokinetics of Pfizer's compound PF2341066. The results are demonstrated in FIG. 4 and n the following tables (Table 16A and 16B)

TABLE 16A rat pharmacokinetics of Compound PF2341066 (Pfizer)
Rat Pharmacokinetics

| Compound | Parameter | Dose_Route | Units | Estimate | SD |
| --- | --- | --- | --- | --- | --- |
| PF2341066 | AUC0-1440 | 10 mg/kg IV | min*ug/mL | 1236 | 706 |
| PF2341066 | AUC0-1440 | 10 mg/kg PO | min*ug/mL | 33.2 | 21.2 |
| PF2341066 | F | 10 mg/kg PO | % | 3% | |

TABLE 16B rat pharmacokinetics of Compound 53.

| Cmpd 53 | AUC0-1440 | 10 mg/kg IV | min*ug/mL | 531 | 30.7 |
| --- | --- | --- | --- | --- | --- |
| Cmpd 53 | AUC0-1440 | 10 mg/kg PO | min*ug/mL | 2.13 | 0.485 |
| Cmpd 53 | F | 10 mg/kg PO | % | 0.402% | |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed:

1. A method of treating, reducing the severity, or inhibiting the progression of a condition or disorder related to anaplastic lymphoma kinase (ALK) activity in a subject in need thereof comprising administering to the subject an effective amount of compound represented by the structure of formula (45)

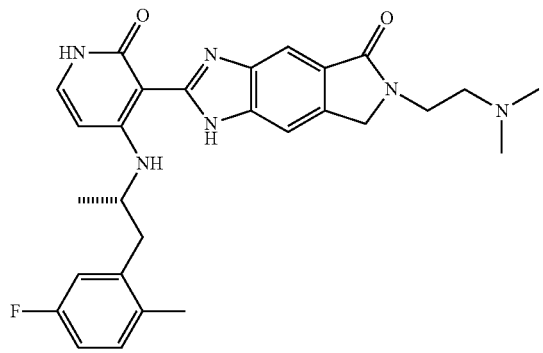

(45)

or its stereoisomer, tautomer, pharmaceutically acceptable salt, or any combination thereof, wherein said condition or disorder is ALK-positive anaplastic large cell lymphoma, non-small cell lung cancer, or neuroblastoma.

2. A method of inhibiting anaplastic lymphoma kinase (ALK) activity comprising contacting the anaplastic lymphoma kinase (ALK) with an effective amount of compound represented by the structure of formula (45)

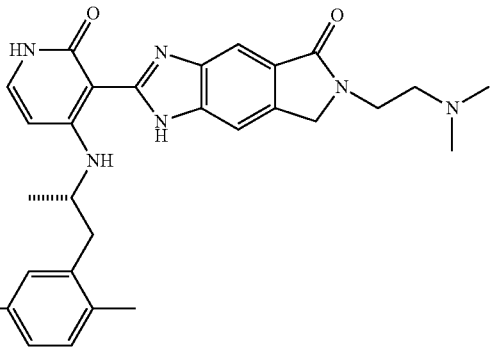

(45)

or its stereoisomer, tautomer, pharmaceutically acceptable salt, or any combination thereof.

3. A method of treating, reducing the severity, or inhibiting the progression of neuroblastoma in a subject in need thereof comprising administering to the subject an effective amount of compound represented by the structure of formula (45)

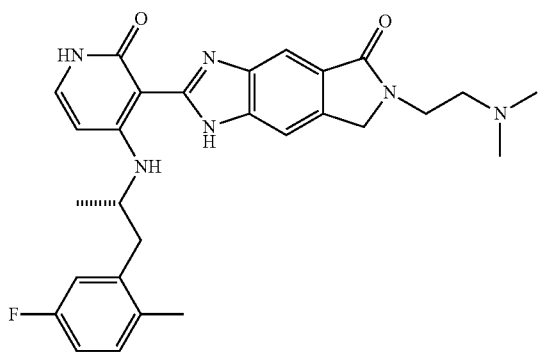

(45)

or its stereoisomer, tautomer, pharmaceutically acceptable salt, or any combination thereof.

* * * * *